US012070455B2

(12) United States Patent
Ammann et al.

(10) Patent No.: US 12,070,455 B2
(45) Date of Patent: Aug. 27, 2024

(54) THIENOPYRROLE COMPOUNDS

(71) Applicant: Gilead Sciences, Inc., Foster City, CA (US)

(72) Inventors: Stephen E. Ammann, Foster City, CA (US); Eda Y. Canales, San Mateo, CA (US); Weng K. Chang, San Lorenzo, CA (US); Henok H. Kinfe, Foster City, CA (US); Scott E. Lazerwith, Burlingame, CA (US); Michael L. Mitchell, Castro Valley, CA (US); Yasamin Moazami, Seattle, WA (US); Scott D. Schroeder, Union City, CA (US); Daniel G. Shore, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 17/930,538

(22) Filed: Sep. 8, 2022

(65) Prior Publication Data

US 2023/0270734 A1    Aug. 31, 2023

Related U.S. Application Data

(60) Provisional application No. 63/242,969, filed on Sep. 10, 2021.

(51) Int. Cl.
| | | |
|---|---|---|
| *C07D 519/00* | (2006.01) | |
| *A61K 31/437* | (2006.01) | |
| *A61K 31/439* | (2006.01) | |
| *A61K 31/4545* | (2006.01) | |
| *A61K 31/4706* | (2006.01) | |
| *A61K 31/496* | (2006.01) | |
| *A61K 31/5377* | (2006.01) | |
| *A61K 45/06* | (2006.01) | |

(52) U.S. Cl.
CPC ........ *A61K 31/4545* (2013.01); *A61K 31/437* (2013.01); *A61K 31/439* (2013.01); *A61K 31/4706* (2013.01); *A61K 31/496* (2013.01); *A61K 31/5377* (2013.01); *A61K 45/06* (2013.01); *C07D 519/00* (2013.01)

(58) Field of Classification Search
CPC .. C07D 519/00; A61K 31/437; A61K 31/439; A61K 31/4545; A61K 31/4706; A61K 31/496; A61K 31/5377; A61K 45/06; A61P 29/00
See application file for complete search history.

(56) References Cited

U.S. PATENT DOCUMENTS

| | | |
|---|---|---|
| 6,329,412 B1 | 12/2001 | Goldstein et al. |
| 6,486,153 B1 | 11/2002 | Castro Pineiro et al. |
| 10,703,755 B2 | 7/2020 | Tojo et al. |
| 2007/0112048 A1 | 5/2007 | Bavari et al. |
| 2008/0194668 A1 | 8/2008 | Marsilje et al. |
| 2015/0105370 A1 | 4/2015 | Carlson et al. |
| 2015/0236272 A1 | 8/2015 | Park et al. |
| 2017/0174653 A1 | 6/2017 | Sherer et al. |
| 2018/0086708 A1 | 3/2018 | Jones et al. |
| 2019/0185469 A1 | 6/2019 | Dyckman et al. |
| 2022/0389034 A1 | 12/2022 | Ammann et al. |

FOREIGN PATENT DOCUMENTS

| | | |
|---|---|---|
| CN | 114075212 A | 2/2022 |
| CN | 114075219 A | 2/2022 |
| EP | 2119703 A1 | 11/2009 |
| SU | 253070 A | 9/1969 |
| WO | WO-2007/048847 A2 | 5/2007 |
| WO | WO-2008/008907 A2 | 1/2008 |
| WO | WO-2008/152471 A1 | 12/2008 |
| WO | WO 2009/111337 A1 | 9/2009 |
| WO | WO-2010/036905 A1 | 4/2010 |
| WO | WO-2011/050245 A1 | 4/2011 |
| WO | WO-2012/167046 A1 | 12/2012 |
| WO | WO-2012/167053 A1 | 12/2012 |
| WO | WO-2013/052263 A2 | 4/2013 |
| WO | WO-2013/052550 A2 | 4/2013 |
| WO | WO-2013/181579 A2 | 12/2013 |
| WO | WO 2014/041518 A1 | 3/2014 |
| WO | WO-2015/057655 A1 | 4/2015 |
| WO | WO-2015/057659 A1 | 4/2015 |
| WO | WO-2016/029077 A1 | 2/2016 |
| WO | WO 2016/128905 A1 | 8/2016 |
| WO | WO-2017/075694 A1 | 5/2017 |
| WO | WO-2017/106607 A1 | 6/2017 |

(Continued)

OTHER PUBLICATIONS

Andrews D M et al. (2009), "Fischer synthesis of isomeric thienopyrrole LHRH antagonists", Tetrahedron 65, 5805-5816.

Beesu M et al. (2015), "Structure-Based Design of Human TLR8-Specific Agonists with Augmented Potency and Adjuvanticity", J. Med. Chem. 2015, 58, 7833-7849.

Beesu M et al. (2016), "Identification of a Human Toll-Like Receptor (TLR) 8-Specific Agonist and a Functional Pan-TLR Inhibitor in 2-Aminoimidazoles", J. Med. Chem. 2016, 59, 3311-3330.

Beutner G L et al. (2021), "A Process Chemistry Benchmark for $sp^2$-$sp^3$ Cross Couplings", The Journal of Organic Chemistry 2021, 86(15), 10380-10396.

Blair J B et al. (1999), "Thieno[3,2-b]- and Thieno[2,3-b]pyrrole Bioisosteric Analogues of the Hallucinogen and Serotonin Agonist N,N-Dimethyltryptamine", J. Med. Chem. 1999, 42, 1106-1111.

(Continued)

*Primary Examiner* — Sarah Pihonak
(74) *Attorney, Agent, or Firm* — Sheppard Mullin Richter & Hampton LLP

(57) ABSTRACT

The present disclosure relates generally to certain compounds, pharmaceutical compositions comprising said compounds, and methods of making and using said compounds and pharmaceutical compositions. The compounds and compositions provided herein may be used for the treatment or prevention of an autoimmune disease and/or inflammatory condition, including systemic lupus erythematosus and cutaneous lupus erythematosus.

29 Claims, No Drawings

(56) References Cited

FOREIGN PATENT DOCUMENTS

| | | |
|---|---|---|
| WO | WO-2017/178844 A1 | 10/2017 |
| WO | WO-2017/188287 A1 | 11/2017 |
| WO | WO-2018/005586 A1 | 1/2018 |
| WO | WO-2018/026620 A1 | 2/2018 |
| WO | WO-2018/031434 A1 | 2/2018 |
| WO | WO-2018/047081 A1 | 3/2018 |
| WO | WO-2018/049089 A1 | 3/2018 |
| WO | WO-2019/018354 A1 | 1/2019 |
| WO | WO-2019/028301 A1 | 2/2019 |
| WO | WO-2019/028302 A1 | 2/2019 |
| WO | WO-2019/088159 A1 | 5/2019 |
| WO | WO-2019/092739 A1 | 5/2019 |
| WO | WO-2019/099336 A1 | 5/2019 |
| WO | WO-2019/118799 A1 | 6/2019 |
| WO | WO-2019/123294 A2 | 6/2019 |
| WO | WO-2019/125849 A1 | 6/2019 |
| WO | WO-2019/125977 A1 | 6/2019 |
| WO | WO-2019/126081 A1 | 6/2019 |
| WO | WO-2019/126082 A1 | 6/2019 |
| WO | WO-2019/126083 A1 | 6/2019 |
| WO | WO-2019/126113 A1 | 6/2019 |
| WO | WO-2019/126242 A1 | 6/2019 |
| WO | WO-2019/126253 A1 | 6/2019 |
| WO | WO-2019/220390 A1 | 11/2019 |
| WO | WO-2020/025517 A1 | 2/2020 |
| WO | WO-2020/086503 A1 | 4/2020 |
| WO | WO-2020/086505 A1 | 4/2020 |
| WO | WO-2020/227337 A1 | 11/2020 |
| WO | WO-2020/227484 A1 | 11/2020 |
| WO | WO-2020/237164 A1 | 11/2020 |
| WO | WO-2021/067326 A1 | 4/2021 |
| WO | WO-2021/067657 A1 | 4/2021 |
| WO | WO-2021/087181 A1 | 5/2021 |
| WO | WO-2021/231941 A1 | 11/2021 |
| WO | WO-2021/252718 A1 | 12/2021 |
| WO | WO-2021/262561 A1 | 12/2021 |
| WO | WO-2022/022489 A1 | 2/2022 |
| WO | WO-2022/040293 A1 | 2/2022 |
| WO | WO-2022/111636 A1 | 6/2022 |
| WO | WO-2022/140325 A1 | 6/2022 |
| WO | WO-2022/140326 A1 | 6/2022 |
| WO | WO-2022221642 A1 * | 10/2022 ........... C07D 495/04 |

OTHER PUBLICATIONS

Ching K-C et al. (2017), "Structural Optimizations of Thieno[3,2-b]pyrrole Derivatives for the Development of Metabolically Stable Inhibitors of Chikungunya Virus", J. Med. Chem. 2017, 60, 7, 3165-3186.

Database Caplus [Online] Chemical Abstracts Service, Columbus, Ohio, US (2007), Koseki Junichi et al.: "Preparation of indolylquinoxaline compounds as VEGF inhibitors and pharmaceutical compositions containing them", JPN. Kokai Tokkyo Koho, 56PP. Coden: JKXXAF, retrieved from STN Database accession No. 2007:431922 Abstract.

Devarapu S K et al. (2018), "Toll-like receptors in lupus nephritis", Journal of Biomedical Science, 25:35.

Dudhgaonkar S et al. (2021), "TLR7 Inhibition With BMS-986256, a Potent and Selective Inhibitor of Human TLR7/8, Provides Robust Efficacy in the MRL/lpr Female Mouse Model of Cutaneous Lupus", Lupus CORA 2021 Presentation, Oct. 6-9, 2021.

Dyckman A J et al. (2021), "Discovery of BMS-986256, a Small Molecule Dual Antagonist of the Toll-Like Receptors 7 and 8 (TLR7/8) Advanced to Clinical Trials for the Treatment of Lupus", Lupus CORA 2021 Presentation, Oct. 6-9, 2021.

Ganapathi L et al. (2015), "The Imidazoquinoline Toll-Like Receptor-7/8 Agonist Hybrid-2 Potently Induces Cytokine Production by Human Newborn and Adult Leukocytes", PLoS One 10(8): e0134640.

Gao W et al. (2017), "Inhibition of Toll-Like Receptor Signaling as a Promising Therapy for Inflammatory Diseases: A Journey from Molecular to Nano Therapeutics", Front. Physiol. 8:508.

Hay D et al. (2014), "Supporting Information—Discovery and optimization of small molecule ligands for the CBP/p300 bromodomains", J. Am. Chem. Soc. 2014, 136, 26, 9308-9319, pp. S1-S99.

Hu Z et al. (2018), "Small-Molecule TLR8 Antagonists via Structure-Based Rational Design", Cell Chemical Biology 25, 1-6.

Huang S et al. (2019), "Subtle differences in chemical pattern between human toll-like receptor 8 agonists and antagonists: Emerging chemical patterns analysis", Chem Biol Drug Des. 2019, 00:1-11.

Kandimalla E R et al. (2013), "Design, synthesis and biological evaluation of novel antagonist compounds of Toll-like receptors 7, 8 and 9", Nucleic Acids Research, vol. 41, No. 6, 3947-3961.

Knoepfel T et al. (2020), "Target-Based Identification and Optimization of 5-Indazol-5-yl Pyridones as Toll-like Receptor 7 and 8 Antagonists Using a Biochemical TLR8 Antagonist Competition Assay", Journal of Medicinal Chemistry 2020, 63(15), 8276-8295.

Kokatla H P et al. (2014), "Structure-Based Design of Novel Human Toll-like Receptor 8 Agonists", ChemMedChem 2014, 9, 719-723.

Kuznik A et al. (2011), "Mechanism of Endosomal TLR Inhibition by Antimalarial Drugs and Imidazoquinolines", J Immunol 186, pp. 1-11.

Liu Z et al. (2012), "Taming lupus—a new understanding of pathogenesis is leading to clinical advances", Nature Medicine, vol. 18, No. 6, 871-882.

Marsilje et al. (2008), "Optimization of small molecule agonists of the thrombopoietin (Tpo) receptor derived from a benzo [a] carbazole hit scaffold", Bioorg. Med. Chem. Lett., vol. 18, No. 19, pp. 5259-5262.

Martin Hernando J I et al. (2009), "Optimization of Thienopyrrole-Based Finger-Loop Inhibitors of the Hepatitis C Virus NS5B Polymerase", ChemMedChem. 2009, 4(10):1695-1713.

Mussari C P et al. (2020), "Discovery of Potent and Orally Bioavailable Small Molecule Antagonists of Toll-like Receptors 7/8/9 (TLR7/8/9)", ACS Med. Chem. Lett. 2020, 11, 9, 1751-1758.

Nguyen et al. (2014), "Synthesis and antibacterial evaluation of new, unsymmetrical triaryl bisamidine compounds", Bioorg. Med. Chem. Lett., vol. 24, No. 15, pp. 3366-3372.

Ohto U et al. (2014), "Structure and function of toll-like receptor 8", Microbes and Infection 16, 273-282.

Pollock J A et al. (2018), "Triaryl Pyrazole Toll-Like Receptor Signaling Inhibitors: Structure-Activity Relationships Governing Pan- and Selective Signaling Inhibitors", ChemMedChem 2018, 13, 2208-2216.

Sacre K et al. (2012), "Hydroxychloroquine is associated with impaired interferon-alpha and tumor necrosis factor-alpha production by plasmacytoid dendritic cells in systemic lupus erythematosus", Arthritis Research & Therapy 2012, 14:R155.

Shukla N M et al. (2009), "Regioisomerism-dependent TLR7 agonism and antagonism in an imidazoquinoline", Bioorganic & Medicinal Chemistry Letters 19, 2211-2214.

Sindac J A et al. (2012), "Novel Inhibitors of Neurotropic Alphavirus Replication That Improve Host Survival in a Mouse Model of Acute Viral Encephalitis", J. Med. Chem. 12, 55, 3535-3545.

Suarez-Farinas M et al. (2013), "Suppression of Molecular Inflammatory Pathways by Toll-Like Receptor 7, 8, and 9 Antagonists in a Model of IL-23-Induced Skin Inflammation", PLoS One 8(12): e84634.

Tojo S et al. (2020), "Structural analysis reveals TLR7 dynamics underlying antagonism", Nature Communications 2020, 11:5204.

Vlach J et al. (2020), "Discovery of M5049: A Novel Selective TLR7/8 Inhibitor for Treatment of Autoimmunity", Journal of Pharmacology and Experimental Therapeutics, 376(3).

Yoo E et al. (2014), "Determinants of Activity at Human Toll-like Receptors 7 and 8: Quantitative Structure-Activity Relationship (QSAR) of Diverse Heterocyclic Scaffolds", J. Med. Chem. 2014, 57, 7955-7970.

Zhang S et al. (2018), "Small-molecule inhibition of TLR8 through stabilization of its resting state", Nature Chemical Biology, vol. 14, pp. 58-64.

Zhang Z et al. (2016), "Structural Analysis Reveals that Toll-like Receptor 7 Is a Dual Receptor for Guanosine and Single-Stranded RNA", Immunity 45, 737-748.

(56) References Cited

OTHER PUBLICATIONS

Zhang Z et al. (2018), "Structural Analyses of Toll-like Receptor 7 Reveal Detailed RNA Sequence Specificity and Recognition Mechanism of Agonistic Ligands", Cell Reports 25, 3371-3381.
Zhou J et al. (2019), "Remote C6-Enantioselective C—H Functionalization of 2,3-Disubstituted Indoles through the Dual H-Bonds and [pi]-[pi] Interaction Strategy Enabled by CPAs", Org. lett., pp. 8662-8666.
Intl. Search Report—Written Opinion dated Dec. 2, 2022 for Intl. Appl. No. PCT/US2022/076099, 9 pages.
Database Registry: 54 compounds RN 2643837-41-4 to RN 2441246-96-2, 18 pages, 2020.

\* cited by examiner

THIENOPYRROLE COMPOUNDS

CROSS REFERENCE TO RELATED APPLICATIONS

This application claims priority to U.S. Provisional Application No. 63/242,969, filed on Sep. 10, 2021, which is incorporated herein in its entirety for all purposes.

FIELD

This disclosure relates generally to novel thienopyrrole compounds, pharmaceutical compositions comprising said compounds, and methods of making and using said compounds and pharmaceutical compositions. In some embodiments, the novel thienopyrrole compounds provided herein may be used in the treatment of certain diseases and disorders, including, but not limited to, an inflammatory condition, systemic lupus erythematosus, cutaneous lupus erythematosus, or lupus nephritis.

BACKGROUND

Toll-like receptors (TLRs) are a family of transmembrane immune receptors that sense pathogens, trigger innate immune responses and prime adaptive immunity. TLR7/8/9 are endosomally localized TLRs that respond to single-stranded RNAs (TLR7/8) or unmethylated DNA containing cytosine-phosphate-guanine (CpG) motifs (TLR9). Activation of TLR7/8/9 leads to inflammatory responses including the production of Type I interferons and proinflammatory cytokines, activation of B cells and antibody production, and neutrophil NETosis. Aberrant activation of TLR7/8/9 contributes to elevated Type I interferon response, increased pro-inflammatory cytokines, and sustained autoantibody production that may fuel the chronic progression of a variety of autoimmune disease and inflammatory conditions leading to broad inflammation and tissue damage. (Kawai et al., 2010, Nat Immunol 11, 373; Joosten et al., 2016, Nat Rev Rheomatol 12, 344; Crow et al., 2019, Lupus Sci Med 6, e000336; Garcia-Romo et al., 2011, Sci Transl Med 3, 73ra20; Kono et al., 2009, PNAS 106, 12061; Koh et al., 2013, J Immunol 190, 4982). Therefore, there is a need for compounds that are potent TLR7, and/or TLR8, and/or TLR9 antagonists that are stable and exhibit effective pharmacokinetic and/or pharmacodynamic profiles.

SUMMARY

In one embodiment, provided herein is a compound of Formula I,

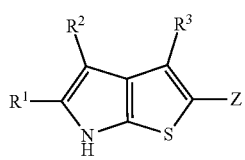

Formula I or a pharmaceutically acceptable salt thereof, wherein
$R^1$ is 8-15 membered fused tricyclic heterocyclyl or 8-15 membered fused tricyclic heteroaryl, wherein the 8-15 membered fused tricyclic heterocyclyl and 8-15 membered fused tricyclic heteroaryl are each independently optionally substituted with 1-4 $R^a$ groups;
$R^2$ is $C_{1-6}$ alkyl, wherein the $C_{1-6}$ alkyl is optionally substituted with 1-4 groups independently selected from halogen and $C_{1-6}$ alkoxy,
  wherein the $C_{1-6}$ alkoxy is optionally substituted with 1-3 halogen groups;
$R^3$ is H, halogen, —CN, $C_{1-6}$ alkyl, and $C_{3-7}$ monocyclic cycloalkyl,
  wherein the $C_{1-6}$ alkyl, and $C_{3-7}$ monocyclic cycloalkyl, are each independently optionally substituted with 1-3 groups independently selected from —OH, halogen, —CN, and $C_{1-4}$ alkoxy,
    wherein the $C_{1-4}$ alkoxy is optionally substituted with 1-3 halogen groups;
Z is $C_{1-6}$ alkyl, —C(O)$R^{13}$—C(O)N$R^6R^7$, $C_{3-7}$ monocyclic cycloalkyl, $C_{7-10}$ fused bicyclic cycloalkyl, $C_{5-10}$ bridged bicyclic cycloalkyl, 4-7 membered monocyclic heterocyclyl, phenyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl,
  wherein the $C_{1-6}$ alkyl is optionally substituted with 1-4 $R^b$ groups;
  wherein the $C_{3-7}$ monocyclic cycloalkyl, $C_{7-10}$ fused bicyclic cycloalkyl, $C_{5-10}$ bridged bicyclic cycloalkyl, 4-7 membered monocyclic heterocyclyl, phenyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-2 $R^8$ groups and are each independently optionally substituted with 1-3 $R^a$ groups;
$R^6$ is $C_{3-7}$ monocyclic cycloalkyl, $C_{7-10}$ fused bicyclic cycloalkyl, $C_{5-10}$ bridged bicyclic cycloalkyl, 4-7 membered monocyclic heterocyclyl, 8-10 membered fused bicyclic heterocyclyl, 6-10 membered bridged bicyclic heterocyclyl, or 7-10 membered spirocyclic heterocyclyl,
  wherein the $C_{3-7}$ monocyclic cycloalkyl, $C_{7-10}$ fused bicyclic cycloalkyl, $C_{5-10}$ bridged bicyclic cycloalkyl, 4-7 membered monocyclic heterocyclyl, 8-10 membered fused bicyclic heterocyclyl, 6-10 membered bridged bicyclic heterocyclyl, and 7-10 membered spirocyclic heterocyclyl are each independently optionally substituted with 1-4 $R^a$ groups;
$R^{13}$ is 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl,
  wherein the 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-4 $R^a$ groups;
$R^7$ is H, $C_{1-6}$ alkyl, $C_{3-7}$ monocyclic cycloalkyl, or 4-6 membered monocyclic heterocyclyl, wherein the $C_{1-6}$ alkyl, $C_{3-7}$ monocyclic cycloalkyl, and 4-6 membered monocyclic heterocyclyl are each independently optionally substituted with 1-4 groups independently selected from —OH, halogen, —CN, and $C_{1-6}$ alkoxy;

each $R^8$ independently is halogen, —C(O)$R^9$, —NR$^{10}$R$^{10}$, $C_{1-6}$ alkyl, $C_{3-7}$ monocyclic cycloalkyl, $C_{7-10}$ fused bicyclic cycloalkyl, $C_{5-10}$ bridged bicyclic cycloalkyl, 4-7 membered monocyclic heterocyclyl, phenyl, 5-6 membered monocyclic heteroaryl, 8-10 membered fused bicyclic heterocyclyl, 6-10 membered bridged bicyclic heterocyclyl, 8-10 membered fused bicyclic heteroaryl, 7-10 membered spirocyclic heterocyclyl, —OR$^5$, —C(O)N(R$^5$)(R$^5$), —N(R$^5$)$_2$(R$^5$)$^+$, —N(R$^5$)C(O)R$^5$, —N(R$^5$)C(O)OR$^5$, —N(R$^5$)C(O)N(R$^5$)(R$^5$), —N(R$^5$)S(O)$_2$(R$^{5a}$), —NR$^5$S(O)$_2$N(R$^5$)(R$^5$), —NR$^5$S(O)$_2$O(R$^{5a}$), —OC(O)N(R$^5$)(R$^5$), —S(O)R$^{5a}$, —S(O)(NH)R$^5$, —S(O)$_2$R$^{5a}$, —S(O)$_2$N(R$^5$)(R$^5$), or —N=S(R$^{5a}$)(R$^{5a}$)=O,
wherein the $C_{1-6}$ alkyl is optionally substituted with 1-4 R$^b$ groups,
wherein the $C_{3-7}$ monocyclic cycloalkyl, $C_{7-10}$ fused bicyclic cycloalkyl, $C_{5-10}$ bridged bicyclic cycloalkyl, 4-7 membered monocyclic heterocyclyl, phenyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-4 R$^a$ groups;
each $R^9$ independently is $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl,
wherein the $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-4 R$^a$ groups;
each $R^5$ and $R^{10}$ independently is H, $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl,
wherein the $C_{1-6}$ alkyl, $C_{2-6}$ alkenyl, and $C_{2-6}$ alkynyl are each independently optionally substituted with 1-4 R$^b$ groups,
wherein the $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-4 R$^a$ groups;
each $R^{5a}$ independently is $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl,
wherein the $C_{1-6}$ alkyl, $C_{2-6}$ alkenyl, and $C_{2-6}$ alkynyl are each independently optionally substituted with 1-4 R$^b$ groups,
wherein the $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-4 R$^a$ groups;
each $R^a$ independently is oxo, imino, halogen, —NO$_2$, —N$_3$, —CN, $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, 7-10 membered spirocyclic heterocyclyl, —OR$^{11}$, —C(O)R$^{11}$, —C(O)OR$^{11}$, —C(O)N(R$^{11}$)(R$^{11}$), —NR$^{11}$R$^{11}$, —N(R$^{11}$)$_2$(R$^{11}$)$^+$, —N(R$^{11}$)C(O)R$^{11}$, —N(R$^{11}$)C(O)OR$^{11}$, —N(R$^{11}$)C(O)N(R$^{11}$)(R$^{11}$), —N(R$^{11}$)S(O)$_2$(R$^{11a}$), —NR$^{11}$S(O)$_2$N(R$^{11}$)(R$^{11}$), —NR$^{11}$S(O)$_2$O(R$^{11a}$), —OC(O)R$^{11}$, —OC(O)OR$^{11}$, —OC(O)N(R$^{11}$)(R$^{11}$), —SR$^{11}$, —S(O)R$^{11a}$, —S(O)(NH)R$^{11}$, —S(O)$_2$R$^{11a}$, —S(O)$_2$N(R$^{11}$)(R$^{11}$) or —N=S(R$^{11a}$)(R$^{11a}$)=O,
wherein the $C_{1-6}$ alkyl, $C_{2-6}$ alkenyl, and $C_{2-6}$ alkynyl are each independently optionally substituted with 1-3 R$^c$ groups,
wherein the $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-3 R$^d$ groups,
each $R^b$ independently is oxo, imino, halogen, —NO$_2$, —N$_3$, —CN, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 8-10 membered bridged bicyclic heterocyclyl, 6-10 membered bridged bicyclic heterocyclyl, 8-10 membered fused bicyclic heteroaryl, 7-10 membered spirocyclic heterocyclyl, —OR$^{11}$, —C(O)R$^{11}$, —C(O)OR$^{11}$, —C(O)N(R$^{11}$)(R$^{11}$), —NR$^{11}$R$^{11}$, —N(R$^{11}$)$_2$(R$^{11}$)$^+$, —N(R$^{11}$)C(O)R$^{11}$, —N(R$^{11}$)C(O)OR$^{11}$, —N(R$^{11}$)C(O)N(R$^{11}$)(R$^{11}$), —N(R$^{11}$)S(O)$_2$(R$^{11a}$), —NR$^{11}$S(O)$_2$N(R$^{11}$)(R$^{11}$), —NR$^{11}$S(O)$_2$O(R$^{11a}$), —OC(O)R$^{11}$, —OC(O)OR$^{11}$, —OC(O)N(R$^{11}$)(R$^{11}$), —SR$^{11}$, —S(O)R$^{11a}$, —S(O)(NH)R$^{11}$, —S(O)$_2$R$^{11a}$, —S(O)$_2$N(R$^{11}$)(R$^{11}$), or —N=S(R$^{11a}$)(R$^{11a}$)=O,
wherein the $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-3 $R^d$ groups;

each $R^e$ independently is halogen, —CN, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, 7-10 membered spirocyclic heterocyclyl, —$OR^{12}$, —$C(O)R^{12}$, —$C(O)OR^{12}$, —$C(O)N(R^{12})(R^{12})$, —$NR^{12}R^{12}$, —$N(R^{12})_2(R^{12})^+$, —$N(R^{12})C(O)R^{12}$, —$N(R^{12})C(O)OR^{12}$, —$N(R^{12})C(O)N(R^{12})(R^{12})$, —$N(R^{12})S(O)_2(R^{12a})$, —$NR^{12}S(O)_2N(R^{12})(R^{12})$, —$NR^{12}S(O)_2O(R^{12a})$, —$OC(O)R^{12}$, —$OC(O)OR^{12}$, —$OC(O)N(R^{12})(R^{12})$, —$SR^{12}$, —$S(O)R^{12a}$, —$S(O)(NH)R^{12}$, —$S(O)_2R^{12a}$, —$S(O)_2N(R^{12})(R^{12})$ or —$N=S(R^{12a})(R^{12a})=O$;

each $R^d$ independently is oxo, halogen, —CN, $C_{1-6}$ alkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, 7-10 membered spirocyclic heterocyclyl, —$OR^{12}$, —$C(O)R^{12}$, —$C(O)OR^{12}$, —$C(O)N(R^{12})(R^{12})$, —$NR^{12}R^{12}$, —$N(R^{12})_2(R^{12})^+$, —$N(R^{12})C(O)R^{12}$, —$N(R^{12})C(O)OR^{12}$, —$N(R^{12})C(O)N(R^{12})(R^{12})$, —$N(R^{12})S(O)_2(R^{12a})$, —$NR^{12}S(O)_2N(R^{12})(R^{12})$, —$NR^{12}S(O)_2O(R^{12a})$, —$OC(O)R^{12}$, —$OC(O)OR^{12}$, —$OC(O)N(R^{12})(R^{12})$, —$SR^{12}$, —$S(O)R^{12a}$, —$S(O)(NH)R^{12}$, —$S(O)_2R^{12a}$, —$S(O)_2N(R^{12})(R^{12})$ or —$N=S(R^{12a})(R^{12a})=O$, wherein the $C_{1-6}$ alkyl is optionally substituted with 1-3 groups independently selected from —OH, halogen, —CN, and $C_{1-3}$ alkoxy;

each $R^{11}$ independently is H, $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl, wherein the $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-3 $R^c$ groups;

each $R^{11a}$ independently is $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl, wherein the $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-3 $R^c$ groups;

each $R^{12}$ independently is H, $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl;

each $R^{12}$, independently is $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl;

wherein each 4-membered monocyclic heterocyclyl independently has 1 ring heteroatom selected from N, O, and S;

wherein each 5-7 membered monocyclic heterocyclyl independently has 1-2 ring heteroatoms independently selected from N, O, and S;

wherein each 6-membered bridged bicyclic heterocyclyl independently has 1 ring heteroatom selected from N, O, and S;

wherein each 7-membered bridged bicyclic heterocyclyl independently has 1-2 ring heteroatoms independently selected from N, O, and S;

wherein each 5-6 membered monocyclic heteroaryl, 8-10 membered fused bicyclic heterocyclyl, 8-10 membered bridged bicyclic heterocyclyl, 8-10 membered fused bicyclic heteroaryl, and 7-10 membered spirocyclic heterocyclyl independently have 1-4 ring heteroatoms independently selected from N, O, and S; and wherein each 8-15 membered fused tricyclic heterocyclyl and 8-15 membered fused tricyclic heteroaryl independently have 1-7 ring heteroatoms independently selected from N, O, and S.

In one embodiment, provided herein is a pharmaceutical composition comprising a compound provided herein, or a pharmaceutically acceptable salt thereof, and a pharmaceutically acceptable excipient or carrier.

In one embodiment, provided herein is a method of inhibiting toll-like receptor 7 and/or 8 activity in a subject in need thereof, comprising administering to the subject a therapeutically effective amount of a compound provided herein, or a pharmaceutically acceptable salt thereof, or a therapeutically effective amount of a pharmaceutical composition provided herein.

In one embodiment, provided herein is a method of inhibiting toll-like receptor 7 activity in a subject in need thereof, comprising administering to the subject a therapeutically effective amount of a compound provided herein, or a pharmaceutically acceptable salt thereof, or a therapeutically effective amount of a pharmaceutical composition provided herein.

In one embodiment, provided herein is a method of inhibiting toll-like receptor 8 activity in a subject in need thereof, comprising administering to the subject a therapeutically effective amount of a compound provided herein, or a pharmaceutically acceptable salt thereof, or a therapeutically effective amount of a pharmaceutical composition provided herein.

In one embodiment, provided herein is a method of treating a disease or disorder associated with elevated toll-like receptor 7 and/or 8 activity in a subject in need thereof, comprising administering to the subject a therapeutically effective amount of a compound provided herein, or a pharmaceutically acceptable salt thereof, or a therapeutically effective amount of a pharmaceutical composition provided herein.

In one embodiment, provided herein is a method of treating a disease or disorder associated with elevated toll-like receptor 7 activity in a subject in need thereof, comprising administering to the subject a therapeutically effective amount of a compound provided herein, or a pharmaceutically acceptable salt thereof, or a therapeutically effective amount of a pharmaceutical composition provided herein.

In one embodiment, provided herein is a method of treating a disease or disorder associated with elevated toll-like receptor 8 activity in a subject in need thereof, comprising administering to the subject a therapeutically effective amount of a compound provided herein, or a pharmaceutically acceptable salt thereof, or a therapeutically effective amount of a pharmaceutical composition provided herein.

In one embodiment, provided herein is a method of treating an inflammatory condition in a subject in need thereof, comprising administering to the subject a therapeutically effective amount of a compound provided herein, or a pharmaceutically acceptable salt thereof, or a therapeutically effective amount of a pharmaceutical composition provided herein.

In one embodiment, provided herein is a method of treating systemic lupus erythematosus in a subject in need thereof, comprising administering to the subject a therapeutically effective amount of a compound provided herein, or a pharmaceutically acceptable salt thereof, or a therapeutically effective amount of a pharmaceutical composition provided herein.

In one embodiment, provided herein is a method of treating cutaneous lupus erythematosus in a subject in need thereof, comprising administering to the subject a therapeutically effective amount of a compound provided herein, or a pharmaceutically acceptable salt thereof, or a therapeutically effective amount of a pharmaceutical composition provided herein.

In one embodiment, provided herein is a method of treating lupus nephritis in a subject in need thereof, comprising administering to the subject a therapeutically effective amount of a compound provided herein, or a pharmaceutically acceptable salt thereof, or a therapeutically effective amount of a pharmaceutical composition provided herein.

In one embodiment, provided herein is a compound provided herein, or a pharmaceutically acceptable salt thereof, or a pharmaceutical composition provided herein for use in therapy.

In one embodiment, provided herein is a compound provided herein, or a pharmaceutically acceptable salt thereof, or a pharmaceutical composition provided herein for use in a method of inhibiting toll-like receptor 7 and/or 8 activity in a subject in need thereof, comprising administering to the subject a therapeutically effective amount of the compound, or a pharmaceutically acceptable salt thereof, or a therapeutically effective amount of the pharmaceutical composition.

In one embodiment, provided herein is a compound provided herein, or a pharmaceutically acceptable salt thereof, or a pharmaceutical composition provided herein for use in a method of inhibiting toll-like receptor 7 activity in a subject in need thereof, comprising administering to the subject a therapeutically effective amount of the compound, or a pharmaceutically acceptable salt thereof, or a therapeutically effective amount of the pharmaceutical composition.

In one embodiment, provided herein is a compound provided herein, or a pharmaceutically acceptable salt thereof, or a pharmaceutical composition provided herein for use in a method of inhibiting toll-like receptor 8 activity in a subject in need thereof, comprising administering to the subject a therapeutically effective amount of the compound, or a pharmaceutically acceptable salt thereof, or a therapeutically effective amount of the pharmaceutical composition.

In one embodiment, provided herein is a compound provided herein, or a pharmaceutically acceptable salt thereof, or a pharmaceutical composition provided herein for use in a method of treating a disease or disorder associated with elevated toll-like receptor 7 and/or 8 activity in a subject in need thereof, comprising administering to the subject a therapeutically effective amount of the compound, or a pharmaceutically acceptable salt thereof, or a therapeutically effective amount of the pharmaceutical composition.

In one embodiment, provided herein is a compound provided herein, or a pharmaceutically acceptable salt thereof, or a pharmaceutical composition provided herein for use in a method of treating a disease or disorder associated with elevated toll-like receptor 7 activity in a subject in need thereof, comprising administering to the subject a therapeutically effective amount of the compound, or a pharmaceutically acceptable salt thereof, or a therapeutically effective amount of the pharmaceutical composition.

In one embodiment, provided herein is a compound provided herein, or a pharmaceutically acceptable salt thereof, or a pharmaceutical composition provided herein for use in a method of treating a disease or disorder associated with elevated toll-like receptor 8 activity in a subject in need thereof, comprising administering to the subject a therapeutically effective amount of the compound, or a pharmaceutically acceptable salt thereof, or a therapeutically effective amount of the pharmaceutical composition.

In one embodiment, provided herein is a compound provided herein, or a pharmaceutically acceptable salt thereof, or a pharmaceutical composition provided herein for use in a method of treating an inflammatory condition in a subject in need thereof, comprising administering to the subject a therapeutically effective amount of the compound, or a pharmaceutically acceptable salt thereof, or a therapeutically effective amount of the pharmaceutical composition.

In one embodiment, provided herein is a compound provided herein, or a pharmaceutically acceptable salt thereof, or a pharmaceutical composition provided herein for use in a method of treating systemic lupus erythematosus in a subject in need thereof, comprising administering to the subject a therapeutically effective amount of the compound, or a pharmaceutically acceptable salt thereof, or a therapeutically effective amount of the pharmaceutical composition.

In one embodiment, provided herein is a compound provided herein, or a pharmaceutically acceptable salt thereof, or a pharmaceutical composition provided herein for use in a method of treating cutaneous lupus erythematosus in a subject in need thereof, comprising administering to the subject a therapeutically effective amount of the compound, or a pharmaceutically acceptable salt thereof, or a therapeutically effective amount of the pharmaceutical composition therapeutically effective amount of the pharmaceutical composition.

DETAILED DESCRIPTION

I. Definitions

The description below is made with the understanding that the present disclosure is to be considered as an exemplification of the claimed subject matter, and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

As used in the present disclosure, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named. A solid line coming out of the center of a ring (including a fused, bridged or spirocyclic ring system) indicates that the point of attachment for a substituent on the ring can be at any ring atom. For example, $R^{aa}$ in the below structure can be attached to any of the five carbon ring atoms or $R^{aa}$ can replace the hydrogen attached to the nitrogen ring atom:

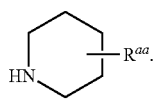

As another example, $R^{aa}$ in the below structure:

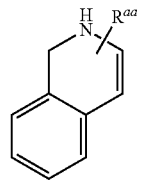

$R^{aa}$ can be attached to any of the numbered positions shown below:

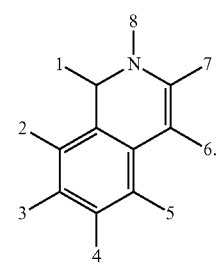

A solid line coming out of the center of a ring (including a fused, bridged, or spirocyclic ring system) indicates that the point of attachment for the ring system to the rest of the compound can be at any ring atom of the fused, bridged, or spirocyclic ring system. For example, in the below structure:

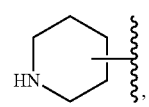

the monocyclic heterocyclyl can be attached to the rest of the compound at any of the numbered positions shown below:

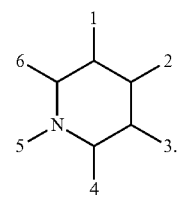

As another example, in the below fused bicyclic heterocyclic structure,

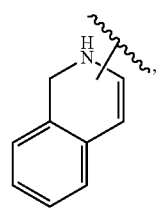

the fused bicyclic heterocyclyl can be attached to the rest of the compound at any of the eight numbered positions shown below:

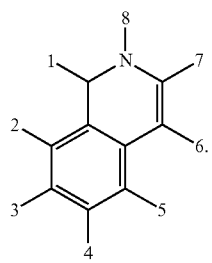

The prefix "C$_{u-v}$" indicates that the following group has from u to v carbon atoms. For example, "C$_{1-6}$ alkyl" indicates that the alkyl group has from 1 to 6 carbon atoms. Likewise, the term "x-y membered" rings, wherein x and y are numerical ranges, such as "3 to 12-membered heterocyclyl", refers to a ring containing x-y atoms (i.e., 3-12), of which up to 80% may be heteroatoms, such as N, O, S, P, and the remaining atoms are carbon.

Also, certain commonly used alternative chemical names may or may not be used. For example, a divalent group such as a divalent "alkyl" group, a divalent "aryl" group, etc., may also be referred to as an "alkylene" group or an "alkylenyl" group, or alkylyl group, an "arylene" group or an "arylenyl" group, or arylyl group, respectively.

"A compound disclosed herein" or "a compound of the present disclosure" or "a compound provided herein" or "a compound described herein" refers to the compounds of Formula I. Also included are the specific compounds of Examples 1 to 68.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, the term "about X" includes description of "X".

"Alkyl" refers to an unbranched or branched saturated hydrocarbon chain. As used herein, alkyl has 1 to 20 carbon atoms (i.e., C$_{1-20}$ alkyl), 1 to 12 carbon atoms (i.e., C$_{1-12}$ alkyl), 1 to 8 carbon atoms (i.e., C$_{1-8}$ alkyl), 1 to 6 carbon atoms (i.e., C$_{1-6}$ alkyl), 1 to 4 carbon atoms (i.e., C$_{1-4}$ alkyl), 1 to 3 carbon atoms (i.e., C$_{1-3}$ alkyl), or 1 to 2 carbon atoms (i.e., C$_{1-2}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —(CH$_2$)$_3$CH$_3$), sec-butyl (i.e. —CH(CH$_3$)CH$_2$CH$_3$), isobutyl (i.e. —CH$_2$CH(CH$_3$)$_2$) and tert-butyl (i.e. —C(CH$_3$)$_3$); and "propyl" includes n-propyl (i.e. —(CH$_2$)$_2$CH$_3$) and isopropyl (i.e. —CH(CH$_3$)$_2$).

"Alkenyl" refers to an aliphatic group containing at least one carbon-carbon double bond and having from 2 to 20 carbon atoms (i.e., C$_{2-20}$ alkenyl), 2 to 8 carbon atoms (i.e., C$_{2-8}$ alkenyl), 2 to 6 carbon atoms (i.e., C$_{2-6}$ alkenyl), or 2 to 4 carbon atoms (i.e., C$_{2-4}$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., C$_{2-20}$ alkynyl), 2 to 8 carbon atoms (i.e., C$_{2-8}$ alkynyl), 2 to 6 carbon atoms (i.e., C$_{2-6}$ alkynyl), or 2 to 4 carbon atoms (i.e., C$_{2-4}$ alkynyl). The term "alkynyl" also includes those groups having one triple bond and one double bond.

"Alkylene" refers to a divalent and unbranched saturated hydrocarbon chain. As used herein, alkylene has 1 to 20 carbon atoms (i.e., C$_{1-20}$ alkylene), 1 to 12 carbon atoms (i.e., C$_{1-12}$ alkylene), 1 to 8 carbon atoms (i.e., C$_{1-8}$ alkylene), 1 to 6 carbon atoms (i.e., C$_{1-6}$ alkylene), 1 to 4 carbon atoms (i.e., C$_{1-4}$ alkylene), 1 to 3 carbon atoms (i.e., C$_{1-3}$ alkylene), or 1 to 2 carbon atoms (i.e., C$_{1-2}$ alkylene). Examples of alkylene groups include methylene, ethylene, propylene, butylene, pentylene, and hexylene. In some embodiments, an alkylene is optionally substituted with an alkyl group. Examples of substituted alkylene groups include —CH(CH$_3$)CH$_2$—, —CH$_2$CH(CH$_3$)—, —CH$_2$CH(CH$_2$CH$_3$)—, —CH$_2$C(CH$_3$)$_2$—, —C(CH$_3$)$_2$CH$_2$—, —CH(CH$_3$)CH(CH$_3$)—, —CH$_2$C(CH$_2$CH$_3$)(CH$_3$)—, and —CH$_2$C(CH$_2$CH$_3$)$_2$.

"Alkoxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy. "Haloalkoxy" refers to an alkoxy group as defined above, wherein one or more hydrogen atoms are replaced by a halogen.

"Acyl" refers to a group —C(=O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amido" refers to both a "C-amido" group which refers to the group —C(=O)NR$^y$R$^z$ and an "N-amido" group which refers to the group —NR$^y$C(=O)R$^z$, wherein R$^y$ and R$^z$ are independently selected from the group consisting of hydrogen, alkyl, aryl, haloalkyl, heteroaryl, cycloalkyl, or heterocyclyl; each of which may be optionally substituted.

"Amino" refers to the group —NR$^y$R$^z$ wherein R$^y$ and R$^z$ are independently selected from the group consisting of hydrogen, alkyl, haloalkyl, aryl, heteroaryl, cycloalkyl, or heterocyclyl; each of which may be optionally substituted.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., C$_{6-20}$ aryl), 6 to 12 carbon ring atoms (i.e., C$_{6-12}$ aryl), or 6 to 10 carbon ring atoms (i.e., C$_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Cyano" or "carbonitrile" refers to the group —CN.

"Cycloalkyl" refers to a saturated or partially saturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., C$_{3-20}$ cycloalkyl), 3 to 12 ring carbon atoms (i.e., C$_{3-12}$ cycloalkyl), 3 to 10 ring carbon atoms (i.e., C$_{3-10}$ cycloalkyl), 3 to 8 ring carbon atoms (i.e., C$_{3-8}$ cycloalkyl), or 3 to 6 ring carbon atoms (i.e., C$_{3-6}$ cycloalkyl). Examples of cycloalkyl groups include cyclopropyl, cyclobutyl, cyclopentyl, and cyclohexyl.

"Cycloalkoxy" refers to the group "cycloalkyl-O—". Examples of cycloalkoxy groups include but are not limited to:

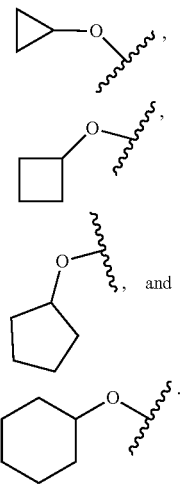

"Bridged" refers to a ring fusion wherein different atoms on a ring are joined by a divalent substituent, such as an alkylenyl group, an alkylenyl group containing one or two heteroatoms, or a single heteroatom. Quinuclidinyl and adamantanyl are examples of bridged ring systems.

The term "fused" refers to a ring which is bound to an adjacent ring.

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents.

"Halogen" or "halo" includes fluoro, chloro, bromo, and iodo.

"Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Heteroalkylene" refers to a divalent and unbranched saturated hydrocarbon chain having one, two, or three heteroatoms selected from NH, O, or S. As used herein, a heteroalkylene has 1 to 20 carbon atoms and one, two, or three heteroatoms selected from NH, O, and S (i.e., C$_{1-20}$ heteroalkylene); 1 to 8 carbon atoms and one, two, or three heteroatoms selected from NH, O, and S (i.e., C$_{1-8}$ heteroalkylene); 1 to 6 carbon atoms and one, two, or three heteroatoms selected from NH, O, and S (i.e., C$_{1-6}$ heteroalkylene); 1 to 4 carbon atoms and one, two, or three heteroatoms selected from NH, O, and S (i.e., C$_{1-4}$ heteroalkylene); 1 to 3 carbon atoms and one, two, or three heteroatoms selected from NH, O, and S (i.e., C$_{1-3}$ heteroalkylene); or 1 to 2 carbon atoms and one, two, or three heteroatoms selected from NH, O, and S (i.e., C$_{1-3}$ heteroalkylene). For example, —CH$_2$O— is a C$_1$ heteroalkylene and —CH$_2$SCH$_2$— is a C$_2$ heteroalkylene. Examples of heteroalkylene groups include —CH$_2$CH$_2$OCH$_2$—, —CH$_2$SCH$_2$OCH$_2$—, —CH$_2$O—, and —CH$_2$NHCH$_2$—. In some embodiments, a heteroalkylene is optionally substituted with an alkyl group. Examples of substituted heteroalkylene groups include —CH(CH$_3$)N(CH$_3$)CH$_2$—, —CH$_2$OCH(CH$_3$)—, —CH$_2$CH(CH$_2$CH$_3$)S—, —CH$_2$NHC(CH$_3$)$_2$—, —C(CH$_3$)$_2$ SCH$_2$—, —CH(CH$_3$)N(CH$_3$)CH(CH$_3$)O—, —CH$_2$SC(CH$_2$CH$_3$)(CH$_3$)—, and —CH$_2$C(CH$_2$CH$_3$)$_2$ NH—.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 carbon ring atoms (i.e., C$_{1-20}$ heteroaryl), 3 to 12 carbon ring atoms (i.e., C$_{3-12}$ heteroaryl), or 3 to 8 carbon ring atoms (i.e., C$_{3-8}$ heteroaryl); and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

"Heterocyclyl" or "heterocyclic ring" or "heterocycle" refers to a non-aromatic cyclic alkyl group, with one or more ring heteroatoms independently selected from nitrogen, oxygen and sulfur. As used herein, "heterocyclyl" or "heterocyclic ring" or "heterocycle" refer to rings that are saturated or partially saturated unless otherwise indicated, e.g., in some embodiments "heterocyclyl" or "heterocyclic ring" or "heterocycle" refers to rings that are partially saturated where specified. The term "heterocyclyl" or "heterocyclic ring" or "heterocycle" includes heterocycloalkenyl groups (i.e., the heterocyclyl group having at least one double bond). A heterocyclyl may be a single ring or multiple rings wherein the multiple rings may be fused, bridged, or spiro. As used herein, heterocyclyl has 2 to 20 carbon ring atoms (i.e., C$_{2-20}$ heterocyclyl), 2 to 12 carbon ring atoms (i.e., C$_{2-12}$ heterocyclyl), 2 to 10 carbon ring atoms (i.e., C$_{2-10}$ heterocyclyl), 2 to 8 carbon ring atoms (i.e., C$_{2-8}$ heterocyclyl), 3 to 12 carbon ring atoms (i.e., C$_{3-12}$ heterocyclyl), 3 to 8 carbon ring atoms (i.e., C$_{3-8}$ heterocyclyl), or 3 to 6 carbon ring atoms (i.e., C$_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include pyrrolidinyl, piperidinyl, piperazinyl, oxetanyl, dioxolanyl, azetidinyl, and morpholinyl. As used herein, the term "bridged-heterocyclyl" refers to a four- to ten-membered cyclic moiety connected at two non-adjacent atoms of the heterocyclyl with one or more (e.g., 1 or 2) four- to ten-membered cyclic moiety having at least one heteroatom where each heteroatom is independently selected from nitrogen, oxygen, and sulfur. As used herein, "bridged-heterocyclyl" includes bicyclic and tricyclic ring systems. Also as used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl. As used herein, the terms "heterocycle", "heterocyclyl", and "heterocyclic ring" are used interchangeably. In some embodiments, a heterocyclyl is substituted with an oxo group.

"Heterocycloxy" refers to the group "—O(heterocyclyl)". Examples of heterocycloxy groups include but are not limited to —O(pyrrolidinyl), —O(tetrahydrofuranyl), —O(piperidinyl), —O(morpholinyl), —O(oxetanyl), and —O(2-oxa-7-azaspiro[3.5]nonanyl).

"Hydroxy" or "hydroxyl" refers to the group —OH.

"Oxo" refers to the group (=O) or (O).

"Sulfonyl" refers to the group —S(O)$_2$R$^{bb}$, where R$^{bb}$ is alkyl, haloalkyl, heterocyclyl, cycloalkyl, heteroaryl, or aryl. Examples of sulfonyl are methylsulfonyl, ethylsulfonyl, phenylsulfonyl, and toluenesulfonyl.

Whenever the graphical representation of a group terminates in a singly bonded nitrogen atom, that group represents an —NH group unless otherwise indicated. Similarly, unless otherwise expressed, hydrogen atom(s) are implied and deemed present where necessary in view of the knowledge of one of skill in the art to complete valency or provide stability.

The terms "optional" or "optionally" mean that the subsequently described event or circumstance may or may not occur, and that the description includes instances where said event or circumstance occurs and instances in which it does not. Also, the term "optionally substituted" means that any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

In some embodiments, a substituted cycloalkyl, a substituted heterocyclyl, a substituted aryl, and/or a substituted heteroaryl includes a cycloalkyl, a heterocyclyl, an aryl, and/or a heteroaryl that has a substituent on the ring atom to which the cycloalkyl, heterocyclyl, aryl, and/or heteroaryl is attached to the rest of the compound. For example, in the below moiety, the cyclopropyl is substituted with a methyl group:

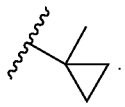

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

"Enantiomers" are a pair of stereoisomers that are non-superimposable mirror images of each other. A 1:1 mixture of a pair of enantiomers is a "racemic" mixture. A mixture of enantiomers at a ratio other than 1:1 is a "scalemic" mixture.

"Diastereoisomers" are stereoisomers that have at least two asymmetric atoms, but which are not mirror-images of each other.

A "tautomer" refers to a proton shift from one atom of a molecule to another atom of the same molecule. The present disclosure includes tautomers of any compounds provided herein.

Some of the compounds provided herein exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

A "solvate" is formed by the interaction of a solvent and a compound. Solvates of salts of the compounds provided herein are also provided. Hydrates of the compounds provided herein are also provided.

Any formula or structure provided herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^2$H, $^3$H, $^{13}$C and $^{14}$C are incorporated, are also provided herein. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The present disclosure also includes compounds of Formula I, in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the present disclosure may have improved DMPK (drug metabolism and pharmacokinetics) properties, relating to absorption, distribution, metabolism and excretion (ADME). Substitution with heavier isotopes such as deuterium may afford certain therapeutic advantages resulting from greater metabolic stability, for example, increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure, any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure, any atom specifically designated as a deuterium (D) is meant to represent deuterium.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, mono, di or tri cycloalkyl amines, mono, di or tri arylamines or mixed amines, and the like. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Treatment" or "treating" is an approach for obtaining beneficial or desired results including clinical results. Beneficial or desired clinical results may include one or more of the following: a) inhibiting the disease or condition (i.e., decreasing one or more symptoms resulting from the disease or condition, and/or diminishing the extent of the disease or condition); b) slowing or arresting the development of one or more clinical symptoms associated with the disease or condition (i.e., stabilizing the disease or condition, preventing or delaying the worsening or progression of the disease or condition, and/or preventing or delaying the spread (i.e., metastasis) of the disease or condition); and/or c) relieving the disease, that is, causing the regression of clinical symptoms (i.e., ameliorating the disease state, providing partial or total remission of the disease or condition, enhancing effect of another medication, delaying the progression of the disease, increasing the quality of life, and/or prolonging survival).

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or pharmaceutically acceptable salts, isomer, or a mixture thereof means an amount sufficient to effect treatment when administered to a subject, to provide a therapeutic benefit such as amelioration of symptoms or slowing of disease progression. For example, a therapeutically effective amount may be an amount sufficient to improve a symptom of a disease or condition responsive to inhibition of toll-like receptor 7, 8, and/or 9. The therapeutically effective amount may vary depending on the subject, and the disease or condition being treated, the weight and age of the subject, the severity of the disease or condition, and the manner of administering, which can readily be determined by one of ordinary skill in the art.

II. Compounds

In one embodiment, provided herein is a compound of Formula I,

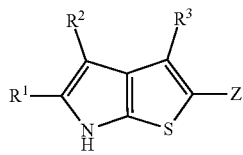

Formula I or a pharmaceutically acceptable salt thereof,
wherein
$R^1$ is 8-15 membered fused tricyclic heterocyclyl or 8-15 membered fused tricyclic heteroaryl, wherein the 8-15 membered fused tricyclic heterocyclyl and 8-15 membered fused tricyclic heteroaryl are each independently optionally substituted with 1-4 $R^a$ groups;
$R^2$ is $C_{1-6}$ alkyl, wherein the $C_{1-6}$ alkyl is optionally substituted with 1-4 groups independently selected from halogen and $C_{1-6}$ alkoxy, wherein the $C_{1-6}$ alkoxy is optionally substituted with 1-3 halogen groups;
$R^3$ is H, halogen, —CN, $C_{1-6}$ alkyl, and $C_{3-7}$ monocyclic cycloalkyl,
wherein the $C_{1-6}$ alkyl and $C_{3-7}$ monocyclic cycloalkyl are each independently optionally substituted with 1-3 groups independently selected from —OH, halogen, —CN, and $C_{1-4}$ alkoxy,
wherein the $C_{1-4}$ alkoxy is optionally substituted with 1-3 halogen groups;
Z is $C_{1-6}$ alkyl, —C(O)$R^{13}$—C(O)N$R^6R^7$, $C_{3-7}$ monocyclic cycloalkyl, $C_{7-10}$ fused bicyclic cycloalkyl, $C_{5-10}$ bridged bicyclic cycloalkyl, 4-7 membered monocyclic heterocyclyl, phenyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl,
wherein the $C_{1-6}$ alkyl is optionally substituted with 1-4 $R^b$ groups;
wherein the $C_{3-7}$ monocyclic cycloalkyl, $C_{7-10}$ fused bicyclic cycloalkyl, $C_{5-10}$ bridged bicyclic cycloalkyl, 4-7 membered monocyclic heterocyclyl, phenyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-2 $R^8$ groups and are each independently optionally substituted with 1-3 $R^a$ groups;
$R^6$ is $C_{3-7}$ monocyclic cycloalkyl, $C_{7-10}$ fused bicyclic cycloalkyl, $C_{5-10}$ bridged bicyclic cycloalkyl, 4-7 membered monocyclic heterocyclyl, 8-10 membered fused bicyclic heterocyclyl, 6-10 membered bridged bicyclic heterocyclyl, or 7-10 membered spirocyclic heterocyclyl,
wherein the $C_{3-7}$ monocyclic cycloalkyl, $C_{7-10}$ fused bicyclic cycloalkyl, $C_{5-10}$ bridged bicyclic cycloalkyl, 4-7 membered monocyclic heterocyclyl, 8-10 membered fused bicyclic heterocyclyl, 6-10 membered bridged bicyclic heterocyclyl, and 7-10 membered spirocyclic heterocyclyl are each independently optionally substituted with 1-4 $R^a$ groups;
$R^{13}$ is 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl,
wherein the 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-4 $R^a$ groups;
$R^7$ is H, $C_{1-6}$ alkyl, $C_{3-7}$ monocyclic cycloalkyl, or 4-6 membered monocyclic heterocyclyl, wherein the $C_{1-6}$ alkyl, $C_{3-7}$ monocyclic cycloalkyl, and 4-6 membered monocyclic heterocyclyl are each independently optionally substituted with 1-4 groups independently selected from —OH, halogen, —CN, and $C_{1-6}$ alkoxy;
each $R^8$ independently is halogen, —C(O)$R^9$, —NR$^{10}$R$^{10}$, $C_{1-6}$ alkyl, $C_{3-7}$ monocyclic cycloalkyl, $C_{7-10}$ fused bicyclic cycloalkyl, $C_{5-10}$ bridged bicyclic cycloalkyl, 4-7 membered monocyclic heterocyclyl, phenyl, 5-6 membered monocyclic heteroaryl, 8-10 membered fused bicyclic heterocyclyl, 6-10 membered bridged bicyclic heterocyclyl, 8-10 membered fused bicyclic heteroaryl, 7-10 membered spirocyclic heterocyclyl, —OR$^5$, —C(O)N(R$^5$)(R$^5$), —N(R$^5$)$_2$(R$^5$)$^+$, —N(R$^5$)C(O)R$^5$, —N(R$^5$)C(O)OR$^5$, —N(R$^5$)C(O)N(R$^5$)(R$^5$), —N(R$^5$)S(O)$_2$(R$^{5a}$), —NR$^5$S(O)$_2$N(R$^5$)(R$^5$), —NR$^5$S(O)$_2$O(R$^{5a}$), —OC(O)N(R$^5$)(R$^5$), —S(O)R$^{5a}$, —S(O)(NH)R$^5$, —S(O)$_2$R$^{5a}$, —S(O)$_2$N(R$^5$)(R$^5$), or —N=S(R$^{5a}$)(R$^{5a}$)=O,
wherein the $C_{1-6}$ alkyl is optionally substituted with 1-4 $R^b$ groups,
wherein the $C_{3-7}$ monocyclic cycloalkyl, $C_{7-10}$ fused bicyclic cycloalkyl, $C_{5-10}$ bridged bicyclic cycloalkyl, 4-7 membered monocyclic heterocyclyl, phenyl, 5-6 membered monocyclic heteroaryl, 8-10 membered fused bicyclic heterocyclyl, 6-10 membered bridged bicyclic heteroaryl, 8-10 membered fused bicyclic heteroaryl, and 7-10 membered spirocyclic heterocyclyl are each independently optionally substituted with 1-4 $R^a$ groups;

each $R^9$ independently is $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl, wherein the $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-4 $R^a$ groups;

each $R^5$ and $R^{10}$ independently is H, $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl, wherein the $C_{1-6}$ alkyl, $C_{2-6}$ alkenyl, and $C_{2-6}$ alkynyl are each independently optionally substituted with 1-4 $R^b$ groups, wherein the $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-4 $R^a$ groups;

each $R^{5a}$ independently is $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl, wherein the $C_{1-6}$ alkyl, $C_{2-6}$ alkenyl, and $C_{2-6}$ alkynyl are each independently optionally substituted with 1-4 $R^b$ groups, wherein the $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-4 $R^a$ groups;

each $R^a$ independently is oxo, imino, halogen, —$NO_2$, —$N_3$, —CN, $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, 7-10 membered spirocyclic heterocyclyl, —$OR^{11}$, —$C(O)R^{11}$, —$C(O)OR^{11}$, —$C(O)N(R^{11})(R^{11})$, —$NR^{11}R^{11}$, —$N(R^{11})_2(R^{11})^+$, —$N(R^{11})C(O)R^{11}$, —$N(R^{11})C(O)OR^{11}$, —$N(R^{11})C(O)N(R^{11})(R^{11})$, —$N(R^{11})S(O)_2(R^{11a})$, —$NR^{11}S(O)_2N(R^{11})(R^{11})$, —$NR^{11}S(O)_2O(R^{11a})$, —$OC(O)R^{11}$, —$OC(O)OR^{11}$, —$OC(O)N(R^{11})(R^{11})$, —$SR^{11}$, —$S(O)R^{11a}$, —$S(O)(NH)R^{11}$, —$S(O)_2R^{11a}$, —$S(O)_2N(R^{11})(R^{11})$, or —$N=S(R^{11a})(R^{11a})=O$, wherein the $C_{1-6}$ alkyl, $C_{2-6}$ alkenyl, and $C_{2-6}$ alkynyl are each independently optionally substituted with 1-3 $R^c$ groups, wherein the $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-3 $R^d$ groups, each $R^b$ independently is oxo, imino, halogen, —$NO_2$, —$N_3$, —CN, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 8-10 membered bridged bicyclic heterocyclyl, 6-10 membered bridged bicyclic heterocyclyl, 8-10 membered fused bicyclic heteroaryl, 7-10 membered spirocyclic heterocyclyl, —$OR^{11}$, —$C(O)R^{11}$, —$C(O)OR^{11}$, —$C(O)N(R^{11})(R^{11})$, —$NR^{11}R^{11}$, —$N(R^{11})_2(R^{11})^+$, —$N(R^{11})C(O)R^{11}$, —$N(R^{11})C(O)OR^{11}$, —$N(R^{11})C(O)N(R^{11})(R^{11})$, —$N(R^{11})S(O)_2(R^{11a})$, —$NR^{11}S(O)_2N(R^{11})(R^{11})$, —$NR^{11}S(O)_2O(R^{11a})$, —$OC(O)R^{11}$, —$OC(O)OR^{11}$, —$OC(O)N(R^{11})(R^{11})$, —$SR^{11}$, —$S(O)R^{11a}$, —$S(O)(NH)R^{11}$, —$S(O)_2R^{11a}$, —$S(O)_2N(R^{11})(R^{11})$, or —$N=S(R^{11a})(R^{11a})=O$, wherein the $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-3 $R^d$ groups;

each $R^c$ independently is halogen, —CN, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, 7-10 membered spirocyclic heterocyclyl, —$OR^{12}$, —$C(O)R^{12}$, —$C(O)OR^{12}$, —$C(O)N(R^{12})(R^{12})$, —$NR^{12}R^{12}$, —$N(R^{12})_2(R^{12})^+$, —$N(R^{12})C(O)R^{12}$, —$N(R^{12})C(O)OR^{12}$, —$N(R^{12})C(O)N(R^{12})(R^{12})$, —$N(R^{12})S(O)_2(R^{12a})$, —$NR^{12}S(O)_2N(R^{12})(R^{12})$, —$NR^{12}S(O)_2O(R^{12a})$, —$OC(O)R^{12}$, —$OC(O)OR^{12}$, —$OC(O)N(R^{12})(R^{12})$, —$SR^{12}$, —$S(O)R^{12a}$, —$S(O)(NH)R^{12}$, —$S(O)_2R^{12a}$, —$S(O)_2N(R^{12})(R^{12})$ or —$N=S(R^{12a})(R^{12a})=O$;

each $R^d$ independently is oxo, halogen, —CN, $C_{1-6}$ alkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, 7-10 membered spirocyclic heterocyclyl, —OR$^{12}$, —C(O)R$^{12}$, —C(O)OR$^{12}$, —C(O)N(R$^{12}$)(R$^{12}$), —NR$^{12}$R$^{12}$—N(R$^{12}$)$_2$(R$^{12}$)$^+$, —N(R$^{12}$)C(O)R$^{12}$, —N(R$^{12}$)C(O)OR$^{12}$, —N(R$^{12}$)C(O)N(R$^{12}$)(R$^{12}$), —N(R$^{12}$)S(O)$_2$(R$^{12a}$), —NR$^{12}$S(O)$_2$N(R$^{12}$)(R$^{12}$), —NR$^{12}$S(O)$_2$O(R$^{12a}$), —OC(O)R$^{12}$, —OC(O)OR$^{12}$, —OC(O)N(R$^{12}$)(R$^{12}$), —SR$^{12}$, —S(O)R$^{12a}$, —S(O)(NH)R$^{12}$, —S(O)$_2$R$^{12a}$, —S(O)$_2$N(R$^{12}$)(R$^{12}$) or —N═S(R$^{12a}$)(R$^{12a}$)═O,
wherein the C$_{1-6}$ alkyl is optionally substituted with 1-3 groups independently selected from —OH, halogen, —CN, and C$_{1-3}$ alkoxy;
each R$^{11}$ independently is H, C$_{1-6}$ alkyl, C$_{2-6}$ alkenyl, C$_{2-6}$ alkynyl, C$_{3-7}$ monocyclic cycloalkyl, C$_{7-10}$ fused bicyclic cycloalkyl, C$_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl,
wherein the C$_{1-6}$ alkyl, C$_{2-6}$ alkenyl, C$_{2-6}$ alkynyl, C$_{3-7}$ monocyclic cycloalkyl, C$_{7-10}$ fused bicyclic cycloalkyl, C$_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-3 R$^c$ groups;
each R$^{11a}$ independently is C$_{1-6}$ alkyl, C$_{2-6}$ alkenyl, C$_{2-6}$ alkynyl, C$_{3-7}$ monocyclic cycloalkyl, C$_{7-10}$ fused bicyclic cycloalkyl, C$_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl,
wherein the C$_{1-6}$ alkyl, C$_{2-6}$ alkenyl, C$_{2-6}$ alkynyl, C$_{3-7}$ monocyclic cycloalkyl, C$_{7-10}$ fused bicyclic cycloalkyl, C$_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-3 R$^c$ groups;
each R$^{12}$ independently is H, C$_{1-6}$ alkyl, C$_{2-6}$ alkenyl, C$_{2-6}$ alkynyl, C$_{3-7}$ monocyclic cycloalkyl, C$_{7-10}$ fused bicyclic cycloalkyl, C$_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl;
each R$^{12}$, independently is C$_{1-6}$ alkyl, C$_{2-6}$ alkenyl, C$_{2-6}$ alkynyl, C$_{3-7}$ monocyclic cycloalkyl, C$_{7-10}$ fused bicyclic cycloalkyl, C$_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl;
wherein each 4-membered monocyclic heterocyclyl independently has 1 ring heteroatom selected from N, O, and S;
wherein each 5-7 membered monocyclic heterocyclyl independently has 1-2 ring heteroatoms independently selected from N, O, and S;
wherein each 6-membered bridged bicyclic heterocyclyl independently has 1 ring heteroatom selected from N, O, and S;
wherein each 7-membered bridged bicyclic heterocyclyl independently has 1-2 ring heteroatoms independently selected from N, O, and S;
wherein each 5-6 membered monocyclic heteroaryl, 8-10 membered fused bicyclic heterocyclyl, 8-10 membered bridged bicyclic heterocyclyl, 8-10 membered fused bicyclic heteroaryl, and 7-10 membered spirocyclic heterocyclyl independently have 1-4 ring heteroatoms independently selected from N, O, and S; and
wherein each 8-15 membered fused tricyclic heterocyclyl and 8-15 membered fused tricyclic heteroaryl independently have 1-7 ring heteroatoms independently selected from N, O, and S.
In some embodiments of a compound of Formula I, or a pharmaceutically acceptable salt thereof, Z is C$_{7-10}$ fused bicyclic cycloalkyl, 8-10 membered fused bicyclic heterocyclyl, 6-10 membered bridged bicyclic heterocyclyl, or 8-10 membered fused bicyclic heteroaryl,
wherein the C$_{7-10}$ fused bicyclic cycloalkyl, 8-10 membered fused bicyclic heterocyclyl, 6-10 membered bridged bicyclic heterocyclyl, and 8-10 membered fused bicyclic heteroaryl are each independently optionally substituted with 1-2 R$^8$ groups and are each independently optionally substituted with 1-3 R$^a$ groups.
In some embodiments of a compound of Formula I, or a pharmaceutically acceptable salt thereof,
R$^1$ is 8-15 membered fused tricyclic heterocyclyl optionally substituted with 1-4 R$^a$ groups;
R$^2$ is C$_{1-6}$ alkyl, wherein the C$_{1-6}$ alkyl is optionally substituted with 1-4 groups independently selected from halogen and C$_{1-6}$ alkoxy, wherein the C$_{1-6}$ alkoxy is optionally substituted with 1-3 halogen groups;
R$^3$ is H or C$_{1-6}$ alkyl,
wherein the C$_{1-6}$ alkyl is optionally substituted with 1-3 groups independently selected from —OH, halogen, —CN, and C$_{1-4}$ alkoxy,
wherein the C$_{1-4}$ alkoxy is optionally substituted with 1-3 halogen groups;
Z is 4-7 membered monocyclic heterocyclyl, phenyl, 5-6 membered monocyclic heteroaryl, 8-10 membered fused bicyclic heterocyclyl, 6-10 membered bridged bicyclic heterocyclyl, or 7-10 membered spirocyclic heterocyclyl,
wherein the 4-7 membered monocyclic heterocyclyl, phenyl, 5-6 membered monocyclic heteroaryl, 8-10 membered fused bicyclic heterocyclyl, 6-10 membered bridged bicyclic heterocyclyl, and 7-10 membered spirocyclic heterocyclyl are each independently optionally substituted with 1-2 R$^8$ groups and are each independently optionally substituted with 1-3 R$^a$ groups;
each R$^8$ independently is —C(O)R$^9$, C$_{1-6}$ alkyl, 4-7 membered monocyclic heterocyclyl, or —S(O)$_2$R$^{5a}$, wherein the $C_{1-6}$ alkyl is optionally substituted with 1-4 $R^b$ groups,
wherein the 4-7 membered monocyclic heterocyclyl is optionally substituted with 1-4 $R^a$ groups;
each $R^9$ independently is $C_{3-7}$ monocyclic cycloalkyl or 4-7 membered monocyclic heterocyclyl,
wherein the $C_{3-7}$ monocyclic cycloalkyl and 4-7 membered monocyclic heterocyclyl are each independently optionally substituted with 1-4 $R^a$ groups;
$R^{5a}$ is 4-7 membered monocyclic heterocyclyl, wherein the 4-7 membered monocyclic heterocyclyl is optionally substituted with 1-4 $R^a$ groups;
each $R^a$ independently is oxo, imino, halogen, $-NO_2$, $-N_3$, $-CN$, $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, 7-10 membered spirocyclic heterocyclyl, $-OR^{11}$, $-C(O)R^{11}$, $-C(O)OR^{11}$, $-C(O)N(R^{11})(R^{11})$, $-NR^{11}R^{11}$, $-N(R^{11})_2(R^{11})^+$, $-N(R^{11})C(O)R^{11}$, $-N(R^{11})C(O)OR^{11}$, $-N(R^{11})C(O)N(R^{11})(R^{11})$, $-N(R^{11})S(O)_2(R^{11a})$, $-NR^{11}S(O)_2N(R^{11})(R^{11})$, $-NR^{11}S(O)_2O(R^{11a})$, $-OC(O)R^{11}$, $-OC(O)OR^{11}$, $-OC(O)N(R^{11})(R^{11})$, $-SR^{11}$, $-S(O)R^{11a}$, $-S(O)(NH)R^{11}$, $-S(O)_2R^{11a}$, $-S(O)_2N(R^{11})(R^{11})$, or $-N=S(R^{11a})(R^{11a})=O$,
wherein the $C_{1-6}$ alkyl, $C_{2-6}$ alkenyl, and $C_{2-6}$ alkynyl are each independently optionally substituted with 1-3 $R^c$ groups,
wherein the $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-3 $R^d$ groups,
each $R^b$ independently is oxo, imino, halogen, $-NO_2$, $-N_3$, $-CN$, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 8-10 membered bridged bicyclic heterocyclyl, 6-10 membered bridged bicyclic heterocyclyl, 8-10 membered fused bicyclic heteroaryl, 7-10 membered spirocyclic heterocyclyl, $-OR^{11}$, $-C(O)R^{11}$, $-C(O)OR^{11}$, $-C(O)N(R^{11})(R^{11})$, $-NR^{11}R^{11}$, $-N(R^{11})_2(R^{11})^+$, $-N(R^{11})C(O)R^{11}$, $-N(R^{11})C(O)OR^{11}$, $-N(R^{11})C(O)N(R^{11})(R^{11})$, $-N(R^{11})S(O)_2(R^{11a})$, $-NR^{11}S(O)_2N(R^{11})(R^{11})$, $-NR^{11}S(O)_2O(R^{11a})$, $-OC(O)R^{11}$, $-OC(O)OR^{11}$, $-OC(O)N(R^{11})(R^{11})$, $-SR^{11}$, $-S(O)R^{11a}$, $-S(O)(NH)R^{11}$, $-S(O)_2R^{11a}$, $-S(O)_2N(R^{11})(R^{11})$, or $-N=S(R^{11a})(R^{11a})=O$,
wherein the $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-3 $R^d$ groups;

each $R^c$ independently is halogen, $-CN$, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, 7-10 membered spirocyclic heterocyclyl, $-OR^{12}$, $-C(O)R^{12}$, $-C(O)OR^{12}$, $-C(O)N(R^{12})(R^{12})$, $-NR^{12}R^{12}$, $-N(R^{12})_2(R^{12})^+$, $-N(R^{12})C(O)R^{12}$, $-N(R^{12})C(O)OR^{12}$, $-N(R^{12})C(O)N(R^{12})(R^{12})$, $-N(R^{12})S(O)_2(R^{12a})$, $-NR^{12}S(O)_2N(R^{12})(R^{12})$, $-NR^{12}S(O)_2O(R^{12a})$, $-OC(O)R^{12}$, $-OC(O)OR^{12}$, $-OC(O)N(R^{12})(R^{12})$, $-SR^{12}$, $-S(O)R^{12a}$, $-S(O)(NH)R^{12}$, $-S(O)_2R^{12a}$, $-S(O)_2N(R^{12})(R^{12})$ or $-N=S(R^{12a})(R^{12a})=O$;
each $R^d$ independently is oxo, halogen, $-CN$, $C_{1-6}$ alkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, 7-10 membered spirocyclic heterocyclyl, $-OR^{12}$, $-C(O)R^{12}$, $-C(O)OR^{12}$, $-C(O)N(R^{12})(R^{12})$, $-NR^{12}R^{12}$, $-N(R^{12})_2(R^{12})^+$, $-N(R^{12})C(O)R^{12}$, $-N(R^{12})C(O)OR^{12}$, $-N(R^{12})C(O)N(R^{12})(R^{12})$, $-N(R^{12})S(O)_2(R^{12a})$, $-NR^{12}S(O)_2N(R^{12})(R^{12})$, $-NR^{12}S(O)_2O(R^{12a})$, $-OC(O)R^{12}$, $-OC(O)OR^{12}$, $-OC(O)N(R^{12})(R^{12})$, $-SR^{12}$, $-S(O)R^{12a}$, $-S(O)(NH)R^{12}$, $-S(O)_2R^{12a}$, $-S(O)_2N(R^{12})(R^{12})$ or $-N=S(R^{12a})(R^{12a})=O$;
each $R^{11}$ independently is H, $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl,
wherein the $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-3 $R^c$ groups;
each $R^{11a}$ independently is $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl,
wherein the $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heteroaryl, 6-10 membered bridged bicyclic heterocyclyl, 8-10 membered fused bicyclic heteroaryl, and 7-10 membered spirocyclic heterocyclyl are each independently optionally substituted with 1-3 $R^c$ groups;

each $R^{12}$ independently is H, $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl;

each $R^{12a}$ independently is $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl;

wherein each 4-membered monocyclic heterocyclyl independently has 1 ring heteroatom selected from N, O, and S;

wherein each 5-7 membered monocyclic heterocyclyl independently has 1-2 ring heteroatoms independently selected from N, O, and S;

wherein each 6-membered bridged bicyclic heterocyclyl independently has 1 ring heteroatom selected from N, O, and S;

wherein each 7-membered bridged bicyclic heterocyclyl independently has 1-2 ring heteroatoms independently selected from N, O, and S;

wherein each 5-6 membered monocyclic heteroaryl, 8-10 membered fused bicyclic heterocyclyl, 8-10 membered bridged bicyclic heterocyclyl, 8-10 membered fused bicyclic heteroaryl, and 7-10 membered spirocyclic heterocyclyl independently have 1-4 ring heteroatoms independently selected from N, O, and S; and wherein each 8-15 membered fused tricyclic heterocyclyl and 8-15 membered fused tricyclic heteroaryl independently have 1-7 ring heteroatoms independently selected from N, O, and S.

In some embodiments of a compound of Formula I, or a pharmaceutically acceptable salt thereof, $R^1$ is 8-15 membered fused tricyclic heterocyclyl optionally substituted with 1-3 groups independently selected from —OH, halogen, —CN, oxo, —$NR^{11}R^{11}$, $C_{1-4}$ alkoxy, $C_{1-6}$ alkyl, and $C_{3-7}$ monocyclic cycloalkyl;

$R^2$ is $C_{1-6}$ alkyl, wherein the $C_{1-6}$ alkyl is optionally substituted with 1-4 groups independently selected from halogen and $C_{1-6}$ alkoxy;

$R^3$ is H or $C_{1-6}$ alkyl, wherein the $C_{1-6}$ alkyl is optionally substituted with 1-3 groups independently selected from —OH, halogen, —CN, and $C_{1-4}$ alkoxy;

Z is 4-7 membered monocyclic heterocyclyl, phenyl, 5-6 membered monocyclic heteroaryl, 8-10 membered fused bicyclic heterocyclyl, 6-10 membered bridged bicyclic heterocyclyl, or 7-10 membered spirocyclic heterocyclyl, wherein the 4-7 membered monocyclic heterocyclyl, phenyl, 5-6 membered monocyclic heteroaryl, 8-10 membered fused bicyclic heterocyclyl, 6-10 membered bridged bicyclic heterocyclyl, and 7-10 membered spirocyclic heterocyclyl are each independently optionally substituted with 1-2 $R^8$ groups and are each independently optionally substituted with 1-3 groups independently selected from —OH, halogen, —CN, oxo, —$NR^{11}R^{11}$, $C_{1-4}$ alkoxy, and $C_{1-5}$ alkyl;

each $R^8$ independently is —$C(O)R^9$, $C_{1-6}$ alkyl, 4-7 membered monocyclic heterocyclyl, or —$S(O)_2R^{5a}$, wherein the $C_{1-6}$ alkyl is optionally substituted with 1-3 groups independently selected from —OH, halogen, —CN, oxo, —$NR^{11}R^{11}$, —$C(O)NR^{11}R^{11}$, $C_{1-4}$ alkoxy, and $R^{8a}$, wherein the 4-7 membered monocyclic heterocyclyl is optionally substituted with 1-3 groups independently selected from —OH, halogen, —CN, oxo, —$NR^{11}R^{11}$, $C_{1-4}$ alkoxy, and $C_{1-5}$ alkyl;

each $R^{8a}$ independently is 4-7 membered monocyclic heterocyclyl or 5-6 membered monocyclic heteroaryl, wherein the 4-7 membered monocyclic heterocyclyl and 5-6 membered monocyclic heteroaryl are each independently optionally substituted with 1-3 groups independently selected from —OH, halogen, $C_{1-4}$ alkoxy, and $C_{1-5}$ alkyl;

each $R^9$ independently is $C_{3-7}$ monocyclic cycloalkyl or 4-7 membered monocyclic heterocyclyl, wherein the $C_{3-7}$ monocyclic cycloalkyl and 4-7 membered monocyclic heterocyclyl are each independently optionally substituted with 1-3 groups independently selected from —OH, halogen, —CN, oxo, —$NR^{11}R^{11}$, $C_{1-4}$ alkoxy, $C_{1-5}$ alkyl, and 4-7 membered monocyclic heterocyclyl;

$R^{5a}$ is 4-7 membered monocyclic heterocyclyl, wherein the 4-7 membered monocyclic heterocyclyl is optionally substituted with 1-3 groups independently selected from —OH, halogen, —CN, oxo, —$NR^{11}R^{11}$, $C_{1-4}$ alkoxy, and $C_{1-5}$ alkyl;

each $R^{11}$ independently is H or $C_{1-6}$ alkyl;

each $R^{12}$ independently is H or $C_{1-4}$ alkyl;

wherein each 4-membered monocyclic heterocyclyl independently has 1 ring heteroatom selected from N, O, and S;

wherein each 5-7 membered monocyclic heterocyclyl independently has 1-2 ring heteroatoms independently selected from N, O, and S;

wherein each 6-membered bridged bicyclic heterocyclyl independently has 1 ring heteroatom selected from N, O, and S;

wherein each 7-membered bridged bicyclic heterocyclyl independently has 1-2 ring heteroatoms independently selected from N, O, and S;

wherein each 5-6 membered monocyclic heteroaryl, 8-10 membered fused bicyclic heterocyclyl, 8-10 membered bridged bicyclic heterocyclyl, 8-10 membered fused bicyclic heteroaryl, and 7-10 membered spirocyclic heterocyclyl independently have 1-4 ring heteroatoms independently selected from N, O, and S; and wherein each 8-15 membered fused tricyclic heterocyclyl and 8-15 membered fused tricyclic heteroaryl independently have 1-7 ring heteroatoms independently selected from N, O, and S.

Unless specified otherwise, each 4-membered monocyclic heterocyclyl as used herein has 1 ring heteroatom selected from N, O, and S. Unless specified otherwise, each 5-7 membered monocyclic heterocyclyl as used herein has 1-2 ring heteroatoms independently selected from N, O, and S. Unless specified otherwise, each 6-membered bridged bicyclic heterocyclyl as used herein has 1 ring heteroatom selected from N, O, and S. Unless specified otherwise, each 7-membered bridged bicyclic heterocyclyl as used herein has 1-2 ring heteroatoms independently selected from N, O, and S. Unless specified otherwise, each 5-6 membered monocyclic heteroaryl, 8-10 membered fused bicyclic heterocyclyl, 8-10 membered bridged bicyclic heterocyclyl, 8-10 membered fused bicyclic heteroaryl, and 7-10 membered spirocyclic heterocyclyl as used herein independently have 1-4 ring heteroatoms independently selected from N, O, and S.

In some embodiments of a compound of Formula I, or a pharmaceutically acceptable salt thereof, $R^1$ is 8-15 membered fused tricyclic heterocyclyl, wherein the 8-15 membered fused tricyclic heterocyclyl is optionally substituted with 1-4 $R^a$ groups. In some embodiments of a compound of Formula I, or a pharmaceutically acceptable salt thereof, $R^1$ is 8-15 membered fused tricyclic heterocyclyl, wherein the 8-15 membered fused tricyclic heterocyclyl is optionally substituted with 1-3 $R^a$ groups. In some embodiments of a compound of Formula I, or a pharmaceutically acceptable salt thereof, $R^1$ is 8-15 membered fused tricyclic heterocyclyl, wherein the 8-15 membered fused tricyclic heterocyclyl is optionally substituted with 1-3 groups independently selected from —OH, halogen, —CN, oxo, —NR$^{11}$R$^{11}$, C$_{1-4}$ alkoxy, C$_{1-6}$ alkyl, and C$_{3-7}$ monocyclic cycloalkyl.

In some embodiments of a compound of Formula I, or a pharmaceutically acceptable salt thereof, $R^1$ is 8-15 membered fused tricyclic heterocyclyl, wherein the 8-15 membered fused tricyclic heterocyclyl is substituted with 1-4 $R^a$ groups. In some embodiments of a compound of Formula I, or a pharmaceutically acceptable salt thereof, $R^1$ is 8-15 membered fused tricyclic heterocyclyl, wherein the 8-15 membered fused tricyclic heterocyclyl is substituted with 1-3 $R^a$ groups. In some embodiments of a compound of Formula I, or a pharmaceutically acceptable salt thereof, $R^1$ is 8-15 membered fused tricyclic heterocyclyl, wherein the 8-15 membered fused tricyclic heterocyclyl is substituted with 1-3 groups independently selected from —OH, halogen, —CN, oxo, —NR$^{11}$R$^{11}$, C$_{1-4}$ alkoxy, C$_{1-6}$ alkyl, and C$_{3-7}$ monocyclic cycloalkyl.

In some embodiments of a compound of Formula I, or a pharmaceutically acceptable salt thereof, $R^1$ is 8-15 membered fused tricyclic heterocyclyl.

In some embodiments of a compound of Formula I, or a pharmaceutically acceptable salt thereof, $R^1$ is 8-15 membered fused tricyclic heteroaryl, wherein the 8-15 membered fused tricyclic heteroaryl is optionally substituted with 1-4 $R^a$ groups. In some embodiments of a compound of Formula I, or a pharmaceutically acceptable salt thereof, $R^1$ is 8-15 membered fused tricyclic heteroaryl, wherein the 8-15 membered fused tricyclic heteroaryl is optionally substituted with 1-3 $R^a$ groups. In some embodiments of a compound of Formula I, or a pharmaceutically acceptable salt thereof, $R^1$ is 8-15 membered fused tricyclic heteroaryl, wherein the 8-15 membered fused tricyclic heteroaryl is optionally substituted with 1-3 groups independently selected from —OH, halogen, —CN, oxo, —NR$^{11}$R$^{11}$, C$_{1-4}$ alkoxy, C$_{1-6}$ alkyl, and C$_{3-7}$ monocyclic cycloalkyl.

In some embodiments of a compound of Formula I, or a pharmaceutically acceptable salt thereof, $R^1$ is 8-15 membered fused tricyclic heteroaryl, wherein the 8-15 membered fused tricyclic heteroaryl is substituted with 1-4 $R^a$ groups. In some embodiments of a compound of Formula I, or a pharmaceutically acceptable salt thereof, $R^1$ is 8-15 membered fused tricyclic heteroaryl, wherein the 8-15 membered fused tricyclic heteroaryl is substituted with 1-3 $R^a$ groups. In some embodiments of a compound of Formula I, or a pharmaceutically acceptable salt thereof, $R^1$ is 8-15 membered fused tricyclic heteroaryl, wherein the 8-15 membered fused tricyclic heteroaryl is substituted with 1-3 groups independently selected from —OH, halogen, —CN, oxo, —NR$^{11}$R$^{11}$, C$_{1-4}$ alkoxy, C$_{1-6}$ alkyl, and C$_{3-7}$ monocyclic cycloalkyl.

In some embodiments of a compound of Formula I, or a pharmaceutically acceptable salt thereof, $R^1$ is

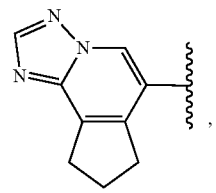

which is optionally substituted with 1-3 groups independently selected from halogen, C$_{1-3}$ alkyl, and C$_{1-3}$ alkoxy, wherein the C$_{1-3}$ alkyl is optionally substituted with 1-3 halogen groups.

In some embodiments of a compound of Formula I, or a pharmaceutically acceptable salt thereof, $R^1$ is

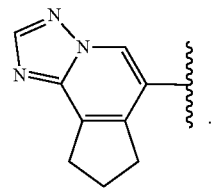 [SMILES: *c1cn2ncnc2c2c1CCC2]

In some embodiments of a compound of Formula I, or a pharmaceutically acceptable salt thereof, $R^1$ is

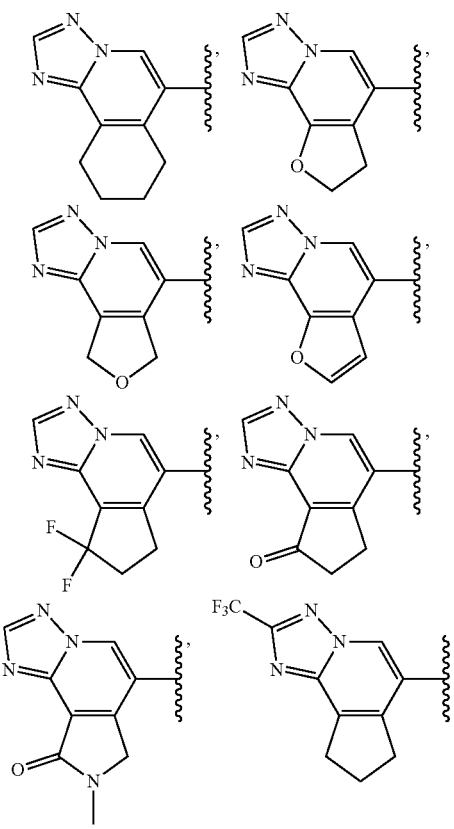

-continued

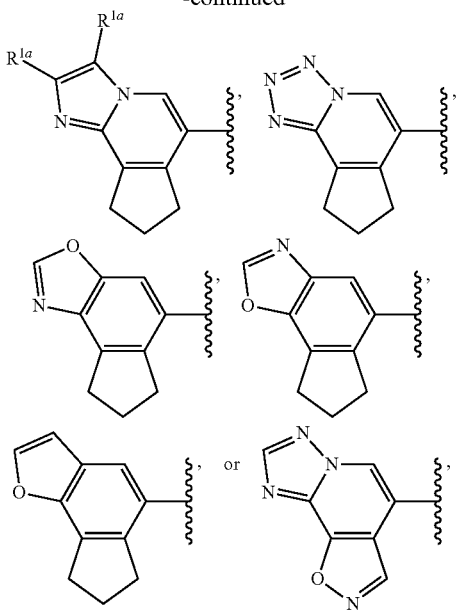

wherein each $R^{1a}$ independently is H, —CN, $C_{1-6}$ alkyl, $C_{1-5}$ alkoxy, or $C_{3-7}$ monocyclic cycloalkyl, wherein the $C_{1-6}$ alkyl and $C_{1-5}$ alkoxy are each optionally substituted with 1-3 halogen groups.

In some embodiments of a compound of Formula I, or a pharmaceutically acceptable salt thereof, each $R^{1a}$ independently is H, —CN, —CHF$_2$, —CF$_3$, methyl, methoxy, or cyclopropyl.

In some embodiments of a compound of Formula I, or a pharmaceutically acceptable salt thereof, $R^1$ is

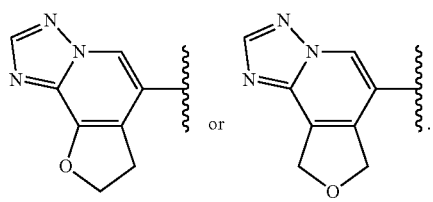 [SMILES: *c1cn2ncnc2c2c1CCO2 ; *c1cn2ncnc2c2c1COC2]

In some embodiments of a compound of Formula I, or a pharmaceutically acceptable salt thereof, $R^2$ is $C_{1-6}$ alkyl, wherein the $C_{1-6}$ alkyl is optionally substituted with 1-4 groups independently selected from halogen and $C_{1-6}$ alkoxy, wherein the $C_{1-6}$ alkoxy is optionally substituted with 1-3 halogen groups. In some embodiments of a compound of Formula I, or a pharmaceutically acceptable salt thereof, $R^2$ is $C_{1-6}$ alkyl, wherein the $C_{1-6}$ alkyl is optionally substituted with 1-3 groups independently selected from halogen and $C_{1-6}$ alkoxy, wherein the $C_{1-6}$ alkoxy is optionally substituted with 1-3 halogen groups. In some embodiments of a compound of Formula I, or a pharmaceutically acceptable salt thereof, $R^2$ is $C_{1-6}$ alkyl, wherein the $C_{1-6}$ alkyl is optionally substituted with 1-3 groups independently selected from halogen and $C_{1-3}$ alkoxy, wherein the $C_{1-3}$ alkoxy is optionally substituted with 1-3 halogen groups. In some embodiments of a compound of Formula I, or a pharmaceutically acceptable salt thereof, $R^2$ is $C_{1-6}$ alkyl, wherein the $C_{1-6}$ alkyl is substituted with 1-4 groups independently selected from halogen and $C_{1-6}$ alkoxy, wherein the $C_{1-6}$ alkoxy is optionally substituted with 1-3 halogen groups. In some embodiments of a compound of Formula I, or a pharmaceutically acceptable salt thereof, $R^2$ is $C_{1-6}$ alkyl, wherein the $C_{1-6}$ alkyl is substituted with 1-3 groups independently selected from halogen and $C_{1-6}$ alkoxy, wherein the $C_{1-6}$ alkoxy is optionally substituted with 1-3 halogen groups. In some embodiments of a compound of Formula I, or a pharmaceutically acceptable salt thereof, $R^2$ is $C_{1-6}$ alkyl, wherein the $C_{1-6}$ alkyl is substituted with 1-3 groups independently selected from halogen and $C_{1-3}$ alkoxy, wherein the $C_{1-3}$ alkoxy is optionally substituted with 1-3 halogen groups.

In some embodiments of a compound of Formula I, or a pharmaceutically acceptable salt thereof, $R^2$ is $C_{1-6}$ alkyl, wherein the $C_{1-6}$ alkyl is optionally substituted with 1-4 groups independently selected from halogen and $C_{1-6}$ alkoxy. In some embodiments of a compound of Formula I, or a pharmaceutically acceptable salt thereof, $R^2$ is $C_{1-6}$ alkyl, wherein the $C_{1-6}$ alkyl is optionally substituted with 1-3 groups independently selected from halogen and $C_{1-6}$ alkoxy. In some embodiments of a compound of Formula I, or a pharmaceutically acceptable salt thereof, $R^2$ is $C_{1-6}$ alkyl, wherein the $C_{1-6}$ alkyl is optionally substituted with 1-3 groups independently selected from halogen and $C_{1-3}$ alkoxy. In some embodiments of a compound of Formula I, or a pharmaceutically acceptable salt thereof, $R^2$ is $C_{1-6}$ alkyl, wherein the $C_{1-6}$ alkyl is substituted with 1-4 groups independently selected from halogen and $C_{1-6}$ alkoxy. In some embodiments of a compound of Formula I, or a pharmaceutically acceptable salt thereof, $R^2$ is $C_{1-6}$ alkyl, wherein the $C_{1-6}$ alkyl is substituted with 1-3 groups independently selected from halogen and $C_{1-6}$ alkoxy. In some embodiments of a compound of Formula I, or a pharmaceutically acceptable salt thereof, $R^2$ is $C_{1-6}$ alkyl, wherein the $C_{1-6}$ alkyl is substituted with 1-3 groups independently selected from halogen and $C_{1-3}$ alkoxy.

In some embodiments of a compound of Formula I, or a pharmaceutically acceptable salt thereof, $R^2$ is $C_{1-4}$ alkyl, wherein the $C_{1-4}$ alkyl is optionally substituted with 1-4 groups independently selected from halogen and $C_{1-6}$ alkoxy. In some embodiments of a compound of Formula I, or a pharmaceutically acceptable salt thereof, $R^2$ is $C_{1-4}$ alkyl, wherein the $C_{1-4}$ alkyl is optionally substituted with 1-3 groups independently selected from halogen and $C_{1-6}$ alkoxy. In some embodiments of a compound of Formula I, or a pharmaceutically acceptable salt thereof, $R^2$ is $C_{1-4}$ alkyl, wherein the $C_{1-4}$ alkyl is optionally substituted with 1-3 groups independently selected from halogen and $C_{1-3}$ alkoxy.

In some embodiments of a compound of Formula I, or a pharmaceutically acceptable salt thereof, $R^2$ is $C_{1-4}$ alkyl, wherein the $C_{1-4}$ alkyl is substituted with 1-4 groups independently selected from halogen and $C_{1-6}$ alkoxy. In some embodiments of a compound of Formula I, or a pharmaceutically acceptable salt thereof, $R^2$ is $C_{1-4}$ alkyl, wherein the $C_{1-4}$ alkyl is substituted with 1-3 groups independently selected from halogen and $C_{1-6}$ alkoxy. In some embodiments of a compound of Formula I, or a pharmaceutically acceptable salt thereof, $R^2$ is $C_{1-4}$ alkyl, wherein the $C_{1-4}$ alkyl is substituted with 1-3 groups independently selected from halogen and $C_{1-3}$ alkoxy.

In some embodiments of a compound of Formula I, or a pharmaceutically acceptable salt thereof, $R^2$ is $C_{1-6}$ alkyl. In some embodiments of a compound of Formula I, or a pharmaceutically acceptable salt thereof, $R^2$ is $C_{1-4}$ alkyl. In some embodiments of a compound of Formula I, or a pharmaceutically acceptable salt thereof, $R^2$ is $C_{1-3}$ alkyl. In some embodiments of a compound of Formula I, or a pharmaceutically acceptable salt thereof, $R^2$ is ethyl or isopropyl. In some embodiments of a compound of Formula I, or a pharmaceutically acceptable salt thereof, $R^2$ is methyl. In some embodiments of a compound of Formula I, or a pharmaceutically acceptable salt thereof, $R^2$ is ethyl. In some embodiments of a compound of Formula I, or a pharmaceutically acceptable salt thereof, $R^2$ is propyl. In some embodiments of a compound of Formula I, or a pharmaceutically acceptable salt thereof, $R^2$ is isopropyl.

In some embodiments of a compound of Formula I, or a pharmaceutically acceptable salt thereof, $R^3$ is H, halogen, —CN, $C_{1-6}$ alkyl, and $C_{3-7}$ monocyclic cycloalkyl,
wherein the $C_{1-6}$ alkyl and $C_{3-7}$ monocyclic cycloalkyl are each independently optionally substituted with 1-3 groups independently selected from —OH, halogen, —CN, and $C_{1-4}$ alkoxy,
wherein the $C_{1-4}$ alkoxy is optionally substituted with 1-3 halogen groups.

In some embodiments of a compound of Formula I, or a pharmaceutically acceptable salt thereof, $R^3$ is H or $C_{1-6}$ alkyl,
wherein the $C_{1-6}$ alkyl is optionally substituted with 1-3 groups independently selected from —OH, halogen, —CN, and $C_{1-4}$ alkoxy,
wherein the $C_{1-4}$ alkoxy is optionally substituted with 1-3 halogen groups.

In some embodiments of a compound of Formula I, or a pharmaceutically acceptable salt thereof, $R^3$ is H or $C_{1-6}$ alkyl, wherein the $C_{1-6}$ alkyl is optionally substituted with 1-3 groups independently selected from —OH, halogen, —CN, and $C_{1-4}$ alkoxy. In some embodiments of a compound of Formula I, or a pharmaceutically acceptable salt thereof, $R^3$ is H or $C_{1-6}$ alkyl. In some embodiments of a compound of Formula I, or a pharmaceutically acceptable salt thereof, $R^3$ is H or methyl.

In some embodiments of a compound of Formula I, or a pharmaceutically acceptable salt thereof, $R^3$ is H. In some embodiments of a compound of Formula I, or a pharmaceutically acceptable salt thereof, $R^3$ is halogen. In some embodiments of a compound of Formula I, or a pharmaceutically acceptable salt thereof, $R^3$ is —CN.

In some embodiments of a compound of Formula I, or a pharmaceutically acceptable salt thereof, $R^3$ is $C_{3-7}$ monocyclic cycloalkyl, wherein the $C_{3-7}$ monocyclic cycloalkyl is optionally substituted with 1-3 groups independently selected from —OH, halogen, —CN, and $C_{1-4}$ alkoxy, wherein the $C_{1-4}$ alkoxy is optionally substituted with 1-3 halogen groups. In some embodiments of a compound of Formula I, or a pharmaceutically acceptable salt thereof, $R^3$ is $C_{3-7}$ monocyclic cycloalkyl, wherein the $C_{3-7}$ monocyclic cycloalkyl is substituted with 1-3 groups independently selected from —OH, halogen, —CN, and $C_{1-4}$ alkoxy, wherein the $C_{1-4}$ alkoxy is optionally substituted with 1-3 halogen groups. In some embodiments of a compound of Formula I, or a pharmaceutically acceptable salt thereof, $R^3$ is $C_{3-7}$ monocyclic cycloalkyl.

In some embodiments of a compound of Formula I, or a pharmaceutically acceptable salt thereof, $R^3$ is $C_{1-6}$ alkyl, wherein the $C_{1-6}$ alkyl is optionally substituted with 1-3 groups independently selected from —OH, halogen, —CN, and $C_{1-4}$ alkoxy, wherein the $C_{1-4}$ alkoxy is optionally substituted with 1-3 halogen groups. In some embodiments of a compound of Formula I, or a pharmaceutically acceptable salt thereof, $R^3$ is $C_{1-6}$ alkyl, wherein the $C_{1-6}$ alkyl is substituted with 1-3 groups independently selected from —OH, halogen, —CN, and $C_{1-4}$ alkoxy, wherein the $C_{1-4}$ alkoxy is optionally substituted with 1-3 halogen groups.

In some embodiments of a compound of Formula I, or a pharmaceutically acceptable salt thereof, $R^3$ is $C_{1-6}$ alkyl, wherein the $C_{1-6}$ alkyl is optionally substituted with 1-3 groups independently selected from —OH, halogen, —CN, and $C_{1-4}$ alkoxy. In some embodiments of a compound of Formula I, or a pharmaceutically acceptable salt thereof, $R^3$ is $C_{1-6}$ alkyl, wherein the $C_{1-6}$ alkyl is substituted with 1-3 groups independently selected from —OH, halogen, —CN, and $C_{1-4}$ alkoxy.

In some embodiments of a compound of Formula I, or a pharmaceutically acceptable salt thereof, $R^3$ is $C_{1-4}$ alkyl optionally substituted with 1-3 groups independently selected from —OH, halogen, —CN, and $C_{1-3}$ alkoxy. In some embodiments of a compound of Formula I, or a pharmaceutically acceptable salt thereof, $R^3$ is methyl substituted with 1-3 halogen groups. In some embodiments of a compound of Formula I, or a pharmaceutically acceptable salt thereof, $R^3$ is —CHF$_2$.

In some embodiments of a compound of Formula I, or a pharmaceutically acceptable salt thereof, $R^3$ is $C_{1-6}$ alkyl. In some embodiments of a compound of Formula I, or a pharmaceutically acceptable salt thereof, $R^3$ is $C_{1-4}$ alkyl. In some embodiments of a compound of Formula I, or a pharmaceutically acceptable salt thereof, $R^3$ is $C_{1-3}$ alkyl. In some embodiments of a compound of Formula I, or a pharmaceutically acceptable salt thereof, $R^3$ is methyl.

In some embodiments of a compound of Formula I, or a pharmaceutically acceptable salt thereof, Z is $C_{1-6}$ alkyl, —C(O)R$^{13}$, —C(O)NR$^6$R$^7$, $C_{3-7}$ monocyclic cycloalkyl, $C_{7-10}$ fused bicyclic cycloalkyl, $C_{5-10}$ bridged bicyclic cycloalkyl, 4-7 membered monocyclic heterocyclyl, phenyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl,
wherein the $C_{1-6}$ alkyl is optionally substituted with 1-4 R$^b$ groups,
wherein the $C_{3-7}$ monocyclic cycloalkyl, $C_{7-10}$ fused bicyclic cycloalkyl, $C_{5-10}$ bridged bicyclic cycloalkyl, 4-7 membered monocyclic heterocyclyl, phenyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-2 R$^8$ groups and are each independently optionally substituted with 1-3 R$^a$ groups.

In some embodiments of a compound of Formula I, or a pharmaceutically acceptable salt thereof, Z is $C_{7-10}$ fused bicyclic cycloalkyl, 8-10 membered fused bicyclic heterocyclyl, 6-10 membered bridged bicyclic heterocyclyl, or 8-10 membered fused bicyclic heteroaryl,
wherein the $C_{7-10}$ fused bicyclic cycloalkyl, 8-10 membered fused bicyclic heterocyclyl, 6-10 membered bridged bicyclic heterocyclyl, and 8-10 membered fused bicyclic heteroaryl are each independently optionally substituted with 1-2 R$^8$ groups and are each independently optionally substituted with 1-3 R$^a$ groups.

In some embodiments of a compound of Formula I, or a pharmaceutically acceptable salt thereof, Z is 4-7 membered monocyclic heterocyclyl, phenyl, 5-6 membered monocyclic heteroaryl, 8-10 membered fused bicyclic heterocyclyl, 6-10 membered bridged bicyclic heterocyclyl, or 7-10 membered spirocyclic heterocyclyl,
wherein the 4-7 membered monocyclic heterocyclyl, phenyl, 5-6 membered monocyclic heteroaryl, 8-10 membered fused bicyclic heterocyclyl, 6-10 membered bridged bicyclic heterocyclyl, and 7-10 membered spirocyclic heterocyclyl are each independently optionally substituted with 1-2 $R^8$ groups and are each independently optionally substituted with 1-3 $R^a$ groups.

In some embodiments of a compound of Formula I, or a pharmaceutically acceptable salt thereof, Z is 4-7 membered monocyclic heterocyclyl, phenyl, 5-6 membered monocyclic heteroaryl, 8-10 membered fused bicyclic heterocyclyl, 6-10 membered bridged bicyclic heterocyclyl, or 7-10 membered spirocyclic heterocyclyl,
wherein the 4-7 membered monocyclic heterocyclyl, phenyl, 5-6 membered monocyclic heteroaryl, 8-10 membered fused bicyclic heterocyclyl, 6-10 membered bridged bicyclic heterocyclyl, and 7-10 membered spirocyclic heterocyclyl are each independently optionally substituted with 1-2 $R^8$ groups and are each independently optionally substituted with 1-3 groups independently selected from —OH, halogen, —CN, oxo, —$NR^{11}R^{11}$, $C_{1-4}$ alkoxy, and $C_{1-5}$ alkyl.

In some embodiments of a compound of Formula I, or a pharmaceutically acceptable salt thereof, Z is $C_{7-10}$ fused bicyclic cycloalkyl, 8-10 membered fused bicyclic heterocyclyl, 6-10 membered bridged bicyclic heterocyclyl, or 8-10 membered fused bicyclic heteroaryl,
wherein the $C_{7-10}$ fused bicyclic cycloalkyl, 8-10 membered fused bicyclic heterocyclyl, 6-10 membered bridged bicyclic heterocyclyl, and 8-10 membered fused bicyclic heteroaryl are each independently optionally substituted with 1-2 $R^8$ groups and are each independently optionally substituted with 1-3 $R^a$ groups.

In some embodiments of a compound of Formula I, or a pharmaceutically acceptable salt thereof, Z is $C_{1-6}$ alkyl, wherein the $C_{1-6}$ alkyl is optionally substituted with 1-4 $R^b$ groups. In some embodiments of a compound of Formula I, or a pharmaceutically acceptable salt thereof, Z is $C_{1-6}$ alkyl, wherein the $C_{1-6}$ alkyl is optionally substituted with 1-3 $R^b$ groups. In some embodiments of a compound of Formula I, or a pharmaceutically acceptable salt thereof, Z is $C_{1-6}$ alkyl, wherein the $C_{1-6}$ alkyl is substituted with 1-4 $R^b$ groups. In some embodiments of a compound of Formula I, or a pharmaceutically acceptable salt thereof, Z is $C_{1-6}$ alkyl, wherein the $C_{1-10}$ alkyl is substituted with 1-3 $R^b$ groups. In some embodiments of a compound of Formula I, or a pharmaceutically acceptable salt thereof, Z is $C_{1-6}$ alkyl.

In some embodiments of a compound of Formula I, or a pharmaceutically acceptable salt thereof, Z is $C_{3-7}$ monocyclic cycloalkyl, wherein the $C_{3-7}$ monocyclic cycloalkyl is optionally substituted with 1-2 $R^8$ groups and is optionally substituted with 1-3 $R^a$ groups. In some embodiments of a compound of Formula I, or a pharmaceutically acceptable salt thereof, Z is $C_{3-7}$ monocyclic cycloalkyl, wherein the $C_{3-7}$ monocyclic cycloalkyl is optionally substituted with 1-2 $R^8$ groups and is optionally substituted with 1-3 groups independently selected from —OH, halogen, —CN, oxo, —$NR^{11}R^{11}$, $C_{1-4}$ alkoxy, and $C_{1-5}$ alkyl.

In some embodiments of a compound of Formula I, or a pharmaceutically acceptable salt thereof, Z is $C_{3-7}$ monocyclic cycloalkyl, wherein the $C_{3-7}$ monocyclic cycloalkyl is substituted with 1-2 $R^8$ groups and is optionally substituted with 1-3 $R^a$ groups. In some embodiments of a compound of Formula I, or a pharmaceutically acceptable salt thereof, Z is $C_{3-7}$ monocyclic cycloalkyl, wherein the $C_{3-7}$ monocyclic cycloalkyl is substituted with 1-2 $R^8$ groups and is optionally substituted with 1-3 groups independently selected from —OH, halogen, —CN, oxo, —$NR^{11}R^{11}$, $C_{1-4}$ alkoxy, and $C_{1-5}$ alkyl.

In some embodiments of a compound of Formula I, or a pharmaceutically acceptable salt thereof, Z is $C_{3-7}$ monocyclic cycloalkyl, wherein the $C_{3-7}$ monocyclic cycloalkyl is substituted with 1-2 $R^8$ groups and is substituted with 1-3 $R^a$ groups. In some embodiments of a compound of Formula I, or a pharmaceutically acceptable salt thereof, Z is $C_{3-7}$ monocyclic cycloalkyl, wherein the $C_{3-7}$ monocyclic cycloalkyl is substituted with 1-2 $R^8$ groups and is substituted with 1-3 groups independently selected from —OH, halogen, —CN, oxo, —$NR^{11}R^{11}$, $C_{1-4}$ alkoxy, and $C_{1-5}$ alkyl.

In some embodiments of a compound of Formula I, or a pharmaceutically acceptable salt thereof, Z is $C_{3-7}$ monocyclic cycloalkyl, wherein the $C_{3-7}$ monocyclic cycloalkyl is substituted with 1-2 $R^8$ groups. In some embodiments of a compound of Formula I, or a pharmaceutically acceptable salt thereof, Z is $C_{3-7}$ monocyclic cycloalkyl, wherein the $C_{3-7}$ monocyclic cycloalkyl is optionally substituted with 1-3 $R^a$ groups. In some embodiments of a compound of Formula I, or a pharmaceutically acceptable salt thereof, Z is $C_{3-7}$ monocyclic cycloalkyl, wherein the $C_{3-7}$ monocyclic cycloalkyl is optionally substituted with 1-3 groups independently selected from —OH, halogen, —CN, oxo, —$NR^{11}R^{11}$, $C_{1-4}$ alkoxy, and $C_{1-5}$ alkyl. In some embodiments of a compound of Formula I, or a pharmaceutically acceptable salt thereof, Z is $C_{3-7}$ monocyclic cycloalkyl.

In some embodiments of a compound of Formula I, or a pharmaceutically acceptable salt thereof, Z is cyclobutanyl, cyclopentanyl, or cyclohexanyl, each of which is optionally substituted with 1-2 $R^8$ groups and optionally substituted with 1-3 groups independently selected from —OH, halogen, —CN, oxo, —$NR^{11}R^{11}$, $C_{1-4}$ alkoxy, and $C_{1-5}$ alkyl. In some embodiments of a compound of Formula I, or a pharmaceutically acceptable salt thereof, Z is cyclobutanyl, cyclopentanyl, or cyclohexanyl, each of which is substituted with 1-2 $R^8$ groups and is optionally substituted with 1-3 groups independently selected from —OH, halogen, —CN, oxo, —$NR^{11}R^{11}$, $C_{1-4}$ alkoxy, and $C_{1-5}$ alkyl. In some embodiments of a compound of Formula I, or a pharmaceutically acceptable salt thereof, Z is cyclobutanyl, cyclopentanyl, or cyclohexanyl, each of which is optionally substituted with 1-2 $R^8$ groups. In some embodiments of a compound of Formula I, or a pharmaceutically acceptable salt thereof, Z is cyclobutanyl, cyclopentanyl, or cyclohexanyl, each of which is optionally substituted with 1-3 groups independently selected from —OH, halogen, —CN, oxo, —$NR^{11}R^{11}$, $C_{1-4}$ alkoxy, and $C_{1-5}$ alkyl.

In some embodiments of a compound of Formula I, or a pharmaceutically acceptable salt thereof, Z is $C_{7-10}$ fused bicyclic cycloalkyl, wherein the $C_{7-10}$ fused bicyclic cycloalkyl is optionally substituted with 1-2 $R^8$ groups and is optionally substituted with 1-3 $R^a$ groups. In some embodiments of a compound of Formula I, or a pharmaceutically acceptable salt thereof, Z is $C_{7-10}$ fused bicyclic cycloalkyl, wherein the $C_{7-10}$ fused bicyclic cycloalkyl is substituted with 1-2 $R^8$ groups and is optionally substituted with 1-3 $R^a$ groups. In some embodiments of a compound of Formula I, or a pharmaceutically acceptable salt thereof, Z is $C_{7-10}$ fused bicyclic cycloalkyl, wherein the $C_{7-10}$ fused bicyclic cycloalkyl is substituted with 1-2 $R^8$ groups and is substituted with 1-3 $R^a$ groups. In some embodiments of a compound of Formula I, or a pharmaceutically acceptable salt thereof, Z is $C_{7-10}$ fused bicyclic cycloalkyl, wherein the $C_{7-10}$ fused bicyclic cycloalkyl is substituted with 1-2 $R^8$ groups. In some embodiments of a compound of Formula I, or a pharmaceutically acceptable salt thereof, Z is $C_{7-10}$ fused bicyclic cycloalkyl, wherein the $C_{7-10}$ fused bicyclic cycloalkyl is optionally substituted with 1-3 $R^a$ groups. In some embodiments of a compound of Formula I, or a pharmaceutically acceptable salt thereof, Z is $C_{7-10}$ fused bicyclic cycloalkyl.

In some embodiments of a compound of Formula I, or a pharmaceutically acceptable salt thereof, Z is $C_{5-10}$ bridged bicyclic cycloalkyl, wherein the $C_{5-10}$ bridged bicyclic cycloalkyl is optionally substituted with 1-2 $R^8$ groups and is optionally substituted with 1-3 $R^a$ groups. In some embodiments of a compound of Formula I, or a pharmaceutically acceptable salt thereof, Z is $C_{5-10}$ bridged bicyclic cycloalkyl, wherein the $C_{5-10}$ bridged bicyclic cycloalkyl is substituted with 1-2 $R^8$ groups and is optionally substituted with 1-3 $R^a$ groups. In some embodiments of a compound of Formula I, or a pharmaceutically acceptable salt thereof, Z is $C_{5-10}$ bridged bicyclic cycloalkyl, wherein the $C_{5-10}$ bridged bicyclic cycloalkyl is substituted with 1-2 $R^8$ groups and is substituted with 1-3 $R^a$ groups. In some embodiments of a compound of Formula I, or a pharmaceutically acceptable salt thereof, Z is $C_{5-10}$ bridged bicyclic cycloalkyl, wherein the $C_{5-10}$ bridged bicyclic cycloalkyl is substituted with 1-2 $R^8$ groups. In some embodiments of a compound of Formula I, or a pharmaceutically acceptable salt thereof, Z is $C_{5-10}$ bridged bicyclic cycloalkyl, wherein the $C_{5-10}$ bridged bicyclic cycloalkyl is optionally substituted with 1-3 $R^a$ groups. In some embodiments of a compound of Formula I, or a pharmaceutically acceptable salt thereof, Z is $C_{5-10}$ bridged bicyclic cycloalkyl.

In some embodiments of a compound of Formula I, or a pharmaceutically acceptable salt thereof, Z is 4-7 membered monocyclic heterocyclyl, wherein the 4-7 membered monocyclic heterocyclyl is optionally substituted with 1-2 $R^8$ groups and is optionally substituted with 1-3 $R^a$ groups. In some embodiments of a compound of Formula I, or a pharmaceutically acceptable salt thereof, Z is 4-7 membered monocyclic heterocyclyl, wherein the 4-7 membered monocyclic heterocyclyl is substituted with 1-2 $R^8$ groups and is optionally substituted with 1-3 $R^a$ groups. In some embodiments of a compound of Formula I, or a pharmaceutically acceptable salt thereof, Z is 4-7 membered monocyclic heterocyclyl, wherein the 4-7 membered monocyclic heterocyclyl is substituted with 1-2 $R^8$ groups and is substituted with 1-3 $R^a$ groups. In some embodiments of a compound of Formula I, or a pharmaceutically acceptable salt thereof, Z is 4-7 membered monocyclic heterocyclyl, wherein the 4-7 membered monocyclic heterocyclyl is substituted with 1-2 $R^8$ groups. In some embodiments of a compound of Formula I, or a pharmaceutically acceptable salt thereof, Z is 4-7 membered monocyclic heterocyclyl, wherein the 4-7 membered monocyclic heterocyclyl is optionally substituted with 1-3 $R^a$ groups. In some embodiments of a compound of Formula I, or a pharmaceutically acceptable salt thereof, Z is 4-7 membered monocyclic heterocyclyl.

In some embodiments of a compound of Formula I, or a pharmaceutically acceptable salt thereof, Z is 5-6 membered monocyclic heterocyclyl, wherein the 5-6 membered monocyclic heterocyclyl is optionally substituted with 1-2 $R^8$ groups and is optionally substituted with 1-3 $R^a$ groups. In some embodiments of a compound of Formula I, or a pharmaceutically acceptable salt thereof, Z is 5-6 membered monocyclic heterocyclyl, wherein the 5-6 membered monocyclic heterocyclyl is optionally substituted with 1-2 $R^8$ groups and is optionally substituted with 1-3 groups independently selected from —OH, halogen, —CN, oxo, —NR$^{11}$R$^{11}$, $C_{1-4}$ alkoxy, and $C_{1-5}$ alkyl.

In some embodiments of a compound of Formula I, or a pharmaceutically acceptable salt thereof, Z is 5-6 membered monocyclic heterocyclyl, wherein the 5-6 membered monocyclic heterocyclyl is substituted with 1-2 $R^8$ groups and is optionally substituted with 1-3 $R^a$ groups. In some embodiments of a compound of Formula I, or a pharmaceutically acceptable salt thereof, Z is 5-6 membered monocyclic heterocyclyl, wherein the 5-6 membered monocyclic heterocyclyl is substituted with 1-2 $R^8$ groups and is optionally substituted with 1-3 groups independently selected from —OH, halogen, —CN, oxo, —NR$^{11}$R$^{11}$, $C_{1-4}$ alkoxy, and $C_{1-5}$ alkyl.

In some embodiments of a compound of Formula I, or a pharmaceutically acceptable salt thereof, Z is 5-6 membered monocyclic heterocyclyl, wherein the 5-6 membered monocyclic heterocyclyl is substituted with 1-2 $R^8$ groups and is substituted with 1-3 $R^a$ groups. In some embodiments of a compound of Formula I, or a pharmaceutically acceptable salt thereof, Z is 5-6 membered monocyclic heterocyclyl, wherein the 5-6 membered monocyclic heterocyclyl is substituted with 1-2 $R^8$ groups and is substituted with 1-3 groups independently selected from —OH, halogen, —CN, oxo, —NR$^{11}$R$^{11}$, $C_{1-4}$ alkoxy, and $C_{1-5}$ alkyl.

In some embodiments of a compound of Formula I, or a pharmaceutically acceptable salt thereof, Z is 5-6 membered monocyclic heterocyclyl, wherein the 5-6 membered monocyclic heterocyclyl is substituted with 1-2 $R^8$ groups. In some embodiments of a compound of Formula I, or a pharmaceutically acceptable salt thereof, Z is 5-6 membered monocyclic heterocyclyl, wherein the 5-6 membered monocyclic heterocyclyl is optionally substituted with 1-3 groups independently selected from —OH, halogen, —CN, oxo, —NR$^{11}$R$^{11}$, $C_{1-4}$ alkoxy, and $C_{1-5}$ alkyl. In some embodiments of a compound of Formula I, or a pharmaceutically acceptable salt thereof, Z is 5-6 membered monocyclic heterocyclyl.

In some embodiments of a compound of Formula I, or a pharmaceutically acceptable salt thereof, Z is phenyl, wherein the phenyl is optionally substituted with 1-2 $R^8$ groups and is optionally substituted with 1-3 $R^a$ groups. In some embodiments of a compound of Formula I, or a pharmaceutically acceptable salt thereof, Z is phenyl, wherein the phenyl is optionally substituted with 1-2 $R^8$ groups and is optionally substituted with 1-3 groups independently selected from —OH, halogen, —CN, oxo, —NR$^{11}$R$^{11}$, $C_{1-4}$ alkoxy, and $C_{1-5}$ alkyl.

In some embodiments of a compound of Formula I, or a pharmaceutically acceptable salt thereof, Z is phenyl, wherein the phenyl is substituted with 1-2 $R^8$ groups and is optionally substituted with 1-3 $R^a$ groups. In some embodiments of a compound of Formula I, or a pharmaceutically acceptable salt thereof, Z is phenyl, wherein the phenyl is substituted with 1-2 $R^8$ groups and is optionally substituted with 1-3 groups independently selected from —OH, halogen, —CN, oxo, —NR$^{11}$R$^{11}$, $C_{1-4}$ alkoxy, and $C_{1-5}$ alkyl.

In some embodiments of a compound of Formula I, or a pharmaceutically acceptable salt thereof, Z is phenyl, wherein the phenyl is substituted with 1-2 $R^8$ groups and is substituted with 1-3 $R^a$ groups. In some embodiments of a compound of Formula I, or a pharmaceutically acceptable salt thereof, Z is phenyl, wherein the phenyl is substituted with 1-2 $R^8$ groups and is substituted with 1-3 groups independently selected from —OH, halogen, —CN, oxo, —NR$^{11}$R$^{11}$, $C_{1-4}$ alkoxy, and $C_{1-5}$ alkyl.

In some embodiments of a compound of Formula I, or a pharmaceutically acceptable salt thereof, Z is phenyl, wherein the phenyl is substituted with 1-2 $R^8$ groups. In some embodiments of a compound of Formula I, or a pharmaceutically acceptable salt thereof, Z is phenyl, wherein the phenyl is optionally substituted with 1-3 $R^a$ groups. In some embodiments of a compound of Formula I, or a pharmaceutically acceptable salt thereof, Z is phenyl, wherein the phenyl is optionally substituted with 1-3 groups independently selected from —OH, halogen, —CN, oxo, —$NR^{11}R^{11}$, $C_{1-4}$ alkoxy, and $C_{1-5}$ alkyl. In some embodiments of a compound of Formula I, or a pharmaceutically acceptable salt thereof, Z is phenyl.

In some embodiments of a compound of Formula I, or a pharmaceutically acceptable salt thereof, Z is 5-6 membered monocyclic heteroaryl, wherein the 5-6 membered monocyclic heteroaryl is optionally substituted with 1-2 $R^8$ groups and is optionally substituted with 1-3 $R^a$ groups. In some embodiments of a compound of Formula I, or a pharmaceutically acceptable salt thereof, Z is 5-6 membered monocyclic heteroaryl, wherein the 5-6 membered monocyclic heteroaryl is substituted with 1-2 $R^8$ groups and is optionally substituted with 1-3 $R^a$ groups. In some embodiments of a compound of Formula I, or a pharmaceutically acceptable salt thereof, Z is 5-6 membered monocyclic heteroaryl, wherein the 5-6 membered monocyclic heteroaryl is substituted with 1-2 $R^8$ groups and is substituted with 1-3 $R^a$ groups. In some embodiments of a compound of Formula I, or a pharmaceutically acceptable salt thereof, Z is 5-6 membered monocyclic heteroaryl, wherein the 5-6 membered monocyclic heteroaryl is substituted with 1-2 $R^8$ groups. In some embodiments of a compound of Formula I, or a pharmaceutically acceptable salt thereof, Z is 5-6 membered monocyclic heteroaryl, wherein the 5-6 membered monocyclic heteroaryl is optionally substituted with 1-3 $R^a$ groups. In some embodiments of a compound of Formula I, or a pharmaceutically acceptable salt thereof, Z is 5-6 membered monocyclic heteroaryl.

In some embodiments of a compound of Formula I, or a pharmaceutically acceptable salt thereof, Z is 5-6 membered monocyclic heteroaryl, wherein the 5-6 membered monocyclic heteroaryl is optionally substituted with 1-2 $R^8$ groups and is optionally substituted with 1-3 groups independently selected from —OH, halogen, —CN, oxo, —$NR^{11}R^{11}$, $C_{1-4}$ alkoxy, and $C_{1-5}$ alkyl.

In some embodiments of a compound of Formula I, or a pharmaceutically acceptable salt thereof, Z is 5-6 membered monocyclic heteroaryl, wherein the 5-6 membered monocyclic heteroaryl is substituted with 1-2 $R^8$ groups and is optionally substituted with 1-3 groups independently selected from —OH, halogen, —CN, oxo, —$NR^{11}R^{11}$, $C_{1-4}$ alkoxy, and $C_{1-5}$ alkyl.

In some embodiments of a compound of Formula I, or a pharmaceutically acceptable salt thereof, Z is 5-6 membered monocyclic heteroaryl, wherein the 5-6 membered monocyclic heteroaryl is substituted with 1-2 $R^8$ groups and is substituted with 1-3 groups independently selected from —OH, halogen, —CN, oxo, —$NR^{11}R^{11}$, $C_{1-4}$ alkoxy, and $C_{1-5}$ alkyl.

In some embodiments of a compound of Formula I, or a pharmaceutically acceptable salt thereof, Z is 5-6 membered monocyclic heteroaryl, wherein the 5-6 membered monocyclic heteroaryl is optionally substituted with 1-3 groups independently selected from —OH, halogen, —CN, oxo, —$NR^{11}R^{11}$, $C_{1-4}$ alkoxy, and $C_{1-5}$ alkyl.

In some embodiments of a compound of Formula I, or a pharmaceutically acceptable salt thereof, Z is 8-10 membered fused bicyclic heterocyclyl, wherein the 8-10 membered fused bicyclic heterocyclyl is optionally substituted with 1-2 $R^8$ groups and is optionally substituted with 1-3 $R^a$ groups. In some embodiments of a compound of Formula I, or a pharmaceutically acceptable salt thereof, Z is 8-10 membered fused bicyclic heterocyclyl, wherein the 8-10 membered fused bicyclic heterocyclyl is optionally substituted with 1-2 $R^8$ groups and is optionally substituted with 1-3 groups independently selected from —OH, halogen, —CN, oxo, —$NR^{11}R^{11}$, $C_{1-4}$ alkoxy, and $C_{1-5}$ alkyl.

In some embodiments of a compound of Formula I, or a pharmaceutically acceptable salt thereof, Z is 8-10 membered fused bicyclic heterocyclyl, wherein the 8-10 membered fused bicyclic heterocyclyl is substituted with 1-2 $R^8$ groups and is optionally substituted with 1-3 $R^a$ groups. In some embodiments of a compound of Formula I, or a pharmaceutically acceptable salt thereof, Z is 8-10 membered fused bicyclic heterocyclyl, wherein the 8-10 membered fused bicyclic heterocyclyl is substituted with 1-2 $R^8$ groups and is optionally substituted with 1-3 groups independently selected from —OH, halogen, —CN, oxo, —$NR^{11}R^{11}$, $C_{1-4}$ alkoxy, and $C_{1-5}$ alkyl.

In some embodiments of a compound of Formula I, or a pharmaceutically acceptable salt thereof, Z is 8-10 membered fused bicyclic heterocyclyl, wherein the 8-10 membered fused bicyclic heterocyclyl is substituted with 1-2 $R^8$ groups and is substituted with 1-3 $R^a$ groups. In some embodiments of a compound of Formula I, or a pharmaceutically acceptable salt thereof, Z is 8-10 membered fused bicyclic heterocyclyl, wherein the 8-10 membered fused bicyclic heterocyclyl is substituted with 1-2 $R^8$ groups and is substituted with 1-3 groups independently selected from —OH, halogen, —CN, oxo, —$NR^{11}R^{11}$, $C_{1-4}$ alkoxy, and $C_{1-5}$ alkyl.

In some embodiments of a compound of Formula I, or a pharmaceutically acceptable salt thereof, Z is 8-10 membered fused bicyclic heterocyclyl, wherein the 8-10 membered fused bicyclic heterocyclyl is substituted with 1-2 $R^8$ groups. In some embodiments of a compound of Formula I, or a pharmaceutically acceptable salt thereof, Z is 8-10 membered fused bicyclic heterocyclyl, wherein the 8-10 membered fused bicyclic heterocyclyl is optionally substituted with 1-3 groups independently selected from —OH, halogen, —CN, oxo, —$NR^{11}R^{11}$, $C_{1-4}$ alkoxy, and $C_{1-5}$ alkyl. In some embodiments of a compound of Formula I, or a pharmaceutically acceptable salt thereof, Z is 8-10 membered fused bicyclic heterocyclyl.

In some embodiments of a compound of Formula I, or a pharmaceutically acceptable salt thereof, Z is 6-10 membered bridged bicyclic heterocyclyl, wherein the 6-10 membered bridged bicyclic heterocyclyl is optionally substituted with 1-2 $R^8$ groups and is optionally substituted with 1-3 $R^a$ groups. In some embodiments of a compound of Formula I, or a pharmaceutically acceptable salt thereof, Z is 6-10 membered bridged bicyclic heterocyclyl, wherein the 6-10 membered bridged bicyclic heterocyclyl is optionally substituted with 1-2 $R^8$ groups and is optionally substituted with 1-3 groups independently selected from —OH, halogen, —CN, oxo, —$NR^{11}R^{11}$, $C_{1-4}$ alkoxy, and $C_{1-5}$ alkyl.

In some embodiments of a compound of Formula I, or a pharmaceutically acceptable salt thereof, Z is 6-10 membered bridged bicyclic heterocyclyl, wherein the 6-10 membered bridged bicyclic heterocyclyl is substituted with 1-2 $R^8$ groups and is optionally substituted with 1-3 $R^a$ groups. In some embodiments of a compound of Formula I, or a pharmaceutically acceptable salt thereof, Z is 6-10 membered bridged bicyclic heterocyclyl, wherein the 6-10 membered bridged bicyclic heterocyclyl is substituted with 1-2 $R^8$ groups and is optionally substituted with 1-3 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, Z is 6-10 membered bridged bicyclic heterocyclyl, wherein the 6-10 membered bridged bicyclic heterocyclyl is substituted with 1-2 $R^8$ groups and is substituted with 1-3 $R^a$ groups. In some embodiments of a compound of Formula I, or a pharmaceutically acceptable salt thereof, Z is 6-10 membered bridged bicyclic heterocyclyl, wherein the 6-10 membered bridged bicyclic heterocyclyl is substituted with 1-2 $R^8$ groups and is substituted with 1-3 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, Z is 6-10 membered bridged bicyclic heterocyclyl, wherein the 6-10 membered bridged bicyclic heterocyclyl is substituted with 1-2 $R^8$ groups. In some embodiments of a compound of Formula I, or a pharmaceutically acceptable salt thereof, Z is 6-10 membered bridged bicyclic heterocyclyl, wherein the 6-10 membered bridged bicyclic heterocyclyl is optionally substituted with 1-3 groups independently selected from —OH, halogen, —CN, oxo, —NR$^{11}$R$^{11}$, C$_{1-4}$ alkoxy, and C$_{1-5}$ alkyl. In some embodiments of a compound of Formula I, or a pharmaceutically acceptable salt thereof, Z is 6-10 membered bridged bicyclic heterocyclyl.

In some embodiments of a compound of Formula I, or a pharmaceutically acceptable salt thereof, Z is 8-10 membered fused bicyclic heteroaryl, wherein the 8-10 membered fused bicyclic heteroaryl is optionally substituted with 1-2 $R^8$ groups and is optionally substituted with 1-3 $R^a$ groups. In some embodiments of a compound of Formula I, or a pharmaceutically acceptable salt thereof, Z is 8-10 membered fused bicyclic heteroaryl, wherein the 8-10 membered fused bicyclic heteroaryl is optionally substituted with 1-2 $R^8$ groups and is optionally substituted with 1-3 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, Z is 8-10 membered fused bicyclic heteroaryl, wherein the 8-10 membered fused bicyclic heteroaryl is substituted with 1-2 $R^8$ groups and is optionally substituted with 1-3 $R^a$ groups. In some embodiments of a compound of Formula I, or a pharmaceutically acceptable salt thereof, Z is 8-10 membered fused bicyclic heteroaryl, wherein the 8-10 membered fused bicyclic heteroaryl is substituted with 1-2 $R^8$ groups and is optionally substituted with 1-3 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, Z is 8-10 membered fused bicyclic heteroaryl, wherein the 8-10 membered fused bicyclic heteroaryl is substituted with 1-2 $R^8$ groups and is substituted with 1-3 $R^a$ groups. In some embodiments of a compound of Formula I, or a pharmaceutically acceptable salt thereof, Z is 8-10 membered fused bicyclic heteroaryl, wherein the 8-10 membered fused bicyclic heteroaryl is substituted with 1-2 $R^8$ groups and is substituted with 1-3 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, Z is 8-10 membered fused bicyclic heteroaryl, wherein the 8-10 membered fused bicyclic heteroaryl is substituted with 1-2 $R^8$ groups. In some embodiments of a compound of Formula I, or a pharmaceutically acceptable salt thereof, Z is 8-10 membered fused bicyclic heteroaryl, wherein the 8-10 membered fused bicyclic heteroaryl is optionally substituted with 1-3 $R^a$ groups. In some embodiments of a compound of Formula I, or a pharmaceutically acceptable salt thereof, Z is 8-10 membered fused bicyclic heteroaryl, wherein the 8-10 membered fused bicyclic heteroaryl is optionally substituted with 1-3 groups independently selected from —OH, halogen, —CN, oxo, —NR$^{11}$R$^{11}$, C$_{1-4}$ alkoxy, and C$_{1-5}$ alkyl. In some embodiments of a compound of Formula I, or a pharmaceutically acceptable salt thereof, Z is 8-10 membered fused bicyclic heteroaryl.

In some embodiments of a compound of Formula I, or a pharmaceutically acceptable salt thereof, Z is 7-10 membered spirocyclic heterocyclyl, wherein the 7-10 membered spirocyclic heterocyclyl is optionally substituted with 1-2 $R^8$ groups and is optionally substituted with 1-3 $R^a$ groups. In some embodiments of a compound of Formula I, or a pharmaceutically acceptable salt thereof, Z is 7-10 membered spirocyclic heterocyclyl, wherein the 7-10 membered spirocyclic heterocyclyl is optionally substituted with 1-2 $R^8$ groups and is optionally substituted with 1-3 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, Z is 7-10 membered spirocyclic heterocyclyl, wherein the 7-10 membered spirocyclic heterocyclyl is substituted with 1-2 $R^8$ groups and is optionally substituted with 1-3 $R^a$ groups. In some embodiments of a compound of Formula I, or a pharmaceutically acceptable salt thereof, Z is 7-10 membered spirocyclic heterocyclyl, wherein the 7-10 membered spirocyclic heterocyclyl is substituted with 1-2 $R^8$ groups and is optionally substituted with 1-3 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, Z is 7-10 membered spirocyclic heterocyclyl, wherein the 7-10 membered spirocyclic heterocyclyl is substituted with 1-2 $R^8$ groups and is substituted with 1-3 $R^a$ groups. In some embodiments of a compound of Formula I, or a pharmaceutically acceptable salt thereof, Z is 7-10 membered spirocyclic heterocyclyl, wherein the 7-10 membered spirocyclic heterocyclyl is substituted with 1-2 $R^8$ groups and is substituted with 1-3 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, Z is 7-10 membered spirocyclic heterocyclyl, wherein the 7-10 membered spirocyclic heterocyclyl is substituted with 1-2 $R^8$ groups. In some embodiments of a compound of Formula I, or a pharmaceutically acceptable salt thereof, Z is 7-10 membered spirocyclic heterocyclyl, wherein the 7-10 membered spirocyclic heterocyclyl is optionally substituted with 1-3 groups independently selected from —OH, halogen, —CN, oxo, —NR$^{11}$R$^{11}$, C$_{1-4}$ alkoxy, and C$_{1-5}$ alkyl. In some embodiments of a compound of Formula I, or a pharmaceutically acceptable salt thereof, Z is 7-10 membered spirocyclic heterocyclyl.

In some embodiments of a compound of Formula I, or a pharmaceutically acceptable salt thereof, Z is 4-7 membered monocyclic heterocyclyl, wherein the 4-7 membered monocyclic heterocyclyl is optionally substituted with one $R^8$ group and optionally substituted with 1-3 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, Z is 4-7 membered monocyclic heterocyclyl,
wherein the 4-7 membered monocyclic heterocyclyl is optionally substituted with one R$^8$ group and optionally substituted with 1-3 groups independently selected from —OH, halogen, —CN, oxo, —NR$^{11}$R$^{11}$, C$_{1-4}$ alkoxy, and C$_{1-5}$ alkyl, and
wherein the 4-7 membered monocyclic heterocyclyl has one or two ring heteroatoms that is N.

In some embodiments of a compound of Formula I, or a pharmaceutically acceptable salt thereof, Z is 5-6 membered monocyclic heterocyclyl,
wherein the 5-6 membered monocyclic heterocyclyl is optionally substituted with one R$^8$ groups and is optionally substituted with 1-2 groups independently selected from —OH, halogen, —CN, oxo, —NR$^{11}$R$^{11}$, C$_{1-4}$ alkoxy, and C$_{1-5}$ alkyl, and
wherein the 5-6 membered monocyclic heterocyclyl has one or two ring heteroatoms that is N.

In some embodiments of a compound of Formula I, or a pharmaceutically acceptable salt thereof, Z is piperidinyl, wherein the piperidinyl is optionally substituted with one R$^8$ group.

In some embodiments of a compound of Formula I, or a pharmaceutically acceptable salt thereof, Z is phenyl or 5-6 membered monocyclic heteroaryl, each of which is optionally substituted with one R$^8$ group and is optionally substituted with 1-2 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, Z is phenyl optionally substituted with one R$^8$ group.

In some embodiments of a compound of Formula I, or a pharmaceutically acceptable salt thereof, Z is 5-6 membered monocyclic heteroaryl, wherein the 5-6 membered monocyclic heteroaryl is optionally substituted with one R$^8$ group and has one, two, or three ring heteroatoms that is N.

In some embodiments of a compound of Formula I, or a pharmaceutically acceptable salt thereof, Z is pyridinyl or

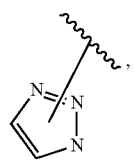

each of which is optionally substituted with one R$^8$ group.

In some embodiments of a compound of Formula I, or a pharmaceutically acceptable salt thereof, Z is 8-10 membered fused bicyclic heterocyclyl optionally substituted with one R$^8$ groups and is optionally substituted with 1-2 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, Z is 8-10 membered fused bicyclic heterocyclyl,
wherein the 8-10 membered fused bicyclic heterocyclyl is optionally substituted with one R$^8$ groups and is optionally substituted with 1-2 groups independently selected from —OH, halogen, —CN, oxo, —NR$^{11}$R$^{11}$, C$_{1-4}$ alkoxy, and C$_{1-5}$ alkyl, and
wherein the 8-10 membered fused bicyclic heterocyclyl has one or two ring heteroatoms that is N.

In some embodiments of a compound of Formula I, or a pharmaceutically acceptable salt thereof, Z is

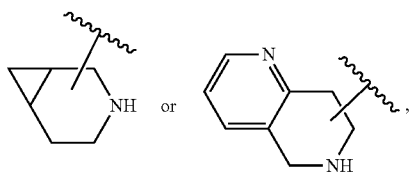

each of which is optionally substituted with one R$^8$ group.

In some embodiments of a compound of Formula I, or a pharmaceutically acceptable salt thereof, Z is 6-10 membered bridged bicyclic heterocyclyl optionally substituted with one R$^8$ groups and optionally substituted with 1-2 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, Z is 6-10 membered bridged bicyclic heterocyclyl,
wherein the 6-10 membered bridged bicyclic heterocyclyl is optionally substituted with one R$^8$ groups and is optionally substituted with 1-2 groups independently selected from —OH, halogen, —CN, oxo, —NR$^{11}$R$^{11}$, C$_{1-4}$ alkoxy, and C$_{1-5}$ alkyl, and
wherein the 6-10 membered bridged bicyclic heterocyclyl has one or two ring heteroatoms that is N.

In some embodiments of a compound of Formula I, or a pharmaceutically acceptable salt thereof, Z is

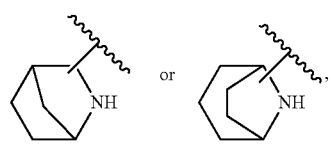

each of which is optionally substituted with one R$^8$ group.

In some embodiments of a compound of Formula I, or a pharmaceutically acceptable salt thereof, Z is 7-10 membered spirocyclic heterocyclyl optionally substituted with one R$^8$ group and optionally substituted with 1-2 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, Z is 7-10 membered spirocyclic heterocyclyl,
wherein the 7-10 membered spirocyclic heterocyclyl is optionally substituted with one R$^8$ groups and is optionally substituted with 1-2 groups independently selected from —OH, halogen, —CN, oxo, —NR$^{11}$R$^{11}$, C$_{1-4}$ alkoxy, and C$_{1-5}$ alkyl, and
wherein the 7-10 membered spirocyclic heterocyclyl has one or two ring heteroatoms that is N.

In some embodiments of a compound of Formula I, or a pharmaceutically acceptable salt thereof, Z is

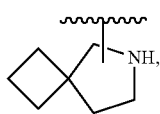

which is optionally substituted with one $R^8$ group.

In some embodiments of a compound of Formula I, or a pharmaceutically acceptable salt thereof, Z is

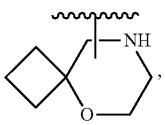

which is optionally substituted with one $R^8$ group.

In some embodiments of a compound of Formula I, or a pharmaceutically acceptable salt thereof, Z substituted with one $R^8$ group is

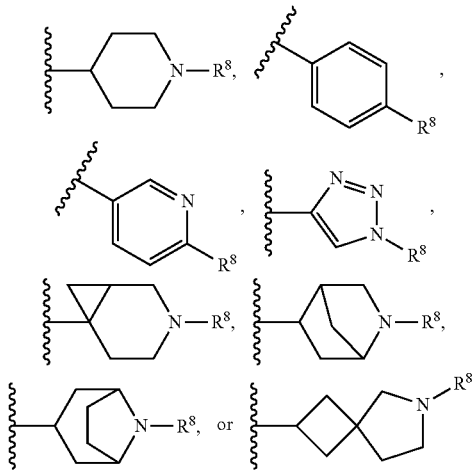

In some embodiments of a compound of Formula I, or a pharmaceutically acceptable salt thereof, each $R^8$ independently is halogen, —C(O)$R^9$, —N$R^{10}R^{10}$, $C_{1-6}$ alkyl, $C_{3-7}$ monocyclic cycloalkyl, $C_{7-10}$ fused bicyclic cycloalkyl, $C_{5-10}$ bridged bicyclic cycloalkyl, 4-7 membered monocyclic heterocyclyl, phenyl, 5-6 membered monocyclic heteroaryl, 8-10 membered fused bicyclic heterocyclyl, 6-10 membered bridged bicyclic heterocyclyl, 8-10 membered fused bicyclic heteroaryl, 7-10 membered spirocyclic heterocyclyl, —O$R^5$, —C(O)N($R^5$)($R^5$), —N($R^5$)$_2$($R^5$)$^+$, —N($R^5$)C(O)$R^5$, —N($R^5$)C(O)O$R^5$, —N($R^5$)C(O)N($R^5$)($R^5$), —N$R^5$S(O)$_2$($R^{5a}$), —N$R^5$S(O)$_2$N($R^5$)($R^5$), —N$R^5$S(O)$_2$O($R^{5a}$), —OC(O)N($R^5$)($R^5$), —S(O)$R^{5a}$, —S(O)(NH)$R^5$, —S(O)$_2R^{5a}$, —S(O)$_2$N($R^5$)($R^5$), or —N=S($R^{5a}$)($R^{5a}$)=O, wherein the $C_{1-6}$ alkyl is optionally substituted with 1-4 $R^b$ groups, wherein the $C_{3-7}$ monocyclic cycloalkyl, $C_{7-10}$ fused bicyclic cycloalkyl, $C_{5-10}$ bridged bicyclic cycloalkyl, 4-7 membered monocyclic heterocyclyl, phenyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-4 $R^a$ groups.

In some embodiments of a compound of Formula I, or a pharmaceutically acceptable salt thereof, each $R^8$ independently is —C(O)$R^9$, $C_{1-6}$ alkyl, 4-7 membered monocyclic heterocyclyl, or —S(O)$_2R^{5a}$, wherein the $C_{1-6}$ alkyl is optionally substituted with 1-4 $R^b$ groups, and wherein the 4-7 membered monocyclic heterocyclyl is optionally substituted with 1-4 $R^a$ groups.

In some embodiments of a compound of Formula I, or a pharmaceutically acceptable salt thereof, each $R^8$ independently is —C(O)$R^9$, $C_{1-6}$ alkyl, 4-7 membered monocyclic heterocyclyl, or —S(O)$_2R^{5a}$, wherein the $C_{1-6}$ alkyl is optionally substituted with 1-3 groups independently selected from —OH, halogen, —CN, oxo, —N$R^{11}R^{11}$, —C(O)N$R^{11}R^{11}$, $C_{1-4}$ alkoxy, and $R^{8a}$, and wherein the 4-7 membered monocyclic heterocyclyl is optionally substituted with 1-3 groups independently selected from —OH, halogen, —CN, oxo, —N$R^{11}R^{11}$, $C_{1-4}$ alkoxy, and $C_{1-5}$ alkyl.

In some embodiments of a compound of Formula I, or a pharmaceutically acceptable salt thereof, one or both $R^8$ is halogen. In some embodiments of a compound of Formula I, or a pharmaceutically acceptable salt thereof, one or both $R^8$ is —O$R^5$. In some embodiments of a compound of Formula I, or a pharmaceutically acceptable salt thereof, one or both $R^B$ is —C(O)N($R^5$)($R^5$). In some embodiments of a compound of Formula I, or a pharmaceutically acceptable salt thereof, one or both $R^8$ is —N($R^5$)$_2$($R^5$)$^+$. In some embodiments of a compound of Formula I, or a pharmaceutically acceptable salt thereof, one or both $R^8$ is —N($R^5$)C(O)$R^5$. In some embodiments of a compound of Formula I, or a pharmaceutically acceptable salt thereof, one or both $R^8$ is —N($R^5$)C(O)O$R^5$. In some embodiments of a compound of Formula I, or a pharmaceutically acceptable salt thereof, one or both $R^8$ is —N($R^5$)C(O)N($R^5$)($R^5$). In some embodiments of a compound of Formula I, or a pharmaceutically acceptable salt thereof, one or both $R^8$ is —N($R^5$)S(O)$_2$($R^{5a}$). In some embodiments of a compound of Formula I, or a pharmaceutically acceptable salt thereof, one or both $R^B$ is —N$R^5$S(O)$_2$N($R^5$)($R^5$). In some embodiments of a compound of Formula I, or a pharmaceutically acceptable salt thereof, one or both $R^8$ is —N$R^5$S(O)$_2$O($R^{5a}$). In some embodiments of a compound of Formula I, or a pharmaceutically acceptable salt thereof, one or both $R^8$ is —OC(O)N($R^5$)($R^5$). In some embodiments of a compound of Formula I, or a pharmaceutically acceptable salt thereof, one or both $R^8$ is —S(O)$R^{5a}$. In some embodiments of a compound of Formula I, or a pharmaceutically acceptable salt thereof, one or both $R^8$ is —S(O)(NH)$R^5$. In some embodiments of a compound of Formula I, or a pharmaceutically acceptable salt thereof, one or both $R^8$ is —S(O)$_2$N($R^5$)($R^5$). In some embodiments of a compound of Formula I, or a pharmaceutically acceptable salt thereof, one or both $R^8$ is —N=S($R^{5a}$)($R^{5a}$)=O.

In some embodiments of a compound of Formula I, or a pharmaceutically acceptable salt thereof, one or both $R^8$ is $C_{1-6}$ alkyl, wherein the $C_{1-6}$ alkyl is optionally substituted with 1-4 $R^b$ groups. In some embodiments of a compound of Formula I, or a pharmaceutically acceptable salt thereof, one or both $R^8$ is $C_{1-6}$ alkyl, wherein the $C_{1-6}$ alkyl is optionally substituted with 1-3 $R^b$ groups. In some embodiments of a compound of Formula I, or a pharmaceutically acceptable salt thereof, one or both $R^8$ is $C_{1-6}$ alkyl, wherein the $C_{1-6}$ alkyl is optionally substituted with 1-3 groups independently selected from —OH, halogen, —CN, oxo, —N$R^{11}R^{11}$, —C(O)N($R^{11}$)($R^{11}$), $C_{1-4}$ alkoxy, and $R^{8a}$. In some embodiments of a compound of Formula I, or a pharmaceutically acceptable salt thereof, one or both $R^8$ is $C_{1-3}$ alkyl, wherein the $C_{1-3}$ alkyl is optionally substituted with 1-3 groups independently selected from —OH, halogen, —CN, oxo, —NR$^{11}$R$^{11}$, —C(O)N(R$^{11}$)(R$^{11}$), $C_{1-4}$ alkoxy, and R$^{8a}$. In some embodiments of a compound of Formula I, or a pharmaceutically acceptable salt thereof, one or both $R^8$ is $C_{1-3}$ alkyl, wherein the $C_{1-3}$ alkyl is optionally substituted with 1-2 groups independently selected from oxo, —NR$^{11}$R$^{11}$, —C(O)N(R$^{11}$)(R$^{11}$), and R$^{8a}$. In some embodiments of a compound of Formula I, or a pharmaceutically acceptable salt thereof, one or both $R^8$ is $C_{1-6}$ alkyl, wherein the $C_{1-6}$ alkyl is substituted with 1-4 R$^b$ groups. In some embodiments of a compound of Formula I, or a pharmaceutically acceptable salt thereof, one or both $R^8$ is $C_{1-6}$ alkyl, wherein the $C_{1-6}$ alkyl is substituted with 1-3 R$^b$ groups. In some embodiments of a compound of Formula I, or a pharmaceutically acceptable salt thereof, one or both $R^8$ is $C_{1-6}$ alkyl, wherein the $C_{1-6}$ alkyl is substituted with 1-3 groups independently selected from —OH, halogen, —CN, oxo, —NR$^{11}$R$^{11}$, —C(O)N(R$^{11}$)(R$^{11}$), $C_{1-4}$ alkoxy, and R$^{8a}$. In some embodiments of a compound of Formula I, or a pharmaceutically acceptable salt thereof, one or both $R^8$ is $C_{1-6}$ alkyl, wherein the $C_{1-6}$ alkyl is substituted with 1-3 groups independently selected from —OH, oxo, —NH$_2$, —N(CH$_3$)$_2$, —C(O)NH$_2$, —C(O)N(CH$_3$)$_2$, and R$^{8a}$. In some embodiments of a compound of Formula I, or a pharmaceutically acceptable salt thereof, one or both $R^8$ is $C_{1-6}$ alkyl, wherein the $C_{1-6}$ alkyl is substituted with 1-3 groups independently selected from —OH, oxo, —N(CH$_3$)$_2$, —C(O)NH$_2$, and R$^{8a}$. In some embodiments of a compound of Formula I, or a pharmaceutically acceptable salt thereof, one or both $R^8$ is $C_{1-3}$ alkyl, wherein the $C_{1-3}$ alkyl is substituted with 1-3 groups independently selected from —OH, halogen, —CN, oxo, —NR$^{11}$R$^{11}$, —C(O)N(R$^{11}$)(R$^{11}$), $C_{1-4}$ alkoxy, and R$^{8a}$. In some embodiments of a compound of Formula I, or a pharmaceutically acceptable salt thereof, one or both $R^8$ is $C_{1-3}$ alkyl, wherein the $C_{1-3}$ alkyl is substituted with 1-2 groups independently selected from oxo, —NR$^{11}$R$^{11}$, —C(O)N(R$^{11}$)(R$^{11}$), and R$^{8a}$. In some embodiments of a compound of Formula I, or a pharmaceutically acceptable salt thereof, one or both $R^8$ is $C_{1-6}$ alkyl. In some embodiments of a compound of Formula I, or a pharmaceutically acceptable salt thereof, one or both $R^8$ is $C_{1-3}$ alkyl.

In some embodiments of a compound of Formula I, or a pharmaceutically acceptable salt thereof, one or both $R^8$ is $C_{1-6}$ alkyl, wherein the $C_{1-6}$ alkyl is substituted with 1-3 groups independently selected from —OH, oxo, —N(CH$_3$)$_2$, —C(O)NH$_2$, —C(O)NHCH$_3$, and R$^{8a}$. In some embodiments of a compound of Formula I, or a pharmaceutically acceptable salt thereof, $R^8$ is $C_{1-6}$ alkyl, wherein the $C_{1-6}$ alkyl is substituted with 1-3 groups independently selected from —OH, oxo, —N(CH$_3$)$_2$, —C(O)NH$_2$, —C(O)NHCH$_3$, and R$^{8a}$.

In some embodiments of a compound of Formula I, or a pharmaceutically acceptable salt thereof, one or both $R^8$ is $C_{3-7}$ monocyclic cycloalkyl, wherein the $C_{3-7}$ monocyclic cycloalkyl is optionally substituted with 1-4 R$^a$ groups. In some embodiments of a compound of Formula I, or a pharmaceutically acceptable salt thereof, one or both $R^8$ is $C_{3-7}$ monocyclic cycloalkyl, wherein the $C_{3-7}$ monocyclic cycloalkyl is substituted with 1-4 R$^a$ groups. In some embodiments of a compound of Formula I, or a pharmaceutically acceptable salt thereof, one or both $R^8$ is $C_{3-7}$ monocyclic cycloalkyl.

In some embodiments of a compound of Formula I, or a pharmaceutically acceptable salt thereof, one or both $R^8$ is $C_{7-10}$ fused bicyclic cycloalkyl, wherein the $C_{7-10}$ fused bicyclic cycloalkyl is optionally substituted with 1-4 R$^a$ groups. In some embodiments of a compound of Formula I, or a pharmaceutically acceptable salt thereof, one or both $R^8$ is $C_{7-10}$ fused bicyclic cycloalkyl, wherein the $C_{7-10}$ fused bicyclic cycloalkyl is substituted with 1-4 R$^a$ groups. In some embodiments of a compound of Formula I, or a pharmaceutically acceptable salt thereof, one or both $R^8$ is $C_{7-10}$ fused bicyclic cycloalkyl.

In some embodiments of a compound of Formula I, or a pharmaceutically acceptable salt thereof, one or both $R^8$ is $C_{5-10}$ bridged bicyclic cycloalkyl, wherein the $C_{5-10}$ bridged bicyclic cycloalkyl is optionally substituted with 1-4 R$^a$ groups. In some embodiments of a compound of Formula I, or a pharmaceutically acceptable salt thereof, one or both $R^8$ is $C_{5-10}$ bridged bicyclic cycloalkyl, wherein the $C_{5-10}$ bridged bicyclic cycloalkyl is substituted with 1-4 R$^a$ groups. In some embodiments of a compound of Formula I, or a pharmaceutically acceptable salt thereof, one or both $R^8$ is $C_{5-10}$ bridged bicyclic cycloalkyl.

In some embodiments of a compound of Formula I, or a pharmaceutically acceptable salt thereof, one or both $R^8$ is 4-7 membered monocyclic heterocyclyl, wherein the 4-7 membered monocyclic heterocyclyl is optionally substituted with 1-4 R$^a$ groups. In some embodiments of a compound of Formula I, or a pharmaceutically acceptable salt thereof, one or both $R^8$ is 4-7 membered monocyclic heterocyclyl, wherein the 4-7 membered monocyclic heterocyclyl is optionally substituted with 1-3 R$^a$ groups. In some embodiments of a compound of Formula I, or a pharmaceutically acceptable salt thereof, one or both $R^8$ is 4-7 membered monocyclic heterocyclyl, wherein the 4-7 membered monocyclic heterocyclyl is optionally substituted with 1-3 groups independently selected from —OH, halogen, —CN, oxo, —NR$^{11}$R$^{11}$, $C_{1-4}$ alkoxy, and $C_{1-5}$ alkyl.

In some embodiments of a compound of Formula I, or a pharmaceutically acceptable salt thereof, one or both $R^8$ is 4-7 membered monocyclic heterocyclyl, wherein the 4-7 membered monocyclic heterocyclyl is substituted with 1-4 R$^a$ groups. In some embodiments of a compound of Formula I, or a pharmaceutically acceptable salt thereof, one or both $R^8$ is 4-7 membered monocyclic heterocyclyl, wherein the 4-7 membered monocyclic heterocyclyl is substituted with 1-3 R$^a$ groups. In some embodiments of a compound of Formula I, or a pharmaceutically acceptable salt thereof, one or both $R^8$ is 4-7 membered monocyclic heterocyclyl, wherein the 4-7 membered monocyclic heterocyclyl is substituted with 1-3 groups independently selected from —OH, halogen, —CN, oxo, —NR$^{11}$R$^{11}$, $C_{1-4}$ alkoxy, and $C_{1-5}$ alkyl.

In some embodiments of a compound of Formula I, or a pharmaceutically acceptable salt thereof, one or both $R^8$ is 4-7 membered monocyclic heterocyclyl.

In some embodiments of a compound of Formula I, or a pharmaceutically acceptable salt thereof, one or both $R^8$ is 5-6 membered monocyclic heterocyclyl, wherein the 5-6 membered monocyclic heterocyclyl is optionally substituted with 1-4 R$^a$ groups. In some embodiments of a compound of Formula I, or a pharmaceutically acceptable salt thereof, one or both $R^8$ is 5-6 membered monocyclic heterocyclyl, wherein the 5-6 membered monocyclic heterocyclyl is optionally substituted with 1-3 R$^a$ groups. In some embodiments of a compound of Formula I, or a pharmaceutically acceptable salt thereof, one or both $R^8$ is 5-6 membered monocyclic heterocyclyl, wherein the 5-6 membered monocyclic heterocyclyl is optionally substituted with 1-3 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, one or both R$^8$ is 5-6 membered monocyclic heterocyclyl, wherein the 5-6 membered monocyclic heterocyclyl is substituted with 1-4 R$^a$ groups. In some embodiments of a compound of Formula I, or a pharmaceutically acceptable salt thereof, one or both R$^8$ is 5-6 membered monocyclic heterocyclyl, wherein the 5-6 membered monocyclic heterocyclyl is substituted with 1-3 R$^a$ groups. In some embodiments of a compound of Formula I, or a pharmaceutically acceptable salt thereof, one or both R$^8$ is 5-6 membered monocyclic heterocyclyl, wherein the 5-6 membered monocyclic heterocyclyl is substituted with 1-3 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, one or both R$^8$ is 5-6 membered monocyclic heterocyclyl.

In some embodiments of a compound of Formula I, or a pharmaceutically acceptable salt thereof, one or both R$^8$ is phenyl, wherein the phenyl is optionally substituted with 1-4 R$^a$ groups. In some embodiments of a compound of Formula I, or a pharmaceutically acceptable salt thereof, one or both R$^8$ is phenyl, wherein the phenyl is substituted with 1-4 R$^a$ groups. In some embodiments of a compound of Formula I, or a pharmaceutically acceptable salt thereof, one or both R$^8$ is phenyl.

In some embodiments of a compound of Formula I, or a pharmaceutically acceptable salt thereof, one or both R$^8$ is 5-6 membered monocyclic heteroaryl, wherein the 5-6 membered monocyclic heteroaryl is optionally substituted with 1-4 R$^a$ groups. In some embodiments of a compound of Formula I, or a pharmaceutically acceptable salt thereof, one or both R$^8$ is 5-6 membered monocyclic heteroaryl, wherein the 5-6 membered monocyclic heteroaryl is substituted with 1-4 R$^a$ groups. In some embodiments of a compound of Formula I, or a pharmaceutically acceptable salt thereof, one or both R$^8$ is 5-6 membered monocyclic heteroaryl.

In some embodiments of a compound of Formula I, or a pharmaceutically acceptable salt thereof, one or both R$^8$ is 8-10 membered fused bicyclic heterocyclyl, wherein the 8-10 membered fused bicyclic heterocyclyl is optionally substituted with 1-4 R$^a$ groups. In some embodiments of a compound of Formula I, or a pharmaceutically acceptable salt thereof, one or both R$^8$ is 8-10 membered fused bicyclic heterocyclyl, wherein the 8-10 membered fused bicyclic heterocyclyl is optionally substituted with 1-3 R$^a$ groups. In some embodiments of a compound of Formula I, or a pharmaceutically acceptable salt thereof, one or both R$^8$ is 8-10 membered fused bicyclic heterocyclyl, wherein the 8-10 membered fused bicyclic heterocyclyl is optionally substituted with 1-3 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, one or both R$^8$ is 8-10 membered fused bicyclic heterocyclyl, wherein the 8-10 membered fused bicyclic heterocyclyl is substituted with 1-4 R$^a$ groups. In some embodiments of a compound of Formula I, or a pharmaceutically acceptable salt thereof, one or both R$^8$ is 8-10 membered fused bicyclic heterocyclyl, wherein the 8-10 membered fused bicyclic heterocyclyl is substituted with 1-3 R$^a$ groups. In some embodiments of a compound of Formula I, or a pharmaceutically acceptable salt thereof, one or both R$^8$ is 8-10 membered fused bicyclic heterocyclyl, wherein the 8-10 membered fused bicyclic heterocyclyl is substituted with 1-3 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, one or both R$^8$ is 8-10 membered fused bicyclic heterocyclyl.

In some embodiments of a compound of Formula I, or a pharmaceutically acceptable salt thereof, one or both R$^8$ is 6-10 membered bridged bicyclic heterocyclyl, wherein the 6-10 membered bridged bicyclic heterocyclyl is optionally substituted with 1-4 R$^a$ groups. In some embodiments of a compound of Formula I, or a pharmaceutically acceptable salt thereof, one or both R$^8$ is 6-10 membered bridged bicyclic heterocyclyl, wherein the 6-10 membered bridged bicyclic heterocyclyl is optionally substituted with 1-3 R$^a$ groups. In some embodiments of a compound of Formula I, or a pharmaceutically acceptable salt thereof, one or both R$^8$ is 6-10 membered bridged bicyclic heterocyclyl, wherein the 6-10 membered bridged bicyclic heterocyclyl is optionally substituted with 1-3 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, one or both R$^8$ is 6-10 membered bridged bicyclic heterocyclyl, wherein the 6-10 membered bridged bicyclic heterocyclyl is substituted with 1-4 R$^a$ groups. In some embodiments of a compound of Formula I, or a pharmaceutically acceptable salt thereof, one or both R$^8$ is 6-10 membered bridged bicyclic heterocyclyl, wherein the 6-10 membered bridged bicyclic heterocyclyl is substituted with 1-3 R$^a$ groups. In some embodiments of a compound of Formula I, or a pharmaceutically acceptable salt thereof, one or both R$^8$ is 6-10 membered bridged bicyclic heterocyclyl, wherein the 6-10 membered bridged bicyclic heterocyclyl is substituted with 1-3 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, one or both R$^8$ is 6-10 membered bridged bicyclic heterocyclyl.

In some embodiments of a compound of Formula I, or a pharmaceutically acceptable salt thereof, one or both R$^8$ is 7-8 membered bridged bicyclic heterocyclyl, wherein the 7-8 membered bridged bicyclic heterocyclyl is optionally substituted with 1-4 R$^a$ groups. In some embodiments of a compound of Formula I, or a pharmaceutically acceptable salt thereof, one or both R$^8$ is 7-8 membered bridged bicyclic heterocyclyl, wherein the 7-8 membered bridged bicyclic heterocyclyl is optionally substituted with 1-3 R$^a$ groups. In some embodiments of a compound of Formula I, or a pharmaceutically acceptable salt thereof, one or both R$^8$ is 7-8 membered bridged bicyclic heterocyclyl, wherein the 7-8 membered bridged bicyclic heterocyclyl is optionally substituted with 1-3 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, one or both R$^8$ is 7-8 membered bridged bicyclic heterocyclyl, wherein the 7-8 membered bridged bicyclic heterocyclyl is substituted with 1-4 R$^a$ groups. In some embodiments of a compound of Formula I, or a pharmaceutically acceptable salt thereof, one or both R$^8$ is 7-8 membered bridged bicyclic heterocyclyl, wherein the 7-8 membered bridged bicyclic heterocyclyl is substituted with 1-3 R$^a$ groups. In some embodiments of a compound of Formula I, or a pharmaceutically acceptable salt thereof, one or both $R^8$ is 7-8 membered bridged bicyclic heterocyclyl, wherein the 7-8 membered bridged bicyclic heterocyclyl is substituted with 1-3 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, one or both $R^8$ is 7-8 membered bridged bicyclic heterocyclyl.

In some embodiments of a compound of Formula I, or a pharmaceutically acceptable salt thereof, one or both $R^8$ is 7-10 membered spirocyclic heterocyclyl, wherein the 7-10 membered spirocyclic heterocyclyl is optionally substituted with 1-4 $R^a$ groups. In some embodiments of a compound of Formula I, or a pharmaceutically acceptable salt thereof, one or both $R^8$ is 7-10 membered spirocyclic heterocyclyl, wherein the 7-10 membered spirocyclic heterocyclyl is substituted with 1-4 $R^a$ groups. In some embodiments of a compound of Formula I, or a pharmaceutically acceptable salt thereof, one or both $R^8$ is 7-10 membered spirocyclic heterocyclyl.

In some embodiments of a compound of Formula I, or a pharmaceutically acceptable salt thereof, one or both $R^8$ is 7-10 membered spirocyclic heterocyclyl, wherein the 7-10 membered spirocyclic heterocyclyl is optionally substituted with 1-3 groups independently selected from —OH, halogen, —CN, oxo, —NR$^{11}$R$^{11}$, C$_{1-4}$ alkoxy, and C$_{1-5}$ alkyl. In some embodiments of a compound of Formula I, or a pharmaceutically acceptable salt thereof, one or both $R^8$ is 7-10 membered spirocyclic heterocyclyl, wherein the 7-10 membered spirocyclic heterocyclyl is substituted with 1-3 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, one or both $R^8$ is 7-10 membered spirocyclic heterocyclyl, wherein the 7-10 membered spirocyclic heterocyclyl is optionally substituted with 1-3 groups independently selected from oxo and methyl. In some embodiments of a compound of Formula I, or a pharmaceutically acceptable salt thereof, one or both $R^8$ is 7-10 membered spirocyclic heterocyclyl, wherein the 7-10 membered spirocyclic heterocyclyl is substituted with 1-3 groups independently selected from oxo and methyl.

In some embodiments of a compound of Formula I, or a pharmaceutically acceptable salt thereof, one or both $R^8$ is

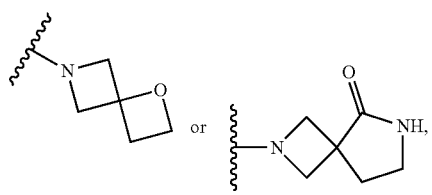 [SMILES: *N1CC2(CCO2)C1 ; *N1CC2(CCNC2=O)C1]

each of which is optionally substituted with one methyl group. In some embodiments of a compound of Formula I, or a pharmaceutically acceptable salt thereof, one or both $R^8$ is

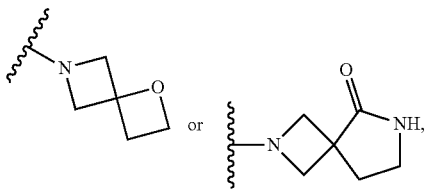 [SMILES: *N1CC2(CCO2)C1 ; *N1CC2(CCNC2=O)C1]

each of which is substituted with one methyl group.

In some embodiments of a compound of Formula I, or a pharmaceutically acceptable salt thereof, $R^8$ is 4-7 membered monocyclic heterocyclyl, wherein the 4-7 membered monocyclic heterocyclyl is optionally substituted with 1-3 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, $R^8$ is 4-7 membered monocyclic heterocyclyl,
  wherein the 4-7 membered monocyclic heterocyclyl is optionally substituted with 1-3 groups independently selected from —OH, halogen, —CN, oxo, —NR$^{11}$R$^{11}$, C$_{1-4}$ alkoxy, and C$_{1-5}$ alkyl, and
  wherein the 4-7 membered monocyclic heterocyclyl has one or two ring heteroatoms independently selected from N and S.

In some embodiments of a compound of Formula I, or a pharmaceutically acceptable salt thereof, $R^8$ is 5-6 membered monocyclic heterocyclyl, wherein the 5-6 membered monocyclic heterocyclyl is optionally substituted with 1-2 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, $R^8$ is piperidinyl or piperazinyl, each of which is optionally substituted with 1-2 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, $R^8$ is piperidinyl or piperazinyl.

In some embodiments of a compound of Formula I, or a pharmaceutically acceptable salt thereof, $R^8$ is C$_{1-6}$ alkyl, wherein the C$_{1-6}$ alkyl is optionally substituted with 1-3 groups independently selected from —OH, halogen, —CN, oxo, —NR$^{11}$R$^{11}$, —C(O)NR$^{11}$R$^{11}$, C$_{1-4}$ alkoxy, and R$^{8a}$.

In some embodiments of a compound of Formula I, or a pharmaceutically acceptable salt thereof, $R^8$ is C$_{1-6}$ alkyl, wherein the C$_{1-6}$ alkyl is substituted with 1-2 groups independently selected from —C(O)NR$^{11}$R$^{11}$ and R$^{8a}$.

In some embodiments of a compound of Formula I, or a pharmaceutically acceptable salt thereof, $R^8$ is C$_{1-4}$ alkyl, wherein the C$_{1-4}$ alkyl is substituted with 1-2 groups independently selected from —C(O)NH$_2$, 4-7 membered monocyclic heterocyclyl, and 5-6 membered monocyclic heteroaryl, and
  wherein the 4-7 membered monocyclic heterocyclyl and 5-6 membered monocyclic heteroaryl are each independently optionally substituted with one group selected from —OH, halogen, C$_{1-3}$ alkoxy, and C$_{1-3}$ alkyl.

In some embodiments of a compound of Formula I, or a pharmaceutically acceptable salt thereof, each R$^{8a}$ independently is 4-7 membered monocyclic heterocyclyl or 5-6 membered monocyclic heteroaryl, wherein the 4-7 membered monocyclic heterocyclyl and 5-6 membered monocyclic heteroaryl are each independently optionally substituted with 1-3 groups independently selected from —OH, halogen, $C_{1-4}$ alkoxy, and $C_{1-5}$ alkyl.

In some embodiments of a compound of Formula I, or a pharmaceutically acceptable salt thereof, each $R^{8a}$ independently is 4-membered monocyclic heterocyclyl or 5-membered monocyclic heteroaryl, each of which is optionally substituted with one $C_{1-3}$ alkyl.

In some embodiments of a compound of Formula I, or a pharmaceutically acceptable salt thereof, each $R^{8a}$ independently is oxetanyl or 5-membered monocyclic heteroaryl having two ring heteroatoms that is N, and wherein the oxetanyl and the 5-membered monocyclic heteroaryl are each optionally substituted with methyl.

In some embodiments of a compound of Formula I, or a pharmaceutically acceptable salt thereof, each $R^{8a}$ independently is oxetanyl or pyrazolyl, wherein the oxetanyl and pyrazolyl are each optionally substituted with methyl.

In some embodiments of a compound of Formula I, or a pharmaceutically acceptable salt thereof, one or both $R^8$ is —C(O)$R^9$. In some embodiments of a compound of Formula I, or a pharmaceutically acceptable salt thereof, $R^8$ is —C(O)$R^9$.

In some embodiments of a compound of Formula I, or a pharmaceutically acceptable salt thereof, each $R^9$ independently is $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl,
wherein the $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-4 $R^a$ groups.

In some embodiments of a compound of Formula I, or a pharmaceutically acceptable salt thereof, each $R^9$ independently is $C_{3-7}$ monocyclic cycloalkyl or 4-7 membered monocyclic heterocyclyl, wherein the $C_{3-7}$ monocyclic cycloalkyl and 4-7 membered monocyclic heterocyclyl are each independently optionally substituted with 1-4 $R^a$ groups.

In some embodiments of a compound of Formula I, or a pharmaceutically acceptable salt thereof, each $R^9$ independently is $C_{3-7}$ monocyclic cycloalkyl or 4-7 membered monocyclic heterocyclyl, wherein the $C_{3-7}$ monocyclic cycloalkyl and 4-7 membered monocyclic heterocyclyl are each independently optionally substituted with 1-3 groups independently selected from —OH, halogen, —CN, oxo, —NR$^{11}$R$^{11}$, $C_{1-4}$ alkoxy, $C_{1-5}$ alkyl, and 4-7 membered monocyclic heterocyclyl.

In some embodiments of a compound of Formula I, or a pharmaceutically acceptable salt thereof, one or both $R^9$ is $C_{3-7}$ monocyclic cycloalkyl, wherein the $C_{3-7}$ monocyclic cycloalkyl is optionally substituted with 1-4 $R^a$ groups. In some embodiments of a compound of Formula I, or a pharmaceutically acceptable salt thereof, one or both $R^9$ is $C_{3-7}$ monocyclic cycloalkyl, wherein the $C_{3-7}$ monocyclic cycloalkyl is optionally substituted with 1-3 groups independently selected from —OH, halogen, —CN, oxo, —NR$^{11}$R$^{11}$, $C_{1-4}$ alkoxy, $C_{1-5}$ alkyl, and 4-7 membered monocyclic heterocyclyl. In some embodiments of a compound of Formula I, or a pharmaceutically acceptable salt thereof, one or both $R^9$ is $C_{3-7}$ monocyclic cycloalkyl, wherein the $C_{3-7}$ monocyclic cycloalkyl is substituted with 1-4 $R^a$ groups. In some embodiments of a compound of Formula I, or a pharmaceutically acceptable salt thereof, one or both $R^9$ is $C_{3-7}$ monocyclic cycloalkyl, wherein the $C_{3-7}$ monocyclic cycloalkyl is substituted with 1-3 groups independently selected from —OH, halogen, —CN, oxo, —NR$^{11}$R$^{11}$, $C_{1-4}$ alkoxy, $C_{1-5}$ alkyl, and 4-7 membered monocyclic heterocyclyl. In some embodiments of a compound of Formula I, or a pharmaceutically acceptable salt thereof, one or both $R^9$ is $C_{3-7}$ monocyclic cycloalkyl.

In some embodiments of a compound of Formula I, or a pharmaceutically acceptable salt thereof, one or both $R^9$ is $C_{7-10}$ fused bicyclic cycloalkyl, wherein the $C_{7-10}$ fused bicyclic cycloalkyl is optionally substituted with 1-4 $R^a$ groups. In some embodiments of a compound of Formula I, or a pharmaceutically acceptable salt thereof, one or both $R^9$ is $C_{7-10}$ fused bicyclic cycloalkyl, wherein the $C_{7-10}$ fused bicyclic cycloalkyl is substituted with 1-4 $R^a$ groups. In some embodiments of a compound of Formula I, or a pharmaceutically acceptable salt thereof, one or both $R^9$ is $C_{7-10}$ fused bicyclic cycloalkyl.

In some embodiments of a compound of Formula I, or a pharmaceutically acceptable salt thereof, one or both $R^9$ is $C_{5-10}$ bridged bicyclic cycloalkyl, wherein the $C_{5-10}$ bridged bicyclic cycloalkyl is optionally substituted with 1-4 $R^a$ groups. In some embodiments of a compound of Formula I, or a pharmaceutically acceptable salt thereof, one or both $R^9$ is $C_{5-10}$ bridged bicyclic cycloalkyl, wherein the $C_{5-10}$ bridged bicyclic cycloalkyl is substituted with 1-4 $R^a$ groups. In some embodiments of a compound of Formula I, or a pharmaceutically acceptable salt thereof, one or both $R^9$ is $C_{5-10}$ bridged bicyclic cycloalkyl.

In some embodiments of a compound of Formula I, or a pharmaceutically acceptable salt thereof, one or both $R^9$ is phenyl, wherein the phenyl is optionally substituted with 1-4 $R^a$ groups. In some embodiments of a compound of Formula I, or a pharmaceutically acceptable salt thereof, one or both $R^9$ is phenyl, wherein the phenyl is substituted with 1-4 $R^a$ groups. In some embodiments of a compound of Formula I, or a pharmaceutically acceptable salt thereof, one or both $R^9$ is phenyl.

In some embodiments of a compound of Formula I, or a pharmaceutically acceptable salt thereof, one or both $R^9$ is naphthalenyl, wherein the naphthalenyl is optionally substituted with 1-4 $R^a$ groups. In some embodiments of a compound of Formula I, or a pharmaceutically acceptable salt thereof, one or both $R^9$ is naphthalenyl, wherein the naphthalenyl is substituted with 1-4 $R^a$ groups. In some embodiments of a compound of Formula I, or a pharmaceutically acceptable salt thereof, one or both $R^9$ is naphthalenyl.

In some embodiments of a compound of Formula I, or a pharmaceutically acceptable salt thereof, one or both $R^9$ is 5-6 membered monocyclic heteroaryl, wherein the 5-6 membered monocyclic heteroaryl is optionally substituted with 1-4 $R^a$ groups. In some embodiments of a compound of Formula I, or a pharmaceutically acceptable salt thereof, one or both $R^9$ is 5-6 membered monocyclic heteroaryl, wherein the 5-6 membered monocyclic heteroaryl is substituted with 1-4 $R^a$ groups. In some embodiments of a compound of Formula I, or a pharmaceutically acceptable salt thereof, one or both $R^9$ is 5-6 membered monocyclic heteroaryl.

In some embodiments of a compound of Formula I, or a pharmaceutically acceptable salt thereof, one or both $R^9$ is 8-10 membered fused bicyclic heterocyclyl, wherein the 8-10 membered fused bicyclic heterocyclyl is optionally substituted with 1-4 R$^a$ groups. In some embodiments of a compound of Formula I, or a pharmaceutically acceptable salt thereof, one or both R$^9$ is 8-10 membered fused bicyclic heterocyclyl, wherein the 8-10 membered fused bicyclic heterocyclyl is substituted with 1-4 R$^a$ groups. In some embodiments of a compound of Formula I, or a pharmaceutically acceptable salt thereof, one or both R$^9$ is 8-10 membered fused bicyclic heterocyclyl.

In some embodiments of a compound of Formula I, or a pharmaceutically acceptable salt thereof, one or both R$^9$ is 8-10 membered fused bicyclic heteroaryl, wherein the 8-10 membered fused bicyclic heteroaryl is optionally substituted with 1-4 R$^a$ groups. In some embodiments of a compound of Formula I, or a pharmaceutically acceptable salt thereof, one or both R$^9$ is 8-10 membered fused bicyclic heteroaryl, wherein the 8-10 membered fused bicyclic heteroaryl is substituted with 1-4 R$^a$ groups. In some embodiments of a compound of Formula I, or a pharmaceutically acceptable salt thereof, one or both R$^9$ is 8-10 membered fused bicyclic heteroaryl.

In some embodiments of a compound of Formula I, or a pharmaceutically acceptable salt thereof, one or both R$^9$ is 7-10 membered spirocyclic heterocyclyl, wherein the 7-10 membered spirocyclic heterocyclyl is optionally substituted with 1-4 R$^a$ groups. In some embodiments of a compound of Formula I, or a pharmaceutically acceptable salt thereof, one or both R$^9$ is 7-10 membered spirocyclic heterocyclyl, wherein the 7-10 membered spirocyclic heterocyclyl is substituted with 1-4 R$^a$ groups. In some embodiments of a compound of Formula I, or a pharmaceutically acceptable salt thereof, one or both R$^9$ is 7-10 membered spirocyclic heterocyclyl.

In some embodiments of a compound of Formula I, or a pharmaceutically acceptable salt thereof, one or both R$^9$ is 7-10 membered spirocyclic heterocyclyl, wherein the 7-10 membered spirocyclic heterocyclyl has 1-2 ring heteroatoms independently selected from N and O.

In some embodiments of a compound of Formula I, or a pharmaceutically acceptable salt thereof, R$^9$ is

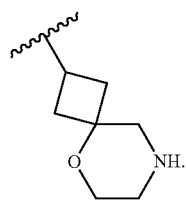 [SMILES: *C1CC2(CNCCO2)C1]

In some embodiments of a compound of Formula I, or a pharmaceutically acceptable salt thereof, one or both R$^9$ is 4-7 membered monocyclic heterocyclyl, wherein the 4-7 membered monocyclic heterocyclyl is optionally substituted with 1-4 R$^a$ groups. In some embodiments of a compound of Formula I, or a pharmaceutically acceptable salt thereof, one or both R$^9$ is 4-7 membered monocyclic heterocyclyl, wherein the 4-7 membered monocyclic heterocyclyl is optionally substituted with 1-3 groups independently selected from —OH, halogen, —CN, oxo, —NR$^{11}$R$^{11}$, C$_{1-4}$ alkoxy, C$_{1-5}$ alkyl, and 4-7 membered monocyclic heterocyclyl. In some embodiments of a compound of Formula I, or a pharmaceutically acceptable salt thereof, one or both R$^9$ is 4-7 membered monocyclic heterocyclyl, wherein the 4-7 membered monocyclic heterocyclyl is substituted with 1-4 R$^a$ groups. In some embodiments of a compound of Formula I, or a pharmaceutically acceptable salt thereof, one or both R$^9$ is 4-7 membered monocyclic heterocyclyl, wherein the 4-7 membered monocyclic heterocyclyl is substituted with 1-3 groups independently selected from —OH, halogen, —CN, oxo, —NR$^{11}$R$^{11}$, C$_{1-4}$ alkoxy, C$_{1-5}$ alkyl, and 4-7 membered monocyclic heterocyclyl. In some embodiments of a compound of Formula I, or a pharmaceutically acceptable salt thereof, one or both R$^9$ is 4-7 membered monocyclic heterocyclyl.

In some embodiments of a compound of Formula I, or a pharmaceutically acceptable salt thereof, one or both R$^9$ is 5-7 membered monocyclic heterocyclyl, wherein the 5-7 membered monocyclic heterocyclyl is optionally substituted with 1-4 R$^a$ groups. In some embodiments of a compound of Formula I, or a pharmaceutically acceptable salt thereof, one or both R$^9$ is 5-7 membered monocyclic heterocyclyl, wherein the 5-7 membered monocyclic heterocyclyl is optionally substituted with 1-3 groups independently selected from —OH, halogen, —CN, —NR$^{11}$R$^{11}$, C$_{1-3}$ alkoxy, and C$_{1-3}$ alkyl. In some embodiments of a compound of Formula I, or a pharmaceutically acceptable salt thereof, one or both R$^9$ is 5-7 membered monocyclic heterocyclyl, wherein the 5-7 membered monocyclic heterocyclyl is substituted with 1-4 R$^a$ groups. In some embodiments of a compound of Formula I, or a pharmaceutically acceptable salt thereof, one or both R$^9$ is 5-7 membered monocyclic heterocyclyl, wherein the 5-7 membered monocyclic heterocyclyl is substituted with 1-3 groups independently selected from —OH, halogen, —CN, —NR$^{11}$R$^{11}$, C$_{1-3}$ alkoxy, and C$_{1-3}$ alkyl. In some embodiments of a compound of Formula I, or a pharmaceutically acceptable salt thereof, one or both R$^9$ is 5-7 membered monocyclic heterocyclyl.

In some embodiments of a compound of Formula I, or a pharmaceutically acceptable salt thereof, one or both R$^9$ is 4-6 membered monocyclic heterocyclyl, wherein the 4-6 membered monocyclic heterocyclyl is optionally substituted with 1-4 R$^a$ groups. In some embodiments of a compound of Formula I, or a pharmaceutically acceptable salt thereof, one or both R$^9$ is 4-6 membered monocyclic heterocyclyl, wherein the 4-6 membered monocyclic heterocyclyl is optionally substituted with 1-3 groups independently selected from —OH, halogen, —CN, —NR$^{11}$R$^{11}$, C$_{1-3}$ alkoxy, and C$_{1-3}$ alkyl. In some embodiments of a compound of Formula I, or a pharmaceutically acceptable salt thereof, one or both R$^9$ is 4-6 membered monocyclic heterocyclyl, wherein the 4-6 membered monocyclic heterocyclyl is optionally substituted with 1-2 groups independently selected from —OH, halogen, C$_{1-3}$ alkoxy, and C$_{1-3}$ alkyl. In some embodiments of a compound of Formula I, or a pharmaceutically acceptable salt thereof, one or both R$^9$ is 4-6 membered monocyclic heterocyclyl, wherein the 4-6 membered monocyclic heterocyclyl is substituted with 1-4 R$^a$ groups. In some embodiments of a compound of Formula I, or a pharmaceutically acceptable salt thereof, one or both R$^9$ is 4-6 membered monocyclic heterocyclyl, wherein the 4-6 membered monocyclic heterocyclyl is substituted with 1-3 groups independently selected from —OH, halogen, —CN, —NR$^{11}$R$^{11}$, C$_{1-3}$ alkoxy, and C$_{1-3}$ alkyl. In some embodiments of a compound of Formula I, or a pharmaceutically acceptable salt thereof, one or both R$^9$ is 4-6 membered monocyclic heterocyclyl, wherein the 4-6 membered monocyclic heterocyclyl is substituted with 1-2 groups independently selected from —OH, halogen, C$_{1-3}$ alkoxy, and C$_{1-3}$ alkyl. In some embodiments of a compound of Formula I, or a pharmaceutically acceptable salt thereof, one or both R$^9$ is 4-6 membered monocyclic heterocyclyl.

In some embodiments of a compound of Formula I, or a pharmaceutically acceptable salt thereof, one or both R⁹ is 6-10 membered bridged bicyclic heterocyclyl, wherein the 6-10 membered bridged bicyclic heterocyclyl is optionally substituted with 1-4 R$^a$ groups. In some embodiments of a compound of Formula I, or a pharmaceutically acceptable salt thereof, one or both R⁹ is 6-10 membered bridged bicyclic heterocyclyl, wherein the 6-10 membered bridged bicyclic heterocyclyl is optionally substituted with 1-3 groups independently selected from —OH, halogen, —CN, oxo, —NR¹¹R¹¹, C$_{1-4}$ alkoxy, and C$_{1-5}$ alkyl. In some embodiments of a compound of Formula I, or a pharmaceutically acceptable salt thereof, one or both R⁹ is 6-10 membered bridged bicyclic heterocyclyl, wherein the 6-10 membered bridged bicyclic heterocyclyl is optionally substituted with 1-3 groups independently selected from —OH, halogen, —CN, —NR¹¹R¹¹, C$_{1-3}$ alkoxy, and C$_{1-3}$ alkyl. In some embodiments of a compound of Formula I, or a pharmaceutically acceptable salt thereof, one or both R⁹ is 6-10 membered bridged bicyclic heterocyclyl, wherein the 6-10 membered bridged bicyclic heterocyclyl is substituted with 1-4 R$^a$ groups. In some embodiments of a compound of Formula I, or a pharmaceutically acceptable salt thereof, one or both R⁹ is 6-10 membered bridged bicyclic heterocyclyl, wherein the 6-10 membered bridged bicyclic heterocyclyl is substituted with 1-3 groups independently selected from —OH, halogen, —CN, oxo, —NR¹¹R¹¹, C$_{1-4}$ alkoxy, and C$_{1-5}$ alkyl. In some embodiments of a compound of Formula I, or a pharmaceutically acceptable salt thereof, one or both R⁹ is 6-10 membered bridged bicyclic heterocyclyl, wherein the 6-10 membered bridged bicyclic heterocyclyl is substituted with 1-3 groups independently selected from —OH, halogen, —CN, —NR¹¹R¹¹, C$_{1-3}$ alkoxy, and C$_{1-3}$ alkyl. In some embodiments of a compound of Formula I, or a pharmaceutically acceptable salt thereof, one or both R⁹ is 6-10 membered bridged bicyclic heterocyclyl.

In some embodiments of a compound of Formula I, or a pharmaceutically acceptable salt thereof, R⁹ is 4-7 membered monocyclic heterocyclyl, wherein the 4-7 membered monocyclic heterocyclyl is optionally substituted with 1-3 groups independently selected from —OH, halogen, —CN, oxo, —NR¹¹R¹¹, C$_{1-4}$ alkoxy, C$_{1-5}$ alkyl, and 4-7 membered monocyclic heterocyclyl.

In some embodiments of a compound of Formula I, or a pharmaceutically acceptable salt thereof, R⁹ is 4-7 membered monocyclic heterocyclyl,
 wherein the 4-7 membered monocyclic heterocyclyl is optionally substituted with 1-3 groups independently selected from —OH, halogen, —CN, oxo, —NR¹¹R¹¹, C$_{1-4}$ alkoxy, and C$_{1-5}$ alkyl, and
 wherein the 4-7 membered monocyclic heterocyclyl has one or two ring heteroatoms that is N.

In some embodiments of a compound of Formula I, or a pharmaceutically acceptable salt thereof, R⁹ is 5-6 membered monocyclic heterocyclyl, wherein the 5-6 membered monocyclic heterocyclyl is optionally substituted with 1-2 groups independently selected from —OH, halogen, C$_{1-3}$ alkoxy, and C$_{1-3}$ alkyl, and wherein the 5-6 membered monocyclic heterocyclyl has one or two ring heteroatoms that is N.

In some embodiments of a compound of Formula I, or a pharmaceutically acceptable salt thereof, R⁹ is pyrrolidinyl or morpholinyl, each of which is optionally substituted with 1-2 groups independently selected from —OH, halogen, C$_{1-3}$ alkoxy, and C$_{1-3}$ alkyl.

In some embodiments of a compound of Formula I, or a pharmaceutically acceptable salt thereof, R⁹ is azetidinyl or pyrrolidinyl, each of which is optionally substituted with 1-2 groups independently selected from —OH, halogen, C$_{1-3}$ alkoxy, and C$_{1-3}$ alkyl. In some embodiments of a compound of Formula I, or a pharmaceutically acceptable salt thereof, R⁹ is azetidinyl or pyrrolidinyl, each of which is substituted with 1-2 groups independently selected from —OH, halogen, C$_{1-3}$ alkoxy, and C$_{1-3}$ alkyl.

In some embodiments of a compound of Formula I, or a pharmaceutically acceptable salt thereof, R⁹ is

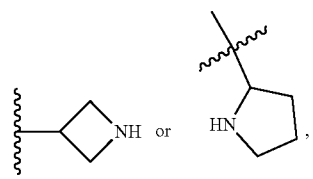 [SMILES: *C1CNC1 ; *C1CCCN1]

each of which is optionally substituted with 1-2 groups independently selected from —OH, methyl, and trifluoromethyl. In some embodiments of a compound of Formula I, or a pharmaceutically acceptable salt thereof, R⁹ is

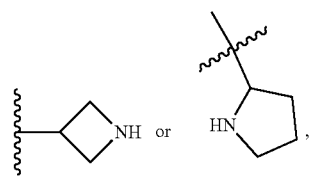 [SMILES: *C1CNC1 ; *C1CCCN1]

each of which is substituted with 1-2 groups independently selected from —OH, methyl, and trifluoromethyl.

In some embodiments of a compound of Formula I, or a pharmaceutically acceptable salt thereof, R⁹ is C$_{3-7}$ monocyclic cycloalkyl optionally substituted with 1-3 groups independently selected from —OH, halogen, —CN, oxo, —NR¹¹R¹¹, C$_{1-4}$ alkoxy, C$_{1-5}$ alkyl, and 4-7 membered monocyclic heterocyclyl.

In some embodiments of a compound of Formula I, or a pharmaceutically acceptable salt thereof, R⁹ is cyclopropyl, cyclobutyl, or cyclopentanyl, each of which is optionally substituted with 1-2 groups independently selected from —OH, halogen, C$_{1-3}$ alkoxy, C$_{1-3}$ alkyl, and 4-7 membered monocyclic heterocyclyl.

In some embodiments of a compound of Formula I, or a pharmaceutically acceptable salt thereof, R⁹ is cyclopropyl, cyclobutyl, or cyclopentanyl, each of which is optionally substituted with 1-2 groups independently selected from —OH, halogen, C$_{1-3}$ alkoxy, C$_{1-3}$ alkyl, and 5-7 membered monocyclic heterocyclyl, wherein the 5-7 membered monocyclic heterocyclyl has one or two ring heteroatoms that is N.

In some embodiments of a compound of Formula I, or a pharmaceutically acceptable salt thereof, R⁹ is cyclopropyl optionally substituted with 6 membered monocyclic heterocyclyl, wherein the 6 membered monocyclic heterocyclyl has one ring heteroatom that is N.

In some embodiments of a compound of Formula I, or a pharmaceutically acceptable salt thereof, R⁹ is cyclopropyl optionally substituted with morpholinyl.

In some embodiments of a compound of Formula I, or a pharmaceutically acceptable salt thereof, one or both R⁸ is —NR¹⁰R¹⁰.

In some embodiments of a compound of Formula I, or a pharmaceutically acceptable salt thereof, one or both $R^8$ is —S(O)$_2$R$^{5a}$.

In some embodiments of a compound of Formula I, or a pharmaceutically acceptable salt thereof, $R^8$ is —S(O)$_2$R$^{5a}$.

In some embodiments of a compound of Formula I, or a pharmaceutically acceptable salt thereof, $R^{5a}$ is 4-7 membered monocyclic heterocyclyl,
  wherein the 4-7 membered monocyclic heterocyclyl is optionally substituted with 1-3 groups independently selected from —OH, halogen, —CN, oxo, —NR$^{11}$R$^{11}$, C$_{1-4}$ alkoxy, and C$_{1-5}$ alkyl, and
  wherein the 4-7 membered monocyclic heterocyclyl has one or two ring heteroatoms that is N.

In some embodiments of a compound of Formula I, or a pharmaceutically acceptable salt thereof, $R^{5a}$ is 5-6 membered monocyclic heterocyclyl,
  wherein the 5-6 membered heterocyclyl is optionally substituted with 1-2 groups independently selected from —OH, halogen, —CN, and C$_{1-5}$ alkyl, and
  wherein the 5-6 membered heterocyclyl has one or two ring heteroatoms that is N.

In some embodiments of a compound of Formula I, or a pharmaceutically acceptable salt thereof, $R^{5a}$ is piperazinyl.

In some embodiments of a compound of Formula I, or a pharmaceutically acceptable salt thereof, Z is —C(O)NR$^6$R$^7$. In some embodiments of a compound of Formula I, or a pharmaceutically acceptable salt thereof, Z is —C(O)N(H)R$^6$. In some embodiments of a compound of Formula I, or a pharmaceutically acceptable salt thereof, Z is —C(O)N(CH$_3$)R$^6$.

In some embodiments of a compound of Formula I, or a pharmaceutically acceptable salt thereof, $R^6$ is C$_{3-7}$ monocyclic cycloalkyl, C$_{7-10}$ fused bicyclic cycloalkyl, C$_{5-10}$ bridged bicyclic cycloalkyl, 4-7 membered monocyclic heterocyclyl, 8-10 membered fused bicyclic heterocyclyl, 6-10 membered bridged bicyclic heterocyclyl or 7-10 membered spirocyclic heterocyclyl,
  wherein the C$_{3-7}$ monocyclic cycloalkyl, C$_{7-10}$ fused bicyclic cycloalkyl, C$_{5-10}$ bridged bicyclic cycloalkyl, 4-7 membered monocyclic heterocyclyl, 8-10 membered fused bicyclic heterocyclyl, 6-10 membered bridged bicyclic heterocyclyl, and 7-10 membered spirocyclic heterocyclyl are each independently optionally substituted with 1-4 R$^a$ groups.

In some embodiments of a compound of Formula I, or a pharmaceutically acceptable salt thereof, $R^6$ is 4-7 membered monocyclic heterocyclyl,
  wherein the C$_{1-6}$ alkyl is optionally substituted with 1-3 R$^b$ groups,
  wherein the 4-7 membered monocyclic heterocyclyl is optionally substituted with 1-3 R$^a$ groups.

In some embodiments of a compound of Formula I, or a pharmaceutically acceptable salt thereof, $R^6$ is 4-7 membered monocyclic heterocyclyl,
  wherein the C$_{1-6}$ alkyl is optionally substituted with 1-2 groups independently selected from —OH, halogen, —NR$^{11}$R$^{11}$, and C$_{1-3}$ alkoxy,
  wherein the 4-7 membered monocyclic heterocyclyl is optionally substituted with 1-3 groups independently selected from —OH, halogen, —CN, —NR$^{11}$R$^{11}$, C$_{1-3}$ alkoxy, and C$_{1-3}$ alkyl.

In some embodiments of a compound of Formula I, or a pharmaceutically acceptable salt thereof, $R^6$ is 4-7 membered monocyclic heterocyclyl, wherein the 4-7 membered monocyclic heterocyclyl is optionally substituted with 1-3 groups independently selected from —OH, halogen, —CN, oxo, —NR$^{11}$R$^{11}$, C$_{1-4}$ alkoxy, and C$_{1-5}$ alkyl, and
  wherein the C$_{1-4}$ alkoxy and C$_{1-5}$ alkyl are each independently optionally substituted with 1-3 groups independently selected from —OH, halogen, —CN, and —NR$^{12}$R$^{12}$.

In some embodiments of a compound of Formula I, or a pharmaceutically acceptable salt thereof, $R^6$ is 4-7 membered monocyclic heterocyclyl, wherein the 4-7 membered monocyclic heterocyclyl is optionally substituted with 1-3 groups independently selected from —OH, halogen, —CN, oxo, —NR$^{11}$R$^{11}$, C$_{1-4}$ alkoxy, and C$_{1-5}$ alkyl. In some embodiments of a compound of Formula I, or a pharmaceutically acceptable salt thereof, $R^6$ is 4-7 membered monocyclic heterocyclyl, wherein the 4-7 membered monocyclic heterocyclyl is substituted with 1-3 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, $R^6$ is C$_{3-7}$ monocyclic cycloalkyl, wherein the C$_{3-7}$ monocyclic cycloalkyl is optionally substituted with 1-4 R$^a$ groups. In some embodiments of a compound of Formula I, or a pharmaceutically acceptable salt thereof, $R^6$ is C$_{3-7}$ monocyclic cycloalkyl, wherein the C$_{3-7}$ monocyclic cycloalkyl is substituted with 1-4 R$^a$ groups. In some embodiments of a compound of Formula I, or a pharmaceutically acceptable salt thereof, $R^6$ is C$_{3-7}$ monocyclic cycloalkyl.

In some embodiments of a compound of Formula I, or a pharmaceutically acceptable salt thereof, $R^6$ is C$_{7-10}$ fused bicyclic cycloalkyl, wherein the C$_{7-10}$ fused bicyclic cycloalkyl is optionally substituted with 1-4 R$^a$ groups. In some embodiments of a compound of Formula I, or a pharmaceutically acceptable salt thereof, $R^6$ is C$_{7-10}$ fused bicyclic cycloalkyl, wherein the C$_{7-10}$ fused bicyclic cycloalkyl is substituted with 1-4 R$^a$ groups. In some embodiments of a compound of Formula I, or a pharmaceutically acceptable salt thereof, $R^6$ is C$_{7-10}$ fused bicyclic cycloalkyl.

In some embodiments of a compound of Formula I, or a pharmaceutically acceptable salt thereof, $R^6$ is C$_{5-10}$ bridged bicyclic cycloalkyl, wherein the C$_{5-10}$ bridged bicyclic cycloalkyl is optionally substituted with 1-4 R$^a$ groups. In some embodiments of a compound of Formula I, or a pharmaceutically acceptable salt thereof, $R^6$ is C$_{5-10}$ bridged bicyclic cycloalkyl, wherein the C$_{5-10}$ bridged bicyclic cycloalkyl is substituted with 1-4 R$^a$ groups. In some embodiments of a compound of Formula I, or a pharmaceutically acceptable salt thereof, $R^6$ is C$_{5-10}$ bridged bicyclic cycloalkyl.

In some embodiments of a compound of Formula I, or a pharmaceutically acceptable salt thereof, $R^6$ is 4-7 membered monocyclic heterocyclyl, wherein the 4-7 membered monocyclic heterocyclyl is optionally substituted with 1-4 R$^a$ groups. In some embodiments of a compound of Formula I, or a pharmaceutically acceptable salt thereof, $R^6$ is 4-7 membered monocyclic heterocyclyl, wherein the 4-7 membered monocyclic heterocyclyl is optionally substituted with 1-3 R$^a$ groups. In some embodiments of a compound of Formula I, or a pharmaceutically acceptable salt thereof, $R^6$ is 4-7 membered monocyclic heterocyclyl, wherein the 4-7 membered monocyclic heterocyclyl is optionally substituted with 1-3 groups independently selected from —OH, halogen, —CN, oxo, —NR$^{11}$R$^{11}$, C$_{1-4}$ alkoxy, and C$_{1-5}$ alkyl, wherein the C$_{1-4}$ alkoxy and C$_{1-5}$ alkyl are each independently optionally substituted with 1-3 groups independently selected from —OH, halogen, —CN, and —NR$^{12}$R$^{12}$. In some embodiments of a compound of Formula I, or a pharmaceutically acceptable salt thereof, $R^6$ is 4-7 membered monocyclic heterocyclyl, wherein the 4-7 membered monocyclic heterocyclyl is optionally substituted 1-3 groups independently selected from —OH, halogen, —CN, —NR$^{11}$R$^{11}$, $C_{1-3}$ alkoxy, and $C_{1-3}$ alkyl, wherein the $C_{1-3}$ alkoxy and $C_{1-3}$ alkyl are each independently optionally substituted with 1-3 groups independently selected from —OH, halogen, —CN, and —NR$^{12}$R$^{12}$. In some embodiments of a compound of Formula I, or a pharmaceutically acceptable salt thereof, $R^6$ is 5-6 membered monocyclic heterocyclyl, wherein the 5-6 membered monocyclic heterocyclyl is optionally substituted 1-3 groups independently selected from —OH, halogen, —CN, —NR$^{11}$R$^{11}$, $C_{1-3}$ alkoxy, and $C_{1-3}$ alkyl, wherein the $C_{1-3}$ alkoxy and $C_{1-3}$ alkyl are each independently optionally substituted with 1-3 groups independently selected from —OH, halogen, —CN, and —NR$^{12}$R$^{12}$.

In some embodiments of a compound of Formula I, or a pharmaceutically acceptable salt thereof, $R^6$ is 4-7 membered monocyclic heterocyclyl, wherein the 4-7 membered monocyclic heterocyclyl is substituted with 1-4 $R^a$ groups. In some embodiments of a compound of Formula I, or a pharmaceutically acceptable salt thereof, $R^6$ is 4-7 membered monocyclic heterocyclyl, wherein the 4-7 membered monocyclic heterocyclyl is substituted with 1-3 $R^a$ groups. In some embodiments of a compound of Formula I, or a pharmaceutically acceptable salt thereof, $R^6$ is 4-7 membered monocyclic heterocyclyl, wherein the 4-7 membered monocyclic heterocyclyl is substituted with 1-3 groups independently selected from —OH, halogen, —CN, oxo, —NR$^{11}$R$^{11}$, $C_{1-4}$ alkoxy, and $C_{1-5}$ alkyl, wherein the $C_{1-4}$ alkoxy and $C_{1-5}$ alkyl are each independently optionally substituted with 1-3 groups independently selected from —OH, halogen, —CN, and —NR$^{12}$R$^{12}$. In some embodiments of a compound of Formula I, or a pharmaceutically acceptable salt thereof, $R^6$ is 4-7 membered monocyclic heterocyclyl, wherein the 4-7 membered monocyclic heterocyclyl is substituted with 1-3 groups independently selected from —OH, halogen, —CN, —NR$^{11}$R$^{11}$, $C_{1-3}$ alkoxy, and $C_{1-3}$ alkyl, wherein the $C_{1-3}$ alkoxy and $C_{1-3}$ alkyl are each independently optionally substituted with 1-3 groups independently selected from —OH, halogen, —CN, and —NR$^{12}$R$^{12}$. In some embodiments of a compound of Formula I, or a pharmaceutically acceptable salt thereof, $R^6$ is 5-6 membered monocyclic heterocyclyl, wherein the 5-6 membered monocyclic heterocyclyl is substituted with 1-3 groups independently selected from —OH, halogen, —CN, —NR$^{11}$R$^{11}$, $C_{1-3}$ alkoxy, and $C_{1-3}$ alkyl, wherein the $C_{1-3}$ alkoxy and $C_{1-3}$ alkyl are each independently optionally substituted with 1-3 groups independently selected from —OH, halogen, —CN, and —NR$^{12}$R$^{12}$ In some embodiments of a compound of Formula I, or a pharmaceutically acceptable salt thereof, $R^6$ is 4-7 membered monocyclic heterocyclyl. In some embodiments of a compound of Formula I, or a pharmaceutically acceptable salt thereof, $R^6$ is 5-6 membered monocyclic heterocyclyl.

In some embodiments of a compound of Formula I, or a pharmaceutically acceptable salt thereof, $R^6$ is 4-7 membered monocyclic heterocyclyl,
  wherein the 4-7 membered monocyclic heterocyclyl is optionally substituted with 1-3 groups independently selected from —OH, halogen, —CN, oxo, —NR$^{11}$R$^{11}$, $C_{1-4}$ alkoxy, and $C_{1-5}$ alkyl, wherein the $C_{1-4}$ alkoxy and $C_{1-5}$ alkyl are each independently optionally substituted with 1-3 groups independently selected from —OH, halogen, —CN, and —NR$^{12}$R$^{12}$, and
  wherein the 4-7 membered monocyclic heterocyclyl has one or two ring heteroatoms that is N.

In some embodiments of a compound of Formula I, or a pharmaceutically acceptable salt thereof, $R^6$ is 5-6 membered monocyclic heterocyclyl,
  wherein the 5-6 membered heterocyclyl is optionally substituted with 1-2 groups independently selected from —OH, halogen, —CN, and $C_{1-5}$ alkyl, and
  wherein the $C_{1-5}$ alkyl is optionally substituted with 1-2 groups independently selected from —OH and halogen.

In some embodiments of a compound of Formula I, or a pharmaceutically acceptable salt thereof, $R^6$ is pyrrolidinyl, piperidinyl, or piperazinyl, each of which is optionally substituted with 1-2 groups independently selected from —OH, halogen, —CN, and $C_{1-5}$ alkyl, wherein the $C_{1-5}$ alkyl is optionally substituted with 1-2 groups independently selected from —OH and halogen.

In some embodiments of a compound of Formula I, or a pharmaceutically acceptable salt thereof, $R^6$ is pyrrolidinyl, piperidinyl, or piperazinyl, each of which is optionally substituted with one $C_{1-3}$ alkyl group, wherein the $C_{1-3}$ alkyl is optionally substituted with 1-2 groups independently selected from —OH and halogen.

In some embodiments of a compound of Formula I, or a pharmaceutically acceptable salt thereof, $R^6$ is

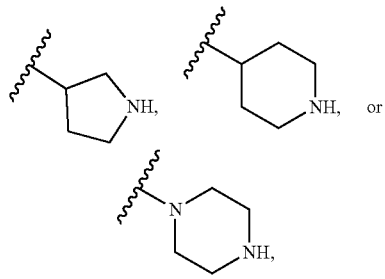

each of which is optionally substituted with $C_{1-3}$ alkyl, wherein the $C_{1-3}$ alkyl is substituted with one —OH group.

In some embodiments of a compound of Formula I, or a pharmaceutically acceptable salt thereof, $R^6$ is piperidinyl.

In some embodiments of a compound of Formula I, or a pharmaceutically acceptable salt thereof, $R^6$ is 8-10 membered fused bicyclic heterocyclyl, wherein the 8-10 membered fused bicyclic heterocyclyl is optionally substituted with 1-4 $R^a$ groups. In some embodiments of a compound of Formula I, or a pharmaceutically acceptable salt thereof, $R^6$ is 8-10 membered fused bicyclic heterocyclyl, wherein the 8-10 membered fused bicyclic heterocyclyl is optionally substituted with 1-3 $R^a$ groups. In some embodiments of a compound of Formula I, or a pharmaceutically acceptable salt thereof, $R^6$ is 8-10 membered fused bicyclic heterocyclyl, wherein the 8-10 membered fused bicyclic heterocyclyl is optionally substituted with 1-3 groups independently selected from —OH, halogen, —CN, oxo, —NR$^{11}$R$^{11}$, $C_{1-4}$ alkoxy, and $C_{1-5}$ alkyl.

In some embodiments of a compound of Formula I, or a pharmaceutically acceptable salt thereof, $R^6$ is 8-10 membered fused bicyclic heterocyclyl, wherein the 8-10 membered fused bicyclic heterocyclyl is substituted with 1-4 $R^a$ groups. In some embodiments of a compound of Formula I, or a pharmaceutically acceptable salt thereof, $R^6$ is 8-10 membered fused bicyclic heterocyclyl, wherein the 8-10 membered fused bicyclic heterocyclyl is substituted with 1-3

$R^a$ groups. In some embodiments of a compound of Formula I, or a pharmaceutically acceptable salt thereof, $R^6$ is 8-10 membered fused bicyclic heterocyclyl, wherein the 8-10 membered fused bicyclic heterocyclyl is substituted with 1-3 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, $R^6$ is 8-10 membered fused bicyclic heterocyclyl.

In some embodiments of a compound of Formula I, or a pharmaceutically acceptable salt thereof, $R^6$ is 6-10 membered bridged bicyclic heterocyclyl, wherein the 6-10 membered bridged bicyclic heterocyclyl is optionally substituted with 1-4 $R^a$ groups. In some embodiments of a compound of Formula I, or a pharmaceutically acceptable salt thereof, $R^6$ is 6-10 membered bridged bicyclic heterocyclyl, wherein the 6-10 membered bridged bicyclic heterocyclyl is optionally substituted with 1-3 $R^a$ groups. In some embodiments of a compound of Formula I, or a pharmaceutically acceptable salt thereof, $R^6$ is 6-10 membered bridged bicyclic heterocyclyl, wherein the 6-10 membered bridged bicyclic heterocyclyl is optionally substituted with 1-3 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, $R^6$ is 6-10 membered bridged bicyclic heterocyclyl, wherein the 6-10 membered bridged bicyclic heterocyclyl is substituted with 1-4 $R^a$ groups. In some embodiments of a compound of Formula I, or a pharmaceutically acceptable salt thereof, $R^6$ is 6-10 membered bridged bicyclic heterocyclyl, wherein the 6-10 membered bridged bicyclic heterocyclyl is substituted with 1-3 $R^a$ groups. In some embodiments of a compound of Formula I, or a pharmaceutically acceptable salt thereof, $R^6$ is 6-10 membered bridged bicyclic heterocyclyl, wherein the 6-10 membered bridged bicyclic heterocyclyl is substituted with 1-3 groups independently selected from —OH, halogen, —CN, oxo, —NR$^{11}$R$^{11}$, C$_{1-4}$ alkoxy, and C$_{1-5}$ alkyl.

In some embodiments of a compound of Formula I, or a pharmaceutically acceptable salt thereof, $R^6$ is 6-10 membered bridged bicyclic heterocyclyl.

In some embodiments of a compound of Formula I, or a pharmaceutically acceptable salt thereof, $R^6$ is 7-10 membered spirocyclic heterocyclyl, wherein the 7-10 membered spirocyclic heterocyclyl is optionally substituted with 1-4 $R^a$ groups. In some embodiments of a compound of Formula I, or a pharmaceutically acceptable salt thereof, $R^6$ is 7-10 membered spirocyclic heterocyclyl, wherein the 7-10 membered spirocyclic heterocyclyl is substituted with 1-4 $R^a$ groups. In some embodiments of a compound of Formula I, or a pharmaceutically acceptable salt thereof, $R^6$ is 7-10 membered spirocyclic heterocyclyl.

In some embodiments of a compound of Formula I, or a pharmaceutically acceptable salt thereof, $R^7$ is H, C$_{1-6}$ alkyl, C$_{3-7}$ monocyclic cycloalkyl, or 4-6 membered monocyclic heterocyclyl, wherein the C$_{1-6}$ alkyl, C$_{3-7}$ monocyclic cycloalkyl, and 4-6 membered monocyclic heterocyclyl are each independently optionally substituted with 1-4 groups independently selected from —OH, halogen, —CN, and C$_{1-6}$ alkoxy. In some embodiments of a compound of Formula I, or a pharmaceutically acceptable salt thereof, $R^7$ is H or C$_{1-6}$ alkyl, wherein the C$_{1-6}$ alkyl is optionally substituted with 1-4 groups independently selected from —OH, halogen, —CN, and C$_{1-6}$ alkoxy.

In some embodiments of a compound of Formula I, or a pharmaceutically acceptable salt thereof, $R^7$ is H or C$_{1-3}$ alkyl. In some embodiments of a compound of Formula I, or a pharmaceutically acceptable salt thereof, $R^7$ is H or methyl.

In some embodiments of a compound of Formula I, or a pharmaceutically acceptable salt thereof, $R^7$ is H.

In some embodiments of a compound of Formula I, or a pharmaceutically acceptable salt thereof, $R^7$ is C$_{1-6}$ alkyl, wherein the C$_{1-6}$ alkyl is optionally substituted with 1-4 groups independently selected from —OH, halogen, —CN, and C$_{1-6}$ alkoxy. In some embodiments of a compound of Formula I, or a pharmaceutically acceptable salt thereof, $R^7$ is C$_{1-6}$ alkyl, wherein the C$_{1-6}$ alkyl is substituted with 1-4 groups independently selected from —OH, halogen, —CN, and C$_{1-6}$ alkoxy. In some embodiments of a compound of Formula I, or a pharmaceutically acceptable salt thereof, $R^7$ is C$_{1-6}$ alkyl. In some embodiments of a compound of Formula I, or a pharmaceutically acceptable salt thereof, $R^7$ is C$_{1-3}$ alkyl. In some embodiments of a compound of Formula I, or a pharmaceutically acceptable salt thereof, $R^7$ is methyl.

In some embodiments of a compound of Formula I, or a pharmaceutically acceptable salt thereof, $R^7$ is C$_{3-7}$ monocyclic cycloalkyl, wherein the C$_{3-7}$ monocyclic cycloalkyl is optionally substituted with 1-4 groups independently selected from —OH, halogen, —CN, and C$_{1-6}$ alkoxy. In some embodiments of a compound of Formula I, or a pharmaceutically acceptable salt thereof, $R^7$ is C$_{3-7}$ monocyclic cycloalkyl, wherein the C$_{3-7}$ monocyclic cycloalkyl is substituted with 1-4 groups independently selected from —OH, halogen, —CN, and C$_{1-6}$ alkoxy. In some embodiments of a compound of Formula I, or a pharmaceutically acceptable salt thereof, $R^7$ is C$_{3-7}$ monocyclic cycloalkyl.

In some embodiments of a compound of Formula I, or a pharmaceutically acceptable salt thereof, $R^7$ is 4-6 membered monocyclic heterocyclyl, wherein the 4-6 membered monocyclic heterocyclyl is optionally substituted with 1-4 groups independently selected from —OH, halogen, —CN, and C$_{1-6}$ alkoxy. In some embodiments of a compound of Formula I, or a pharmaceutically acceptable salt thereof, $R^7$ is 4-6 membered monocyclic heterocyclyl, wherein the 4-6 membered monocyclic heterocyclyl is substituted with 1-4 groups independently selected from —OH, halogen, —CN, and C$_{1-6}$ alkoxy. In some embodiments of a compound of Formula I, or a pharmaceutically acceptable salt thereof, $R^7$ is 4-6 membered monocyclic heterocyclyl. In some embodiments of a compound of Formula I, or a pharmaceutically acceptable salt thereof, $R^7$ is oxetanyl.

In some embodiments of a compound of Formula I, or a pharmaceutically acceptable salt thereof, Z is —C(O)R$^{13}$.

In some embodiments of a compound of Formula I, or a pharmaceutically acceptable salt thereof, R$^{13}$ is 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl,
  wherein the 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-4 $R^a$ groups.

In some embodiments of a compound of Formula I, or a pharmaceutically acceptable salt thereof, R$^{13}$ is 4-7 membered monocyclic heterocyclyl, 8-10 membered fused bicyclic heterocyclyl, 6-10 membered bridged bicyclic heterocyclyl, or 7-10 membered spirocyclic heterocyclyl,
   wherein the 4-7 membered monocyclic heterocyclyl, 8-10 membered fused bicyclic heterocyclyl, 6-10 membered bridged bicyclic heterocyclyl, and 7-10 membered spirocyclic heterocyclyl are each independently optionally substituted with 1-3 $R^a$ groups.

In some embodiments of a compound of Formula I, or a pharmaceutically acceptable salt thereof, $R^{13}$ is 4-7 membered monocyclic heterocyclyl, 8-10 membered fused bicyclic heterocyclyl, 6-10 membered bridged bicyclic heterocyclyl, or 7-10 membered spirocyclic heterocyclyl,
   wherein the 4-7 membered monocyclic heterocyclyl, 8-10 membered fused bicyclic heterocyclyl, 6-10 membered bridged bicyclic heterocyclyl, and 7-10 membered spirocyclic heterocyclyl are each independently optionally substituted with 1-3 groups independently selected from —OH, halogen, —CN, oxo, —NR$^{11}$R$^{11}$, $C_{1-4}$ alkoxy, and $C_{1-5}$ alkyl,
      wherein the $C_{1-5}$ alkyl is optionally substituted with 1-3 groups independently selected from —OH, halogen, —CN, oxo, and —NR$^{12}$R$^{12}$.

In some embodiments of a compound of Formula I, or a pharmaceutically acceptable salt thereof, $R^{13}$ is 4-7 membered monocyclic heterocyclyl, 8-10 membered fused bicyclic heterocyclyl, 6-10 membered bridged bicyclic heterocyclyl, or 7-10 membered spirocyclic heterocyclyl,
   wherein the 4-7 membered monocyclic heterocyclyl, 8-10 membered fused bicyclic heterocyclyl, 6-10 membered bridged bicyclic heterocyclyl, and 7-10 membered spirocyclic heterocyclyl are each independently optionally substituted with 1-3 groups independently selected from —OH, halogen, —CN, oxo, —NR$^{11}$R$^{11}$, $C_{1-4}$ alkoxy, and $C_{1-5}$ alkyl,
      wherein the $C_{1-5}$ alkyl is optionally substituted with 1-2 groups independently selected from —OH, halogen, —CN, and —NR$^{12}$R$^{12}$, and
      wherein each $R^{12}$ independently is H or $C_{1-3}$ alkyl.

In some embodiments of a compound of Formula I, or a pharmaceutically acceptable salt thereof, $R^{13}$ is 4-7 membered monocyclic heterocyclyl, wherein the 4-7 membered monocyclic heterocyclyl is optionally substituted with 1-4 $R^a$ groups. In some embodiments of a compound of Formula I, or a pharmaceutically acceptable salt thereof, $R^{13}$ is 4-7 membered monocyclic heterocyclyl, wherein the 4-7 membered monocyclic heterocyclyl is optionally substituted with 1-3 $R^a$ groups. In some embodiments of a compound of Formula I, or a pharmaceutically acceptable salt thereof, $R^{13}$ is 4-7 membered monocyclic heterocyclyl, wherein the 4-7 membered monocyclic heterocyclyl is optionally substituted with 1-3 groups independently selected from —OH, halogen, —CN, oxo, —NR$^{11}$R$^{11}$, $C_{1-4}$ alkoxy, and $C_{1-5}$ alkyl, wherein the $C_{1-5}$ alkyl is optionally substituted with 1-3 groups independently selected from —OH, halogen, —CN, oxo, and —NR$^{12}$R$^{12}$. In some embodiments of a compound of Formula I, or a pharmaceutically acceptable salt thereof, $R^{13}$ is 4-7 membered monocyclic heterocyclyl, wherein the 4-7 membered monocyclic heterocyclyl is optionally substituted with 1-3 groups independently selected from —OH, halogen, —CN, oxo, —NR$^{11}$R$^{11}$, $C_{1-4}$ alkoxy, and $C_{1-5}$ alkyl, wherein the $C_{1-5}$ alkyl is optionally substituted with 1-2 groups independently selected from —OH, halogen, —CN, oxo, and —NR$^{12}$R$^{12}$, and wherein each $R^{12}$ independently is H or $C_{1-3}$ alkyl. In some embodiments of a compound of Formula I, or a pharmaceutically acceptable salt thereof, $R^{13}$ is 4-7 membered monocyclic heterocyclyl, wherein the 4-7 membered monocyclic heterocyclyl is optionally substituted with 1-3 groups independently selected from —OH, halogen, —CN, oxo, —NR$^{11}$R$^{11}$, $C_{1-4}$ alkoxy, and $C_{1-5}$ alkyl.

In some embodiments of a compound of Formula I, or a pharmaceutically acceptable salt thereof, $R^{13}$ is 4-7 membered monocyclic heterocyclyl, wherein the 4-7 membered monocyclic heterocyclyl is substituted with 1-4 $R^a$ groups. In some embodiments of a compound of Formula I, or a pharmaceutically acceptable salt thereof, $R^{13}$ is 4-7 membered monocyclic heterocyclyl, wherein the 4-7 membered monocyclic heterocyclyl is substituted with 1-3 $R^a$ groups. In some embodiments of a compound of Formula I, or a pharmaceutically acceptable salt thereof, $R^{13}$ is 4-7 membered monocyclic heterocyclyl, wherein the 4-7 membered monocyclic heterocyclyl is substituted with 1-3 groups independently selected from —OH, halogen, —CN, oxo, —NR$^{11}$R$^{11}$, $C_{1-4}$ alkoxy, and $C_{1-5}$ alkyl, wherein the $C_{1-5}$ alkyl is optionally substituted with 1-3 groups independently selected from —OH, halogen, —CN, oxo, and —NR$^{12}$R$^{12}$. In some embodiments of a compound of Formula I, or a pharmaceutically acceptable salt thereof, $R^{13}$ is 4-7 membered monocyclic heterocyclyl, wherein the 4-7 membered monocyclic heterocyclyl is substituted with 1-3 groups independently selected from —OH, halogen, —CN, oxo, —NR$^{11}$R$^{11}$, $C_{1-4}$ alkoxy, and $C_{1-5}$ alkyl, wherein the $C_{1-5}$ alkyl is optionally substituted with 1-2 groups independently selected from —OH, halogen, —CN, oxo, and —NR$^{12}$R$^{12}$, and wherein each $R^{12}$ independently is H or $C_{1-3}$ alkyl. In some embodiments of a compound of Formula I, or a pharmaceutically acceptable salt thereof, $R^{13}$ is 4-7 membered monocyclic heterocyclyl, wherein the 4-7 membered monocyclic heterocyclyl is substituted with 1-3 groups independently selected from —OH, halogen, —CN, oxo, —NR$^{11}$R$^{11}$, $C_{1-4}$ alkoxy, and $C_{1-5}$ alkyl.

In some embodiments of a compound of Formula I, or a pharmaceutically acceptable salt thereof, $R^{13}$ is 4-7 membered monocyclic heterocyclyl, wherein the 4-7 membered monocyclic heterocyclyl is optionally substituted with 1-3 groups independently selected from —OH, halogen, —CN, oxo, —NR$^{11}$R$^{11}$, $C_{1-4}$ alkoxy, and $C_{1-5}$ alkyl. In some embodiments of a compound of Formula I, or a pharmaceutically acceptable salt thereof, $R^{13}$ is 4-7 membered monocyclic heterocyclyl, wherein the 4-7 membered monocyclic heterocyclyl is substituted with 1-3 groups independently selected from —OH, halogen, —CN, oxo, —NR$^{11}$R$^{11}$, $C_{1-4}$ alkoxy, and $C_{1-5}$ alkyl.

In some embodiments of a compound of Formula I, or a pharmaceutically acceptable salt thereof, $R^{13}$ is 4-7 membered monocyclic heterocyclyl,
   wherein the 4-7 membered monocyclic heterocyclyl is optionally substituted with 1-3 groups independently selected from —OH, halogen, —CN, oxo, —NR$^{11}$R$^{11}$, $C_{1-4}$ alkoxy, and $C_{1-5}$ alkyl, and
   wherein the 4-7 membered monocyclic heterocyclyl has one or two ring heteroatoms that is N.

In some embodiments of a compound of Formula I, or a pharmaceutically acceptable salt thereof, $R^{13}$ is 5-6 membered monocyclic heterocyclyl, wherein the 5-6 membered monocyclic heterocyclyl is optionally substituted with 1-3 groups independently selected from —OH, halogen, —CN, oxo, —NR$^{11}$R$^{11}$, $C_{1-4}$ alkoxy, and $C_{1-5}$ alkyl.

In some embodiments of a compound of Formula I, or a pharmaceutically acceptable salt thereof, $R^{13}$ is 4-7 membered monocyclic heterocyclyl. In some embodiments of a compound of Formula I, or a pharmaceutically acceptable salt thereof, $R^{13}$ is 5-6 membered monocyclic heterocyclyl.

In some embodiments of a compound of Formula I, or a pharmaceutically acceptable salt thereof, $R^{13}$ is piperazinyl.

In some embodiments of a compound of Formula I, or a pharmaceutically acceptable salt thereof, $R^{13}$ is 5-6 membered monocyclic heteroaryl, wherein the 5-6 membered monocyclic heteroaryl is optionally substituted with 1-4 $R^a$ groups. In some embodiments of a compound of Formula I, or a pharmaceutically acceptable salt thereof, $R^{13}$ is 5-6 membered monocyclic heteroaryl, wherein the 5-6 membered monocyclic heteroaryl is substituted with 1-4 $R^a$ groups. In some embodiments of a compound of Formula I, or a pharmaceutically acceptable salt thereof, $R^{13}$ is 5-6 membered monocyclic heteroaryl.

In some embodiments of a compound of Formula I, or a pharmaceutically acceptable salt thereof, $R^{13}$ is 8-10 membered fused bicyclic heterocyclyl, wherein the 8-10 membered fused bicyclic heterocyclyl is optionally substituted with 1-4 $R^a$ groups. In some embodiments of a compound of Formula I, or a pharmaceutically acceptable salt thereof, $R^{13}$ is 8-10 membered fused bicyclic heterocyclyl, wherein the 8-10 membered fused bicyclic heterocyclyl is optionally substituted with 1-3 $R^a$ groups. In some embodiments of a compound of Formula I, or a pharmaceutically acceptable salt thereof, $R^{13}$ is 8-10 membered fused bicyclic heterocyclyl, wherein the 8-10 membered fused bicyclic heterocyclyl is optionally substituted with 1-3 groups independently selected from —OH, halogen, —CN, oxo, —NR$^{11}$R$^{11}$, C$_{1-4}$ alkoxy, and C$_{1-5}$ alkyl, wherein the C$_{1-5}$ alkyl is optionally substituted with 1-3 groups independently selected from —OH, halogen, —CN, oxo, and —NR$^{12}$R$^{12}$. In some embodiments of a compound of Formula I, or a pharmaceutically acceptable salt thereof, $R^{13}$ is 8-10 membered fused bicyclic heterocyclyl, wherein the 8-10 membered fused bicyclic heterocyclyl is optionally substituted with 1-3 groups independently selected from —OH, halogen, —CN, oxo, —NR$^{11}$R$^{11}$, C$_{1-4}$ alkoxy, and C$_{1-5}$ alkyl, wherein the C$_{1-5}$ alkyl is optionally substituted with 1-2 groups independently selected from —OH, halogen, —CN, oxo, and —NR$^{12}$R$^{12}$, and wherein each R$^{12}$ independently is H or C$_{1-3}$ alkyl.

In some embodiments of a compound of Formula I, or a pharmaceutically acceptable salt thereof, $R^{13}$ is 8-10 membered fused bicyclic heterocyclyl, wherein the 8-10 membered fused bicyclic heterocyclyl is substituted with 1-4 $R^a$ groups. In some embodiments of a compound of Formula I, or a pharmaceutically acceptable salt thereof, $R^{13}$ is 8-10 membered fused bicyclic heterocyclyl, wherein the 8-10 membered fused bicyclic heterocyclyl is substituted with 1-3 $R^a$ groups. In some embodiments of a compound of Formula I, or a pharmaceutically acceptable salt thereof, $R^{13}$ is 8-10 membered fused bicyclic heterocyclyl, wherein the 8-10 membered fused bicyclic heterocyclyl is substituted with 1-3 groups independently selected from —OH, halogen, —CN, oxo, —NR$^{11}$R$^{11}$, C$_{1-4}$ alkoxy, and C$_{1-5}$ alkyl, wherein the C$_{1-5}$ alkyl is optionally substituted with 1-3 groups independently selected from —OH, halogen, —CN, oxo, and —NR$^{12}$R$^{12}$. In some embodiments of a compound of Formula I, or a pharmaceutically acceptable salt thereof, $R^{13}$ is 8-10 membered fused bicyclic heterocyclyl, wherein the 8-10 membered fused bicyclic heterocyclyl is substituted with 1-3 groups independently selected from —OH, halogen, —CN, oxo, —NR$^{11}$R$^{11}$, C$_{1-4}$ alkoxy, and C$_{1-5}$ alkyl, wherein the C$_{1-5}$ alkyl is optionally substituted with 1-2 groups independently selected from —OH, halogen, —CN, oxo, and —NR$^{12}$R$^{12}$, and wherein each R$^{12}$ independently is H or C$_{1-3}$ alkyl.

In some embodiments of a compound of Formula I, or a pharmaceutically acceptable salt thereof, $R^{13}$ is 8-10 membered fused bicyclic heterocyclyl.

In some embodiments of a compound of Formula I, or a pharmaceutically acceptable salt thereof, $R^{13}$ is 6-10 membered bridged bicyclic heterocyclyl, wherein the 6-10 membered bridged bicyclic heterocyclyl is optionally substituted with 1-4 $R^a$ groups. In some embodiments of a compound of Formula I, or a pharmaceutically acceptable salt thereof, $R^{13}$ is 6-10 membered bridged bicyclic heterocyclyl, wherein the 6-10 membered bridged bicyclic heterocyclyl is optionally substituted with 1-3 $R^a$ groups. In some embodiments of a compound of Formula I, or a pharmaceutically acceptable salt thereof, $R^{13}$ is 6-10 membered bridged bicyclic heterocyclyl, wherein the 6-10 membered bridged bicyclic heterocyclyl is optionally substituted with 1-3 groups independently selected from —OH, halogen, —CN, oxo, —NR$^{11}$R$^{11}$, C$_{1-4}$ alkoxy, and C$_{1-5}$ alkyl, wherein the C$_{1-5}$ alkyl is optionally substituted with 1-3 groups independently selected from —OH, halogen, —CN, oxo, and —NR$^{12}$R$^{12}$. In some embodiments of a compound of Formula I, or a pharmaceutically acceptable salt thereof, $R^{13}$ is 6-10 membered bridged bicyclic heterocyclyl, wherein the 6-10 membered bridged bicyclic heterocyclyl is optionally substituted with 1-3 groups independently selected from —OH, halogen, —CN, oxo, —NR$^{11}$R$^{11}$, C$_{1-4}$ alkoxy, and C$_{1-5}$ alkyl, wherein the C$_{1-5}$ alkyl is optionally substituted with 1-2 groups independently selected from —OH, halogen, —CN, oxo, and —NR$^{12}$R$^{12}$, and wherein each R$^{12}$ independently is H or C$_{1-3}$ alkyl.

In some embodiments of a compound of Formula I, or a pharmaceutically acceptable salt thereof, $R^{13}$ is 6-10 membered bridged bicyclic heterocyclyl, wherein the 6-10 membered bridged bicyclic heterocyclyl is substituted with 1-4 $R^a$ groups. In some embodiments of a compound of Formula I, or a pharmaceutically acceptable salt thereof, $R^{13}$ is 6-10 membered bridged bicyclic heterocyclyl, wherein the 6-10 membered bridged bicyclic heterocyclyl is substituted with 1-3 $R^a$ groups. In some embodiments of a compound of Formula I, or a pharmaceutically acceptable salt thereof, $R^{13}$ is 6-10 membered bridged bicyclic heterocyclyl, wherein the 6-10 membered bridged bicyclic heterocyclyl is substituted with 1-3 groups independently selected from —OH, halogen, —CN, oxo, —NR$^{11}$R$^{11}$, C$_{1-4}$ alkoxy, and C$_{1-5}$ alkyl, wherein the C$_{1-5}$ alkyl is optionally substituted with 1-3 groups independently selected from —OH, halogen, —CN, oxo, and —NR$^{12}$R$^{12}$. In some embodiments of a compound of Formula I, or a pharmaceutically acceptable salt thereof, $R^{13}$ is 6-10 membered bridged bicyclic heterocyclyl, wherein the 6-10 membered bridged bicyclic heterocyclyl is substituted with 1-3 groups independently selected from —OH, halogen, —CN, oxo, —NR$^{11}$R$^{11}$, C$_{1-4}$ alkoxy, and C$_{1-5}$ alkyl, wherein the C$_{1-5}$ alkyl is optionally substituted with 1-2 groups independently selected from —OH, halogen, —CN, oxo, and —NR$^{12}$R$^{12}$, and wherein each R$^{12}$ independently is H or C$_{1-3}$ alkyl.

In some embodiments of a compound of Formula I, or a pharmaceutically acceptable salt thereof, $R^{13}$ is 6-10 membered bridged bicyclic heterocyclyl.

In some embodiments of a compound of Formula I, or a pharmaceutically acceptable salt thereof, $R^{13}$ is 7-10 membered spirocyclic heterocyclyl, wherein the 7-10 membered spirocyclic heterocyclyl is optionally substituted with 1-4 $R^a$ groups. In some embodiments of a compound of Formula I, or a pharmaceutically acceptable salt thereof, $R^{13}$ is 7-10 membered spirocyclic heterocyclyl, wherein the 7-10 membered spirocyclic heterocyclyl is optionally substituted with 1-3 $R^a$ groups. In some embodiments of a compound of Formula I, or a pharmaceutically acceptable salt thereof, $R^{13}$ is 7-10 membered spirocyclic heterocyclyl, wherein the 7-10 membered spirocyclic heterocyclyl is optionally substituted with 1-3 groups independently selected from —OH, halogen, —CN, oxo, —NR$^{11}$R$^{11}$, C$_{1-4}$ alkoxy, and C$_{1-5}$ alkyl, wherein the C$_{1-5}$ alkyl is optionally substituted with 1-3 groups independently selected from —OH, halogen, —CN, oxo, and —NR$^{12}$R$^{12}$. In some embodiments of a compound of Formula I, or a pharmaceutically acceptable salt thereof, $R^{13}$ is 7-10 membered spirocyclic heterocyclyl, wherein the 7-10 membered spirocyclic heterocyclyl is optionally substituted with 1-3 groups independently selected from —OH, halogen, —CN, oxo, —NR$^{11}$R$^{11}$, C$_{1-4}$ alkoxy, and C$_{1-5}$ alkyl, wherein the C$_{1-5}$ alkyl is optionally substituted with 1-2 groups independently selected from —OH, halogen, —CN, oxo, and —NR$^{12}$R$^{12}$, and wherein each $R^{12}$ independently is H or C$_{1-3}$ alkyl.

In some embodiments of a compound of Formula I, or a pharmaceutically acceptable salt thereof, $R^{13}$ is 7-10 membered spirocyclic heterocyclyl, wherein the 7-10 membered spirocyclic heterocyclyl is substituted with 1-4 $R^a$ groups. In some embodiments of a compound of Formula I, or a pharmaceutically acceptable salt thereof, $R^{13}$ is 7-10 membered spirocyclic heterocyclyl, wherein the 7-10 membered spirocyclic heterocyclyl is substituted with 1-3 $R^a$ groups. In some embodiments of a compound of Formula I, or a pharmaceutically acceptable salt thereof, $R^{13}$ is 7-10 membered spirocyclic heterocyclyl, wherein the 7-10 membered spirocyclic heterocyclyl is substituted with 1-3 groups independently selected from —OH, halogen, —CN, oxo, —NR$^{11}$R$^{11}$, C$_{1-4}$ alkoxy, and C$_{1-5}$ alkyl, wherein the C$_{1-5}$ alkyl is optionally substituted with 1-3 groups independently selected from —OH, halogen, —CN, oxo, and —NR$^{12}$R$^{12}$. In some embodiments of a compound of Formula I, or a pharmaceutically acceptable salt thereof, $R^{13}$ is 7-10 membered spirocyclic heterocyclyl, wherein the 7-10 membered spirocyclic heterocyclyl is substituted with 1-3 groups independently selected from —OH, halogen, —CN, oxo, —NR$^{11}$R$^{11}$, C$_{1-4}$ alkoxy, and C$_{1-5}$ alkyl, wherein the C$_{1-5}$ alkyl is optionally substituted with 1-2 groups independently selected from —OH, halogen, —CN, oxo, and —NR$^{12}$R$^{12}$, and wherein each $R^{12}$ independently is H or C$_{1-3}$ alkyl.

In some embodiments of a compound of Formula I, or a pharmaceutically acceptable salt thereof, $R^{13}$ is 7-10 membered spirocyclic heterocyclyl.

In some embodiments of a compound of Formula I, or a pharmaceutically acceptable salt thereof, each $R^5$ independently is H, C$_{1-6}$ alkyl, C$_{2-6}$ alkenyl, C$_{2-6}$ alkynyl, C$_{3-7}$ monocyclic cycloalkyl, C$_{7-10}$ fused bicyclic cycloalkyl, C$_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl,
wherein the C$_{1-6}$ alkyl, C$_{2-6}$ alkenyl, and C$_{2-6}$ alkynyl are each independently optionally substituted with 1-4 $R^b$ groups,
wherein the C$_{3-7}$ monocyclic cycloalkyl, C$_{7-10}$ fused bicyclic cycloalkyl, C$_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-4 $R^a$ groups.

In some embodiments of a compound of Formula I, or a pharmaceutically acceptable salt thereof, one or more $R^5$ is H. In some embodiments of a compound of Formula I, or a pharmaceutically acceptable salt thereof, one or more $R^5$ is C$_{1-6}$ alkyl, wherein the C$_{1-6}$ alkyl is optionally substituted with 1-4 $R^b$ groups. In some embodiments of a compound of Formula I, or a pharmaceutically acceptable salt thereof, one or more $R^5$ is C$_{2-6}$ alkenyl, wherein the C$_{2-6}$ alkenyl is optionally substituted with 1-4 $R^b$ groups. In some embodiments of a compound of Formula I, or a pharmaceutically acceptable salt thereof, one or more $R^5$ is C$_{2-6}$ alkynyl, wherein the C$_{2-6}$ alkynyl is optionally substituted with 1-4 $R^b$ groups. In some embodiments of a compound of Formula I, or a pharmaceutically acceptable salt thereof, one or more $R^5$ is C$_{3-7}$ monocyclic cycloalkyl, wherein the C$_{3-7}$ monocyclic cycloalkyl is optionally substituted with 1-4 $R^a$ groups. In some embodiments of a compound of Formula I, or a pharmaceutically acceptable salt thereof, one or more $R^5$ is C$_{7-10}$ fused bicyclic cycloalkyl, wherein the C$_{7-10}$ fused bicyclic cycloalkyl is optionally substituted with 1-4 $R^a$ groups. In some embodiments of a compound of Formula I, or a pharmaceutically acceptable salt thereof, one or more $R^5$ is C$_{5-10}$ bridged bicyclic cycloalkyl, wherein the C$_{5-10}$ bridged bicyclic cycloalkyl is optionally substituted with 1-4 $R^a$ groups. In some embodiments of a compound of Formula I, or a pharmaceutically acceptable salt thereof, one or more $R^5$ is phenyl, wherein the phenyl is optionally substituted with 1-4 $R^a$ groups. In some embodiments of a compound of Formula I, or a pharmaceutically acceptable salt thereof, one or more $R^5$ is naphthalenyl, wherein the naphthalenyl is optionally substituted with 1-4 $R^a$ groups. In some embodiments of a compound of Formula I, or a pharmaceutically acceptable salt thereof, one or more $R^5$ is 4-7 membered monocyclic heterocyclyl, wherein the 4-7 membered monocyclic heterocyclyl is optionally substituted with 1-4 $R^a$ groups. In some embodiments of a compound of Formula I, or a pharmaceutically acceptable salt thereof, one or more $R^5$ is 5-6 membered monocyclic heteroaryl, wherein the 5-6 membered monocyclic heteroaryl is optionally substituted with 1-4 $R^a$ groups. In some embodiments of a compound of Formula I, or a pharmaceutically acceptable salt thereof, one or more $R^5$ is 8-10 membered fused bicyclic heterocyclyl, wherein the 8-10 membered fused bicyclic heterocyclyl is optionally substituted with 1-4 $R^a$ groups. In some embodiments of a compound of Formula I, or a pharmaceutically acceptable salt thereof, one or more $R^5$ is 6-10 membered bridged bicyclic heterocyclyl, wherein the 6-10 membered bridged bicyclic heterocyclyl is optionally substituted with 1-4 $R^a$ groups. In some embodiments of a compound of Formula I, or a pharmaceutically acceptable salt thereof, one or more $R^5$ is 8-10 membered fused bicyclic heteroaryl, wherein the 8-10 membered fused bicyclic heteroaryl is optionally substituted with 1-4 $R^a$ groups. In some embodiments of a compound of Formula I, or a pharmaceutically acceptable salt thereof, one or more $R^5$ is 7-10 membered spirocyclic heterocyclyl, wherein the 7-10 membered spirocyclic heterocyclyl is optionally substituted with 1-4 $R^a$ groups.

In some embodiments of a compound of Formula I, or a pharmaceutically acceptable salt thereof, each $R^{10}$ independently is H, C$_{1-6}$ alkyl, C$_{2-6}$ alkenyl, C$_{2-6}$ alkynyl, C$_{3-7}$ monocyclic cycloalkyl, C$_{7-10}$ fused bicyclic cycloalkyl, C$_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl,
wherein the $C_{1-6}$ alkyl, $C_{2-6}$ alkenyl, and $C_{2-6}$ alkynyl are each independently optionally substituted with 1-4 $R^b$ groups,
wherein the $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-4 $R^a$ groups.

In some embodiments of a compound of Formula I, or a pharmaceutically acceptable salt thereof, each $R^{10}$ independently is H or $C_{1-6}$ alkyl. In some embodiments of a compound of Formula I, or a pharmaceutically acceptable salt thereof, each $R^{10}$ independently is H or $C_{1-3}$ alkyl.

In some embodiments of a compound of Formula I, or a pharmaceutically acceptable salt thereof, one or both $R^{10}$ is H. In some embodiments of a compound of Formula I, or a pharmaceutically acceptable salt thereof, one or both $R^{10}$ is $C_{1-6}$ alkyl, wherein the $C_{1-6}$ alkyl is optionally substituted with 1-4 $R^b$ groups. In some embodiments of a compound of Formula I, or a pharmaceutically acceptable salt thereof, one or both $R^{10}$ is $C_{1-3}$ alkyl, wherein the $C_{1-3}$ alkyl is optionally substituted with 1-4 $R^b$ groups. In some embodiments of a compound of Formula I, or a pharmaceutically acceptable salt thereof, one or both $R^{10}$ is $C_{1-3}$ alkyl. In some embodiments of a compound of Formula I, or a pharmaceutically acceptable salt thereof, one or both $R^{10}$ is $C_{2-6}$ alkenyl, wherein the $C_{2-6}$ alkenyl is optionally substituted with 1-4 $R^b$ groups. In some embodiments of a compound of Formula I, or a pharmaceutically acceptable salt thereof, one or both $R^{10}$ is $C_{2-6}$ alkynyl, wherein the $C_{2-6}$ alkynyl is optionally substituted with 1-4 $R^b$ groups. In some embodiments of a compound of Formula I, or a pharmaceutically acceptable salt thereof, one or both $R^{10}$ is $C_{3-7}$ monocyclic cycloalkyl, wherein the $C_{3-7}$ monocyclic cycloalkyl is optionally substituted with 1-4 $R^a$ groups. In some embodiments of a compound of Formula I, or a pharmaceutically acceptable salt thereof, one or both $R^{10}$ is $C_{7-10}$ fused bicyclic cycloalkyl, wherein the $C_{7-10}$ fused bicyclic cycloalkyl is optionally substituted with 1-4 $R^a$ groups. In some embodiments of a compound of Formula I, or a pharmaceutically acceptable salt thereof, one or both $R^{10}$ is $C_{5-10}$ bridged bicyclic cycloalkyl, wherein the $C_{5-10}$ bridged bicyclic cycloalkyl is optionally substituted with 1-4 $R^a$ groups. In some embodiments of a compound of Formula I, or a pharmaceutically acceptable salt thereof, one or both $R^{10}$ is phenyl, wherein the phenyl is optionally substituted with 1-4 $R^a$ groups. In some embodiments of a compound of Formula I, or a pharmaceutically acceptable salt thereof, one or both $R^{10}$ is naphthalenyl, wherein the naphthalenyl is optionally substituted with 1-4 $R^a$ groups. In some embodiments of a compound of Formula I, or a pharmaceutically acceptable salt thereof, one or both $R^{10}$ is 4-7 membered monocyclic heterocyclyl, wherein the 4-7 membered monocyclic heterocyclyl is optionally substituted with 1-4 $R^a$ groups. In some embodiments of a compound of Formula I, or a pharmaceutically acceptable salt thereof, one or both $R^{10}$ is 5-6 membered monocyclic heteroaryl, wherein the 5-6 membered monocyclic heteroaryl is optionally substituted with 1-4 $R^a$ groups. In some embodiments of a compound of Formula I, or a pharmaceutically acceptable salt thereof, one or both $R^{10}$ is 8-10 membered fused bicyclic heterocyclyl, wherein the 8-10 membered fused bicyclic heterocyclyl is optionally substituted with 1-4 $R^a$ groups. In some embodiments of a compound of Formula I, or a pharmaceutically acceptable salt thereof, one or both $R^{10}$ is 6-10 membered bridged bicyclic heterocyclyl, wherein the 6-10 membered bridged bicyclic heterocyclyl is optionally substituted with 1-4 $R^a$ groups. In some embodiments of a compound of Formula I, or a pharmaceutically acceptable salt thereof, one or both $R^{10}$ is 8-10 membered fused bicyclic heteroaryl, wherein the 8-10 membered fused bicyclic heteroaryl is optionally substituted with 1-4 $R^a$ groups. In some embodiments of a compound of Formula I, or a pharmaceutically acceptable salt thereof, one or both $R^{10}$ is 7-10 membered spirocyclic heterocyclyl, wherein the 7-10 membered spirocyclic heterocyclyl is optionally substituted with 1-4 $R^a$ groups.

In some embodiments of a compound of Formula I, or a pharmaceutically acceptable salt thereof, each $R^{5a}$ independently is $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl,
wherein the $C_{1-6}$ alkyl, $C_{2-6}$ alkenyl, and $C_{2-6}$ alkynyl are each independently optionally substituted with 1-4 $R^b$ groups,
wherein the $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-4 $R^a$ groups.

In some embodiments of a compound of Formula I, or a pharmaceutically acceptable salt thereof, one or more $R^{5a}$ is $C_{1-6}$ alkyl, wherein the $C_{1-6}$ alkyl is optionally substituted with 1-4 $R^b$ groups. In some embodiments of a compound of Formula I, or a pharmaceutically acceptable salt thereof, one or more $R^{5a}$ is $C_{2-6}$ alkenyl, wherein the $C_{2-6}$ alkenyl is optionally substituted with 1-4 $R^b$ groups. In some embodiments of a compound of Formula I, or a pharmaceutically acceptable salt thereof, one or more $R^{5a}$ is $C_{2-6}$ alkynyl, wherein the $C_{2-6}$ alkynyl is optionally substituted with 1-4 $R^b$ groups. In some embodiments of a compound of Formula I, or a pharmaceutically acceptable salt thereof, one or more $R^{5a}$ is $C_{3-7}$ monocyclic cycloalkyl, wherein the $C_{3-7}$ monocyclic cycloalkyl is optionally substituted with 1-4 $R^a$ groups. In some embodiments of a compound of Formula I, or a pharmaceutically acceptable salt thereof, one or more $R^{5a}$ is $C_{7-10}$ fused bicyclic cycloalkyl, wherein the $C_{7-10}$ fused bicyclic cycloalkyl is optionally substituted with 1-4 $R^a$ groups. In some embodiments of a compound of Formula I, or a pharmaceutically acceptable salt thereof, one or more $R^{5a}$ is $C_{5-10}$ bridged bicyclic cycloalkyl, wherein the $C_{5-10}$ bridged bicyclic cycloalkyl is optionally substituted with 1-4 $R^a$ groups. In some embodiments of a compound of Formula I, or a pharmaceutically acceptable salt thereof, one or more $R^{5a}$ is phenyl, wherein the phenyl is optionally substituted with 1-4 $R^a$ groups. In some embodiments of a compound of Formula I, or a pharmaceutically acceptable salt thereof, one or more $R^{5a}$ is naphthalenyl, wherein the naphthalenyl is optionally substituted with 1-4 $R^a$ groups. In some embodiments of a compound of Formula I, or a pharmaceutically acceptable salt thereof, one or more $R^{5a}$ is 4-7 membered monocyclic heterocyclyl, wherein the 4-7 membered monocyclic heterocyclyl is optionally substituted with 1-4 $R^a$ groups. In some embodiments of a compound of Formula I, or a pharmaceutically acceptable salt thereof, one or more $R^{5a}$ is 5-6 membered monocyclic heteroaryl, wherein the 5-6 membered monocyclic heteroaryl is optionally substituted with 1-4 $R^a$ groups. In some embodiments of a compound of Formula I, or a pharmaceutically acceptable salt thereof, one or more $R^{5a}$ is 8-10 membered fused bicyclic heterocyclyl, wherein the 8-10 membered fused bicyclic heterocyclyl is optionally substituted with 1-4 $R^a$ groups. In some embodiments of a compound of Formula I, or a pharmaceutically acceptable salt thereof, one or more $R^{5a}$ is 6-10 membered bridged bicyclic heterocyclyl, wherein the 6-10 membered bridged bicyclic heterocyclyl is optionally substituted with 1-4 $R^a$ groups. In some embodiments of a compound of Formula I, or a pharmaceutically acceptable salt thereof, one or more $R^{5a}$ is 8-10 membered fused bicyclic heteroaryl, wherein the 8-10 membered fused bicyclic heteroaryl is optionally substituted with 1-4 $R^a$ groups. In some embodiments of a compound of Formula I, or a pharmaceutically acceptable salt thereof, one or more $R^{5a}$ is 7-10 membered spirocyclic heterocyclyl, wherein the 7-10 membered spirocyclic heterocyclyl is optionally substituted with 1-4 $R^a$ groups.

In some embodiments of a compound of Formula I, or a pharmaceutically acceptable salt thereof, each $R^a$ independently is oxo, imino, halogen, $-NO_2$, $-N_3$, $-CN$, $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, 7-10 membered spirocyclic heterocyclyl, $-OR^{11}$, $-C(O)R^{11}$, $-C(O)OR^{11}$, $-C(O)N(R^{11})(R^{11})$, $-NR^{11}R^{11}$, $-N(R^{11})_2(R^{11})^+$, $-N(R^{11})C(O)R^{11}$, $-N(R^{11})C(O)OR^{11}$, $-N(R^{11})C(O)N(R^{11})(R^{11})$, $-N(R^{11})S(O)_2(R^{11a})$, $-NR^{11}S(O)_2N(R^{11})(R^{11})$, $-NR^{11}S(O)_2O(R^{11a})$, $-OC(O)R^{11}$, $-OC(O)OR^{11}$, $-OC(O)N(R^{11})(R^{11})$, $-SR^{11}$, $-S(O)R^{11a}$, $-S(O)(NH)R^{11}$, $-S(O)_2R^{11a}$, $-S(O)_2N(R^{11})(R^{11})$, or $-N=S(R^{11a})(R^{11a})=O$,
- wherein the $C_{1-6}$ alkyl, $C_{2-6}$ alkenyl, and $C_{2-6}$ alkynyl are each independently optionally substituted with 1-3 $R^c$ groups, and
- wherein the $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-3 $R^d$ groups.

In some embodiments of a compound of Formula I or II, or a pharmaceutically acceptable salt thereof, each $R^a$ independently is $-OH$, halogen, $-CN$, oxo, $-NR^{11}R^{11}$, $C_{1-4}$ alkoxy, or $C_{1-5}$ alkyl. In some embodiments of a compound of Formula I, or a pharmaceutically acceptable salt thereof, each $R^a$ independently is $-OH$, halogen, $-CN$, oxo, $-NR^{11}R^{11}$, $C_{1-3}$ alkoxy, or $C_{1-3}$ alkyl.

In some embodiments of a compound of Formula I, or a pharmaceutically acceptable salt thereof, one or more $R^a$ is oxo. In some embodiments of a compound of Formula I, or a pharmaceutically acceptable salt thereof, one or more $R^a$ is imino. In some embodiments of a compound of Formula I, or a pharmaceutically acceptable salt thereof, one or more $R^a$ is halogen. In some embodiments of a compound of Formula I, or a pharmaceutically acceptable salt thereof, one or more $R^a$ is $-NO_2$. In some embodiments of a compound of Formula I, or a pharmaceutically acceptable salt thereof, one or more $R^a$ is $-N_3$. In some embodiments of a compound of Formula I, or a pharmaceutically acceptable salt thereof, one or more $R^a$ is $-CN$. In some embodiments of a compound of Formula I, or a pharmaceutically acceptable salt thereof, one or more $R^a$ is $-OR^{11}$. In some embodiments of a compound of Formula I, or a pharmaceutically acceptable salt thereof, one or more $R^a$ is $-C(O)R^{11}$. In some embodiments of a compound of Formula I, or a pharmaceutically acceptable salt thereof, one or more $R^a$ is $-C(O)OR^{11}$. In some embodiments of a compound of Formula I, or a pharmaceutically acceptable salt thereof, one or more $R^a$ is $-C(O)N(R^{11})(R^{11})$. In some embodiments of a compound of Formula I, or a pharmaceutically acceptable salt thereof, one or more $R^a$ is $-NR^{11}R^{11}$. In some embodiments of a compound of Formula I, or a pharmaceutically acceptable salt thereof, one or more $R^a$ is $-N(R^{11})_2(R^{11})$. In some embodiments of a compound of Formula I, or a pharmaceutically acceptable salt thereof, one or more $R^a$ is $-N(R^{11})C(O)R^{11}$. In some embodiments of a compound of Formula I, or a pharmaceutically acceptable salt thereof, one or more $R^a$ is $-N(R^{11})C(O)OR^{11}$. In some embodiments of a compound of Formula I, or a pharmaceutically acceptable salt thereof, one or more $R^a$ is $-N(R^{11})C(O)N(R^{11})(R^{11})$. In some embodiments of a compound of Formula I, or a pharmaceutically acceptable salt thereof, one or more $R^a$ is $-N(R^{11})S(O)_2(R^{11a})$. In some embodiments of a compound of Formula I, or a pharmaceutically acceptable salt thereof, one or more $R^a$ is $-NR^{11}S(O)_2N(R^{11})(R^{11})$. In some embodiments of a compound of Formula I, or a pharmaceutically acceptable salt thereof, one or more $R^a$ is $-NR^{11}S(O)_2O(R^{11a})$. In some embodiments of a compound of Formula I, or a pharmaceutically acceptable salt thereof, one or more $R^a$ is $-OC(O)R^{11}$. In some embodiments of a compound of Formula I, or a pharmaceutically acceptable salt thereof, one or more $R^a$ is $-OC(O)OR^{11}$. In some embodiments of a compound of Formula I, or a pharmaceutically acceptable salt thereof, one or more $R^a$ is $-OC(O)N(R^{11})(R^{11})$. In some embodiments of a compound of Formula I, or a pharmaceutically acceptable salt thereof, one or more $R^a$ is $-SR^{11}$. In some embodiments of a compound of Formula I, or a pharmaceutically acceptable salt thereof, one or more $R^a$ is $-S(O)R^{11a}$. In some embodiments of a compound of Formula I, or a pharmaceutically acceptable salt thereof, one or more $R^a$ is $-S(O)(NH)R^{11}$. In some embodiments of a compound of Formula I, or a pharmaceutically acceptable salt thereof, one or more $R^a$ is $-S(O)_2R^{11a}$. In some embodiments of a compound of Formula I, or a pharmaceutically acceptable salt thereof, one or more $R^a$ is $-S(O)_2N(R^{11})(R^{11})$. In some embodiments of a compound of Formula I, or a pharmaceutically acceptable salt thereof, one or more $R^a$ is $-N=S(R^{11a})(R^{11a})=O$.

In some embodiments of a compound of Formula I, or a pharmaceutically acceptable salt thereof, one or more $R^a$ is $C_{1-6}$ alkyl, wherein the $C_{1-6}$ alkyl is optionally substituted with 1-3 $R^c$ groups. In some embodiments of a compound of Formula I, or a pharmaceutically acceptable salt thereof, one or more $R^a$ is $C_{2-6}$ alkenyl, wherein the $C_{2-6}$ alkenyl is optionally substituted with 1-3 $R^c$ groups. In some embodiments of a compound of Formula I, or a pharmaceutically acceptable salt thereof, one or more $R^a$ is $C_{2-6}$ alkynyl, wherein the $C_{2-6}$ alkynyl is optionally substituted with 1-3 $R^c$ groups.

In some embodiments of a compound of Formula I, or a pharmaceutically acceptable salt thereof, one or more $R^a$ is $C_{3-7}$ monocyclic cycloalkyl, wherein the $C_{3-7}$ monocyclic cycloalkyl is optionally substituted with 1-3 $R^d$ groups. In some embodiments of a compound of Formula I, or a pharmaceutically acceptable salt thereof, one or more $R^a$ is $C_{7-10}$ fused bicyclic cycloalkyl, wherein the $C_{7-10}$ fused bicyclic cycloalkyl is optionally substituted with 1-3 $R^d$ groups. In some embodiments of a compound of Formula I, or a pharmaceutically acceptable salt thereof, one or more $R^a$ is $C_{5-10}$ bridged bicyclic cycloalkyl, wherein the $C_{5-10}$ bridged bicyclic cycloalkyl is optionally substituted with 1-3 $R^d$ groups. In some embodiments of a compound of Formula I, or a pharmaceutically acceptable salt thereof, one or more $R^a$ is phenyl, wherein the phenyl is optionally substituted with 1-3 $R^d$ groups. In some embodiments of a compound of Formula I, or a pharmaceutically acceptable salt thereof, one or more $R^a$ is naphthalenyl, wherein the naphthalenyl is optionally substituted with 1-3 $R^d$ groups. In some embodiments of a compound of Formula I, or a pharmaceutically acceptable salt thereof, one or more $R^a$ is 4-7 membered monocyclic heterocyclyl, wherein the 4-7 membered monocyclic heterocyclyl is optionally substituted with 1-3 $R^d$ groups. In some embodiments of a compound of Formula I, or a pharmaceutically acceptable salt thereof, one or more $R^a$ is 5-6 membered monocyclic heteroaryl, wherein the 5-6 membered monocyclic heteroaryl is optionally substituted with 1-3 $R^d$ groups. In some embodiments of a compound of Formula I, or a pharmaceutically acceptable salt thereof, one or more $R^a$ is 8-10 membered fused bicyclic heterocyclyl, wherein the 8-10 membered fused bicyclic heterocyclyl is optionally substituted with 1-3 $R^d$ groups. In some embodiments of a compound of Formula I, or a pharmaceutically acceptable salt thereof, one or more $R^a$ is 6-10 membered bridged bicyclic heterocyclyl, wherein the 6-10 membered bridged bicyclic heterocyclyl is optionally substituted with 1-3 $R^d$ groups. In some embodiments of a compound of Formula I, or a pharmaceutically acceptable salt thereof, one or more $R^a$ is 8-10 membered fused bicyclic heteroaryl, wherein the 8-10 membered fused bicyclic heteroaryl is optionally substituted with 1-3 $R^d$ groups. In some embodiments of a compound of Formula I, or a pharmaceutically acceptable salt thereof, one or more $R^a$ is 7-10 membered spirocyclic heterocyclyl, wherein the 7-10 membered spirocyclic heterocyclyl is optionally substituted with 1-3 $R^d$ groups.

In some embodiments of a compound of Formula I, or a pharmaceutically acceptable salt thereof, each $R^b$ independently is oxo, imino, halogen, —$NO_2$, —$N_3$, —CN, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, 7-10 membered spirocyclic heterocyclyl, —$OR^{11}$, —$C(O)R^{11}$, —$C(O)OR^{11}$, —$C(O)N(R^{11})(R^{11})$, —$NR^{11}R^{11}$, —$N(R^{11})_2(R^{11})^+$, —$N(R^{11})C(O)R^{11}$, —$N(R^{11})C(O)OR^{11}$, —$N(R^{11})C(O)N(R^{11})(R^{11})$, —$N(R^{11})S(O)_2(R^{11a})$, —$NR^{11}S(O)_2N(R^{11})(R^{11})$, —$NR^{11}S(O)_2O(R^{11a})$, —$OC(O)R^{11}$, —$OC(O)OR^{11}$, —$OC(O)N(R^{11})(R^{11})$, —$SR^{11}$, —$S(O)R^{11a}$, —$S(O)(NH)R^{11}$, —$S(O)_2R^{11a}$, —$S(O)_2N(R^{11})(R^{11})$, or —$N=S(R^{11a})(R^{11a})=O$, wherein the $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-3 $R^d$ groups.

In some embodiments of a compound of Formula I, or a pharmaceutically acceptable salt thereof, each $R^b$ independently is —OH, halogen, —CN, oxo, —$NR^{11}R^{11}$, $C_{1-4}$ alkoxy, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 8-10 membered bridged bicyclic heterocyclyl, 6-10 membered bridged bicyclic heterocyclyl, 8-10 membered fused bicyclic heteroaryl, or 7-10 membered spirocyclic heterocyclyl.

In some embodiments of a compound of Formula I, or a pharmaceutically acceptable salt thereof, each $R^b$ independently is —OH, halogen, —CN, oxo, —$NR^{11}R^{11}$, —$C(O)N(R^{11})(R^{11})$, $C_{1-4}$ alkoxy, or 4-7 membered monocyclic heterocyclyl. In some embodiments of a compound of Formula I, or a pharmaceutically acceptable salt thereof, each $R^b$ independently is —OH, halogen, —CN, oxo, —$NR^{11}R^{11}$, or $C_{1-4}$ alkoxy. In some embodiments of a compound of Formula I, or a pharmaceutically acceptable salt thereof, each $R^b$ independently is —OH, halogen, —CN, oxo, —$NR^{11}R^{11}$, or $C_{1-3}$ alkoxy. In some embodiments of a compound of Formula I, or a pharmaceutically acceptable salt thereof, each $R^b$ independently is halogen or $C_{1-3}$ alkoxy.

In some embodiments of a compound of Formula I, or a pharmaceutically acceptable salt thereof, each $R^b$ independently is 4-7 membered monocyclic heterocyclyl, 8-10 membered fused bicyclic heterocyclyl, or 6-10 membered bridged bicyclic heterocyclyl. In some embodiments of a compound of Formula I, or a pharmaceutically acceptable salt thereof, one or more $R^b$ is 4-7 membered monocyclic heterocyclyl. In some embodiments of a compound of Formula I, or a pharmaceutically acceptable salt thereof, one or more $R^b$ is 5-7 membered monocyclic heterocyclyl. In some embodiments of a compound of Formula I, or a pharmaceutically acceptable salt thereof, one or more $R^b$ is 8-10 membered fused bicyclic heterocyclyl. In some embodiments of a compound of Formula I, or a pharmaceutically acceptable salt thereof, one or more $R^b$ is 6-10 membered bridged bicyclic heterocyclyl.

In some embodiments of a compound of Formula I, or a pharmaceutically acceptable salt thereof, one or more $R^b$ is oxo. In some embodiments of a compound of Formula I, or a pharmaceutically acceptable salt thereof, one or more $R^b$ is imino. In some embodiments of a compound of Formula I, or a pharmaceutically acceptable salt thereof, one or more $R^b$ is halogen. In some embodiments of a compound of Formula I, or a pharmaceutically acceptable salt thereof, one or more $R^b$ is —$NO_2$. In some embodiments of a compound of Formula I, or a pharmaceutically acceptable salt thereof, one or more $R^b$ is —$N_3$. In some embodiments of a compound of Formula I, or a pharmaceutically acceptable salt thereof, one or more $R^b$ is —CN. In some embodiments of a compound of Formula I, or a pharmaceutically acceptable salt thereof, one or more $R^b$ is —$OR^{11}$. In some embodiments of a compound of Formula I, or a pharmaceutically acceptable salt thereof, one or more $R^b$ is —$C(O)R^{11}$. In some embodiments of a compound of Formula I, or a pharmaceutically acceptable salt thereof, one or more $R^b$ is —C(O)OR$^{11}$. In some embodiments of a compound of Formula I, or a pharmaceutically acceptable salt thereof, one or more $R^b$ is —C(O)N(R$^{11}$)(R$^{11}$). In some embodiments of a compound of Formula I, or a pharmaceutically acceptable salt thereof, one or more $R^b$ is —NR$^{11}$R$^{11}$. In some embodiments of a compound of Formula I, or a pharmaceutically acceptable salt thereof, one or more $R^b$ is —N(R$^{11}$)$_2$(R$^{11}$). In some embodiments of a compound of Formula I, or a pharmaceutically acceptable salt thereof, one or more $R^b$ is —N(R$^{11}$)C(O)R$^{11}$. In some embodiments of a compound of Formula I, or a pharmaceutically acceptable salt thereof, one or more $R^b$ is —N(R$^{11}$)C(O)OR$^{11}$. In some embodiments of a compound of Formula I, or a pharmaceutically acceptable salt thereof, one or more $R^b$ is —N(R$^{11}$)C(O)N(R$^1$)(R$^{11}$). In some embodiments of a compound of Formula I, or a pharmaceutically acceptable salt thereof, one or more $R^b$ is —N(R$^{11}$)S(O)$_2$(R$^{11a}$). In some embodiments of a compound of Formula I, or a pharmaceutically acceptable salt thereof, one or more $R^b$ is —NR$^{11}$S(O)$_2$N(R$^{11}$)(R$^{11}$). In some embodiments of a compound of Formula I, or a pharmaceutically acceptable salt thereof, one or more $R^b$ is —NR$^{11}$S(O)$_2$O(R$^{11a}$). In some embodiments of a compound of Formula I, or a pharmaceutically acceptable salt thereof, one or more $R^b$ is —OC(O)R$^{11}$. In some embodiments of a compound of Formula I, or a pharmaceutically acceptable salt thereof, one or more $R^b$ is —OC(O)OR$^{11}$. In some embodiments of a compound of Formula I, or a pharmaceutically acceptable salt thereof, one or more $R^b$ is —OC(O)N(R$^{11}$)(R$^{11}$). In some embodiments of a compound of Formula I, or a pharmaceutically acceptable salt thereof, one or more $R^b$ is —SR$^{11}$. In some embodiments of a compound of Formula I, or a pharmaceutically acceptable salt thereof, one or more $R^b$ is —S(O)R$^{11a}$. In some embodiments of a compound of Formula I, or a pharmaceutically acceptable salt thereof, one or more $R^b$ is —S(O)(NH)R$^{11}$. In some embodiments of a compound of Formula I, or a pharmaceutically acceptable salt thereof, one or more $R^b$ is —S(O)$_2$R$^{11a}$. In some embodiments of a compound of Formula I, or a pharmaceutically acceptable salt thereof, one or more $R^b$ is —S(O)$_2$N(R$^{11}$)(R$^{11}$). In some embodiments of a compound of Formula I, or a pharmaceutically acceptable salt thereof, one or more $R^b$ is —N=S(R$^{11a}$)(R$^{11a}$)=O.

In some embodiments of a compound of Formula I, or a pharmaceutically acceptable salt thereof, one or more $R^b$ is $C_{3-7}$ monocyclic cycloalkyl, wherein the $C_{3-7}$ monocyclic cycloalkyl is optionally substituted with 1-3 $R^d$ groups. In some embodiments of a compound of Formula I, or a pharmaceutically acceptable salt thereof, one or more $R^b$ is $C_{7-10}$ fused bicyclic cycloalkyl, wherein the $C_{7-10}$ fused bicyclic cycloalkyl is optionally substituted with 1-3 $R^d$ groups. In some embodiments of a compound of Formula I, or a pharmaceutically acceptable salt thereof, one or more $R^b$ is $C_{5-10}$ bridged bicyclic cycloalkyl, wherein the $C_{5-10}$ bridged bicyclic cycloalkyl is optionally substituted with 1-3 $R^d$ groups. In some embodiments of a compound of Formula I, or a pharmaceutically acceptable salt thereof, one or more $R^b$ is phenyl, wherein the phenyl is optionally substituted with 1-3 $R^d$ groups. In some embodiments of a compound of Formula I, or a pharmaceutically acceptable salt thereof, one or more $R^b$ is naphthalenyl, wherein the naphthalenyl is optionally substituted with 1-3 $R^d$ groups. In some embodiments of a compound of Formula I, or a pharmaceutically acceptable salt thereof, one or more $R^b$ is 4-7 membered monocyclic heterocyclyl, wherein the 4-7 membered monocyclic heterocyclyl is optionally substituted with 1-3 $R^d$ groups. In some embodiments of a compound of Formula I, or a pharmaceutically acceptable salt thereof, one or more $R^b$ is 5-6 membered monocyclic heteroaryl, wherein the 5-6 membered monocyclic heteroaryl is optionally substituted with 1-3 $R^d$ groups. In some embodiments of a compound of Formula I, or a pharmaceutically acceptable salt thereof, one or more $R^b$ is 8-10 membered fused bicyclic heterocyclyl, wherein the 8-10 membered fused bicyclic heterocyclyl is optionally substituted with 1-3 $R^d$ groups. In some embodiments of a compound of Formula I, or a pharmaceutically acceptable salt thereof, one or more $R^b$ is 6-10 membered bridged bicyclic heterocyclyl, wherein the 6-10 membered bridged bicyclic heterocyclyl is optionally substituted with 1-3 $R^d$ groups. In some embodiments of a compound of Formula I, or a pharmaceutically acceptable salt thereof, one or more $R^b$ is 8-10 membered fused bicyclic heteroaryl, wherein the 8-10 membered fused bicyclic heteroaryl is optionally substituted with 1-3 $R^d$ groups. In some embodiments of a compound of Formula I, or a pharmaceutically acceptable salt thereof, one or more $R^b$ is 7-10 membered spirocyclic heterocyclyl, wherein the 7-10 membered spirocyclic heterocyclyl is optionally substituted with 1-3 $R^d$ groups.

In some embodiments of a compound of Formula I, or a pharmaceutically acceptable salt thereof, each $R^c$ independently is halogen, —CN, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, 7-10 membered spirocyclic heterocyclyl, —OR$^{12}$, —C(O)R$^{12}$, —C(O)OR$^{12}$, —C(O)N(R$^{12}$)(R$^{12}$), —NR$^{12}$R$^{12}$, —N(R$^{12}$)$_2$(R$^{12}$)$^+$, —N(R$^{12}$)C(O)R$^{12}$, —N(R$^{12}$)C(O)OR$^{12}$, —N(R$^{12}$)C(O)N(R$^{12}$)(R$^{12}$), —N(R$^{12}$)S(O)$_2$(R$^{12a}$), —NR$^{12}$S(O)$_2$N(R$^{12}$)(R$^{12}$), —NR$^{12}$S(O)$_2$O(R$^{12a}$), —OC(O)R$^{12}$, —OC(O)OR$^{12}$, —OC(O)N(R$^{12}$)(R$^{12}$), —SR$^{12}$, —S(O)R$^{12a}$, —S(O)(NH)R$^{12}$, —S(O)$_2$R$^{12a}$, —S(O)$_2$N(R$^{12}$)(R$^{12}$), or —N=S(R$^{12a}$)(R$^{12a}$)=O.

In some embodiments of a compound of Formula I, or a pharmaceutically acceptable salt thereof, one or more $R^c$ is halogen. In some embodiments of a compound of Formula I, or a pharmaceutically acceptable salt thereof, one or more $R^c$ is —CN. In some embodiments of a compound of Formula I, or a pharmaceutically acceptable salt thereof, one or more $R^c$ is $C_{7-10}$ fused bicyclic cycloalkyl. In some embodiments of a compound of Formula I, or a pharmaceutically acceptable salt thereof, one or more $R^c$ is $C_{5-10}$ bridged bicyclic cycloalkyl. In some embodiments of a compound of Formula I, or a pharmaceutically acceptable salt thereof, one or more $R^c$ is phenyl. In some embodiments of a compound of Formula I, or a pharmaceutically acceptable salt thereof, one or more $R^c$ is naphthalenyl. In some embodiments of a compound of Formula I, or a pharmaceutically acceptable salt thereof, one or more $R^c$ is 4-7 membered monocyclic heterocyclyl. In some embodiments of a compound of Formula I, or a pharmaceutically acceptable salt thereof, one or more $R^c$ is 5-6 membered monocyclic heteroaryl. In some embodiments of a compound of Formula I, or a pharmaceutically acceptable salt thereof, one or more $R^c$ is 8-10 membered fused bicyclic heterocyclyl. In some embodiments of a compound of Formula I, or a pharmaceutically acceptable salt thereof, one or more $R^c$ is 6-10 membered bridged bicyclic heterocyclyl. In some embodiments of a compound of Formula I, or a pharmaceutically acceptable salt thereof, one or more $R^c$ is 8-10 membered fused bicyclic heteroaryl. In some embodiments of a compound of Formula I, or a pharmaceutically acceptable salt thereof, one or more $R^c$ is 7-10 membered spirocyclic heterocyclyl. In some embodiments of a compound of Formula I, or a pharmaceutically acceptable salt thereof, one or more $R^c$ is —$OR^{12}$. In some embodiments of a compound of Formula I, or a pharmaceutically acceptable salt thereof, one or more $R^c$ is —$C(O)R^{12}$. In some embodiments of a compound of Formula I, or a pharmaceutically acceptable salt thereof, one or more $R^c$ is —$C(O)OR^{12}$. In some embodiments of a compound of Formula I, or a pharmaceutically acceptable salt thereof, one or more $R^c$ is —$C(O)N(R^{12})(R^{12})$. In some embodiments of a compound of Formula I, or a pharmaceutically acceptable salt thereof, one or more $R^c$ is —$NR^{12}R^{12}$. In some embodiments of a compound of Formula I, or a pharmaceutically acceptable salt thereof, one or more $R^c$ is —$N(R^{12})_2(R^{12})^+$. In some embodiments of a compound of Formula I, or a pharmaceutically acceptable salt thereof, one or more $R^c$ is —$N(R^{12})C(O)R^{12}$. In some embodiments of a compound of Formula I, or a pharmaceutically acceptable salt thereof, one or more $R^c$ is —$N(R^{12})C(O)OR^{12}$. In some embodiments of a compound of Formula I, or a pharmaceutically acceptable salt thereof, one or more $R^c$ is —$N(R^{12})C(O)N(R^{12})(R^{12})$. In some embodiments of a compound of Formula I, or a pharmaceutically acceptable salt thereof, one or more $R^c$ is —$N(R^{12})S(O)_2(R^{12a})$. In some embodiments of a compound of Formula I, or a pharmaceutically acceptable salt thereof, one or more $R^c$ is —$NR^{12}S(O)_2N(R^{12})(R^{12})$. In some embodiments of a compound of Formula I, or a pharmaceutically acceptable salt thereof, one or more $R^c$ is —$NR^{12}S(O)_2O(R^{12a})$. In some embodiments of a compound of Formula I, or a pharmaceutically acceptable salt thereof, one or more $R^c$ is —$OC(O)R^{12}$. In some embodiments of a compound of Formula I, or a pharmaceutically acceptable salt thereof, one or more $R^c$ is —$OC(O)OR^{12}$. In some embodiments of a compound of Formula I, or a pharmaceutically acceptable salt thereof, one or more $R^c$ is —$OC(O)N(R^{12})(R^{12})$. In some embodiments of a compound of Formula I, or a pharmaceutically acceptable salt thereof, one or more $R^c$ is —$SR^{12}$. In some embodiments of a compound of Formula I, or a pharmaceutically acceptable salt thereof, one or more $R^c$ is —$S(O)R^{12a}$. In some embodiments of a compound of Formula I, or a pharmaceutically acceptable salt thereof, one or more $R^c$ is —$S(O)(NH)R^{12}$. In some embodiments of a compound of Formula I, or a pharmaceutically acceptable salt thereof, one or more $R^c$ is —$S(O)_2R^{12a}$. In some embodiments of a compound of Formula I, or a pharmaceutically acceptable salt thereof, one or more $R^c$ is —$S(O)_2N(R^{12})(R^{12})$. In some embodiments of a compound of Formula I, or a pharmaceutically acceptable salt thereof, one or more $R^c$ is —$N=S(R^{12a})(R^{12a})=O$.

In some embodiments of a compound of Formula I or II, or a pharmaceutically acceptable salt thereof, each $R^c$ independently is —OH, halogen, —CN, oxo, or —$NR^{12}R^{12}$. In some embodiments of a compound of Formula I, or a pharmaceutically acceptable salt thereof, each $R^c$ independently is —OH, halogen, —CN, or —$NR^{12}R^{12}$. In some embodiments of a compound of Formula I, or a pharmaceutically acceptable salt thereof, one or more $R^c$ is —OH. In some embodiments of a compound of Formula I, or a pharmaceutically acceptable salt thereof, one or more $R^c$ is halogen.

In some embodiments of a compound of Formula I, or a pharmaceutically acceptable salt thereof, each $R^d$ independently is oxo, halogen, —CN, $C_{1-6}$ alkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, 7-10 membered spirocyclic heterocyclyl, —$OR^{12}$, —$C(O)R^{12}$, —$C(O)OR^{12}$, —$C(O)N(R^{12})(R^{12})$, —$NR^{12}R^{12}$, —$N(R^{12})_2(R^{12})^+$, —$N(R^{12})C(O)R^{12}$, —$N(R^{12})C(O)OR^{12}$, —$N(R^{12})C(O)N(R^{12})(R^{12})$, —$N(R^{12})S(O)_2(R^{12a})$, —$NR^{12}S(O)_2N(R^{12})(R^{12})$, —$NR^{12}S(O)_2O(R^{12a})$, —$OC(O)R^{12}$, —$OC(O)OR^{12}$, —$OC(O)N(R^{12})(R^{12})$, —$SR^{12}$, —$S(O)R^{12a}$, —$S(O)(NH)R^{12}$, —$S(O)_2R^{12a}$, —$S(O)_2N(R^{12})(R^{12})$ or —$N=S(R^{12a})(R^{12a})=O$, wherein the $C_{1-6}$ alkyl is optionally substituted with 1-3 groups independently selected from —OH, halogen, —CN, and $C_{1-3}$ alkoxy.

In some embodiments of a compound of Formula I, or a pharmaceutically acceptable salt thereof, one or more $R^d$ is oxo. In some embodiments of a compound of Formula I, or a pharmaceutically acceptable salt thereof, one or more $R^d$ is halogen. In some embodiments of a compound of Formula I, or a pharmaceutically acceptable salt thereof, one or more $R^d$ is —CN. In some embodiments of a compound of Formula I, or a pharmaceutically acceptable salt thereof, one or more $R^d$ is $C_{7-10}$ fused bicyclic cycloalkyl. In some embodiments of a compound of Formula I, or a pharmaceutically acceptable salt thereof, one or more $R^d$ is $C_{5-10}$ bridged bicyclic cycloalkyl. In some embodiments of a compound of Formula I, or a pharmaceutically acceptable salt thereof, one or more $R^d$ is phenyl. In some embodiments of a compound of Formula I, or a pharmaceutically acceptable salt thereof, one or more $R^d$ is naphthalenyl. In some embodiments of a compound of Formula I, or a pharmaceutically acceptable salt thereof, one or more $R^d$ is 4-7 membered monocyclic heterocyclyl. In some embodiments of a compound of Formula I, or a pharmaceutically acceptable salt thereof, one or more $R^d$ is 5-6 membered monocyclic heteroaryl. In some embodiments of a compound of Formula I, or a pharmaceutically acceptable salt thereof, one or more $R^d$ is 8-10 membered fused bicyclic heterocyclyl. In some embodiments of a compound of Formula I, or a pharmaceutically acceptable salt thereof, one or more $R^d$ is 6-10 membered bridged bicyclic heterocyclyl. In some embodiments of a compound of Formula I, or a pharmaceutically acceptable salt thereof, one or more $R^d$ is 8-10 membered fused bicyclic heteroaryl. In some embodiments of a compound of Formula I, or a pharmaceutically acceptable salt thereof, one or more $R^d$ is 7-10 membered spirocyclic heterocyclyl. In some embodiments of a compound of Formula I, or a pharmaceutically acceptable salt thereof, one or more $R^d$ is —$OR^{12}$. In some embodiments of a compound of Formula I, or a pharmaceutically acceptable salt thereof, one or more $R^d$ is —$C(O)R^{12}$. In some embodiments of a compound of Formula I, or a pharmaceutically acceptable salt thereof, one or more $R^d$ is —$C(O)OR^{12}$. In some embodiments of a compound of Formula I, or a pharmaceutically acceptable salt thereof, one or more $R^d$ is —$C(O)N(R^{12})(R^{12})$. In some embodiments of a compound of Formula I, or a pharmaceutically acceptable salt thereof, one or more $R^d$ is —$NR^{12}R^{12}$. In some embodiments of a compound of Formula I, or a pharmaceutically acceptable salt thereof, one or more $R^d$ is —$N(R^{12})_2(R^{12})^+$. In some embodiments of a compound of Formula I, or a pharmaceutically acceptable salt thereof, one or more $R^d$ is —$N(R^{12})C(O)R^{12}$. In some embodiments of a compound of Formula I, or a pharmaceutically acceptable salt thereof, one or more $R^d$ is —$N(R^{12})C(O)OR^{12}$. In some embodiments of a compound of Formula I, or a pharmaceutically acceptable salt thereof, one or more $R^d$ is —$N(R^{12})C(O)N(R^{12})(R^{12})$. In some embodiments of a compound of Formula I, or a pharmaceutically acceptable salt thereof, one or more $R^d$ is —N($R^{12}$)S(O)$_2$($R^{12a}$). In some embodiments of a compound of Formula I, or a pharmaceutically acceptable salt thereof, one or more $R^d$ is —N$R^{12}$S(O)$_2$N($R^{12}$)($R^{12}$). In some embodiments of a compound of Formula I, or a pharmaceutically acceptable salt thereof, one or more $R^d$ is —N$R^{12}$S(O)$_2$O($R^{12a}$). In some embodiments of a compound of Formula I, or a pharmaceutically acceptable salt thereof, one or more $R^d$ is —OC(O)$R^{12}$. In some embodiments of a compound of Formula I, or a pharmaceutically acceptable salt thereof, one or more $R^d$ is —OC(O)O$R^{12}$. In some embodiments of a compound of Formula I, or a pharmaceutically acceptable salt thereof, one or more $R^d$ is —OC(O)N($R^{12}$)($R^{12}$). In some embodiments of a compound of Formula I, or a pharmaceutically acceptable salt thereof, one or more $R^d$ is —S$R^{12}$. In some embodiments of a compound of Formula I, or a pharmaceutically acceptable salt thereof, one or more $R^d$ is —S(O)$R^{12a}$. In some embodiments of a compound of Formula I, or a pharmaceutically acceptable salt thereof, one or more $R^d$ is —S(O)(NH)$R^{12}$. In some embodiments of a compound of Formula I, or a pharmaceutically acceptable salt thereof, one or more $R^d$ is —S(O)$_2$$R^{12a}$. In some embodiments of a compound of Formula I, or a pharmaceutically acceptable salt thereof, one or more $R^d$ is —S(O)$_2$N($R^{12}$)($R^{12}$). In some embodiments of a compound of Formula I, or a pharmaceutically acceptable salt thereof, one or more $R^d$ is —N=S($R^{12a}$)($R^{12a}$)=O.

In some embodiments of a compound of Formula I, or a pharmaceutically acceptable salt thereof, one or more $R^d$ is $C_{1-6}$ alkyl optionally substituted with 1-3 groups independently selected from —OH, halogen, —CN, and $C_{1-3}$ alkoxy.

In some embodiments of a compound of Formula I, or a pharmaceutically acceptable salt thereof, each $R^{11}$ independently is H, $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl,
  wherein the $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-3 $R^c$ groups.

In some embodiments of a compound of Formula I, or a pharmaceutically acceptable salt thereof, each $R^{11}$ independently is H, $C_{1-6}$ alkyl, $C_{3-7}$ monocyclic cycloalkyl, or 4-7 membered monocyclic heterocyclyl. In some embodiments of a compound of Formula I, or a pharmaceutically acceptable salt thereof, each $R^{11}$ independently is H or $C_{1-4}$ alkyl, wherein the $C_{1-4}$ alkyl is optionally substituted with one group selected from —OH and —N$R^{12}R^{12}$. In some embodiments of a compound of Formula I, or a pharmaceutically acceptable salt thereof, each $R^{11}$ independently is H or $C_{1-4}$ alkyl. In some embodiments of a compound of Formula I, or a pharmaceutically acceptable salt thereof, each $R^{11}$ independently is H or $C_{1-3}$ alkyl. In some embodiments of a compound of Formula I, or a pharmaceutically acceptable salt thereof, each $R^{11}$ independently is H or methyl.

In some embodiments of a compound of Formula I, or a pharmaceutically acceptable salt thereof, each $R^{11}$ independently is H or $C_{1-6}$ alkyl. In some embodiments of a compound of Formula I, or a pharmaceutically acceptable salt thereof, each $R^{11}$ independently is H or $C_{1-3}$ alkyl.

In some embodiments of a compound of Formula I, or a pharmaceutically acceptable salt thereof, each $R^{11}$ of —N$R^{11}R^{11}$ and —C(O)N$R^{11}R^{11}$ independently is H or $C_{1-3}$ alkyl.

In some embodiments of a compound of Formula I, or a pharmaceutically acceptable salt thereof, one or more $R^{11}$ is $C_{1-6}$ alkyl, wherein the $C_{1-6}$ alkyl is optionally substituted with 1-3 $R^c$ groups. In some embodiments of a compound of Formula I, or a pharmaceutically acceptable salt thereof, one or more $R^{11}$ is $C_{1-4}$ alkyl, wherein the $C_{1-4}$ alkyl is optionally substituted with 1-3 $R^c$ groups. In some embodiments of a compound of Formula I, or a pharmaceutically acceptable salt thereof, one or more $R^{11}$ is methyl.

In some embodiments of a compound of Formula I, or a pharmaceutically acceptable salt thereof, one or more $R^{11}$ is H. In some embodiments of a compound of Formula I, or a pharmaceutically acceptable salt thereof, one or more $R^{11}$ is $C_{2-6}$ alkenyl, wherein the $C_{2-6}$ alkenyl is optionally substituted with 1-3 $R^c$ groups. In some embodiments of a compound of Formula I, or a pharmaceutically acceptable salt thereof, one or more $R^{11}$ is $C_{2-6}$ alkynyl, wherein the $C_{2-6}$ alkynyl is optionally substituted with 1-3 $R^c$ groups. In some embodiments of a compound of Formula I, or a pharmaceutically acceptable salt thereof, one or more $R^{11}$ is $C_{3-7}$ monocyclic cycloalkyl, wherein the $C_{3-7}$ monocyclic cycloalkyl is optionally substituted with 1-3 $R^c$ groups. In some embodiments of a compound of Formula I, or a pharmaceutically acceptable salt thereof, one or more $R^{11}$ is $C_{7-10}$ fused bicyclic cycloalkyl, wherein the $C_{7-10}$ fused bicyclic cycloalkyl is optionally substituted with 1-3 $R^c$ groups. In some embodiments of a compound of Formula I, or a pharmaceutically acceptable salt thereof, one or more $R^{11}$ is $C_{5-10}$ bridged bicyclic cycloalkyl, wherein the $C_{5-10}$ bridged bicyclic cycloalkyl is optionally substituted with 1-3 $R^c$ groups. In some embodiments of a compound of Formula I, or a pharmaceutically acceptable salt thereof, one or more $R^{11}$ is phenyl, wherein the phenyl is optionally substituted with 1-3 $R^c$ groups. In some embodiments of a compound of Formula I, or a pharmaceutically acceptable salt thereof, one or more $R^{11}$ is naphthalenyl, wherein the naphthalenyl is optionally substituted with 1-3 $R^c$ groups. In some embodiments of a compound of Formula I, or a pharmaceutically acceptable salt thereof, one or more $R^{11}$ is 4-7 membered monocyclic heterocyclyl, wherein the 4-7 membered monocyclic heterocyclyl is optionally substituted with 1-3 $R^c$ groups. In some embodiments of a compound of Formula I, or a pharmaceutically acceptable salt thereof, one or more $R^{11}$ is 5-6 membered monocyclic heteroaryl, wherein the 5-6 membered monocyclic heteroaryl is optionally substituted with 1-3 $R^c$ groups. In some embodiments of a compound of Formula I, or a pharmaceutically acceptable salt thereof, one or more $R^{11}$ is 8-10 membered fused bicyclic heterocyclyl, wherein the 8-10 membered fused bicyclic heterocyclyl is optionally substituted with 1-3 $R^c$ groups. In some embodiments of a compound of Formula I, or a pharmaceutically acceptable salt thereof, one or more $R^{11}$ is 6-10 membered bridged bicyclic heterocyclyl, wherein the 6-10 membered bridged bicyclic heterocyclyl is optionally substituted with 1-3 $R^c$ groups. In some embodiments of a compound of Formula I, or a pharmaceutically acceptable salt thereof, one or more $R^{11}$ is 8-10 membered fused bicyclic heteroaryl, wherein the 8-10 membered fused bicyclic heteroaryl is optionally substituted with 1-3 $R^c$ groups. In some embodiments of a compound of Formula I, or a pharmaceutically acceptable salt thereof, one or more $R^{11}$ is 7-10 membered spirocyclic heterocyclyl, wherein the 7-10 membered spirocyclic heterocyclyl is optionally substituted with 1-3 $R^c$ groups.

In some embodiments of a compound of Formula I, or a pharmaceutically acceptable salt thereof, each $R^{11a}$ independently is $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl, wherein the $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, and 7-10 membered spirocyclic heterocyclyl are each independently optionally substituted with 1-3 $R^c$ groups.

In some embodiments of a compound of Formula I, or a pharmaceutically acceptable salt thereof, one or more $R^{11a}$ is $C_{1-6}$ alkyl, wherein the $C_{1-6}$ alkyl is optionally substituted with 1-3 $R^c$ groups. In some embodiments of a compound of Formula I, or a pharmaceutically acceptable salt thereof, one or more $R^{11a}$ is $C_{2-6}$ alkenyl, wherein the $C_{2-6}$ alkenyl is optionally substituted with 1-3 $R^c$ groups. In some embodiments of a compound of Formula I, or a pharmaceutically acceptable salt thereof, one or more $R^{11a}$ is $C_{2-6}$ alkynyl, wherein the $C_{2-6}$ alkynyl is optionally substituted with 1-3 $R^c$ groups. In some embodiments of a compound of Formula I, or a pharmaceutically acceptable salt thereof, one or more $R^{11a}$ is $C_{3-7}$ monocyclic cycloalkyl, wherein the $C_{3-7}$ monocyclic cycloalkyl is optionally substituted with 1-3 $R^c$ groups. In some embodiments of a compound of Formula I, or a pharmaceutically acceptable salt thereof, one or more $R^{11a}$ is $C_{7-10}$ fused bicyclic cycloalkyl, wherein the $C_{7-10}$ fused bicyclic cycloalkyl is optionally substituted with 1-3 $R^c$ groups. In some embodiments of a compound of Formula I, or a pharmaceutically acceptable salt thereof, one or more $R^{11a}$ is $C_{5-10}$ bridged bicyclic cycloalkyl, wherein the $C_{5-10}$ bridged bicyclic cycloalkyl is optionally substituted with 1-3 $R^c$ groups. In some embodiments of a compound of Formula I, or a pharmaceutically acceptable salt thereof, one or more $R^{11a}$ is phenyl, wherein the phenyl is optionally substituted with 1-3 $R^c$ groups. In some embodiments of a compound of Formula I, or a pharmaceutically acceptable salt thereof, one or more $R^{11a}$ is naphthalenyl, wherein the naphthalenyl is optionally substituted with 1-3 $R^c$ groups. In some embodiments of a compound of Formula I, or a pharmaceutically acceptable salt thereof, one or more $R^{11a}$ is 4-7 membered monocyclic heterocyclyl, wherein the 4-7 membered monocyclic heterocyclyl is optionally substituted with 1-3 $R^c$ groups. In some embodiments of a compound of Formula I, or a pharmaceutically acceptable salt thereof, one or more $R^{11a}$ is 5-6 membered monocyclic heteroaryl, wherein the 5-6 membered monocyclic heteroaryl is optionally substituted with 1-3 $R^c$ groups. In some embodiments of a compound of Formula I, or a pharmaceutically acceptable salt thereof, one or more $R^{11a}$ is 8-10 membered fused bicyclic heterocyclyl, wherein the 8-10 membered fused bicyclic heterocyclyl is optionally substituted with 1-3 $R^c$ groups. In some embodiments of a compound of Formula I, or a pharmaceutically acceptable salt thereof, one or more $R^{11a}$ is 6-10 membered bridged bicyclic heterocyclyl, wherein the 6-10 membered bridged bicyclic heterocyclyl is optionally substituted with 1-3 $R^c$ groups. In some embodiments of a compound of Formula I, or a pharmaceutically acceptable salt thereof, one or more $R^{11a}$ is 8-10 membered fused bicyclic heteroaryl, wherein the 8-10 membered fused bicyclic heteroaryl is optionally substituted with 1-3 $R^c$ groups. In some embodiments of a compound of Formula I, or a pharmaceutically acceptable salt thereof, one or more $R^{11a}$ is 7-10 membered spirocyclic heterocyclyl, wherein the 7-10 membered spirocyclic heterocyclyl is optionally substituted with 1-3 $R^c$ groups.

In some embodiments of a compound of Formula I, or a pharmaceutically acceptable salt thereof, each $R^{12}$ independently is H, $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl.

In some embodiments of a compound of Formula I, or a pharmaceutically acceptable salt thereof, each $R^{12}$ independently is H or $C_{1-4}$ alkyl. In some embodiments of a compound of Formula I, or a pharmaceutically acceptable salt thereof, each $R^{12}$ independently is H or $C_{1-3}$ alkyl.

In some embodiments of a compound of Formula I, or a pharmaceutically acceptable salt thereof, one or more $R^{12}$ is H. In some embodiments of a compound of Formula I, or a pharmaceutically acceptable salt thereof, one or more $R^{12}$ is $C_{1-6}$ alkyl. In some embodiments of a compound of Formula I, or a pharmaceutically acceptable salt thereof, one or more $R^{12}$ is $C_{1-4}$ alkyl. In some embodiments of a compound of Formula I, or a pharmaceutically acceptable salt thereof, one or more $R^{12}$ is $C_{1-3}$ alkyl. In some embodiments of a compound of Formula I, or a pharmaceutically acceptable salt thereof, one or more $R^{12}$ is $C_{2-6}$ alkenyl. In some embodiments of a compound of Formula I, or a pharmaceutically acceptable salt thereof, one or more $R^{12}$ is $C_{2-6}$ alkynyl. In some embodiments of a compound of Formula I, or a pharmaceutically acceptable salt thereof, one or more $R^{12}$ is $C_{3-7}$ monocyclic cycloalkyl. In some embodiments of a compound of Formula I, or a pharmaceutically acceptable salt thereof, one or more $R^{12}$ is $C_{7-10}$ fused bicyclic cycloalkyl. In some embodiments of a compound of Formula I, or a pharmaceutically acceptable salt thereof, one or more $R^{12}$ is $C_{5-10}$ bridged bicyclic cycloalkyl. In some embodiments of a compound of Formula I, or a pharmaceutically acceptable salt thereof, one or more $R^{12}$ is phenyl. In some embodiments of a compound of Formula I, or a pharmaceutically acceptable salt thereof, one or more $R^{12}$ is naphthalenyl. In some embodiments of a compound of Formula I, or a pharmaceutically acceptable salt thereof, one or more $R^{12}$ is 4-7 membered monocyclic heterocyclyl. In some embodiments of a compound of Formula I, or a pharmaceutically acceptable salt thereof, one or more $R^{12}$ is 5-6 membered monocyclic heteroaryl. In some embodiments of a compound of Formula I, or a pharmaceutically acceptable salt thereof, one or more $R^{12}$ is 8-10 membered fused bicyclic heterocyclyl. In some embodiments of a compound of Formula I, or a pharmaceutically acceptable salt thereof, one or more $R^{12}$ is 6-10 membered bridged bicyclic heterocyclyl. In some embodiments of a compound of Formula I, or a pharmaceutically acceptable salt thereof, one or more $R^{12}$ is 8-10 membered fused bicyclic heteroaryl. In some embodiments of a compound of Formula I, or a pharmaceutically acceptable salt thereof, one or more $R^{12}$ is 7-10 membered spirocyclic heterocyclyl.

In some embodiments of a compound of Formula I, or a pharmaceutically acceptable salt thereof, each $R^{12}$, independently is $C_{1-6}$ alkyl, $C_{2-6}$ alkenyl, $C_{2-6}$ alkynyl, $C_{3-7}$ monocyclic cycloalkyl, $C_{7-10}$ fused bicyclic cycloalkyl, $C_{5-10}$ bridged bicyclic cycloalkyl, phenyl, naphthalenyl, 4-7 membered monocyclic heterocyclyl, 5-6 membered monocyclic heteroaryl, 8-10 membered fused bicyclic heterocyclyl, 6-10 membered bridged bicyclic heterocyclyl, 8-10 membered fused bicyclic heteroaryl, or 7-10 membered spirocyclic heterocyclyl.

In some embodiments of a compound of Formula I, or a pharmaceutically acceptable salt thereof, one or more $R^{12a}$ is $C_{1-6}$ alkyl. In some embodiments of a compound of Formula I, or a pharmaceutically acceptable salt thereof, one or more $R^{12a}$ is $C_{2-6}$ alkenyl. In some embodiments of a compound of Formula I, or a pharmaceutically acceptable salt thereof, one or more $R^{12a}$ is $C_{2-6}$ alkynyl. In some embodiments of a compound of Formula I, or a pharmaceutically acceptable salt thereof, one or more $R^{12a}$ is $C_{3-7}$ monocyclic cycloalkyl. In some embodiments of a compound of Formula I, or a pharmaceutically acceptable salt thereof, one or more $R^{12a}$ is $C_{7-10}$ fused bicyclic cycloalkyl. In some embodiments of a compound of Formula I, or a pharmaceutically acceptable salt thereof, one or more $R^{12a}$ is $C_{5-10}$ bridged bicyclic cycloalkyl. In some embodiments of a compound of Formula I, or a pharmaceutically acceptable salt thereof, one or more $R^{12a}$ is phenyl. In some embodiments of a compound of Formula I, or a pharmaceutically acceptable salt thereof, one or more $R^{12a}$ is naphthalenyl. In some embodiments of a compound of Formula I, or a pharmaceutically acceptable salt thereof, one or more $R^{12a}$ is 4-7 membered monocyclic heterocyclyl. In some embodiments of a compound of Formula I, or a pharmaceutically acceptable salt thereof, one or more $R^{12a}$ is 5-6 membered monocyclic heteroaryl. In some embodiments of a compound of Formula I, or a pharmaceutically acceptable salt thereof, one or more $R^{12a}$ is 8-10 membered fused bicyclic heterocyclyl. In some embodiments of a compound of Formula I, or a pharmaceutically acceptable salt thereof, one or more $R^{12a}$ is 6-10 membered bridged bicyclic heterocyclyl. In some embodiments of a compound of Formula I, or a pharmaceutically acceptable salt thereof, one or more $R^{12a}$ is 8-10 membered fused bicyclic heteroaryl. In some embodiments of a compound of Formula I, or a pharmaceutically acceptable salt thereof, one or more $R^{12a}$ is 7-10 membered spirocyclic heterocyclyl.

In one embodiment, provided herein is a compound selected from the group consisting of:

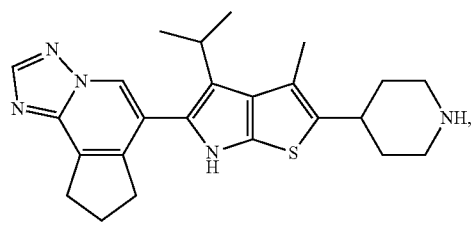

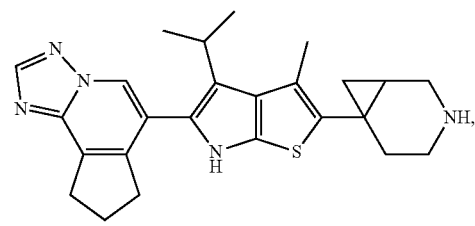

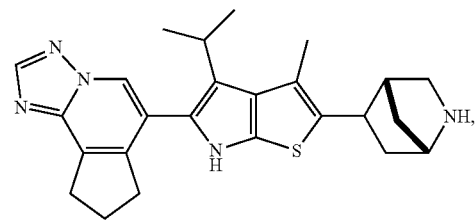

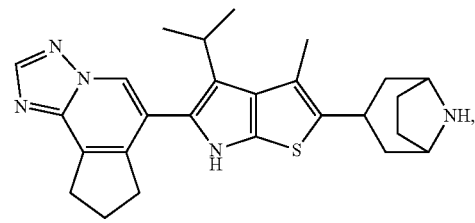

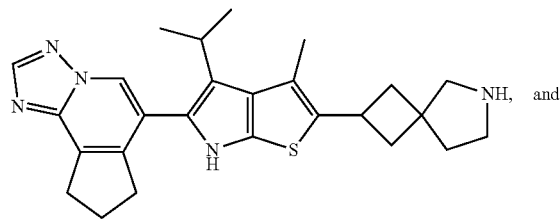

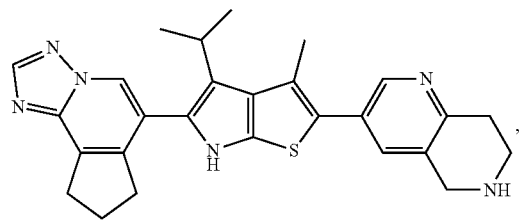

or a pharmaceutically acceptable salt thereof.

In one embodiment, provided herein is a compound selected from the group consisting of:

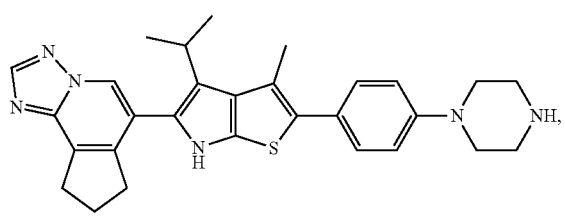

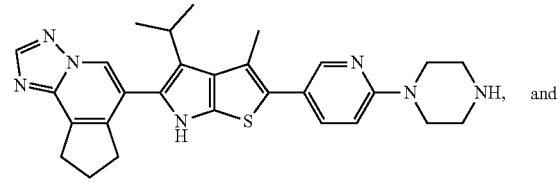

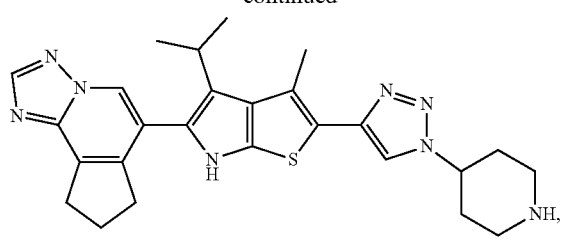
or a pharmaceutically acceptable salt thereof.
In one embodiment, provided herein is a compound selected from the group consisting of:
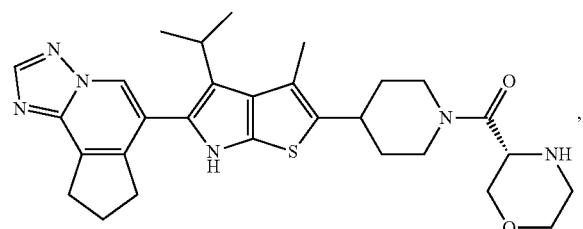
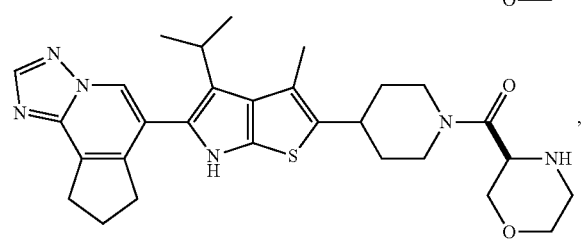
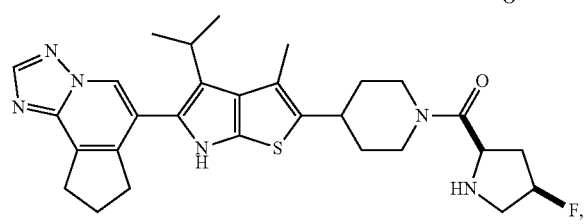
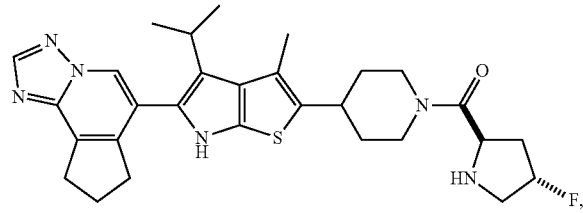
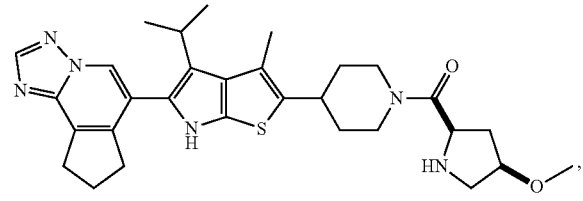
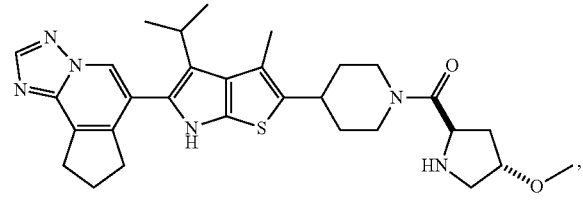
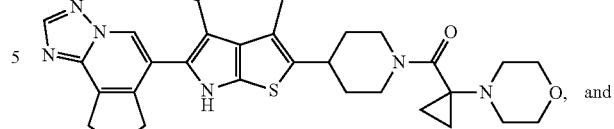
and
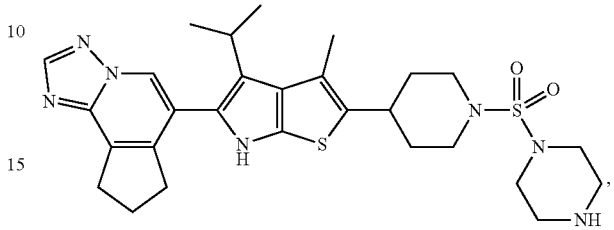
or a pharmaceutically acceptable salt thereof.
In one embodiment, provided herein is a compound selected from the group consisting of:
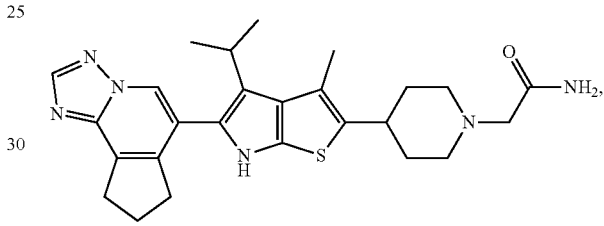
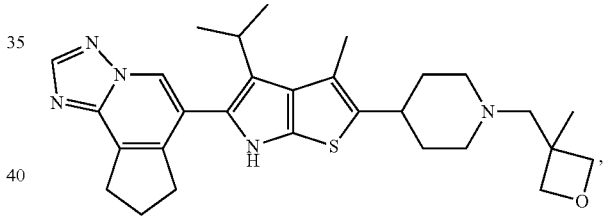
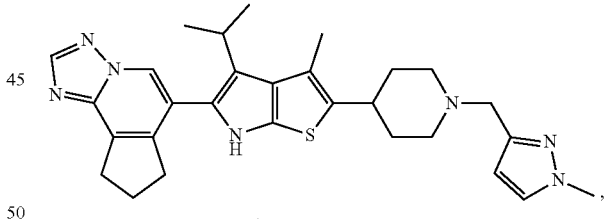
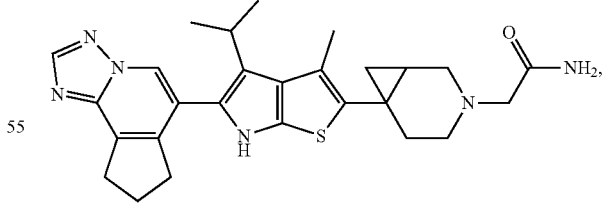
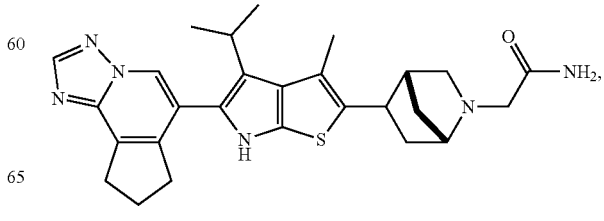

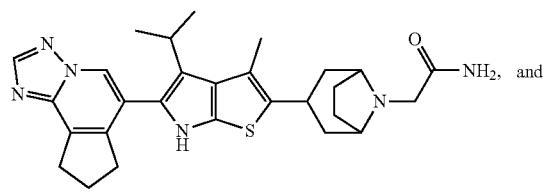
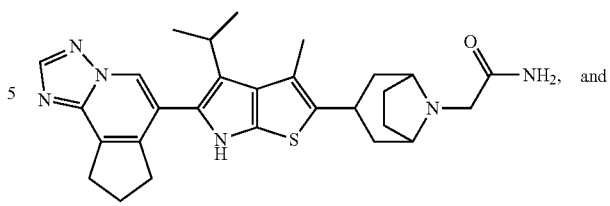
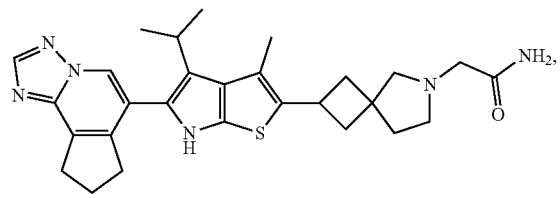
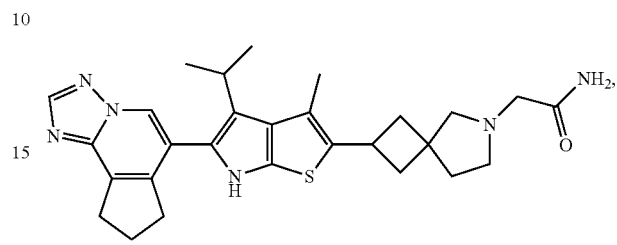
or a pharmaceutically acceptable salt thereof.
In one embodiment, provided herein is a compound selected from the group consisting of:
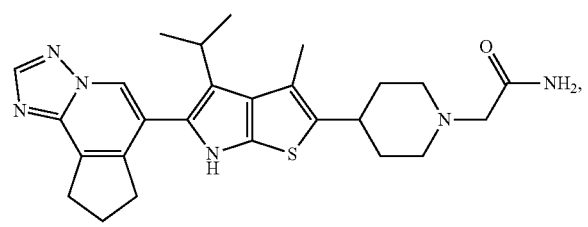
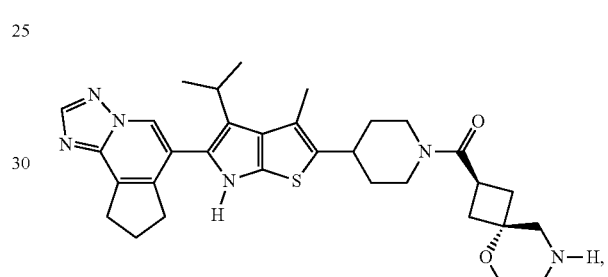
or a pharmaceutically acceptable salt thereof.
In one embodiment, provided herein is a compound selected from the group consisting of:
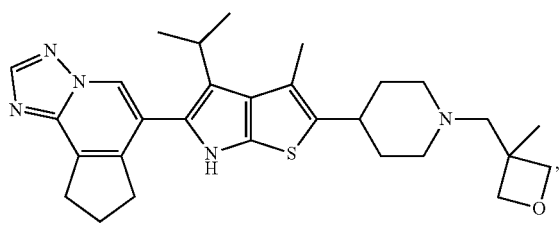
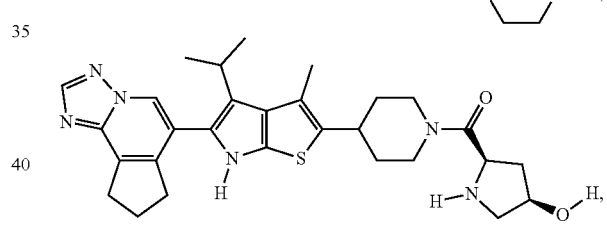
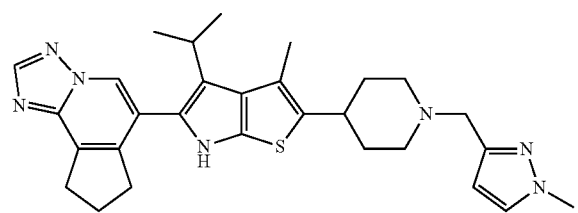
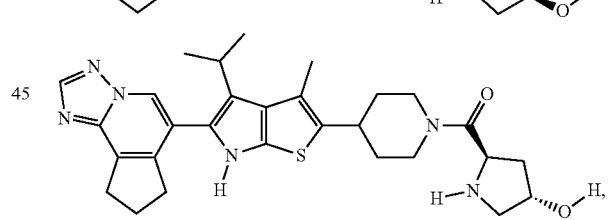
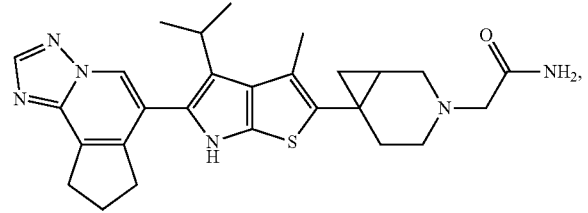
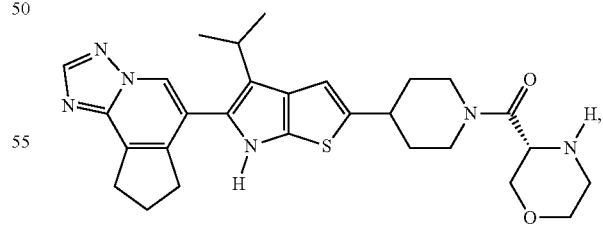
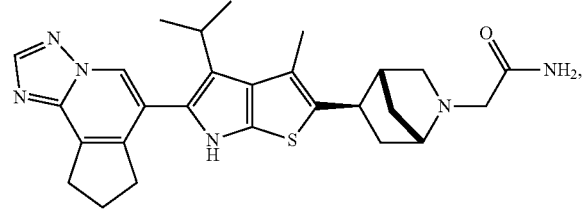
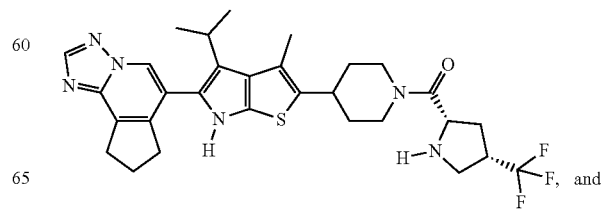

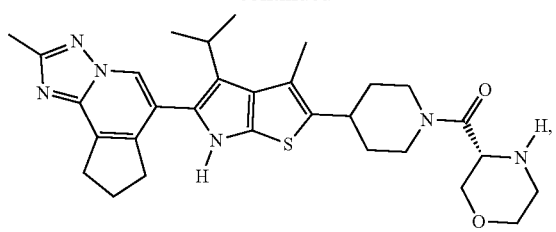

or a pharmaceutically acceptable salt thereof.

In one embodiment, provided herein is a compound selected from the group consisting of:

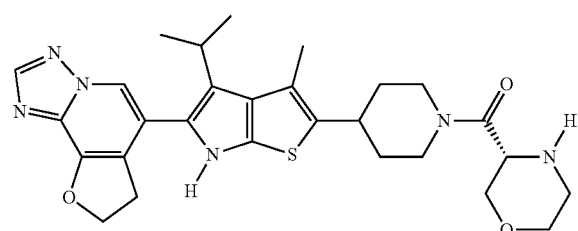

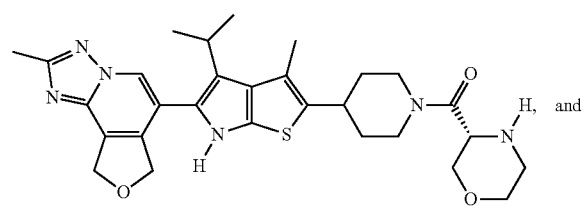

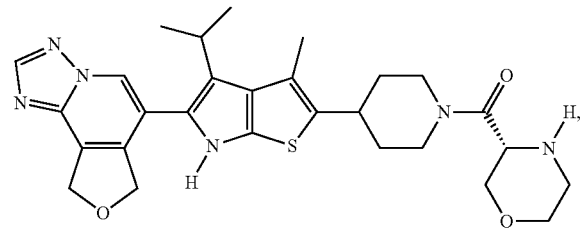

or a pharmaceutically acceptable salt thereof.

In one embodiment, provided herein is a compound selected from the group consisting of:

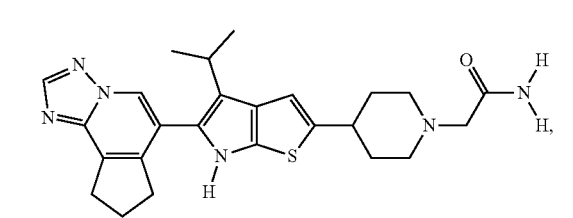

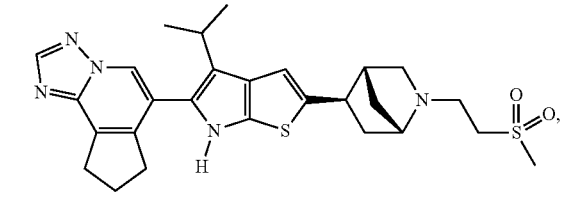

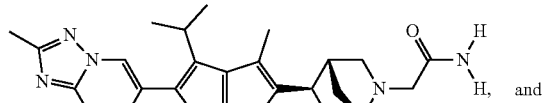

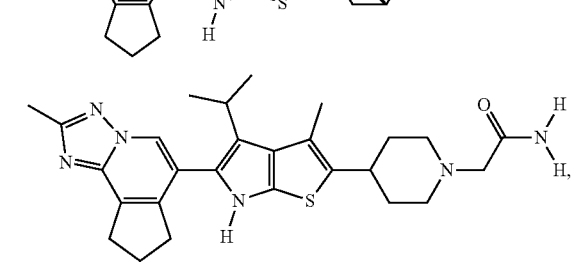

or a pharmaceutically acceptable salt thereof.

In one embodiment, provided herein is a compound selected from the group consisting of:

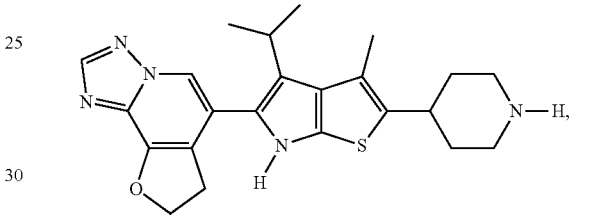

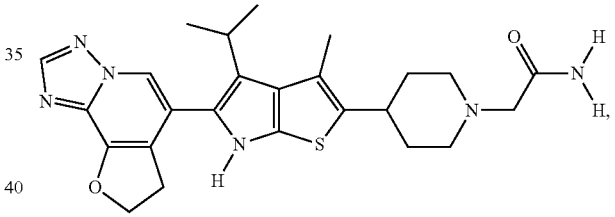

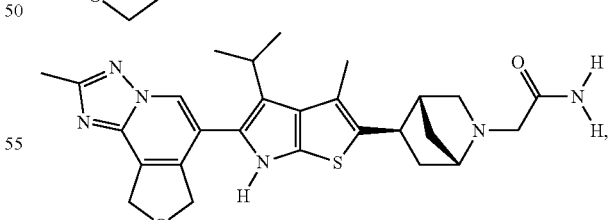

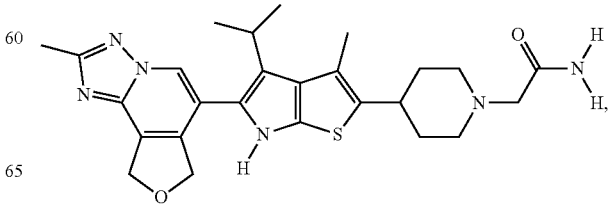

-continued

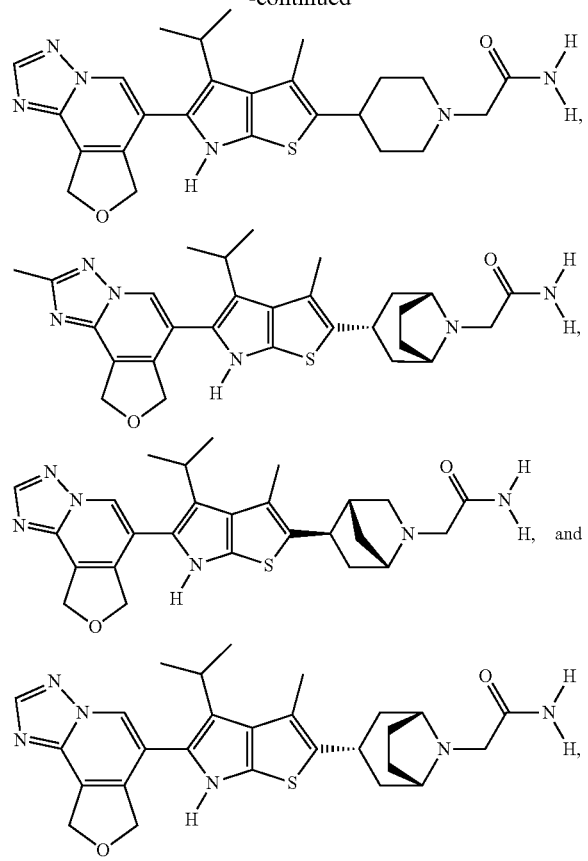

or a pharmaceutically acceptable salt thereof.

In one embodiment, provided herein is a compound selected from the group consisting of:

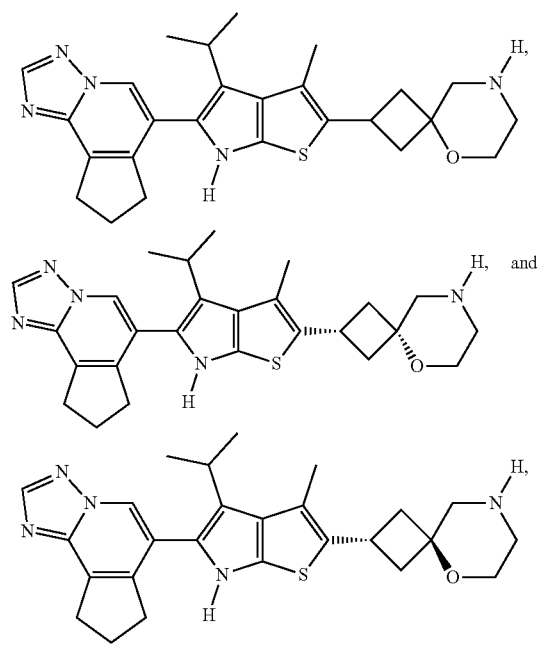

or a pharmaceutically acceptable salt thereof.

In one embodiment, provided herein is a compound selected from the group consisting of:

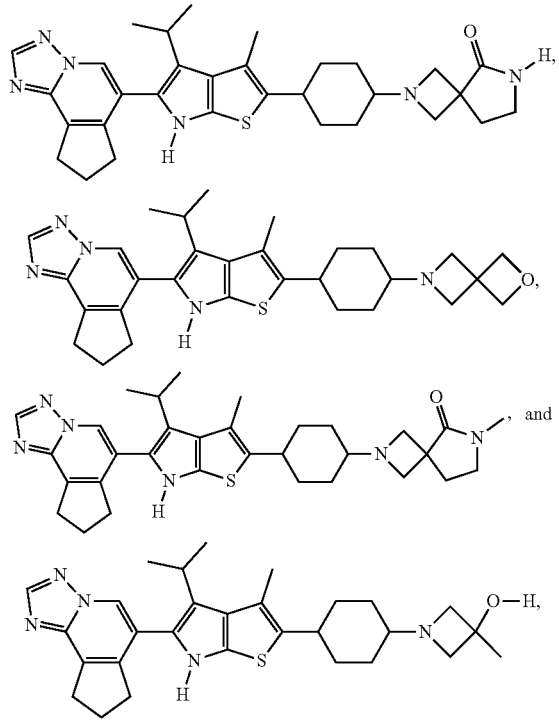

or a pharmaceutically acceptable salt thereof.

In one embodiment, provided herein is a compound selected from the group consisting of:

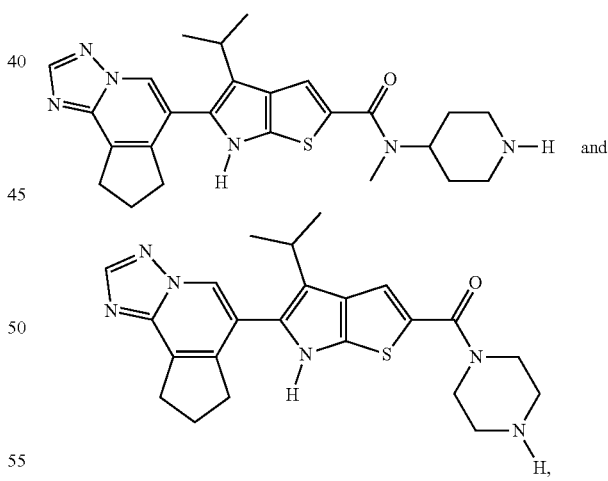

or a pharmaceutically acceptable salt thereof.

III. Compositions and Kits

Compounds provided herein, or pharmaceutically acceptable salts thereof, are usually administered in the form of pharmaceutical compositions. Thus, provided herein are also pharmaceutical compositions that comprise one or more of the compounds provided herein or pharmaceutically acceptable salts, isomer, or a mixture thereof and one or more pharmaceutically acceptable vehicles selected from carriers, adjuvants and excipients. The compounds provided herein, or pharmaceutically acceptable salts thereof, may be the sole active ingredient or one of the active ingredients of the pharmaceutical compositions. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

In one embodiment, provided herein are pharmaceutical compositions comprising a compound provided herein (i.e., a compound of Formula I), or a pharmaceutically acceptable salt thereof, and a pharmaceutically acceptable excipient or carrier. In some embodiments, the pharmaceutical compositions comprise a therapeutically effective amount of a compound provided herein, or a pharmaceutically acceptable salt thereof, and a pharmaceutically acceptable excipient or carrier.

In some embodiments, the pharmaceutical compositions provided herein further comprise one or more (i.e., one, two, three, four; one or two; one to three; or one to four) additional therapeutic agents, or a pharmaceutically acceptable salt thereof. In some embodiments, the pharmaceutical compositions further comprise a therapeutically effective amount of the one or more (i.e., one, two, three, four; one or two; one to three; or one to four) additional therapeutic agents, or a pharmaceutically acceptable salt thereof.

In some embodiments, the one or more additional therapeutic agents comprises an anti-malarial agent. In some embodiments, the anti-malarial agent is selected from chloroquine and hydroxychloroquine, or a pharmaceutically acceptable salt thereof.

In some embodiments, the one or more additional therapeutic agents include agents that are therapeutic for an inflammatory condition. In some embodiments, the one or more additional therapeutic agents is selected from the group consisting of: veltuzumab, PF-06835375, eculizumab, milatuzumab, SM-06, SM-03, BT-063, QX-006-N, BOS-161721, AK-101, TNX-1500, theralizumab, daxdilimab, TAK-079, felzartamab, itolizumab, anifrolumab, iscalimab, dapirolizumab pegol, lanalumab, LY-3361237, JNJ-55920839, UBP-1213, DS-7011, PFI-102, BIIB-059, obexelimab, talacotuzumab, vobarilizumab, TE-2324, PRV-3279, chloroquine, hydroxychloroquine, hydroxychloroquine sulfate, COV-08-0064; GNKS-356, AVO-101, rozibafusp alfa, VRN-02, annexuzlimab, ALPN-101, bendamustine hydrochloride, BMS-986256, NKTR-35, atacicept, telitacicept, BMS-986256, M-5049, KZR-616, KPG-818, verdinexor, ALPN-303, valziflocept, LA-1, cenerimod, prednisone, corticotropin, deucravacitinib, CPL-409116, CS-12192, tofacitinib citrate, ISB-830, DV-1079, julemic acid, iberdomide, TAM-01, BML-258, brepocitinib, SDC-1801, SDC-1802, ICP-330, NTR-441, dalazatide, GSK-2646264, SKI-O-703, lanraplenib (GS-9876), GNS-1653, HMPL-523, RSLV-132, interleukin-2 follow-on biologic, interleukin-2 Anteluke, interking recombinant human interleukin-2, ILT-101, CUG-252, DZ-2002, PEGylated HLA-x (SLE), AC-0058, fenebrutinib, XNW-1011, tirabrutinib hydrochloride, branebrutinib, elsubrutinib, orelabrutinib, DWP-213388, INV-103, R-salbutamol sulphate, anchorins, NIK-SMI1, X-6, INV-17, Oshadi D, baricitinib, upadacitinib, filgotinib, itacitinib, INCB-54707, delgocitinib, DWP-212525, CKD-971, as mometasone, betamethasone, forigerimod, anandamide, DCB-SLE1, arsenic trioxide, tairuimide, TV-4710 (edratide), allogeneic human umbilical cord-derived mesenchymal stem cell therapy (hUC-MSCs), LC-200, BI-705564, SM-934, GX-101, TXR-712, TXR-711, CIT-013, MHV-370, Panzyga®, TPX-6001, TPX-7001, artenimol, and AMG-592, or a pharmaceutically acceptable salt of any of the foregoing, or any combinations thereof.

The pharmaceutical compositions may be administered in either single or multiple doses. The pharmaceutical compositions may be administered by various methods including, for example, rectal, buccal, intranasal and transdermal routes. In some embodiments, the pharmaceutical compositions may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. In some embodiments, the compounds, or pharmaceutically acceptable salts thereof, and pharmaceutical compositions disclosed herein are administered by subcutaneous injection.

The pharmaceutical compositions of the present disclosure may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

In some embodiments, the sterile injectable preparation disclosed herein may also be a sterile injectable solution or suspension prepared from a reconstituted lyophilized powder in a non-toxic parenterally acceptable diluent or solvent, such as a solution in 1,3-butane-diol. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. In certain embodiments the suspension is a microsuspension. In certain embodiments the suspension is a nanosuspension.

In some embodiments, formulations suitable for parenteral administration (e.g., intramuscular (IM) and subcutaneous (SC) administration) will include one or more excipients. Excipients should be compatible with the other ingredients of the formulation and physiologically innocuous to the recipient thereof. Examples of suitable excipients are well known to the person skilled in the art of parenteral formulation and may be found e.g., in Handbook of Pharmaceutical Excipients (eds. Rowe, Sheskey & Quinn), 6th edition 2009. Examples of solubilizing excipients in a parenteral formulation (e.g., an SC or IM formulation) include, but are not limited to, polysorbates (such as polysorbate 20 or 80) and poloxamers (such as poloxamer 338, 188, or 207).

In some embodiments, the compounds, or pharmaceutically acceptable salts thereof, and pharmaceutical compositions disclosed herein are administered with implants.

Oral administration may be another route for administration of the compounds provided herein or pharmaceutically acceptable salts thereof. Administration may be via, for example, capsule or enteric coated tablets. In making the pharmaceutical compositions that include at least one compound provided herein or pharmaceutically acceptable salts, isomer, or a mixture thereof, the active ingredient (such as a compound provided herein) is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the pharmaceutical compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose or any combinations thereof. The pharmaceutical compositions can additionally include lubricating agents such as talc, magnesium stearate, and mineral oil; wetting agents; emulsifying and suspending agents; preserving agents such as methyl and propylhydroxy-benzoates; sweetening agents; and flavoring agents; or any combinations thereof.

The pharmaceutical compositions that include at least one compound described herein or pharmaceutically acceptable salts, isomer, or a mixture thereof can be formulated so as to provide quick, sustained or delayed release of the active ingredient (such as a compound provided herein) after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds provided herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or pharmaceutically acceptable salts, isomer, or a mixture thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds provided herein or pharmaceutically acceptable salts thereof may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with materials such as shellac, cetyl alcohol, and cellulose acetate.

Pharmaceutical compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

In one embodiment, provided herein are kits that comprise a compound provided herein, (i.e., a compound of Formula I), or a pharmaceutically acceptable salt, stereoisomer, prodrug, or solvate thereof, and suitable packaging. In some embodiments, the kit further comprises instructions for use. In some embodiments, the kit comprises a compound provided herein (i.e., a compound of Formula I), or a pharmaceutically acceptable salt, stereoisomer, prodrug, or solvate thereof, and a label and/or instructions for use of the compounds in the treatment of the indications, including the diseases or conditions, described herein.

In some embodiments, the kits further comprise one or more (i.e., one, two, three, four; one or two; one to three; or one to four) additional therapeutic agents, or a pharmaceutically acceptable salt thereof.

In one embodiment, provided herein are articles of manufacture that comprise a compound described herein or pharmaceutically acceptable salts, isomer, or a mixture thereof in a suitable container. In some embodiments, the container may be a vial, jar, ampoule, preloaded syringe, or intravenous bag.

IV. Methods

The methods provided herein may be applied to cell populations in vivo or ex vivo. "In vivo" means within a living individual, as within an animal or human. In this context, the methods provided herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the present disclosure may be used for a variety of purposes, including therapeutic and experimental purposes. For example, the present disclosure may be used ex vivo to determine the optimal schedule and/or dosing of administration of a TLR 7, 8, and/or 9 inhibitor as disclosed herein for a given cell type, individual, and other parameters. Information gleaned from such use may be used for experimental purposes or in the clinic to set protocols for in vivo treatment. Other ex vivo uses for which the present disclosure may be suited are described below or will become apparent to those skilled in the art. The selected compounds may be further characterized to examine the safety or tolerance dosage in human or non-human subjects. Such properties may be examined using commonly known methods to those skilled in the art.

In one embodiment, the present disclosure provides a method of inhibiting toll-like receptor 7, 8, and/or 9 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein. In some embodiments, the present disclosure provides a method of inhibiting toll-like receptor 7, 8, and 9 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein. In some embodiments, the present disclosure provides a method of inhibiting toll-like receptor 7, 8, or 9 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein.

In one embodiment, the present disclosure provides a method of inhibiting toll-like receptor 7 and/or 8 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein. In some embodiments, the present disclosure provides a method of inhibiting toll-like receptor 7 and 8 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein. In some embodiments, the present disclosure provides a method of inhibiting toll-like receptor 7 or 8 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein.

In one embodiment, the present disclosure provides a method of inhibiting toll-like receptor 7 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein. In some embodiments, the present disclosure provides a method of inhibiting toll-like receptor 8 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein.

In one embodiment, the present disclosure provides a method of treating a disease or disorder associated with elevated toll-like receptor 7, 8, and/or 9 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein. In some embodiments, the present disclosure provides a method of treating a disease or disorder associated with elevated toll-like receptor 7, 8, and 9 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein. In some embodiments, the present disclosure provides a method of treating a disease or disorder associated with elevated toll-like receptor 7, 8, or 9 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein.

In one embodiment, the present disclosure provides a method of treating a disease or disorder associated with elevated toll-like receptor 7 and/or 8 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein. In some embodiments, the present disclosure provides a method of treating a disease or disorder associated with elevated toll-like receptor 7 and 8 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein. In some embodiments, the present disclosure provides a method of treating a disease or disorder associated with elevated toll-like receptor 7 or 8 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein.

In one embodiment, the present disclosure provides a method of treating a disease or disorder associated with elevated toll-like receptor 7 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein. In some embodiments, the present disclosure provides a method of treating a disease or disorder associated with elevated toll-like receptor 8 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein.

In one embodiment, the present disclosure provides a method of treating an inflammatory condition in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein.

Non-limiting examples of an inflammatory condition include, without limitation, acne, acid-induced lung injury, Addison's disease, adrenal hyperplasia, adrenocortical insufficiency, adult-onset Still's disease, adult respiratory distress syndrome (ARDS), age-related macular degeneration, aging, alcoholic hepatitis, alcoholic liver disease, allergen-induced asthma, allergic bronchopulmonary, allergic conjunctivitis, allergic contact dermatitis, allergies, allergic encephalomyelitis, allergic neuritis, allograft rejection, alopecia, alopecia areata, Alzheimer's disease, amyloidosis, amyotrophic lateral sclerosis, angina pectoris, angioedema, angiofibroma, anhidrotic ectodermal dysplasia-ill, antiglomerular basement membrane disease, antigen-antibody complex mediated diseases, ankylosing spondylitis, antiphospholipid syndrome, aphthous stomatitis, appendicitis, arthritis, ascites, aspergillosis, asthma, atherosclerosis, atherosclerotic plaques, atopic dermatitis, atrophic thyroiditis, autoimmune diseases, autoimmune hemolytic anemia (immune pancytopenia, paroxysmal nocturnal hemoglobinuria), autoimmune polyendocrinopathies, autoimmune thrombocytopenia (idiopathic thrombocytopenic purpura, immune-mediated thrombocytopenia), autoimmune hepatitis, autoimmune thyroid disorders, autoinflammatory diseases, back pain, *Bacillus anthracis* infection, Bechet's disease, bee sting-induced inflammation, Behçet's syndrome, Bell's palsy, berylliosis, Blau syndrome, bone pain, bronchiolitis, bullous pemphigoid (BP) asthma, burns, bursitis, cardiac hypertrophy, carpal tunnel syndrome, Castleman's disease, catabolic disorders, cataracts, Celiac disease, cerebral aneurysm, chemical irritant-induced inflammation, chorioretinitis, chronic atypical neutrophilic dermatosis with lipodystrophy and elevated temperature (CANDLE) syndrome, chronic heart failure, chronic lung disease of prematurity, chronic obstructive pulmonary disease (COPD), chronic pancreatitis, chronic prostatitis, chronic recurrent multifocal osteomyelitis, cicatricial alopecia, colitis, complex regional pain syndrome, complications of organ transplantation, conjunctivitis, connective tissue disease, contact dermatitis, corneal graft neovascularization, corneal ulcer, Crohn's disease, cryopyrin-associated periodic syndromes, cutaneous lupus erythematosus (CLE), cryptococcosis, cystic fibrosis, deficiency of the interleukin-1 receptor antagonist (DIRA), dermatitis, dermatitis endotoxemia, dermatomyositis, diabetic macular edema, diverticulitis, eczema, encephalitis, endometriosis, endotoxemia, eosinophilic pneumonias, epicondylitis, epidermolysis bullosa, erythema multiforme, erythroblastopenia, esophagitis, familial amyloidotic polyneuropathy, familial cold urticarial, familial Mediterranean fever, fetal growth retardation, fibromyalgia, fistulizing Crohn's disease, food allergies, giant cell arteritis, glaucoma, glioblastoma, glomerular disease, glomerular nephritis, glomerulonephritis, gluten-sensitive enteropathy, gout, gouty arthritis, graft-versus-host disease (GVHD), granulomatous hepatitis, Graves' disease, growth plate injuries, Guillain-Barre syndrome. gut diseases, hair loss, Hashimoto's thyroiditis, head injury, headache, hearing loss, heart disease, hemangioma, hemolytic anemia, hemophilic joints, Henoch-Scholein purpura, hepatitis, hereditary periodic fever syndrome, heritable disorders of connective tissue, herpes zoster and simplex, hidradenitis suppurativa (HS), hip replacement, Hodgkin's disease, Huntington's disease, hyaline membrane disease, hyperactive inflammatory response, hyperammonemia, hypercalcemia, hypercholesterolemia, hypereosinophilic syndrome (HES), hyperimmunoglobulinemia D with recurrent fever (HIDS), hypersensitivity pneumonitis, hypertropic bone formation, hypoplastic and other anemias, hypoplastic anemia, ichthyosis, idiopathic demyelinating polyneuropathy, Idiopathic inflammatory myopathies (dermatomyositis, polymyositis), idiopathic pulmonary fibrosis, idiopathic thrombocytopenic purpura, immunoglobulin nephropathies, immune complex nephritis, immune thrombocytopenic purpura (ITP), incontinentia pigmenti (IP, Bloch-Siemens syndrome), infectious mononucleosis, infectious diseases including viral diseases such as AIDS (HIV infection), hepatitis A, B, C, D, and E, herpes; inflammation, inflammation of the CNS, inflammatory bowel disease (IBD), inflammatory disease of the lower respiratory tract including bronchitis or chronic obstructive pulmonary diseases, inflammatory disease of the upper respiratory tract including the nose and sinuses such as rhinitis or sinusitis, inflammatory diseases of the respiratory tract, inflammatory ischemic event such as stroke or cardiac arrest, inflammatory lung disease, inflammatory myopathy such as myocarditis, inflammatory liver disease, inflammatory neuropathy, inflammatory pain, insect bite-induced inflammation, interstitial cystitis, interstitial lung disease, iritis, irritant-induced inflammation, ischemia/reperfusion, joint replacement, juvenile arthritis, juvenile rheumatoid arthritis, keratitis, kidney injury caused by parasitic infections, kidney transplant rejection, leptospirosis, leukocyte adhesion deficiency, lichen sclerosus (LS), Lambert-Eaton myasthenic syndrome, Loeffler's syndrome, lupus, lupus nephritis, Lyme disease, Marfan syndrome (MFS), mast cell activation syndrome, mastocytosis, meningitis, meningioma, mesothelioma, mixed connective tissue disease, Muckle-Wells syndrome (urticaria deafness amyloidosis), mucositis, multiple organ injury syndrome, multiple sclerosis, muscle wasting, muscular dystrophy, myasthenia gravis (MG), myelodysplastic syndrome, myocarditis, myositis, nasal sinusitis, necrotizing enterocolitis, neonatal onset multisystem inflammatory disease (NOMID), neovascular glaucoma, nephrotic syndrome, neuritis, neuropathological diseases, non-allergen induced asthma, obesity, ocular allergy, optic neuritis, organ transplant rejection, Osier-Weber syndrome, osteoarthritis, osteogenesis imperfecta, osteonecrosis, osteoporosis, osterarthritis, otitis, pachyonychia congenita, Paget's disease, Paget's disease of bone, pancreatitis, Parkinson's disease, pediatric rheumatology, pelvic inflammatory disease, pemphigus, pemphigus vulgaris (PV), bullous pemphigoid (BP), pericarditis, periodic fever, periodontitis, peritoneal endometriosis, pernicious anemia (Addison's disease), pertussis, PFAPA (periodic fever aphthous pharyngitis and cervical adenopathy), pharyngitis and adenitis (PFAPA syndrome), plant irritant-induced inflammation, pneumocystis infection, pneumonia, pneumonitis, poison ivy/urushiol oil-induced inflammation, polyarthritis nodosa, polychondritis, polycystic kidney disease, polymyalgia rheumatic, giant cell arteritis, polymyositis, pouchitis, reperfusion injury and transplant rejection, primary biliary cirrhosis, primary pulmonary hypertension, primary sclerosing cholangitis (PSC), proctitis, psoriasis, psoriasis vulgaris, psoriatic arthritis, psoriatic epidermis, psychosocial stress diseases, pulmonary disease, pulmonary fibrosis, pulmonary hypertension, pyoderma gangrenosum, pyogenic granuloma retrolental fibroplasias, pyogenic sterile arthritis, Raynaud's syndrome, Reiter's disease, reactive arthritis, renal disease, renal graft rejection, reperfusion injury, respiratory distress syndrome, retinal disease, retrolental fibroplasia, Reynaud's syndrome, rheumatic carditis, rheumatic diseases, rheumatic fever, rheumatoid arthritis, rhinitis, rhinitis psoriasis, rosacea, sarcoidosis, Schnitzler syndrome, scleritis, sclerosis, scleroderma, scoliosis, seborrhea, sepsis, septic shock, severe pain, Sézary syndrome, sickle cell anemia, silica-induced disease (Silicosis), Sjogren's syndrome, skin diseases, skin irritation, skin rash, skin sensitization (contact dermatitis or allergic contact dermatitis), sleep apnea, spinal cord injury, spinal stenosis, spondyloarthropathies, sports injuries, sprains and strains, Stevens-Johnson syndrome (SJS), stroke, subarachnoid hemorrhage, sunburn, synovial inflammation, systemic inflammatory response syndrome (SIRS), systemic lupus erythematosus (SLE), systemic mast cell disease (SMCD), systemic vasculitis, systemic-onset juvenile idiopathic arthritis, temporal arteritis, tendinitis, tenosynovitis, thrombocytopenia, thyroditis, thyroiditis, tissue transplant, toxoplasmosis, trachoma, transplantation rejection, traumatic brain injury, tuberculosis, tubulointerstitial nephritis, tumor necrosis factor (TNF) receptor associated periodic syndrome (TRAPS), type 1 diabetes, type 2 diabetes, complications from type 1 or type 2 diabetes, ulcerative colitis, urticaria, uterine fibroids, uveitis, uveoretinitis, vascular restenosis, vasculitis, vasculitis (NHLBI), vitiligo, Wegener's granulomatosis, and Whipple's disease.

In some embodiments, the inflammatory condition is selected from inflammatory bowel disease, psoriasis, psoriatic arthritis, rheumatoid arthritis, glomerulonephritis, mixed connective tissue disease (MCTD), dermatomyositis, polymyositis, systemic sclerosis, antineutrophil cytoplasmic antibody-associated vasculitis, anti-phospholipid syndrome, autoimmune hemolytic anemia, macrophage activation syndrome driven inflammatory anemia, IgA nephropathy, type I diabetes, non-alcoholic steatohepatitis, and Sjogren's syndrome. In some embodiments, the inflammatory condition is inflammatory bowel disease. In some embodiments, the inflammatory condition is psoriasis. In some embodiments, the inflammatory condition is psoriatic arthritis. In some embodiments, the inflammatory condition is rheumatoid arthritis. In some embodiments, the inflammatory condition is glomerulonephritis. In some embodiments, the inflammatory condition is mixed connective tissue disease (MCTD). In some embodiments, the inflammatory condition is dermatomyositis. In some embodiments, the inflammatory condition is polymyositis. In some embodiments, the inflammatory condition is systemic sclerosis. In some embodiments, the inflammatory condition is antineutrophil cytoplasmic antibody-associated vasculitis. In some embodiments, the inflammatory condition is anti-phospholipid syndrome. In some embodiments, the inflammatory condition is autoimmune hemolytic anemia. In some embodiments, the inflammatory condition is macrophage activation syndrome driven inflammatory anemia. In some embodiments, the inflammatory condition is IgA nephropathy. In some embodiments, the inflammatory condition is type I diabetes. In some embodiments, the inflammatory condition is non-alcoholic steatohepatitis. In some embodiments, the inflammatory condition is Sjogren's syndrome.

The compounds provided herein, or pharmaceutically acceptable salts thereof, or the pharmaceutical composition provided herein may treat or ameliorate systemic lupus erythematosus (SLE), cutaneous lupus erythematosus (CLE), lupus nephritis, lupus-related, symptom of SLE, symptom of CLE, or other autoimmune disorder. Symptoms of systemic lupus erythematosus include joint pain, joint swelling, arthritis, fatigue, hair loss, mouth sores, swollen lymph nodes, sensitivity to sunlight, skin rash, headaches, numbness, tingling, seizures, vision problems, personality changes, abdominal pain, nausea, vomiting, abnormal heart rhythms, coughing up blood and difficulty breathing, patchy skin color and Raynaud's phenomenon.

In one embodiment, the present disclosure provides a method of treating systemic lupus erythematosus in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein.

In one embodiment, the present disclosure provides a method of treating cutaneous lupus erythematosus in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein.

In one embodiment, the present disclosure provides a method of treating lupus nephritis in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein.

In some embodiments, the methods provided herein further comprise administering a therapeutically effective amount of one or more additional therapeutic agents, or a pharmaceutically acceptable salt thereof.

In some embodiments, the one or more additional therapeutic agents is selected from the group consisting of veltuzumab, PF-06835375, eculizumab, milatuzumab, SM-06, SM-03, BT-063, QX-006-N, BOS-161721, AK-101, TNX-1500, theralizumab, daxdilimab, TAK-079, felzartamab, itolizumab, anifrolumab, iscalimab, dapirolizumab pegol, lanalumab, LY-3361237, JNJ-55920839, UBP-1213, DS-7011, PFI-102, BIIB-059, obexelimab, talacotuzumab, vobarilizumab, TE-2324, PRV-3279, chloroquine, hydroxychloroquine, hydroxychloroquine sulfate, COV-08-0064; GNKS-356, AVO-101, rozibafusp alfa, VRN-02, annexuzlimab, ALPN-101, bendamustine hydrochloride, BMS-986256, NKTR-35, atacicept, telitacicept, BMS-986256, M-5049, KZR-616, KPG-818, verdinexor, ALPN-303, valziflocept, LA-1, cenerimod, prednisone, corticotropin, deucravacitinib, CPL-409116, CS-12192, tofacitinib citrate, ISB-830, DV-1079, julemic acid, iberdomide, TAM-01, BML-258, brepocitinib, SDC-1801, SDC-1802, ICP-330, NTR-441, dalazatide, GSK-2646264, SKI-O-703, lanraplenib (GS-9876), GNS-1653, HMPL-523, RSLV-132, interleukin-2 follow-on biologic, interleukin-2 Anteluke, interking recombinant human interleukin-2, ILT-101, CUG-252, DZ-2002, PEGylated HLA-x (SLE), AC-0058, fenebrutinib, XNW-1011, tirabrutinib hydrochloride, branebrutinib, elsubrutinib, orelabrutinib, DWP-213388, INV-103, R-salbutamol sulphate, anchorins, NIK-SMI1, X-6, INV-17, Oshadi D, baricitinib, upadacitinib, filgotinib, itacitinib, INCB-54707, delgocitinib, DWP-212525, CKD-971, as mometasone, betamethasone, forigerimod, anandamide, DCB-SLE1, arsenic trioxide, tairuimide, TV-4710 (edratide), allogeneic human umbilical cord-derived mesenchymal stem cell therapy (hUC-MSCs), LC-200, BI-705564, SM-934, GX-101, TXR-712, TXR-711, CIT-013, MHV-370, Panzyga®, TPX-6001, TPX-7001, artenimol, and AMG-592, or a pharmaceutically acceptable salt of any of the foregoing, or any combination thereof.

In some embodiments, the one or more additional therapeutic agents is selected from chloroquine and hydroxychloroquine, or a pharmaceutically acceptable salt thereof. In some embodiments, the one or more additional therapeutic agents is chloroquine. In some embodiments, the one or more additional therapeutic agents is hydroxychloroquine. In some embodiments, the one or more additional therapeutic agent is a pharmaceutically acceptable salt of hydroxychloroquine. In some embodiments, the one or more additional therapeutic agent is hydroxychloroquine sulfate.

In some embodiments of the methods provided herein, the subject is a human.

In some embodiments, the methods provided herein comprise administering a therapeutically effective amount of a compound provided herein (i.e., a compound of Formula I), or a pharmaceutically acceptable salt thereof. In some embodiments, the methods provided herein comprise administering a therapeutically effective amount of a pharmaceutical composition provided herein.

In one embodiment, the present disclosure provides a compound provided herein (i.e., a compound of Formula I), or a pharmaceutically acceptable salt thereof, or a pharmaceutical composition provided herein for use in therapy.

In one embodiment, the present disclosure provides a compound provided herein (i.e., a compound of Formula I), or a pharmaceutically acceptable salt thereof, or a pharmaceutical composition provided herein, for use in a method of inhibiting toll-like receptor 7, 8, and/or 9 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein. In some embodiments, the compound provided herein (i.e., a compound of Formula I), or a pharmaceutically acceptable salt thereof, or the pharmaceutical composition provided herein is for use in a method of inhibiting toll-like receptor 7, 8, and 9 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein. In some embodiments, the compound provided herein (i.e., a compound of Formula I), or a pharmaceutically acceptable salt thereof, or the pharmaceutical composition provided herein is for use in a method of inhibiting toll-like receptor 7, 8, or 9 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein.

In one embodiment, the present disclosure provides a compound provided herein (i.e., a compound of Formula I), or a pharmaceutically acceptable salt thereof, or a pharmaceutical composition provided herein, for use in a method of inhibiting toll-like receptor 7 and/or 8 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein. In some embodiments, the compound provided herein (i.e., a compound of Formula I), or a pharmaceutically acceptable salt thereof, or the pharmaceutical composition provided herein is for use in a method of inhibiting toll-like receptor 7 and 8 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein. In some embodiments, the compound provided herein (i.e., a compound of Formula I), or a pharmaceutically acceptable salt thereof, or the pharmaceutical composition provided herein is for use in a method of inhibiting toll-like receptor 7 or 8 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein.

In one embodiment, the present disclosure provides a compound provided herein (i.e., a compound of Formula I), or a pharmaceutically acceptable salt thereof, or a pharmaceutical composition provided herein, for use in a method of inhibiting toll-like receptor 7 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein. In some embodiments, the compound provided herein (i.e., a compound of Formula I), or a pharmaceutically acceptable salt thereof, or the pharmaceutical composition provided herein is for use in a method of inhibiting toll-like receptor 8 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein.

In one embodiment, the present disclosure provides a compound provided herein (i.e., a compound of Formula I), or a pharmaceutically acceptable salt thereof, or a pharmaceutical composition provided herein, for use in a method of treating a disease or disorder associated with elevated toll-like receptor 7, 8, and/or 9 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein. In some embodiments, the compound provided herein (i.e., a compound of Formula I), or a pharmaceutically acceptable salt thereof, or the pharmaceutical composition provided herein is for use in a method of treating a disease or disorder associated with elevated toll-like receptor 7, 8, and 9 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein. In some embodiments, the compound provided herein (i.e., a compound of Formula I), or a pharmaceutically acceptable salt thereof, or the pharmaceutical composition provided herein is for use in a method of treating a disease or disorder associated with elevated toll-like receptor 7, 8, or 9 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein.

In one embodiment, the present disclosure provides a compound provided herein (i.e., a compound of Formula I), or a pharmaceutically acceptable salt thereof, or a pharmaceutical composition provided herein, for use in a method of treating a disease or disorder associated with elevated toll-like receptor 7 and/or 8 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein. In some embodiments, the compound provided herein (i.e., a compound of Formula I), or a pharmaceutically acceptable salt thereof, or the pharmaceutical composition provided herein is for use in a method of treating a disease or disorder associated with elevated toll-like receptor 7 and 8 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein. In some embodiments, the compound provided herein (i.e., a compound of Formula I), or a pharmaceutically acceptable salt thereof, or the pharmaceutical composition provided herein is for use in a method of treating a disease or disorder associated with elevated toll-like receptor 7 or 8 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein.

In one embodiment, the present disclosure provides a compound provided herein (i.e., a compound of Formula I), or a pharmaceutically acceptable salt thereof, or a pharmaceutical composition provided herein, for use in a method of treating a disease or disorder associated with elevated toll-like receptor 7 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein. In some embodiments, the compound provided herein (i.e., a compound of Formula I), or a pharmaceutically acceptable salt thereof, or the pharmaceutical composition provided herein is for use in a method of treating a disease or disorder associated with elevated toll-like receptor 8 activity in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein.

In one embodiment, the present disclosure provides a compound provided herein (i.e., a compound of Formula I), or a pharmaceutically acceptable salt thereof, or a pharmaceutical composition provided herein, for use in a method of treating an inflammatory condition in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein.

Non-limiting examples of an inflammatory condition include, without limitation, acne, acid-induced lung injury, Addison's disease, adrenal hyperplasia, adrenocortical insufficiency, adult-onset Still's disease, adult respiratory distress syndrome (ARDS), age-related macular degeneration, aging, alcoholic hepatitis, alcoholic liver disease, allergen-induced asthma, allergic bronchopulmonary, allergic conjunctivitis, allergic contact dermatitis, allergies, allergic encephalomyelitis, allergic neuritis, allograft rejection, alopecia, alopecia areata, Alzheimer's disease, amyloidosis, amyotrophic lateral sclerosis, angina pectoris, angioedema, angiofibroma, anhidrotic ectodermal dysplasia-ill, anti-glomerular basement membrane disease, antigen-antibody complex mediated diseases, ankylosing spondylitis, antiphospholipid syndrome, aphthous stomatitis, appendicitis, arthritis, ascites, aspergillosis, asthma, atherosclerosis, atherosclerotic plaques, atopic dermatitis, atrophic thyroiditis, autoimmune diseases, autoimmune hemolytic anemia (immune pancytopenia, paroxysmal nocturnal hemoglobinuria), autoimmune polyendocrinopathies, autoimmune thrombocytopenia (idiopathic thrombocytopenic purpura, immune-mediated thrombocytopenia), autoimmune hepatitis, autoimmune thyroid disorders, autoinflammatory diseases, back pain, *Bacillus anthracis* infection, Bechet's disease, bee sting-induced inflammation, Behçet's syndrome, Bell's palsy, berylliosis, Blau syndrome, bone pain, bronchiolitis, bullous pemphigoid (BP) asthma, burns, bursitis, cardiac hypertrophy, carpal tunnel syndrome, Castleman's disease, catabolic disorders, cataracts, Celiac disease, cerebral aneurysm, chemical irritant-induced inflammation, chorioretinitis, chronic atypical neutrophilic dermatosis with lipodystrophy and elevated temperature (CANDLE) syndrome, chronic heart failure, chronic lung disease of prematurity, chronic obstructive pulmonary disease (COPD), chronic pancreatitis, chronic prostatitis, chronic recurrent multifocal osteomyelitis, cicatricial alopecia, colitis, complex regional pain syndrome, complications of organ transplantation, conjunctivitis, connective tissue disease, contact dermatitis, corneal graft neovascularization, corneal ulcer, Crohn's disease, cryopyrin-associated periodic syndromes, cutaneous lupus erythematosus (CLE), cryptococcosis, cystic fibrosis, deficiency of the interleukin-1 receptor antagonist (DIRA), dermatitis, dermatitis endotoxemia, dermatomyositis, diabetic macular edema, diverticulitis, eczema, encephalitis, endometriosis, endotoxemia, eosinophilic pneumonias, epicondylitis, epidermolysis bullosa, erythema multiforme, erythroblastopenia, esophagitis, familial amyloidotic polyneuropathy, familial cold urticarial, familial Mediterranean fever, fetal growth retardation, fibromyalgia, fistulizing Crohn's disease, food allergies, giant cell arteritis, glaucoma, glioblastoma, glomerular disease, glomerular nephritis, glomerulonephritis, gluten-sensitive enteropathy, gout, gouty arthritis, graft-versus-host disease (GVHD), granulomatous hepatitis, Graves' disease, growth plate injuries, Guillain-Barre syndrome. gut diseases, hair loss, Hashimoto's thyroiditis, head injury, headache, hearing loss, heart disease, hemangioma, hemolytic anemia, hemophilic joints, Henoch-Scholein purpura, hepatitis, hereditary periodic fever syndrome, heritable disorders of connective tissue, herpes zoster and simplex, hidradenitis suppurativa (HS), hip replacement, Hodgkin's disease, Huntington's disease, hyaline membrane disease, hyperactive inflammatory response, hyperammonemia, hypercalcemia, hypercholesterolemia, hypereosinophilic syndrome (HES), hyperimmunoglobulinemia D with recurrent fever (HIDS), hypersensitivity pneumonitis, hypertropic bone formation, hypoplastic and other anemias, hypoplastic anemia, ichthyosis, idiopathic demyelinating polyneuropathy, Idiopathic inflammatory myopathies (dermatomyositis, polymyositis), idiopathic pulmonary fibrosis, idiopathic thrombocytopenic purpura, immunoglobulin nephropathies, immune complex nephritis, immune thrombocytopenic purpura (ITP), incontinentia pigmenti (IP, Bloch-Siemens syndrome), infectious mononucleosis, infectious diseases including viral diseases such as AIDS (HIV infection), hepatitis A, B, C, D, and E, herpes; inflammation, inflammation of the CNS, inflammatory bowel disease (IBD), inflammatory disease of the lower respiratory tract including bronchitis or chronic obstructive pulmonary diseases, inflammatory disease of the upper respiratory tract including the nose and sinuses such as rhinitis or sinusitis, inflammatory diseases of the respiratory tract, inflammatory ischemic event such as stroke or cardiac arrest, inflammatory lung disease, inflammatory myopathy such as myocarditis, inflammatory liver disease, inflammatory neuropathy, inflammatory pain, insect bite-induced inflammation, interstitial cystitis, interstitial lung disease, iritis, irritant-induced inflammation, ischemia/reperfusion, joint replacement, juvenile arthritis, juvenile rheumatoid arthritis, keratitis, kidney injury caused by parasitic infections, kidney transplant rejection, leptospirosis, leukocyte adhesion deficiency, lichen sclerosus (LS), Lambert-Eaton myasthenic syndrome, Loeffler's syndrome, lupus, lupus nephritis, Lyme disease, Marfan syndrome (MFS), mast cell activation syndrome, mastocytosis, meningitis, meningioma, mesothelioma, mixed connective tissue disease, Muckle-Wells syndrome (urticaria deafness amyloidosis), mucositis, multiple organ injury syndrome, multiple sclerosis, muscle wasting, muscular dystrophy, myasthenia gravis (MG), myelodysplastic syndrome, myocarditis, myositis, nasal sinusitis, necrotizing enterocolitis, neonatal onset multisystem inflammatory disease (NOMID), neovascular glaucoma, nephrotic syndrome, neuritis, neuropathological diseases, non-allergen induced asthma, obesity, ocular allergy, optic neuritis, organ transplant rejection, Osler-Weber syndrome, osteoarthritis, osteogenesis imperfecta, osteonecrosis, osteoporosis, osterarthritis, otitis, pachyonychia congenita, Paget's disease, Paget's disease of bone, pancreatitis, Parkinson's disease, pediatric rheumatology, pelvic inflammatory disease, pemphigus, pemphigus vulgaris (PV), bullous pemphigoid (BP), pericarditis, periodic fever, periodontitis, peritoneal endometriosis, pernicious anemia (Addison's disease), pertussis, PFAPA (periodic fever aphthous pharyngitis and cervical adenopathy), pharyngitis and adenitis (PFAPA syndrome), plant irritant-induced inflammation, pneumocystis infection, pneumonia, pneumonitis, poison ivy/urushiol oil-induced inflammation, polyarthritis nodosa, polychondritis, polycystic kidney disease, polymyalgia rheumatic, giant cell arteritis, polymyositis, pouchitis, reperfusion injury and transplant rejection, primary biliary cirrhosis, primary pulmonary hypertension, primary sclerosing cholangitis (PSC), proctitis, psoriasis, psoriasis vulgaris, psoriatic arthritis, psoriatic epidermis, psychosocial stress diseases, pulmonary disease, pulmonary fibrosis, pulmonary hypertension, pyoderma gangrenosum, pyogenic granuloma retrolental fibroplasias, pyogenic sterile arthritis, Raynaud's syndrome, Reiter's disease, reactive arthritis, renal disease, renal graft rejection, reperfusion injury, respiratory distress syndrome, retinal disease, retrolental fibroplasia, Reynaud's syndrome, rheumatic carditis, rheumatic diseases, rheumatic fever, rheumatoid arthritis, rhinitis, rhinitis psoriasis, rosacea, sarcoidosis, Schnitzler syndrome, scleritis, sclerosis, scleroderma, scoliosis, seborrhea, sepsis, septic shock, severe pain, Sézary syndrome, sickle cell anemia, silica-induced disease (Silicosis), Sjogren's syndrome, skin diseases, skin irritation, skin rash, skin sensitization (contact dermatitis or allergic contact dermatitis), sleep apnea, spinal cord injury, spinal stenosis, spondyloarthropathies, sports injuries, sprains and strains, Stevens-Johnson syndrome (SJS), stroke, subarachnoid hemorrhage, sunburn, synovial inflammation, systemic inflammatory response syndrome (SIRS), systemic lupus erythematosus (SLE), systemic mast cell disease (SMCD), systemic vasculitis, systemic-onset juvenile idiopathic arthritis, temporal arteritis, tendinitis, tenosynovitis, thrombocytopenia, thyroditis, thyroiditis, tissue transplant, toxoplasmosis, trachoma, transplantation rejection, traumatic brain injury, tuberculosis, tubulointerstitial nephritis, tumor necrosis factor (TNF) receptor associated periodic syndrome (TRAPS), type 1 diabetes, type 2 diabetes, complications from type 1 or type 2 diabetes, ulcerative colitis, urticaria, uterine fibroids, uveitis, uveoretinitis, vascular restenosis, vasculitis, vasculitis (NHLBI), vitiligo, Wegener's granulomatosis, and Whipple's disease.

In some embodiments, the inflammatory condition is selected from inflammatory bowel disease, psoriasis, psoriatic arthritis, rheumatoid arthritis, glomerulonephritis, mixed connective tissue disease (MCTD), dermatomyositis, polymyositis, systemic sclerosis, antineutrophil cytoplasmic antibody-associated vasculitis, anti-phospholipid syndrome, autoimmune hemolytic anemia, macrophage activation syndrome driven inflammatory anemia, IgA nephropathy, type I diabetes, non-alcoholic steatohepatitis, and Sjogren's syndrome. In some embodiments, the inflammatory condition is inflammatory bowel disease. In some embodiments, the inflammatory condition is psoriasis. In some embodiments, the inflammatory condition is psoriatic arthritis. In some embodiments, the inflammatory condition is rheumatoid arthritis. In some embodiments, the inflammatory condition is glomerulonephritis. In some embodiments, the inflammatory condition is mixed connective tissue disease (MCTD). In some embodiments, the inflammatory condition is dermatomyositis. In some embodiments, the inflammatory condition is polymyositis. In some embodiments, the inflammatory condition is systemic sclerosis. In some embodiments, the inflammatory condition is antineutrophil cytoplasmic antibody-associated vasculitis. In some embodiments, the inflammatory condition is anti-phospholipid syndrome. In some embodiments, the inflammatory condition is autoimmune hemolytic anemia. In some embodiments, the inflammatory condition is macrophage activation syndrome driven inflammatory anemia. In some embodiments, the inflammatory condition is IgA nephropathy. In some embodiments, the inflammatory condition is type I diabetes. In some embodiments, the inflammatory condition is non-alcoholic steatohepatitis. In some embodiments, the inflammatory condition is Sjogren's syndrome.

The compounds provided herein, or pharmaceutically acceptable salts thereof, or the pharmaceutical composition provided herein may treat or ameliorate systemic lupus erythematosus (SLE), cutaneous lupus erythematosus (CLE), lupus nephritis, lupus-related, symptom of SLE, symptom of CLE, or other autoimmune disorder. Symptoms of systemic lupus erythematosus include joint pain, joint swelling, arthritis, fatigue, hair loss, mouth sores, swollen lymph nodes, sensitivity to sunlight, skin rash, headaches, numbness, tingling, seizures, vision problems, personality changes, abdominal pain, nausea, vomiting, abnormal heart rhythms, coughing up blood and difficulty breathing, patchy skin color and Raynaud's phenomenon.

In one embodiment, the present disclosure provides a compound provided herein (i.e., a compound of Formula I), or a pharmaceutically acceptable salt thereof, or a pharmaceutical composition provided herein, for use in a method of treating systemic lupus erythematosus in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein.

In one embodiment, the present disclosure provides a compound provided herein (i.e., a compound of Formula I), or a pharmaceutically acceptable salt thereof, or a pharmaceutical composition provided herein, for use in a method of treating cutaneous lupus erythematosus in a subject in need thereof, comprising administering to the subject a therapeutically effective amount of a compound provided herein (i.e., a compound of Formula I), or a pharmaceutically acceptable salt thereof, or a therapeutically effective amount of a pharmaceutical composition provided herein.

In some embodiments, the uses provided herein further comprise administering a therapeutically effective amount of one or more additional therapeutic agents, or a pharmaceutically acceptable salt thereof.

In some embodiments, the one or more additional therapeutic agents is selected from the group consisting of veltuzumab, PF-06835375, eculizumab, milatuzumab, SM-06, SM-03, BT-063, QX-006-N, BOS-161721, AK-101, TNX-1500, theralizumab, daxdilimab, TAK-079, felzartamab, itolizumab, anifrolumab, iscalimab, dapirolizumab pegol, lanalumab, LY-3361237, JNJ-55920839, UBP-1213, DS-7011, PFI-102, BIIB-059, obexelimab, talacotuzumab, vobarilizumab, TE-2324, PRV-3279, chloroquine, hydroxychloroquine, hydroxychloroquine sulfate, COV-08-0064; GNKS-356, AVO-101, rozibafusp alfa, VRN-02, annexuzlimab, ALPN-101, bendamustine hydrochloride, BMS-986256, NKTR-35, atacicept, telitacicept, BMS-986256, M-5049, KZR-616, KPG-818, verdinexor, ALPN-303, valziflocept, LA-1, cenerimod, prednisone, corticotropin, deucravacitinib, CPL-409116, CS-12192, tofacitinib citrate, ISB-830, DV-1079, julemic acid, iberdomide, TAM-01, BML-258, brepocitinib, SDC-1801, SDC-1802, ICP-330, NTR-441, dalazatide, GSK-2646264, SKI-O-703, lanraplenib (GS-9876), GNS-1653, HMPL-523, RSLV-132, interleukin-2 follow-on biologic, interleukin-2 Anteluke, interking recombinant human interleukin-2, ILT-101, CUG-252, DZ-2002, PEGylated HLA-x (SLE), AC-0058, fenebrutinib, XNW-1011, tirabrutinib hydrochloride, branebrutinib, elsubrutinib, orelabrutinib, DWP-213388, INV-103, R-salbutamol sulphate, anchorins, NIK-SMI1, X-6, INV-17, Oshadi D, baricitinib, upadacitinib, filgotinib, itacitinib, INCB-54707, delgocitinib, DWP-212525, CKD-971, as mometasone, betamethasone, forigerimod, anandamide, DCB-SLE1, arsenic trioxide, tairuimide, TV-4710 (edratide), allogeneic human umbilical cord-derived mesenchymal stem cell therapy (hUC-MSCs), LC-200, BI-705564, SM-934, GX-101, TXR-712, TXR-711, CIT-013, MHV-370, Panzyga®, TPX-6001, TPX-7001, artenimol, and AMG-592, or a pharmaceutically acceptable salt of any of the foregoing, or any combination thereof.

In some embodiments, the one or more additional therapeutic agents is selected from chloroquine and hydroxychloroquine, or a pharmaceutically acceptable salt thereof. In some embodiments, the one or more additional therapeutic agents is chloroquine. In some embodiments, the one or more additional therapeutic agents is hydroxychloroquine. In some embodiments, the one or more additional therapeutic agent is a pharmaceutically acceptable salt of hydroxychloroquine. In some embodiments, the one or more additional therapeutic agent is hydroxychloroquine sulfate.

In some embodiments of the uses provided herein, the subject is a human.

In some embodiments, the uses provided herein comprise administering a therapeutically effective amount of a compound provided herein (i.e., a compound of Formula I), or a pharmaceutically acceptable salt thereof. In some embodiments, the methods provided herein comprise administering a therapeutically effective amount of a pharmaceutical composition provided herein.

V. Administration

The compounds of the present disclosure or pharmaceutically acceptable salts thereof (also referred to herein as the active ingredients) can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with, for example, the condition of the recipient. An advantage of certain compounds disclosed herein, or pharmaceutically acceptable salts thereof, is that they are orally bioavailable and can be dosed orally.

A compound of the present disclosure, or a pharmaceutically acceptable salt thereof, may be administered to an individual in accordance with an effective dosing regimen for a desired period of time or duration, such as at least about one month, at least about 2 months, at least about 3 months, at least about 6 months, or at least about 12 months or longer. In some embodiments, the compound, or a pharmaceutically acceptable salt thereof, is administered on a daily or intermittent schedule for the duration of the individual's life.

The specific dose level of a compound of the present disclosure, or a pharmaceutically acceptable salt thereof, for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound provided herein, or a pharmaceutically acceptable salt thereof, per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein, or a pharmaceutically acceptable salt thereof, administered per dose or per day. Daily dosage of a compound of Formula I, or a pharmaceutically acceptable salt or pharmaceutically acceptable tautomer thereof, may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

The dosage or dosing frequency of a compound of the present disclosure, or a pharmaceutically acceptable salt thereof, may be adjusted over the course of the treatment, based on the judgment of the administering physician.

The compounds of the present disclosure, or pharmaceutically acceptable salts thereof, may be administered to an individual (e.g., a human) in a therapeutically effective amount. In some embodiments, the compound, or a pharmaceutically acceptable salt thereof, is administered once daily.

The compounds provided herein, or pharmaceutically acceptable salts thereof, can be administered by any useful route and means, such as by oral or parenteral (e.g., intravenous) administration. Therapeutically effective amounts of the compound, or a pharmaceutically acceptable salt thereof, may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day. In some embodiments, a therapeutically effective amount of the compounds provided herein, or pharmaceutically acceptable salts thereof, include from about 0.3 mg to about 30 mg per day, or from about 30 mg to about 300 mg per day, or from about 0.3 µg to about 30 mg per day, or from about 30 µg to about 300 µg per day.

A compound of the present disclosure, or a pharmaceutically acceptable salt thereof, may be combined with one or more additional therapeutic agents in any dosage amount of the compound of the present disclosure or a pharmaceutically acceptable salt thereof (e.g., from 1 mg to 1000 mg of compound). Therapeutically effective amounts may include from about 0.1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose, or such as from about 0.01 mg per dose to about 1000 mg per dose, or such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose, or such as from about 1 mg per dose to about 1000 mg per dose. Other therapeutically effective amounts of the compound of Formula I, or a pharmaceutically acceptable salt thereof, are about 1 mg per dose, or about 2, 3, 4, 5, 6, 7, 8, 9, 10, 15, 20, 25, 30, 35, 40, 45, 50, 55, 60, 65, 70, 75, 80, 85, 90, 95, or about 100 mg per dose. Other therapeutically effective amounts of the compound of the present disclosure, or pharmaceutically acceptable salts thereof, are about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or about 1000 mg per dose.

In some embodiments, a therapeutically effective amount of the compound of Formula I, or a pharmaceutically acceptable salt thereof, is about 1 mg to about 600 mg. In some embodiments, a therapeutically effective amount of the compound of Formula I, or a pharmaceutically acceptable salt thereof, is about 1 mg to about 500 mg. In some embodiments, a therapeutically effective amount of the compound of Formula I, or a pharmaceutically acceptable salt thereof, is about 1 mg to about 400 mg. In some embodiments, a therapeutically effective amount of the compound of Formula I, or a pharmaceutically acceptable salt thereof, is about 1 mg to about 300 mg. In some embodiments, a therapeutically effective amount of the compound of Formula I, or a pharmaceutically acceptable salt thereof, is about 1 mg to about 200 mg. In some embodiments, a therapeutically effective amount of the compound of Formula I, or a pharmaceutically acceptable salt thereof, is about 1 mg to about 100 mg. In some embodiments, a therapeutically effective amount of the compound of Formula I, or a pharmaceutically acceptable salt thereof, is about 1 mg to about 75 mg. In some embodiments, a therapeutically effective amount of the compound of Formula I, or a pharmaceutically acceptable salt thereof, is about 1 mg to about 50 mg. In some embodiments, a therapeutically effective amount of the compound of Formula I, or a pharmaceutically acceptable salt thereof, is about 1 mg to about 25 mg. In some embodiments, a therapeutically effective amount of the compound of Formula I, or a pharmaceutically acceptable salt thereof, is about 1 mg to about 20 mg. In some embodiments, a therapeutically effective amount of the compound of Formula I, or a pharmaceutically acceptable salt thereof, is about 1 mg to about 15 mg. In some embodiments, a therapeutically effective amount of the compound of Formula I, or a pharmaceutically acceptable salt thereof, is about 1 mg to about 10 mg. In some embodiments, a therapeutically effective amount of the compound of Formula I, or a pharmaceutically acceptable salt thereof, is about 1 mg to about 5 mg. In some embodiments, a therapeutically effective amount of the compound of Formula I, or a pharmaceutically acceptable salt thereof, is about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, or about 25 mg. In some embodiments, a therapeutically effective amount of the compound of Formula I, or a pharmaceutically acceptable salt thereof, is about 5 mg. In some embodiments, a therapeutically effective amount of the compound of Formula I, or a pharmaceutically acceptable salt thereof, is about 10 mg. In some embodiments, a therapeutically effective amount of the compound of Formula I, or a pharmaceutically acceptable salt thereof, is about 15 mg. In some embodiments, a therapeutically effective amount of the compound of Formula I, or a pharmaceutically acceptable salt thereof, is about 20 mg. In some embodiments, a therapeutically effective amount of the compound of Formula I, or a pharmaceutically acceptable salt thereof, is about 25 mg. In some embodiments, a therapeutically effective amount of the compound of Formula I, or a pharmaceutically acceptable salt thereof, is about 30 mg. In some embodiments, a therapeutically effective amount of the compound of Formula I, or a pharmaceutically acceptable salt thereof, is about 35 mg. In some embodiments, a therapeutically effective amount of the compound of Formula I, or a pharmaceutically acceptable salt thereof, is about 40 mg. In some embodiments, a therapeutically effective amount of the compound of Formula I, or a pharmaceutically acceptable salt thereof, is about 45 mg. In some embodiments, a therapeutically effective amount of the compound of Formula I, or a pharmaceutically acceptable salt thereof, is about 50 mg.

In some embodiments, the methods described herein comprise administering to the subject an initial daily dose of about 1 to 500 mg of a compound provided herein, or a pharmaceutically acceptable salt thereof, and increasing the dose by increments until clinical efficacy is achieved. Increments of about 5, 10, 25, 50, or 100 mg can be used to increase the dose. The dosage can be increased daily, every other day, twice per week, once per week, once every two weeks, once every three weeks, or once a month.

When administered orally, the total daily dosage for a human subject may be between about 1 mg and 1,000 mg, between about 10-500 mg/day, between about 50-300 mg/day, between about 75-200 mg/day, or between about 100-150 mg/day. In some embodiments, the total daily dosage for a human subject may be about 100, 200, 300, 400, 500, 600, 700, 800, 900, or 1000 mg/day administered in a single dose. In some embodiments, the total daily dosage for a human subject may be about 200, 300, 400, 500, 600, 700, or 800 mg/day administered in a single dose. In some embodiments, the total daily dosage for a human subject may be about 300, 400, 500, or 600 mg/day administered in a single dose.

In some embodiments, the total daily dosage for a human subject may be about 100 mg/day administered in a single dose. In some embodiments, the total daily dosage for a human subject may be about 150 mg/day administered in a single dose. In some embodiments, the total daily dosage for a human subject may be about 200 mg/day administered in a single dose. In some embodiments, the total daily dosage for a human subject may be about 250 mg/day administered in a single dose. In some embodiments, the total daily dosage for a human subject may be about 300 mg/day administered in a single dose. In some embodiments, the total daily dosage for a human subject may be about 350 mg/day administered in a single dose. In some embodiments, the total daily dosage for a human subject may be about 400 mg/day administered in a single dose. In some embodiments, the total daily dosage for a human subject may be about 450 mg/day administered in a single dose. In some embodiments, the total daily dosage for a human subject may be about 500 mg/day administered in a single dose. In some embodiments, the total daily dosage for a human subject may be about 550 mg/day administered in a single dose. In some embodiments, the total daily dosage for a human subject may be about 600 mg/day administered in a single dose. In some embodiments, the total daily dosage for a human subject may be about 650 mg/day administered in a single dose. In some embodiments, the total daily dosage for a human subject may be about 700 mg/day administered in a single dose. In some embodiments, the total daily dosage for a human subject may be about 750 mg/day administered in a single dose. In some embodiments, the total daily dosage for a human subject may be about 800 mg/day administered in a single dose. In some embodiments, the total daily dosage for a human subject may be about 850 mg/day administered in a single dose. In some embodiments, the total daily dosage for a human subject may be about 900 mg/day administered in a single dose. In some embodiments, the total daily dosage for a human subject may be about 950 mg/day administered in a single dose. In some embodiments, the total daily dosage for a human subject may be about 1000 mg/day administered in a single dose.

A single dose can be administered hourly, daily, weekly, or monthly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month. In some embodiments, a compound provided herein, or a pharmaceutically acceptable salt thereof, is administered once daily in a method disclosed herein. In some embodiments, a compound provided herein, or a pharmaceutically acceptable salt thereof, is administered twice daily in a method disclosed herein.

The frequency of dosage of the compound of the present disclosure, or a pharmaceutically acceptable salt thereof, will be determined by the needs of the individual patient and can be, for example, once per day or twice, or more times, per day. Administration of the compound, or a pharmaceutically acceptable salt thereof, continues for as long as necessary to treat the inflammatory condition, or any other indication described herein. For example, a compound, or a pharmaceutically acceptable salt thereof, can be administered to a human suffering from an inflammatory condition for a period of from 20 days to 180 days or, for example, for a period of from 20 days to 90 days or, for example, for a period of from 30 days to 60 days.

Administration can be intermittent, with a period of several or more days during which a patient receives a daily dose of the compound of the present disclosure, or a pharmaceutically acceptable salt thereof, followed by a period of several or more days during which a patient does not receive a daily dose of the compound or a pharmaceutically acceptable salt thereof. For example, a patient can receive a dose of the compound, or a pharmaceutically acceptable salt thereof, every other day, or three times per week. Again by way of example, a patient can receive a dose of the compound, or a pharmaceutically acceptable salt thereof, each day for a period of from 1 to 14 days, followed by a period of 7 to 21 days during which the patient does not receive a dose of the compound, or a pharmaceutically acceptable salt thereof, followed by a subsequent period (e.g., from 1 to 14 days) during which the patient again receives a daily dose of the compound, or a pharmaceutically acceptable salt thereof. Alternating periods of administration of the compound, or a pharmaceutically acceptable salt thereof, followed by non-administration of the compound, or a pharmaceutically acceptable salt thereof, can be repeated as clinically required to treat the patient.

The compounds of the present disclosure, or pharmaceutically acceptable salts thereof, or the pharmaceutical compositions of the present disclosure may be administered once, twice, three, or four times daily, using any suitable mode described above. Also, administration or treatment with the compounds, or pharmaceutically acceptable salts thereof, may be continued for a number of days; for example, commonly treatment would continue for at least 7 days, 14 days, or 28 days, for one cycle of treatment. Treatment cycles are well known for inflammatory conditions and other indications described herein. In some embodiments, treatment cycles are frequently alternated with resting periods of about 1 to 28 days, commonly about 7 days or about 14 days, between cycles. The treatment cycles, in other embodiments, may also be continuous.

VI. Combination Therapy

Patients being treated by administration of the compounds provided herein, or pharmaceutically acceptable salts thereof, often exhibit diseases or conditions that benefit from treatment with other therapeutic agents. These diseases or conditions can be of an inflammatory nature or can be related to cancer, metabolic disorders, gastrointestinal disorders and the like. Thus, one embodiment of the disclosure is a method of treating an inflammation related disease or condition, or a metabolic disorder, gastrointestinal disorder, or cancer and the like comprising administering a compound of the present disclosure, or a pharmaceutically acceptable salt thereof, in combination with one or more compounds useful for the treatment of such diseases to a subject, particularly a human subject, in need thereof.

In some embodiments, a compound of the present disclosure, or a pharmaceutically acceptable salt thereof, is combined with one, two, three, four or more additional therapeutic agents. In some embodiments, a compound of the present disclosure, or a pharmaceutically acceptable salt thereof, is combined with two additional therapeutic agents. In some embodiments, a compound of the present disclosure, or a pharmaceutically acceptable salt thereof, is combined with three additional therapeutic agents. In some embodiments, a compound of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In some embodiments, when a compound of the present disclosure, or a pharmaceutically acceptable salt thereof, is combined with one or more additional therapeutic agents as described herein, the components of the composition are administered as a simultaneous or sequential regimen. When administered sequentially, the combination may be administered in two or more administrations.

In some embodiments, a compound of the present disclosure, or a pharmaceutically acceptable salt thereof, is combined with one or more additional therapeutic agents in a unitary dosage form for simultaneous administration to a patient, for example as a solid dosage form for oral administration.

In some embodiments, a compound of the present disclosure, or a pharmaceutically acceptable salt thereof, is co-administered with one or more additional therapeutic agents.

Co-administration includes administration of unit dosages of the compounds provided herein, or pharmaceutically acceptable salts thereof, before or after administration of unit dosages of one or more additional therapeutic agents. The compounds provided herein, or pharmaceutically acceptable salts thereof, may be administered within seconds, minutes, or hours of the administration of one or more additional therapeutic agents. For example, in some embodiments, a unit dose of a compound provided herein, or a pharmaceutically acceptable salt thereof, is administered first, followed within seconds or minutes by administration of a unit dose of one or more additional therapeutic agents. Alternatively, in other embodiments, a unit dose of one or more additional therapeutic agents is administered first, followed by administration of a unit dose of a compound provided herein, or a pharmaceutically acceptable salt thereof, within seconds or minutes. In some embodiments, a unit dose of a compound provided herein, or a pharmaceutically acceptable salt thereof, is administered first, followed, after a period of hours (i.e., 1-12 hours), by administration of a unit dose of one or more additional therapeutic agents. In other embodiments, a unit dose of one or more additional therapeutic agents is administered first, followed, after a period of hours (i.e., 1-12 hours), by administration of a unit dose of a compound provided herein or a pharmaceutically acceptable salt thereof.

In some embodiments, a compound of Formula I, or a pharmaceutically acceptable salt thereof, is formulated as a tablet, which may optionally contain one or more other compounds useful for treating the disease being treated. In certain embodiments, the tablet can contain another active ingredient for treating an inflammatory condition or other indication described herein. In some embodiments, such tablets are suitable for once daily dosing.

Also provided herein are methods of treatment in which a compound of Formula I, or a tautomer or pharmaceutically acceptable salt thereof, is given to a patient in combination with one or more additional therapeutic agents or therapy. In some embodiments, the total daily dosage of a compound of Formula I, or a tautomer, or a pharmaceutically acceptable salt thereof, may be about 1 to about 500 mg/day administered in a single dose for a human subject.

Inflammatory Condition or Disease Combination Therapy

In some embodiments, the compounds provided herein, or pharmaceutically acceptable salts thereof, may be combined with one or more additional therapeutic agents that treat or ameliorate an inflammatory condition. Non-limiting examples of an inflammatory condition include, without limitation, acne, acid-induced lung injury, Addison's disease, adrenal hyperplasia, adrenocortical insufficiency, adult-onset Still's disease, adult respiratory distress syndrome (ARDS), age-related macular degeneration, aging, alcoholic hepatitis, alcoholic liver disease, allergen-induced asthma, allergic bronchopulmonary, allergic conjunctivitis, allergic contact dermatitis, allergies, allergic encephalomyelitis, allergic neuritis, allograft rejection, alopecia, alopecia areata, Alzheimer's disease, amyloidosis, amyotrophic lateral sclerosis, angina pectoris, angioedema, angiofibroma, anhidrotic ectodermal dysplasia-ill, anti-glomerular basement membrane disease, antigen-antibody complex mediated diseases, ankylosing spondylitis, antiphospholipid syndrome, aphthous stomatitis, appendicitis, arthritis, ascites, aspergillosis, asthma, atherosclerosis, atherosclerotic plaques, atopic dermatitis, atrophic thyroiditis, autoimmune diseases, autoimmune hemolytic anemia (immune pancytopenia, paroxysmal nocturnal hemoglobinuria), autoimmune polyendocrinopathies, autoimmune thrombocytopenia (idiopathic thrombocytopenic purpura, immune-mediated thrombocytopenia), autoimmune hepatitis, autoimmune thyroid disorders, autoinflammatory diseases, back pain, *Bacillus anthracis* infection, Bechet's disease, bee sting-induced inflammation, Behçet's syndrome, Bell's palsy, berylliosis, Blau syndrome, bone pain, bronchiolitis, bullous pemphigoid (BP) asthma, burns, bursitis, cardiac hypertrophy, carpal tunnel syndrome, Castleman's disease, catabolic disorders, cataracts, Celiac disease, cerebral aneurysm, chemical irritant-induced inflammation, chorioretinitis, chronic atypical neutrophilic dermatosis with lipodystrophy and elevated temperature (CANDLE) syndrome, chronic heart failure, chronic lung disease of prematurity, chronic obstructive pulmonary disease (COPD), chronic pancreatitis, chronic prostatitis, chronic recurrent multifocal osteomyelitis, cicatricial alopecia, colitis, complex regional pain syndrome, complications of organ transplantation, conjunctivitis, connective tissue disease, contact dermatitis, corneal graft neovascularization, corneal ulcer, Crohn's disease, cryopyrin-associated periodic syndromes, cutaneous lupus erythematosus (CLE), cryptococcosis, cystic fibrosis, deficiency of the interleukin-1 receptor antagonist (DIRA), dermatitis, dermatitis endotoxemia, dermatomyositis, diabetic macular edema, diverticulitis, eczema, encephalitis, endometriosis, endotoxemia, eosinophilic pneumonias, epicondylitis, epidermolysis bullosa, erythema multiforme, erythroblastopenia, esophagitis, familial amyloidotic polyneuropathy, familial cold urticarial, familial Mediterranean fever, fetal growth retardation, fibromyalgia, fistulizing Crohn's disease, food allergies, giant cell arteritis, glaucoma, glioblastoma, glomerular disease, glomerular nephritis, glomerulonephritis, gluten-sensitive enteropathy, gout, gouty arthritis, graft-versus-host disease (GVHD), granulomatous hepatitis, Graves' disease, growth plate injuries, Guillain-Barre syndrome. gut diseases, hair loss, Hashimoto's thyroiditis, head injury, headache, hearing loss, heart disease, hemangioma, hemolytic anemia, hemophilic joints, Henoch-Scholein purpura, hepatitis, hereditary periodic fever syndrome, heritable disorders of connective tissue, herpes zoster and simplex, hidradenitis suppurativa (HS), hip replacement, Hodgkin's disease, Huntington's disease, hyaline membrane disease, hyperactive inflammatory response, hyperammonemia, hypercalcemia, hypercholesterolemia, hypereosinophilic syndrome (HES), hyperimmunoglobulinemia D with recurrent fever (HIDS), hypersensitivity pneumonitis, hypertropic bone formation, hypoplastic and other anemias, hypoplastic anemia, ichthyosis, idiopathic demyelinating polyneuropathy, Idiopathic inflammatory myopathies (dermatomyositis, polymyositis), idiopathic pulmonary fibrosis, idiopathic thrombocytopenic purpura, immunoglobulin nephropathies, immune complex nephritis, immune thrombocytopenic purpura (ITP), incontinentia pigmenti (IP, Bloch-Siemens syndrome), infectious mononucleosis, infectious diseases including viral diseases such as AIDS (HIV infection), hepatitis A, B, C, D, and E, herpes; inflammation, inflammation of the CNS, inflammatory bowel disease (IBD), inflammatory disease of the lower respiratory tract including bronchitis or chronic obstructive pulmonary diseases, inflammatory disease of the upper respiratory tract including the nose and sinuses such as rhinitis or sinusitis, inflammatory diseases of the respiratory tract, inflammatory ischemic event such as stroke or cardiac arrest, inflammatory lung disease, inflammatory myopathy such as myocarditis, inflammatory liver disease, inflammatory neuropathy, inflammatory pain, insect bite-induced inflammation, interstitial cystitis, interstitial lung disease, iritis, irritant-induced inflammation, ischemia/reperfusion, joint replacement, juvenile arthritis, juvenile rheumatoid arthritis, keratitis, kidney injury caused by parasitic infections, kidney transplant rejection, leptospirosis, leukocyte adhesion deficiency, lichen sclerosus (LS), Lambert-Eaton myasthenic syndrome, Loeffler's syndrome, lupus, lupus nephritis, Lyme disease, Marfan syndrome (MFS), mast cell activation syndrome, mastocytosis, meningitis, meningioma, mesothelioma, mixed connective tissue disease, Muckle-Wells syndrome (urticaria deafness amyloidosis), mucositis, multiple organ injury syndrome, multiple sclerosis, muscle wasting, muscular dystrophy, myasthenia gravis (MG), myelodysplastic syndrome, myocarditis, myositis, nasal sinusitis, necrotizing enterocolitis, neonatal onset multisystem inflammatory disease (NOMID), neovascular glaucoma, nephrotic syndrome, neuritis, neuropathological diseases, non-allergen induced asthma, obesity, ocular allergy, optic neuritis, organ transplant rejection, Osier-Weber syndrome, osteoarthritis, osteogenesis imperfecta, osteonecrosis, osteoporosis, osterarthritis, otitis, pachyonychia congenita, Paget's disease, Paget's disease of bone, pancreatitis, Parkinson's disease, pediatric rheumatology, pelvic inflammatory disease, pemphigus, pemphigus vulgaris (PV), bullous pemphigoid (BP), pericarditis, periodic fever, periodontitis, peritoneal endometriosis, pernicious anemia (Addison's disease), pertussis, PFAPA (periodic fever aphthous pharyngitis and cervical adenopathy), pharyngitis and adenitis (PFAPA syndrome), plant irritant-induced inflammation, pneumocystis infection, pneumonia, pneumonitis, poison ivy/urushiol oil-induced inflammation, polyarthritis nodosa, polychondritis, polycystic kidney disease, polymyalgia rheumatic, giant cell arteritis, polymyositis, pouchitis, reperfusion injury and transplant rejection, primary biliary cirrhosis, primary pulmonary hypertension, primary sclerosing cholangitis (PSC), proctitis, psoriasis, psoriasis vulgaris, psoriatic arthritis, psoriatic epidermis, psychosocial stress diseases, pulmonary disease, pulmonary fibrosis, pulmonary hypertension, pyoderma gangrenosum, pyogenic granuloma retrolental fibroplasias, pyogenic sterile arthritis, Raynaud's syndrome, Reiter's disease, reactive arthritis, renal disease, renal graft rejection, reperfusion injury, respiratory distress syndrome, retinal disease, retrolental fibroplasia, Reynaud's syndrome, rheumatic carditis, rheumatic diseases, rheumatic fever, rheumatoid arthritis, rhinitis, rhinitis psoriasis, rosacea, sarcoidosis, Schnitzler syndrome, scleritis, sclerosis, scleroderma, scoliosis, seborrhea, sepsis, septic shock, severe pain, Sézary syndrome, sickle cell anemia, silica-induced disease (Silicosis), Sjogren's syndrome, skin diseases, skin irritation, skin rash, skin sensitization (contact dermatitis or allergic contact dermatitis), sleep apnea, spinal cord injury, spinal stenosis, spondyloarthropathies, sports injuries, sprains and strains, Stevens-Johnson syndrome (SJS), stroke, subarachnoid hemorrhage, sunburn, synovial inflammation, systemic inflammatory response syndrome (SIRS), systemic lupus erythematosus (SLE), systemic mast cell disease (SMCD), systemic vasculitis, systemic-onset juvenile idiopathic arthritis, temporal arteritis, tendinitis, tenosynovitis, thrombocytopenia, thyroditis, thyroiditis, tissue transplant, toxoplasmosis, trachoma, transplantation rejection, traumatic brain injury, tuberculosis, tubulointerstitial nephritis, tumor necrosis factor (TNF) receptor associated periodic syndrome (TRAPS), type 1 diabetes, type 2 diabetes, complications from type 1 or type 2 diabetes, ulcerative colitis, urticaria, uterine fibroids, uveitis, uveoretinitis, vascular restenosis, vasculitis, vasculitis (NHLBI), vitiligo, Wegener's granulomatosis, and Whipple's disease.

Non-limiting examples of therapeutic agents for treatment of an inflammatory disease or condition that can be used in combination with the compounds provided herein, or pharmaceutically acceptable salts thereof, include alpha-fetoprotein modulators; adenosine A3 receptor antagonist; adrenomedullin ligands; AKT1 gene inhibitors; antibiotics; antifungals; ASK1 inhibitors; ATPase inhibitors; beta adrenoceptor antagonists; BTK inhibitors; calcineurin inhibitors; carbohydrate metabolism modulators; cathepsin S inhibitors; CCR9 chemokine antagonists; CD233 modulators; CD29 modulators; CD3 antagonists; CD40 ligand inhibitors; CD40 ligand receptor antagonists; chemokine CXC ligand inhibitors; CHST15 gene inhibitors; collagen modulators; COT protein kinase inhibitors; CSF-1 agonist; CSF-1 antagonists; CX3CR1 chemokine modulators DYRK-1 alpha protein kinase inhibitor, eotaxin ligand inhibitors; EP4 prostanoid receptor agonists; F1F0 ATP synthase modulators; farnesoid X receptor (FXR, NR1H4) agonists or modulators; fecal microbiota transplantation (FMT), fractalkine ligand inhibitors; free fatty acid receptor 2 antagonists; GATA 3 transcription factor inhibitors; glucagon-like peptide 2 agonists; glucocorticoid agonists; Glucocorticoid receptor modulators; guanylate cyclase receptor agonists; HIF prolyl hydroxylase inhibitors; histone deacetylase inhibitors; HLA class II antigen modulators; hypoxia inducible factor-1 stimulator; ICAM1 gene inhibitors; IL-1 beta ligand modulators; IL-12 antagonists; IL-13 antagonists; IL-18 antagonists; IL-18 receptor accessory protein antagonist, IL-22 agonists; IL-23 antagonists; IL-23A inhibitors; IL-6 antagonists; IL-7 receptor antagonists; IL-8 receptor antagonists; IL-36 inhibitors, integrin alpha-4/beta-1 antagonists; integrin alpha-4/beta-7 antagonists; integrin antagonists; interleukin ligand inhibitors; interleukin receptor 17A antagonists; interleukin-1 beta ligands; interleukin 1 like receptor 2 inhibitors; IL-6 receptor modulators; JAK tyrosine kinase inhibitors; Jak1 tyrosine kinase inhibitors; Jak3 tyrosine kinase inhibitors; lactoferrin stimulators; LanC like protein 2 modulators; leukocyte elastase inhibitors; leukocyte proteinase-3 inhibitors; MAdCAM inhibitors; melanin concentrating hormone (MCH-1) antagonist; melanocortin agonists; metalloprotease-9 inhibitors; microbiome-targeting therapeutics; natriuretic peptide receptor C agonists; neuregulin-4 ligands; NLRP3 inhibitors; NKG2 D activating NK receptor antagonists; NR1H4 receptor (FXR) agonists or modulators (deleted); nuclear factor kappa B inhibitors; opioid receptor antagonists; OX40 ligand inhibitors; oxidoreductase inhibitors; P2X7 purinoceptor modulators; PDE 4 inhibitors; Pellino homolog 1 inhibitors; PPAR alpha/delta agonists; PPAR gamma agonists; Protein arginine deiminase IV inhibitor, protein fimH inhibitors; P-selectin glycoprotein ligand-1 inhibitors; Ret tyrosine kinase receptor inhibitors; RIP-1 kinase inhibitors; RIP-2 kinase inhibitors; RNA polymerase inhibitors; sphingosine 1 phosphate phosphatase 1 stimulators; sphingosine-1-phosphate receptor-1 agonists; sphingosine-1-phosphate receptor-5 agonists; sphingosine-1-phosphate receptor-1 antagonists; sphingosine-1-phosphate receptor-1 modulators; stem cell antigen-1 inhibitors; superoxide dismutase modulators; SYK inhibitors; tissue transglutaminase inhibitor; TLR-3 antagonists; TLR-4 antagonists; Toll-like receptor 8 (TLR8) inhibitors; TNF alpha ligand inhibitors; TNF ligand inhibitors; TNF alpha ligand modulators; TNF antagonists; TPL-2 inhibitors; tumor necrosis factor 14 ligand modulators; tumor necrosis factor 15 ligand inhibitors; Tyk2 tyrosine kinase inhibitors; type I IL-1 receptor antagonists; vanilloid VR1 agonists; and zonulin inhibitors; or any combination thereof.

Adenosine A3 receptor antagonists include but are not limited to PBF-677.

Adrenomedullin ligands include but are not limited to adrenomedullin.

Antibiotics include but are not limited to ciprofloxacin, clarithromycin, metronidazole, vancomycin, rifamycin, rifaximin, and tosufloxacin.

ASK1 inhibitors include but are not limited to GS-4997.

Alpha-fetoprotein modulators include but are not limited to ACT-101.

Anti-CD28 inhibitors include but are not limited to JNJ-3133 and abatacept.

Beta adrenoceptor antagonists include but are not limited to NM-001.

BTK inhibitors include but are not limited to GS-4059.

Calcineurin inhibitors include but are not limited to tacrolimus and ciclosporin.

Carbohydrate metabolism modulators include but are not limited to ASD-003.

Cathepsin S inhibitors include but are not limited to VBY-129.

CCR9 chemokine antagonists include but are not limited to CCX-507.

CD233 modulators include but are not limited to GSK-2831781.

CD29 modulators include but are not limited to PF-06687234.

CD3 antagonists include but are not limited to NI-0401, muromonab-CD3, and teplizumab.

CD4 antagonists include but are not limited to IT-1208.

CD40 ligand inhibitors include but are not limited to SAR-441344 and letolizumab.

CD40 gene inhibitors include but are not limited to NJA-730.

CD40 ligand receptor antagonists include but are not limited to FFP-104, BI-655064, ABBV-323, and VIB-4920.

Chaperonin binding immunoglobulin protein include but are not limited to IRL-201805.

Chemokine CXC ligand inhibitors include but are not limited to LY-3041658.

CHST15 gene inhibitors include but are not limited to STNM-01.

Collagen modulators include but are not limited to ECCS-50 (DCCT-10).

COT protein kinase inhibitors include but are not limited to GS-4875.

CSF-1 antagonists include but are not limited to JNJ-40346527 (PRV-6527) and SNDX-6352.

CX3CR1 chemokine modulators include but are not limited to E-6130.

DYRK-1 alpha protein kinase inhibitor include but are not limited to VRN-02.

Microbiome-targeting therapeutics include but are not limited to SER-287, SER-301, and SER-155.

Eotaxin ligand inhibitors include but are not limited to bertilimumab.

EP4 prostanoid receptor agonists include but are not limited to KAG-308.

FIFO ATP synthase modulators include but are not limited to LYC-30937 EC.

Fractalkine ligand inhibitors include but are not limited to quetmolimab (E-6011).

Free fatty acid receptor 2 antagonists include but are not limited to GLPG-0974.

GATA 3 transcription factor inhibitors include but are not limited to SB-012.

Glucagon-like peptide 2 agonists include but are not limited to teduglutide and apraglutide.

Glucocorticoid receptor agonists include but are not limited to budesonide, beclomethasone dipropionate, and dexamethasone sodium phosphate.

Glucocorticoid receptor modulators/TNF ligand inhibitors include but are not limited to ABBV-3373.

Guanylate cyclase receptor agonists include but are not limited to dolcanatide.

HIF prolyl hydroxylase inhibitors include but are not limited to DS-1093 and AKB-4924.

HIF prolyl hydroxylase-2 inhibitors/hypoxia inducible factor-1 stimulators include but are not limited to GB-004.

Histone deacetylase inhibitors include but are not limited to givinostat and NIPEP-CARE.

Histone deacetylase-6 inhibitors include but are not limited to CKD-506.

HLA class II antigen modulators include but are not limited to HLA class II protein modulators.

ICAM1 gene inhibitors include but are not limited to alicaforsen.

IL-12 antagonists include but are not limited to ustekinumab (IL12/IL23).

IL-13 antagonists include but are not limited to tralokinumab.

IL-18 antagonists include but are not limited to GSK-1070806.

IL-18 receptor accessory protein antagonist include but are not limited to anti-IL-1R7 canonical antibody.

IL-22 agonists include but are not limited to AMT-126 and RG-7880.

IL-23 antagonists include but are not limited to tildrakizumab, risankizumab (BI-655066), mirikizumab (LY-3074828), brazikumab (AMG-139), IBI-112, and PTG-200.

IL-23A inhibitors include but are not limited to guselkumab.

IL-6 antagonists include but are not limited to olokizumab.

IL-7 receptor antagonists include but are not limited to OSE-127.

IL-8 receptor antagonists include but are not limited to clotrimazole.

Integrin alpha-4/beta-1 antagonists include but are not limited to natalizumab.

Integrin alpha-4/beta-7 antagonists include but are not limited to etrolizumab (a4b7/aEb7), vedolizumab, carotegrast methyl, TRK-170 (a4b7/a4b1), PTG-100, and PN-10943.

Integrin antagonists include but are not limited to E-6007.

Interleukin ligand inhibitors include but are not limited to bimekizumab (IL-17A/IL-17F).

Interleukin receptor 17A antagonists include but are not limited to brodalumab.

Interleukin-1 beta ligands include but are not limited to K(D)PT.

Interleukin 1 like receptor 2 inhibitors include but are not limited to BI-655130.

IL-6 receptor modulators include but are not limited to Amilo-5MER and olamkicept.

JAK tyrosine kinase inhibitors include but are not limited to tofacitinib (1/3), peficitinib (1/3), TD-3504, and TD-1473.

Jak1 tyrosine kinase inhibitors include but are not limited to a compound disclosed in U.S. Pat. No. 9,238,628.

Jak3 tyrosine kinase inhibitors include but are not limited to OST-122 and PF-06651600.

Jak3 tyrosine kinase inhibitor/TrkA receptor antagonist include but are not limited to SNA-125.

Examples of other JAK inhibitors include but are not limited to AT9283, AZD1480, baricitinib, BMS-911543, fedratinib, filgotinib (GLPG0634), gandotinib (LY2784544), INCB039110, lestaurtinib, momelotinib (CYT0387), NS-018, pacritinib (SB1518), peficitinib (ASP015K), ruxolitinib, tofacitinib (formerly tasocitinib), XL019, upadacitinib (ABT-494), LPG-0555, SHR-0302, and brepocitinib (PF-06700841) (JAK1/Tyk2).

Lactoferrin stimulators include but are not limited to recombinant human lactoferrin (VEN-100).

LanC like protein 2 modulators include but are not limited to BT-11 and BT-104.

Leukocyte elastase inhibitors/Leukocyte proteinase-3 inhibitors include but are not limited to tiprelestat.

MAdCAM inhibitors include but are not limited to SHP-647 (PF-547659).

Melanin concentrating hormone (MCH-1) antagonists include but are not limited to CSTI-100.

Melanocortin MCi receptor agonists include but are not limited to ASP-3291 and PL-8177.

Metalloprotease-9 inhibitors include but are not limited to GS-5745.

Microbiome modulators include but are not limited to ABI-M201.

Natriuretic peptide receptor C agonists include but are not limited to plecanatide.

Neuregulin-4 ligands include but are not limited to NRG-4.

NKG2 D activating NK receptor antagonists include but are not limited to JNJ-4500.

NLRP3 inhibitors include but are not limited to dapansutrile, BMS-986299, SB-414, MCC-950, IFM-514, JT-194, PELA-167, and NBC-6.

Farnesoid X receptor (FXR, NR1H4) agonists or modulators include but are not limited to AGN-242266, cilofexor tromethamine (GS-9674), EDP-305, EYP-001, GNF-5120, MET-409, MET-642, nidufexor (LMB-763), obeticholic acid, TERN-101, and tropifexor.

Nuclear factor kappa B inhibitors include but are not limited to Thetanix.

Opioid receptor antagonists include but are not limited to naltrexone and IRT-103.

OX40 ligand inhibitors include but are not limited to KHK-4083.

Oxidoreductase inhibitors include but are not limited to olsalazine.

Pellino homolog 1 inhibitors include but are not limited to BBT-401.

P2X7 purinoceptor modulators include but are not limited to SGM-1019.

PDE 4 inhibitors include but are not limited to apremilast.

PPAR alpha/delta agonists include but are not limited to elafibranor (GFT-1007).

PPAR gamma agonists include but are not limited to GED-0507-34-Levo.

Protein fimH inhibitors include but are not limited to sibofimloc (EB-8018).

P-selectin glycoprotein ligand-1 inhibitors include but are not limited to SEL-K2, AbGn-168H, and neihulizumab.

Ret tyrosine kinase receptor inhibitors include but are not limited to GSK-3179106.

RIP-1 kinase inhibitors include but are not limited to GSK-2982772 and VRN-04.

RIP-2 kinase inhibitors include but are not limited to GSK-2983559.

Sphingosine 1 phosphate phosphatase 1 stimulators include but are not limited to etrasimod.

Sphingosine-1-phosphate receptor-1 agonists include but are not limited to mocravimod (KRP-203) and BMS-986166.

Sphingosine-1-phosphate receptor-1 agonists/Sphingosine-1-phosphate receptor-5 agonists include but are not limited to ozanimod.

Sphingosine-1-phosphate receptor-1 antagonists include but are not limited to amiselimod (MT-1303).

Sphingosine-1-phosphate receptor-1 modulators include but are not limited to OPL-002, SK1-I.

Stem cell antigen-1 inhibitors include but are not limited to Ampion (DMI-9523).

Superoxide dismutase modulators include but are not limited to midismase.

Syk inhibitors include but are not limited to GS-9876.

tissue transglutaminase inhibitor include but are not limited to zampilimab

TLR-3 antagonists include but are not limited to PRV-300.

TLR-4 antagonists include but are not limited to JKB-122.

Toll-like receptor 8 (TLR8) inhibitors include but are not limited to E-6887, IMO-4200, IMO-8400, IMO-9200, MCT-465, MEDI-9197, motolimod, resiquimod, VTX-1463, and VTX-763.

TNF alpha ligand inhibitors include but are not limited to adalimumab, certolizumab pegol, infliximab, golimumab, DLX-105, Debio-0512, HMPL-004, CYT-020-TNFQb, Hemay-007, and V-565.

TNF alpha ligand modulators/IL-1 beta ligand modulators include but are not limited to PUR-0110.

TNF antagonists include but are not limited to AVX-470, tulinercept, and etanercept.

Tumor necrosis factor 14 ligand modulators include but are not limited to AEVI-002.

Tumor necrosis factor 15 ligand inhibitors include but are not limited to PF-06480605.

Tyk2 tyrosine kinase inhibitors include but are not limited to PF-06826647 and BMS-986165.

Type I IL-1 receptor antagonists include but are not limited to anakinra.

Zonulin inhibitors include but are not limited to larazotide acetate.

In some embodiments, the compounds provided herein, or pharmaceutically acceptable salts thereof, may be combined with one or more anti-inflammatory agents. Anti-inflammatory agents include but are not limited to non-steroidal anti-inflammatory drugs (NSAIDs), non-specific and COX-2 specific cyclooxgenase enzyme inhibitors, gold compounds, corticosteroids, methotrexate, tumor necrosis factor receptor (TNF) receptors antagonists, and immunosuppressants.

Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Additional examples of NSAIDs also include but are not limited to COX-2 specific inhibitors (i.e., a compound that inhibits COX-2 with an $IC_{50}$ that is at least 50-fold lower than the $IC_{50}$ for COX-1), such as celecoxib, valdecoxib, lumiracoxib, etoricoxib and/or rofecoxib.

In some embodiments, the anti-inflammatory agent is a salicylate. Salicylates include but are not limited to acetylsalicylic acid or aspirin, sodium salicylate, choline, and magnesium salicylates.

In some embodiments, the anti-inflammatory agent is a corticosteroid. Non-limiting examples of a corticosteroid include cortisone, dexamethasone, methylprednisolone, prednisolone, prednisolone sodium phosphate, and prednisone.

In some embodiments, the anti-inflammatory agent is a gold compound, e.g., gold sodium thiomalate or auranofin.

In some embodiments, the anti-inflammatory agent is a metabolic inhibitor. Non-limiting examples of a metabolic inhibitor include a dihydrofolate reductase inhibitor, such as methotrexate, or a dihydroorotate dehydrogenase (DHODH) inhibitor, such as leflunomide.

In some embodiments, the anti-inflammatory agent is an anti-C5 monoclonal antibody (such as eculizumab or pexelizumab), a TNF antagonist (such as entanercept), or infliximab, which is an anti-TNF alpha monoclonal antibody.

In some embodiments, the anti-inflammatory agent is an immunosuppressant. Non-limiting examples of an immunosuppressant include methotrexate, leflunomide, cyclosporine, tacrolimus, azathioprine, mycophenolate sodium, mercaptopurine, and mycophenolate mofetil.

Lupus Combination Therapy

In some embodiments, the compounds provided herein, or pharmaceutically acceptable salts thereof, is combined with one or more additional therapeutic agents that target adenosylhomocysteinase, ADP ribosyl cyclase-1 (CD38), adrenocorticotrophic hormone ligands, AIMP multisynthetase complex protein 1, annexin A1 modulators, B and T lymphocyte attenuator (BTLA), BDCA2, beta 2 adrenoceptor, B-lymphocyte antigen CD19, B-lymphocyte antigen CD20, B-lymphocyte cell adhesion molecule (CD22), B-lymphocyte stimulator ligand (BAFF), btk tyrosine kinase, cannabinoid CB2 receptor, CD11b agonists, CD38 Activation-inducible TNF receptor, CD40 (CD154) ligand, CD74, CD79b modulators, CDw123, Collagen VII (Col VII), Complement C5 factor, C-type lectin domain protein 4C, CXCR5 chemokine modulators, deoxyribonuclease modulators, DNA binding protein Ikaros, DYRK-1 alpha protein kinase, dndoplasmin, Exportin 1, FK506 binding protein, glucocorticoid receptor, HLA antigen, IL-10, IL-23m IL-12 receptors, IL-2 receptor, IL-2 receptor alpha subunit, IL-21 modulators, IL-6R, immunoglobulin gamma Fc receptor II modulators, immunoglobulin gamma Fc receptor IIB, inducible T-cell co-stimulator, interferon alpha ligand (INF-alpha), interferon omega ligand (INF omega), interferon type I receptor, interleukin-2 ligand, Itk tyrosine kinase, JAK tyrosine kinase, Jak1 tyrosine kinase, Jak2 tyrosine kinase, Jak3 tyrosine kinase, KCNA voltage-gated potassium channel-3, leukocyte Ig like receptor A4 modulators, mitochondrial 10 kDa heat shock protein, mTOR, non receptor tyrosine kinase TYK2, nuclear export, nuclear factor kappa B inducing kinase, nuclease stimulators, OX-40 receptors, PARP modulators, proteasome modulators, protein arginine deiminase IV (PAD4), protein cereblon modulators, protein MB21D1, retinoid Z receptor gamma inverse, rho associated protein kinase 1, rho associated protein kinase 2, serine threonine protein kinase TBK1 (TBK1), sphingosine kinase 1, sphingosine-1-phosphate receptor-1 modulators, stimulator of interferon genes protein, Syk tyrosine kinase, T cell surface glycoprotein CD28, T-cell differentiation antigen CD6, TLR-7 modulators, TLR-8 modulators, TLR-9 modulators, transcription factor modulators, tumor necrosis factor ligand 13 (APRIL), Tyk2 tyrosine kinase, ubiquitin ligase modulators, and/or zinc finger binding protein Aiolos.

In some embodiments, the compounds provided herein, or pharmaceutically acceptable salts thereof, may be combined with one, two, three, or four additional therapeutic agents selected from:

activation-inducible TNF receptor agonists, including but not limited to BMS-986256;

adenosylhomocysteinase inhibitors, including but not limited to DZ-2002;

adrenocorticotrophic hormone ligands, including but not limited to corticotropin;

AIMP multisynthetase complex protein 1 stimulator/Endoplasmin inhibitors, including but not limited to anchorins;

anti-CDw123 antibodies, including but not limited to talacotuzumab;

annexin A1 modulators, including but not limited to annexuzlimab;

anti-IL-12/IL23 antibodies, including but not limited to AK-101;
anti-BAFF-R antibodies, including but not limited to lanalumab;
anti-BDCA2 antibodies, including but not limited to BIIB-059;
anti-BLys antibodies, including but not limited to belimumab and UBP-1213;
anti-BTLA modulator antibodies, including but not limited to LY-3361237;
anti-C5 antibodies, including but not limited to eculizumab;
anti-CD154 antibodies, including but not limited to TNX-1500;
anti-CD19/CD32b antibodies, including but not limited to obexelimab;
anti-CD20 antibodies, including but not limited to veltuzumab;
anti-CD22 antibodies, including but not limited to SM-06, SM-03;
anti-CD28 antibodies, including but not limited to theralizumab;
anti-CD38 antibodies, including but not limited to TAK-079 and felzartamab;
anti-CD40 antibodies, including but not limited to iscalimab and dapirolizumab pegol;
anti-CD6 antibodies, including but not limited to itolizumab;
anti-CD74 antibodies, including but not limited to milatuzumab;
anti-CXCR5 antibodies, including but not limited to PF-06835375;
anti-IFN-alpha antibodies, including but not limited to QX-006-N;
anti-IFN-alpha/omega antibodies, including but not limited to JNJ-55920839;
anti-IL-10 antibodies, including but not limited to BT-063;
anti-IL-21 antibodies, including but not limited to BOS-161721;
anti-IL-6R nanobodies, including but not limited to vobarilizumab;
anti-ILT7 antibodies, including but not limited to daxdilimab;
anti-interferon alpha vaccines, including but not limited to CKD-971;
anti-interferon receptor type I antibodies, including but not limited to anifrolumab;
anti-PAD4 antibodies, including but not limited to PFI-102;
anti-TLR-7 antibodies, including but not limited to DS-7011;
BAFF/APRIL inhibitors, including but not limited to ALPN-303;
Beta 2 adrenoceptor agonists, including but not limited to R-salbutamol sulphate;
bi-specific antibodies targeting BAFF/ICOSL, including but not limited to rozibafusp alfa;
bi-specific antibodies targeting CD32B/CD79B, including but not limited to PRV-3279;
bi-specific antibodies targeting Col VII/BAFF, including but not limited to TE-2324;
B-lymphocyte stimulator ligand inhibitors, including but not limited to atacicept and telitacicept;
Btk tyrosine kinase inhibitors, including but not limited to AC-0058, fenebrutinib, XNW-1011, tirabrutinib hydrochloride, branebrutinib, elsubrutinib, and orelabrutinib;
Btk/itk tyrosine kinase inhibitors, including but not limited to DWP-213388;
Btk/Jak3 tyrosine kinase inhibitors, including but not limited to DWP-212525;
cannabinoid CB2 receptor agonists, including but not limited to julemic acid;
CD11b agonists, including but not limited to LA-1;
deoxyribonuclease gamma stimulators, including but not limited to NTR-441;
deoxyribonuclease modulators, including but not limited to Oshadi D;
DYRK-1 alpha protein kinase inhibitors, including but not limited to VRN-02;
exportin 1 inhibitors, including but not limited to SINE compounds;
glucocorticoid receptor agonists, including but not limited to prednisone;
HLA antigen modulators, including but not limited to PEGylated HLA-x (SLE);
IL-2 receptor alpha subunit stimulators, including but not limited to NKTR-35;
immunoglobulin gamma Fc receptor IIB modulators, including but not limited to valziflocept;
inducible T-cell co-stimulator inhibitor (ICOS)/T cell surface glycoprotein CD28 inhibitors, including but not limited to ALPN-101;
interferon alpha ligand modulator/TLR-7/TLR-9 modulators, including but not limited to DV-1079;
interleukin-2 ligands, including but not limited to interleukin-2 Anteluke, interking recombinant human interleukin-2, ILT-101, and CUG-252;
interleukin-2 ligands/IL-2 receptor agonists, including but not limited to interleukin-2 follow-on biologic;
JAK 1/2/3 and ROCK 1/2 inhibitors, including but not limited to CPL-409116;
JAK tyrosine kinase inhibitors, including but not limited to delgocitinib;
Jak1/Jak2 tyrosine kinase inhibitors, including but not limited to baricitinib;
Jak1 tyrosine kinase inhibitors, including but not limited to upadacitinib, filgotinib, itacitinib, and INCB-54707;
Jak1/Tyk2 tyrosine kinase inhibitors, including but not limited to brepocitinib, SDC-1801, and SDC-1802;
JAK3/1 and TBK1 kinase inhibitors, including but not limited to CS-12192;
JAK3/JAK1 tyrosine kinase inhibitors, including but not limited to tofacitinib citrate;
KCNA voltage-gated potassium channel-3 inhibitors, including but not limited to dalazatide;
mitochondrial 10 kDa heat shock protein stimulators, including but not limited to INV-103;
mTOR inhibitors, including but not limited to TAM-01;
non-receptor tyrosine kinase TYK2 antagonists, including but not limited to ICP-330;
nuclear export inhibitors, including but not limited to verdinexor;
nuclear factor kappa B inducing kinase inhibitors, including but not limited to NIK-SMI1;
nuclease stimulators, including but not limited to RSLV-132;
OX-40 receptor antagonists, including but not limited to ISB-830;
PARP modulators, including but not limited to bendamustine hydrochloride;
PD-L1 CAR-expressing NK-92 cell therapy;
proteasome inhibitors, including but not limited to KZR-616;

protein cereblon modulators, including but not limited to iberdomide;

protein MB21D1 inhibitors, including but not limited to X-6;

retinoid Z receptor gamma inverse agonists, including but not limited to INV-17;

sphingosine kinase 1 inhibitors, including but not limited to BML-258;

sphingosine-1-phosphate receptor-1 modulator, including but not limited to cenerimod;

Syk tyrosine kinase inhibitors, including but not limited to GSK-2646264, SKI-O-703, lanraplenib (GS-9876), GNS-1653, and HMPL-523;

TLR-9 antagonists, including but not limited to chloroquine, hydroxychloroquine, hydroxychloroquine sulfate, COV-08-0064; GNKS-356, and AVO-101;

TLR7/8 antagonists, including but not limited to M-5049, E-6887, and BMS-986256;

TLR-8 antagonists, including but not limited to ZG-170607;

TLR7/8/9 antagonists, including but not limited to IMO-8400 and IMO-9200;

Tyk2 tyrosine kinase inhibitors, including but not limited to deucravacitinib;

ubiquitin ligase modulators, including but not limited to KPG-818; and other drugs for lupus, including but not limited to mometasone, betamethasone, forigerimod, anandamide, DCB-SLE1, arsenic trioxide, tairuimide, TV-4710 (edratide), allogeneic human umbilical cord-derived mesenchymal stem cell therapy (hUC-MSCs), LC-200, BI-705564, SM-934, GX-101, TXR-712, TXR-711, CIT-013, MHV-370, Panzyga®, TPX-6001, TPX-7001, artenimol, AMG-592, phosphatidylserine-liposome-based immunotherapy, and CD4+CD127lo/-CD25+ polyclonal regulatory T cells.

In some embodiments, the compounds provided herein, or pharmaceutically acceptable salts thereof, may be combined with one, two, three, or four additional therapeutic agents selected from veltuzumab, PF-06835375, eculizumab, milatuzumab, SM-06, SM-03, BT-063, QX-006-N, BOS-161721, AK-101, TNX-1500, theralizumab, daxdilimab, TAK-079, felzartamab, itolizumab, anifrolumab, iscalimab, dapirolizumab pegol, lanalumab, LY-3361237, JNJ-55920839, UBP-1213, DS-7011, PFI-102, BIIB-059, obexelimab, talacotuzumab, vobarilizumab, TE-2324, PRV-3279, chloroquine, hydroxychloroquine, hydroxychloroquine sulfate, COV-08-0064; GNKS-356, AVO-101, rozibafusp alfa, VRN-02, annexuzlimab, ALPN-101, bendamustine hydrochloride, BMS-986256, NKTR-35, atacicept, telitacicept, BMS-986256, M-5049, KZR-616, KPG-818, verdinexor, ALPN-303, valziflocept, LA-1, cenerimod, prednisone, corticotropin, deucravacitinib, CPL-409116, CS-12192, tofacitinib citrate, ISB-830, DV-1079, julemic acid, iberdomide, TAM-01, BML-258, brepocitinib, SDC-1801, SDC-1802, ICP-330, NTR-441, dalazatide, GSK-2646264, SKI-O-703, lanraplenib (GS-9876), GNS-1653, HMPL-523, RSLV-132, interleukin-2 follow-on biologic, interleukin-2 Anteluke, interking recombinant human interleukin-2, ILT-101, CUG-252, DZ-2002, PEGylated HLA-x (SLE), AC-0058, fenebrutinib, XNW-1011, tirabrutinib hydrochloride, branebrutinib, elsubrutinib, orelabrutinib, DWP-213388, INV-103, R-salbutamol sulphate, anchorins, NIK-SMI1, X-6, INV-17, Oshadi D, baricitinib, upadacitinib, filgotinib, itacitinib, INCB-54707, delgocitinib, DWP-212525, CKD-971, as mometasone, betamethasone, forigerimod, anandamide, DCB-SLE1, arsenic trioxide, tairuimide, TV-4710 (edratide), allogeneic human umbilical cord-derived mesenchymal stem cell therapy (hUC-MSCs), LC-200, BI-705564, SM-934, GX-101, TXR-712, TXR-711, CIT-013, MHV-370, Panzyga®, TPX-6001, TPX-7001, artenimol, and AMG-592, or a pharmaceutically acceptable salt of any of the foregoing, or any combination thereof.

Psoriasis Combination Therapy

In some embodiments, the compounds provided herein, or pharmaceutically acceptable salts thereof, may be combined with one, two, three, or four additional therapeutic agents that are useful for treating or ameliorating psoriasis. In some embodiments, the compounds provided herein, or pharmaceutically acceptable salts thereof, may be combined with one, two, three, or four additional therapeutic agents selected from acetaldehyde dehydrogenase inhibitor, adenosine A1 receptor antagonist, adenosine A3 receptor antagonist, adenosine A3 receptor agonists, ADP ribosyl cyclase-1 inhibitors, alpha 2 adrenoceptor modulator, apolipoprotein A antagonist, aryl hydrocarbon receptor agonist, Bcl-xL Bcl-2 associated death promotor modulators, beta amyloid antagonist, beta-catenin inhibitors, bromodomain containing protein inhibitor, Ca2+ release activated Ca2+ channel 1 inhibitors, calcineurin inhibitors, calcium channel inhibitors, cannabinoid CB1 receptor antagonist, cathepsin S inhibitors, CCR3 chemokine antagonists, CXCR2 chemokine antagonist, CXCR1/2 chemokine, CCR6 chemokine antagonist, CD223 modulators, CD40 ligand receptor antagonists, cell adhesion molecule inhibitors, cell surface glycoprotein MUC18 inhibitors, CREB binding protein inhibitors, CXCR4 chemokine modulators, cytokine receptor antagonist, cytosolic phospholipase A2 inhibitors, DHFR inhibitors, DYRK-1 alpha protein kinase inhibitor, EGFR family tyrosine kinase receptor inhibitors, enolase 1 inhibitor, eotaxin ligand inhibitors, FIFO ATP synthase modulator, free fatty acid receptor 2 agonist, free fatty acid receptor 3 agonist, galectin-3 inhibitors, glucocorticoid agonists, GM-CSF ligand inhibitors, GNRH receptor modulators, 5-HT 1a receptor antagonist, FGF receptor antagonist, GroEL protein 2 inhibitor, histamine H1 receptor antagonists, histamine H4 receptor antagonists, histone deacetylase-1 inhibitors, histone deacetylase-2 inhibitors, histone deacetylase-3 inhibitors, histone deacetylase-6 inhibitors, Hsp 90 inhibitor, IL-1 receptor antagonist, interleukin 1 like receptor 2 inhibitor, IL-2 receptor alpha subunit stimulator, IL-2 modulator, IL-10 antagonists, IL-12 antagonists, IL-17 agonist, IL17RA gene inhibitor, IL-17 antagonists, IL-23 antagonists, IL-8 antagonists, immunoglobulin like domain receptor 2 antagonist, insulin receptor substrate-1 inhibitors, interferon gamma receptor antagonists, interleukin 17 ligand inhibitors, interleukin 17A ligand inhibitors, interleukin 17A ligand modulators, interleukin 17F ligand inhibitors, interleukin 23A inhibitors, interleukin receptor 17A antagonists, interleukin receptor 17A modulators, interleukin-1 alpha ligand inhibitors, interleukin-1 beta ligand modulators, IRAK-4 protein kinase inhibitor, Itk tyrosine kinase inhibitor, JAK tyrosine kinase inhibitors, Jak1 tyrosine kinase inhibitors, Jak2 tyrosine kinase inhibitors, Jak3 tyrosine kinase inhibitors, KCNA voltage-gated potassium channel-3 inhibitors, Lck tyrosine kinase inhibitors, lysophosphatidate-1 receptor antagonists, MALT protein 1 inhibitors, MAP kinase inhibitors, membrane copper amine oxidase inhibitors, metalloprotease-1 inhibitors, mitochondrial 10 kDa heat shock protein stimulators, mTOR complex 1 inhibitor, mTOR complex 2 inhibitor, non receptor tyrosine kinase TYK2 antagonists, nuclear erythroid 2-related factor 2 stimulators, nuclear factor kappa B inhibitors, nucleoside reverse transcriptase inhibitors, oncostatin M receptor subunit beta inhibitor, opioid receptor delta antagonists, OX40 ligand inhibitor, parathyroid hormone ligand inhibitors, PDE 4 inhibitors, PDE 4b inhibitor, P2Y6 purinoceptor modulator; P-glycoprotein inhibitors, phosphoinositide-3 kinase delta inhibitors, phosphoinositide-3 kinase gamma inhibitors, phospholipase A2 inhibitors, programmed cell death ligand 1 modulators, programmed cell death protein 1 stimulator, P-selectin glycoprotein ligand-1 stimulators, retinoic acid receptor agonists, retinoic acid receptor gamma antagonists, retinoic acid receptor gamma inverse agonists, retinoid receptor agonists, retinoid X receptor agonists, retinoid X receptor modulators, retinoid Z receptor gamma agonists, retinoid Z receptor gamma inverse agonists, retinoid Z receptor gamma antagonist, rho associated protein kinase 2 inhibitors, ribonuclease P inhibitors, RIP-1 kinase inhibitor, sphingosine-1-phosphate receptor-1 antagonists, sphingosine-1-phosphate receptor-1 modulators, Src tyrosine kinase inhibitors, STAT-3 inhibitors, Syk tyrosine kinase inhibitor, T-box transcription factor TBX21 modulators, T-cell differentiation antigen CD6 inhibitors, T-cell surface glycoprotein CD8 inhibitors, T cell surface glycoprotein CD28 stimulator, TGF beta agonists, TLR-7 antagonists, TLR-8 antagonists, TLR-9 antagonists, TNF alpha ligand inhibitors, TNF alpha ligand modulators, TNF antagonists, TNF binding agents, TNF gene inhibitor, topoisomerase II inhibitors, TrkA receptor antagonists, tubulin binding agents, Tyk2 tyrosine kinase inhibitor, type II TNF receptor modulators, unspecified cytokine receptor antagonists, vitamin D3 receptor agonists, vitamin D3 receptor modulators, Wnt ligand inhibitor, and Wnt 5A ligand inhibitor.

In some embodiments, the compounds provided herein, or pharmaceutically acceptable salts thereof, may be combined with one, two, three, or four additional therapeutic agents selected from AP-005, 18C3 (anti-IL-1 alpha true human antibody), ABX-464, acitretin, adalimumab, adipocell, AFB-035, aganirsen, AKP-11, alefacept, alitretinoin, Amilo-5mer, aminopterin, amiselimod, apremilast, ASKP-1240, AST-005, ATI-2138, AVX-001, baricitinib, belapectin (GR-MD-02), bertilimumab, betamethasone, BI-655066, BI-730357, BI-730460, BI-730460, bimekizumab, BMS-986165, BMX-010, briakinumab, brodalumab, BTT-1023, C-82, calcipotriol, calcitriol, CC-90005, CCL-20LD, CD-10367, certolizumab pegol, CF-101, ciclosporin, CJM-112, CKBA, clobetasol propionate+tretinoin, CM-2489, CPL-409116, crisaborole, CS-12192, CT-327, CTX-101, dalazatide, DFD-06, dimethyl fumarate, dithranol, DLX-105, DSXS-1411, DSXS-1535, DUR-928, EDP-1815, etanercept, fluocinonide, FPP-003, GK-664-S, GLG-801, GLPG-3121, GLPG-3667, GLPG-3970, GLY-2028, GMDP, GSK-2800528, GSK-2831781, GSK-2981278A, guselkumab, halomethasone, HAT-1, IMO-3100, IMO-8400, inecalcitol, infliximab, INV-103, IR-444, IR-502, itolizumab, ixekizumab, JN-2528, KBL-697, KD-025, LAS-41004, LEO-124249, LEO-29102, LEO-32731, LEO-35299, lithium succinate, LNP-1955, LP-0200, M-1095, maxacalcitol, MDX-018, methotrexate, MOL-4249, mometasone, MP-1032, MSB-03, myristyl nicotinate, namilumab, neihulizumab, niclosamide, NLP-91, NP-000888, NVN-1000, olopatadine, orilotimod, P-3072, P-3073, PAT-1657, Pc4, pefcalcitol, PF-06700841, Prurisol, PRX-003, PRX-167700, PUR-0110, recombinant human LFA-3/antibody fusion protein, RON-2315, RTU-1096, 5-414114, secukinumab, SHP-141, SMET-D1, SNK-01, SP-14019, SSS-07, tacalcitol, tazarotene, tildrakizumab, tirbanibulin (KX-01), tofacitinib, toreforant, tregalizumab, TU-2100, UCB-5857, UHE-105, ulobetasol, ustekinumab, VBY-891, voclosporin, VTP-43742, WBI-1001, and ZPL-389, or a pharmaceutically acceptable salt of any of the foregoing, or any combination thereof.

In some embodiments, the compounds provided herein, or pharmaceutically acceptable salts thereof, may be combined with one, two, three, or four additional therapeutic agents selected from:

acetaldehyde dehydrogenase inhibitor, including but not limited to ADX-629;

adenosine A3 receptor agonists, including but not limited to piclidenoson (CF-101);

adenosine A3 receptor antagonist, including but not limited to PBF-1650;

ADP ribosyl cyclase-1 inhibitors, including but not limited to IMO-3100;

5-HT 1a receptor antagonist, including but not limited to AX-1602;

apolipoprotein A antagonist, including but not limited to orticumab;

cytokine receptor antagonist, including but not limited to tapinarof;

aryl hydrocarbon receptor modulator, including but not limited to NTI-528 and RLV-102;

Bcl-xL Bcl-2 associated death promotor modulators, including but not limited to Pc4;

beta-catenin inhibitors, including but not limited to C-82;

bromodomain containing protein inhibitor, including but not limited to BOS-475;

Ca2+ release activated Ca2+ channel 1 inhibitors, including but not limited to CM-2489 and PRCL-02;

calcineurin inhibitors, including but not limited to voclosporin, pimecrolimus, tacrolimus, ciclosporin, HS-378, oxeclosporin, OLO-400, ADV-P3, and CTX-006;

calcium channel inhibitors, including but not limited to RP-3128;

cathepsin S inhibitors, including but not limited to VBY-129, VBY-891, RWJ-445380, and CRA-028129;

CCR3 chemokine antagonists, including but not limited to bertilimumab;

CXCR2 chemokine antagonist, including but not limited to CCX-624;

CD223 modulators, including but not limited to GSK-2831781;

CD40 ligand receptor antagonists, including but not limited to ASKP-1240, lucatumumab, and toralizumab;

cell adhesion molecule inhibitors, including but not limited to BIRT-2584, PC-114, alicaforsen, IC-747, ICM-3, and ISIS-2302;

cell surface glycoprotein MUC18 inhibitors, including but not limited to PRX-003 and imaprelimab;

CREB binding protein inhibitors, including but not limited to C-82;

CXCR1/2 chemokine, including but not limited to LY-3041658;

CXCR4 chemokine modulators, including but not limited to CD184-FK506 ADC;

cytosolic phospholipase A2 inhibitors, including but not limited to AVX-001;

DHFR inhibitors, including but not limited to methotrexate, CH-4051, CePep, CH-1504, MQX-5902, and MPI-2505;

DYRK-1 alpha protein kinase inhibitor, including but not limited to VRN-02;

EGFR family tyrosine kinase receptor inhibitors, including but not limited to erlotinib, icotinib hydrochloride, and SGT-210;

Enolase 1 inhibitor, including but not limited to HuL-001;

Eotaxin ligand inhibitors, including but not limited to bertilimumab;
FIFO ATP synthase modulator, including but not limited to LYC-30937;
FGF receptor antagonist, including but not limited to potassium dobesilate;
free fatty acid receptor 2, 3 agonist, including but not limited to SFA-002;
galectin-3 inhibitors, including but not limited to belapectin (GR-MD-02);
glucocorticoid agonists, including but not limited to betamethasone, clobetasol, auranofin, NM-135, DSXS-1538b, and SEGRA;
GM-CSF ligand inhibitors, including but not limited to namilumab;
GNRH receptor modulators, including but not limited to NL-001;
GroEL protein 2 inhibitor, including but not limited to prozumab;
histamine H1 receptor antagonists, including but not limited to olopatadine and loratadine+nortriptyline;
histamine H4 receptor antagonists, including but not limited to toreforant and ZPL-389;
histone deacetylase-2 inhibitors, including but not limited to KAR-1880;
histone deacetylase 1, 6, 2, 3 inhibitors, including but not limited to remetinostat (SHP-141);
Hsp 90 inhibitor, including but not limited to CTXT-102;
IL-2 receptor alpha subunit stimulator, including but not limited to NKTR-358;
IL-2 modulator; including but not limited to CC-92252;
IL-10 antagonists, including but not limited to pimecrolimus;
IL-12 antagonists, including but not limited to BOW-090, briakinumab, FM-202, and apilimod;
IL-17 antagonists, including but not limited to ixekizumab, secukinumab, AFB-035, KD-025, DLX-3003, EBI-028, M-1095, IMO-3100, GR-1501, 608, vunakizumab, sonelokimab, AK-111, HB-0017, and SIM-335;
IL-17 agonist, including but not limited to ZL-1102;
IL17RA gene inhibitor, including but not limited to XCUR-17;
IL-23 antagonists, including but not limited to tildrakizumab, BI-655066, AMG-139, briakinumab, mirikizumab (LY-3074828), F M-202, apilimod, LY-2525623, risankizumab, and IBI-112;
IL-23 antagonist, including but not limited to ustekinumab and AK-101;
IL-8 antagonists, including but not limited to BMS-986253 (MDX-018), A S-101, ABX-IL8, LI-312, SB-332235, and LF-216;
immunoglobulin like domain receptor 2 antagonist, including but not limited to CGEN-15001;
insulin receptor substrate-1 inhibitors, including but not limited to aganirsen;
interferon gamma receptor antagonists, including but not limited to pimecrolimus, AMG-811, OA-1, AGT-1, mometasone+nortriptyline, and fontolizumab;
interleukin 17 ligand inhibitors, including but not limited to CJM-112, netakimab, and AFB-035;
interleukin 17A ligand inhibitors, including but not limited to COVA-322, JS-005, and ABY-035/AFO2;
interleukin 17A ligand modulators, including but not limited to QX-002-N;
interleukin 17A/17F ligand inhibitors, including but not limited to bimekizumab;
interleukin 23A inhibitors, including but not limited to guselkumab and QX-004-N;
interleukin receptor 17A antagonists, including but not limited to brodalumab and LZM-012;
interleukin 1 like receptor 2 inhibitor, including but not limited to spesolimab and imsidolimab;
interleukin-1 alpha ligand inhibitors, including but not limited to bermekimab (CA-18C3);
interleukin-1 beta ligand modulators, including but not limited to PUR-0110 and AR-100;
IRAK-4 protein kinase inhibitor, including but not limited to BAY-1834845;
Itk tyrosine kinase inhibitor, including but not limited to JTE-051;
JAK tyrosine kinase inhibitors, including but not limited to CS-17380;
Jak1 tyrosine kinase inhibitors, including but not limited to itacitinib, abrocitinib (PF-04965842), solcitinib, SHR-0302, and filgotinib;
JAK1,2,3 tyrosine kinase inhibitor, including but not limited to jaktinib;
JAk1,2 tyrosine kinase inhibitors, including but not limited to baricitinib and ruxolitinib;
TYk2 tyrosine kinase inhibitor, including but not limited to brepocitinib;
Jak1 tyrosine kinase inhibitor, including but not limited to PF-06263276;
JAk 1, 3 tyrosine kinase inhibitor, including but not limited to CS-944X, tofacitinib, and peficitinib;
KCNA voltage-gated potassium channel-3 inhibitors, including but not limited to KPI-150, dalazatide, BNC-164, and SPS-4251;
Lck tyrosine kinase inhibitors, including but not limited to BMS-350751 and NTRC-0625-0;
lysophosphatidate-1 receptor antagonists, including but not limited to BMS-986202;
MAP kinase inhibitors, including but not limited to AIK-33 and KIN-3032;
membrane copper amine oxidase inhibitors, including but not limited to vepalimomab, BTT-1023, RTU-1096, and PRX-167700;
metalloprotease-1 inhibitors, including but not limited to KIN-3032 and HMR-1571;
mitochondrial 10 kDa heat shock protein stimulators, including but not limited to INV-103;
Non receptor tyrosine kinase TYK2 antagonists, including but not limited to SAR-20347, ICP-332, and SDC-1801;
nuclear erythroid 2-related factor 2 stimulators, including but not limited to dimethyl fumarate and XP-23829;
nuclear factor kappa B inhibitors, including but not limited to S-414114, VGX-1027, AKBA, SP-100030, and YP-008;
nucleoside reverse transcriptase inhibitors, including but not limited to Prurisol;
oncostatin M receptor subunit beta inhibitor, including but not limited to vixarelimab;
Opioid receptor delta antagonists, including but not limited to HS-378;
OX40 ligand inhibitor, including but not limited to KY-1005;
P38 MAP kinase inhibitor, including but not limited to AMG-101, AIK-3, VGX-1027, AIK-al, BMS-582949, doramapimod, semapimod, TA-5493, HEP-689, and RWJ-68354;
parathyroid hormone ligand inhibitors, including but not limited to inecalcitol;

PDE 4 inhibitors, including but not limited to apremilast, roflumilast, orismilast, MK-0873, Ro-20-1724, HMR-1571, RPR-122818, HPP-737, crisaborole, and DC-591042;

PDE 4b inhibitor, including but not limited to GRT-6015;

TNF alpha ligand inhibitor, including but not limited to Hemay-005;

P-Glycoprotein inhibitors, including but not limited to boningmycin;

Beta amyloid antagonist, including but not limited to GC-021109;

phosphoinositide-3 kinase delta inhibitors, including but not limited to seletalisib (UCB-5857);

mTOR complex 2 inhibitor, including but not limited to bimiralisib;

phosphoinositide-3 kinase gamma inhibitors, including but not limited to TAT-N25 peptide;

phospholipase A2 inhibitor, including but not limited to ZPL-521, Project P-0229, BMS-181162, and BMS-188184;

programmed cell death ligand 1 modulators, including but not limited to GX-P2;

programmed cell death protein 1 stimulator, including but not limited to LY-3462817 and CC-90006;

P-selectin glycoprotein ligand-1 stimulators, including but not limited toneihulizumab;

P-selectin glycoprotein ligand-1, including but not limited to AbGn-168H;

retinoic acid receptor agonists, including but not limited to acitretin, tazarotene, tretinoin, tazarotene arotinoid trometamol, CD-1599, AM-580, BMS-181163, and CPR-2005;

retinoic acid receptor gamma antagonists, including but not limited to VTP-43742 and BBI-6000;

retinoic acid receptor gamma inverse agonists, including but not limited to GSK-2981278A and JNJ-3534;

retinoid receptor agonists, including but not limited to RASP;

retinoid X receptor agonists, including but not limited to LGD-1550;

retinoid X receptor modulators, including but not limited to bexarotene, alitretinoin, ALRT-1069, LGD-1069, and Net-41B;

retinoid Z receptor gamma agonists, including but not limited to NCE-407;

retinoid Z receptor gamma inverse agonists, including but not limited to ARN-6039, IMU-935, BOS-172767, SAR-441169, and INV-17;

retinoid Z receptor gamma antagonist, including but not limited to AUR-101, JTE-451, ESR-114, ABBV-157, and AZD-0284;

rho associated protein kinase 2 inhibitors, including but not limited to KD-025;

RIP-1 kinase inhibitor, including but not limited to GSK-2982772, DNL-758, and VRN-04;

ribonuclease P inhibitors, including but not limited to RASP;

sphingosine-1-phosphate receptor-1 modulators, including but not limited to amiselimod, AKP-11, FP-253, and CS-0777;

sphingosine-1-phosphate receptor-1 agonist, including but not limited to AK-119, SCD-044, and SYL-927;

sphingosine-1-phosphate receptor-5 modulator, including but not limited to CBP-307;

Src tyrosine kinase inhibitors, including but not limited to tirbanibulin (KX-01);

STAT-3 inhibitors, including but not limited to TAK-114, GLG-801, and MOL-4249;

Syk tyrosine kinase inhibitor, including but not limited to HMPL-523;

T-box transcription factor TBX21 modulators, including but not limited to SB-020;

T-cell differentiation antigen CD6 inhibitors, including but not limited to itolizumab;

T-cell surface glycoprotein CD8 inhibitors, including but not limited to tregalizumab;

T cell surface glycoprotein CD28 stimulator, including but not limited to theralizumab;

TGF beta agonists, including but not limited to tregalizumab;

TLR-7 antagonists, including but not limited to IMO-3100;

TLR-9 antagonists, including but not limited to IMO-3100 and GNKS-356;

TLR 7,8,9 antagonist, including but not limited to IMO-8400;

TNF alpha ligand inhibitors, including but not limited to adalimumab, CHS-1420, BAX-2923, MSB-11022, ABP-501, MYL-1401A, infliximab, certolizumab pegol, AST-005, etanercept, opinercept, ISIS-104838, DLX-105, SSS-07, DLX-2751, DLX-105, Debio-0512, TAQ-588, adalimumab, placulumab, PMI-001, CYT-020-TNFQb, AN-0128, CYT-007-TNFQb, SYI-2074, YP-008, SCT-640A, SBT-104, and T-1649;

TNF alpha ligand modulators, including but not limited to PUR-0110, CDP-571, and ACU-D2;

TNF antagonists, including but not limited to certolizumab pegol, SCB-808, BAX-2200, CT-P05, SCB-131, GSK-2800528, onercept, and ALS-00T2-0501;

TNF binding agents, including but not limited to adalimumab, certolizumab pegol SCB-131, onercept, CT-P17, SBC-808, ABP-501, MYL-1401A, MSB-11022, BAX-2923, CHS-1420, and BCD-057;

TNF gene inhibitor, including but not limited to AST-005;

topoisomerase II inhibitors, including but not limited to GPX-150;

TrkA receptor antagonists, including but not limited to VM-902A, CT-327, K-252a, and lestaurtinib;

tubulin binding agents, including but not limited to KX-01 and paclitaxel;

Tyk2 tyrosine kinase inhibitor, including but not limited to deucravacitinib, PF-06826647, ABBV-712, and CS-43001;

type II TNF receptor modulators, including but not limited to TNR-001, BAX-2200, and SCB-131;

unspecified cytokine receptor antagonists, including but not limited to tetrathiomolybdate, JD-4000, X-083-NAB, SPHD-400, pimecrolimus, and HMPL-010;

vitamin D3 receptor agonists, including but not limited to inecalcitol, maxacalcitol, calcipotriol, falecalcitriol, maxacalcitol, calcitriol NS-78, tacalcitol, calcipotriol, calcithiazol, ecalcidene, lexacalcitol, atocalcitol, and Ro-65-2299;

vitamin D, D3 receptor modulators, including but not limited to VS-320 and VS-105;

Wnt ligand inhibitor, including but not limited to SM-04755; and

Wnt 5A ligand inhibitor, including but not limited to Box-5.

Rheumatoid Arthritis Combination Therapy

In some embodiments, the compounds provided herein, or pharmaceutically acceptable salts thereof, may be combined with one, two, three, or four additional therapeutic agents that are useful for treating or ameliorating rheumatoid arthritis. In some embodiments, the compounds provided herein, or pharmaceutically acceptable salts thereof, may be combined with one, two, three, or four additional therapeutic agents selected from 14-3-3 protein eta inhibitors, 5-lipoxygenase inhibitors, abl tyrosine kinase inhibitors, ACTH receptor agonists, adenosine A3 receptor agonists, adenosine deaminase inhibitors, ADP ribosyl cyclase-1 inhibitors, ADP ribosyl cyclase-1 modulators, ADP ribosylation factor 6 inhibitors, adrenocorticotrophic hormone ligands, aggrecanase-2 inhibitors, albumin modulators, anti-TNF steroid conjugate, adenosine A1 receptor antagonist, annexin A1 modulator, AP1 transcription factor inhibitors, apolipoprotein B modulator, aryl hydrocarbon receptor agonist plus autoantigen, basigin inhibitors, bcr protein inhibitors, B-lymphocyte antigen CD19 inhibitors, B-lymphocyte antigen CD20 inhibitors, B-lymphocyte antigen CD20 modulators, B-lymphocyte cell adhesion molecule inhibitor, B-lymphocyte stimulator ligand inhibitors, bradykinin receptor modulators, BRAF gene inhibitors, branched amino acid aminotransferase 1 inhibitors, bromodomain containing protein inhibitors, Btk tyrosine kinase inhibitors, cadherin-11 antagonists, calcineurin inhibitors, calcium channel inhibitors, calreticulin inhibitor, carbonic anhydrase inhibitors, cathepsin K inhibitors, cathepsin S inhibitors, CCR1 chemokine antagonists, CCR2 chemokine antagonists, CCR3 gene modulators, CCR5 chemokine antagonists, CD126 antagonists, CD29 modulators, CD3 modulators, CD39 agonists, CD4 agonists, CD4 antagonists, CD40 ligand inhibitors, CD40 ligand receptor antagonists, CD40 ligand receptor modulators, CD52 antagonists, CD73 agonists, CD79b modulators, CD80 antagonists, CD86 antagonists, CD95 antagonists, cell adhesion molecule inhibitors, chaperonin modulator, choline kinase inhibitors, clusterin stimulators, complement C5 factor inhibitors, complement factor stimulators, C-reactive protein inhibitors, CSF-1 antagonists, CXC10 chemokine ligand inhibitors, CXCR4 chemokine antagonists, cyclin-dependent kinase inhibitor 1 inhibitors, cyclin-dependent kinase-2 inhibitors, cyclin-dependent kinase-4 inhibitors, cyclin-dependent kinase-5 inhibitors, cyclin-dependent kinase-6 inhibitors, cyclin-dependent kinase-7 inhibitors, cyclin-dependent kinase-9 inhibitors, cyclooxygenase 2 inhibitors, cyclooxygenase 2 modulators, cyclooxygenase inhibitors, cytosolic phospholipase A2 inhibitors, cytotoxic T-lymphocyte protein-4 modulators, cytotoxic T-lymphocyte protein-4 stimulators, deoxyribonuclease gamma stimulator, DHFR inhibitors, diamine acetyltransferase inhibitors, dihydroorotate dehydrogenase inhibitors, DYRK-1 alpha protein kinase inhibitor, elongation factor 2 inhibitors, enolase 1 inhibitor, eotaxin 2 ligand inhibitors, EP4 prostanoid receptor antagonists, erythropoietin receptor agonists, factor XIIa antagonist, Fas ligands, FGF-2 ligand inhibitors, FK506 binding protein-12 modulators, folate antagonists, folate receptor agonists, folate receptor beta antagonists, folate receptor modulators, fractalkine ligand inhibitors, fyn tyrosine kinase inhibitors, G protein coupled receptor 15 antagonists, GABA A receptor modulators, glucocorticoid agonists, glucocorticoid antagonists, glucocorticoid induced leucine zipper stimulators, GM-CSF ligand inhibitors, GM-CSF receptor antagonists, GM-CSF receptor modulators, growth regulated protein alpha ligand inhibitors, H+K+ ATPase inhibitors, histamine H4 receptor antagonists, histone deacetylase inhibitors, histone deacetylase-6 inhibitors, HIV-1 gp120 protein inhibitors, HLA class II antigen DQ-2 alpha modulators, HLA class II antigen inhibitors, HLA class II antigen modulators, Hsp 70 family inhibitors, hypoxia inducible factor-1 inhibitors, IFNB gene stimulators, I-kappa B kinase beta inhibitors, I-kappa B kinase inhibitors, IL-1 antagonists, IL-10 agonists, IL-11 agonists, IL-12 antagonists, IL-15 antagonists, IL-17 antagonists, IL-17 receptor modulators, IL-18 receptor accessory protein antagonist, IL-8 ligand inhibitors, IL-2 agonists, IL-2 antagonists, IL-21 antagonists, IL-23 antagonists, IL-3 antagonists, IL-4 agonists, IL-6 antagonists, IL-6 receptor modulators, IL-6 neutralizing human antibodies, anti-IL6 antibody, immunoglobulin antagonists, immunoglobulin G1 agonists, immunoglobulin G1 antagonists, immunoglobulin G1 modulators, immunoglobulin G2 antagonists, immunoglobulin G2 modulators, immunoglobulin gamma Fc receptor II modulators, immunoglobulin gamma Fc receptor IIB antagonists, immunoglobulin kappa modulators, immunoglobulin M antagonists, inducible nitric oxide synthase inhibitors (iNOS inhibitors), inosine monophosphate dehydrogenase inhibitors, insulin sensitizers, integrin alpha-1/beta-1 antagonists, integrin alpha-4/beta-1 antagonists, integrin alpha-9 antagonist, integrin antagonists, interferon beta ligands, interferon gamma ligands, interleukin 17A ligand inhibitors, interleukin 17F ligand inhibitors, interleukin 23A inhibitors, interleukin ligands, interleukin receptor 17A antagonists, interleukin-1 beta ligand inhibitors, interleukin-10 ligands, interleukin-2 ligands, interleukin-4 ligands, Interleukin-6 ligand inhibitors, Itk tyrosine kinase inhibitors, JAK tyrosine kinase inhibitors, Jak1 tyrosine kinase inhibitors, Jak2 tyrosine kinase inhibitors, JAK3 gene inhibitors, Jak3 tyrosine kinase inhibitors, Jun N terminal kinase inhibitors, KCNA voltage-gated potassium channel-3 modulators, kelch like ECH associated protein 1 modulators, kit tyrosine kinase inhibitors, LanC like protein 2 modulators, leukotriene BLT receptor antagonist, LITAF gene inhibitors, lymphocyte function antigen-3 receptor antagonists, Lyn tyrosine kinase inhibitors, macrophage-drug conjugate (MDC), macrophage mannose receptor 1 modulators, MAdCAM inhibitors, MAP kinase modulators, MAP3K2 gene inhibitors, MAPKAPK5 inhibitors, matrix metalloprotease inhibitors, MCL1 gene inhibitors, MEK protein kinase inhibitors, MEK-1 protein kinase inhibitors, MEK-2 protein kinase inhibitors, membrane copper amine oxidase inhibitors, metalloprotease-2 inhibitors, metalloprotease-9 inhibitors, methylprednisolone, midkine ligand inhibitors, mitochondrial 10 kDa heat shock protein stimulators, mTOR complex 1 inhibitors, mTOR inhibitors, NAD ADP ribosyltransferase stimulators, NAMPT gene inhibitors, NF kappa B inhibitor stimulators, NFAT gene inhibitors, NFE2L2 gene stimulators, nicotinic acetylcholine receptor antagonists, NK cell receptor modulators, NKG2 A B activating NK receptor antagonists, NKG2 D activating NK receptor antagonists, nuclear erythroid 2-related factor 2 stimulators, nuclear factor kappa B inhibitors, nuclear factor kappa B modulators, nuclear factor kappa B p105 inhibitors, opioid growth factor receptor agonists, opioid receptor delta antagonists, osteoclast differentiation factor antagonists, osteoclast differentiation factor ligand inhibitors, oxidoreductase inhibitors, P2X7 purinoceptor agonists, p38 MAP kinase alpha inhibitors, p38 MAP kinase inhibitors, PDE 4 inhibitors, PDE 5 inhibitors, PDGF receptor agonists, PDGF receptor antagonists, PDGF-B ligand inhibitors, PERK gene inhibitors, phosphoinositide-3 kinase delta inhibitors, phosphoinositide-3 kinase gamma inhibitors, phospholipase A2 inhibitors, platelet activating factor receptor antagonists, PPAR gamma agonists, programmed cell death protein 1 modulators, prostaglandin D synthase stimulators, protein arginine deiminase inhibitors, protein tyrosine kinase inhibitors, protease-activated receptor-2 antagonist, PurH purine biosynthesis protein inhibitors, rho associated protein kinase 2 inhibitors, seprase inhibitors, signal transducer CD24 modulators, signal transduction inhibitors, sodium glucose transporter-2 inhibitors, sphingosine 1 phosphate phosphatase modulators, STAT3 gene inhibitors, serum amyloid A protein modulator, superoxide dismutase stimulators, SYK family tyrosine kinase inhibitors, Syk tyrosine kinase inhibitors, syndecan-1 inhibitors, T cell receptor antagonists, T cell receptor modulators, T cell surface glycoprotein CD28 inhibitors, T cell surface glycoprotein CD28 stimulators, TAK1 binding protein modulators, talin modulators, T-cell differentiation antigen CD6 inhibitors, T-cell surface glycoprotein CD8 inhibitors, tenascin modulators, TGF beta agonists, thymulin agonists, TLR-2 antagonists, TLR-4 antagonists, TLR-9 antagonists, TNF alpha ligand inhibitors, TNF alpha ligand modulators, TNF antagonists, TNF gene inhibitors, TNF receptor modulators, TNFSF11 gene inhibitors, transcription factor p65 inhibitors, transcription factor RelB inhibitors, transferrin modulators, transthyretin modulator, tumor necrosis factor 13C receptor antagonists, tumor necrosis factor 15 ligand inhibitors, tumor necrosis factor ligand 13 inhibitors, tumor necrosis factor ligand inhibitors, type I IL-1 receptor antagonists, type I TNF receptor antagonists, type II TNF receptor modulators, unspecified GPCR agonists, VEGF receptor antagonists, VEGF-2 receptor antagonists, VEGF-2 receptor modulators, VEGF-B ligand inhibitors, X-linked inhibitor of apoptosis protein inhibitors, and zap70 tyrosine kinase inhibitors.

In some embodiments, the compounds provided herein, or pharmaceutically acceptable salts thereof, may be combined with one, two, three, or four additional therapeutic agents selected from 99mTc labelled annexin V-128, abatacept, abatacept biosimilar, ABBV-257, ABT-122, ABT-494, acalabrutinib, aceclofenac, actarit, AdMSCs, MS-392, adalimumab, adalimumab biosimilar, adalimumab follow-on biologic, AK-106, ALX-0061, Amilo-5MER, aminopterin, AMT-101, anakinra, anakinra biosimilar, anakinra follow-on biologic, annexuzlimab, ARG-301, ARQ-250, ASLAN-003, ASP-5094, AT-132, AZD-9567, baricitinib, BI-655064, bimekizumab, BiP (rheumatoid arthritis), BLHP-006, blisibimod, BMS-986104, BMS-986142, ABBV-105, BTT-1023, canakinumab, Cartistem, CCX-354, CD24-IgFc, celecoxib, cerdulatinib, certolizumab pegol, CF-101, CFZ-533, CHR-5154, cibinetide, ciclosporin, clazakizumab, CNTO-6785, corticotropin, CR-6086, CreaVax-RA, CWG-92, CWG-940, Cx-611, DE-098, DEN-181, deflazacort, Rheumavax, denosumab, diacerein, diclofenac, DWJ-1421, E-6011, eicosapentaenoic acid monoglycerides, etanercept, etanercept biosimilar, etanercept follow-on biologic, etodolac, etoricoxib, filgotinib, fosdagrocorat, GLPG-3970, gerilimzumab, ginsenoside C-K, givinostat, GLPG-4399, goat polyclonal antibodies, golimumab, GS-5745, GS-9876, GSK-3196165, HHT-109, HM-71224, HMPL-523, HST-003, hyaluronate sodium, (S)-hydroxychloroquine, IB-RA (injectable, rheumatoid arthritis), IB-RA (oral, rheumatoid arthritis), IcanoMAB, ICP-022, iguratimod, IMD-2560, imidazole salicylate, infliximab, infliximab biobetter, infliximab biosimilar, CT-P13, INSIX RA, interferon gamma follow-on biologic, interleukin-2 (injectable), interleukin-2 follow-on biologic, INV-103, IR-501, itolizumab, JNJ-40346527, Ka Shu Ning, KB-312, KD-025, ketoprofen+omeprazole, KINE-101, LB-600, leflunomide, lenzilumab, LLDT-8, LNK-01001, LNP-1955, lumiracoxib, LY-3090106, masitinib, mavrilimumab, MBS-2320, MEDI-5117, meloxicam, methotrexate, MGD-010, misoprostol+diclofenac, MM-A01-01, monalizumab, MORAb-022, MPC-300-IV, MRC-375, nabumetone, namilumab, naproxen+esomeprazole, naproxen+esomeprazole strontium, NIP-046, ocaratuzumab, ofatumumab, OHR-118, olokizumab, OM-89, once-daily naproxen (oral controlled release, pain), ONO-4059, Oralgam, ozoralizumab, PAR-2 inhibitors, peficitinib, pelubiprofen, PF-06687234, piperidone hydrochloridum, piroxicam, prednisolone, prednisone, Procell, Prosorba, PRT-2607, PRTX-100, PRX-167700, QBSAU, rabeximod, RCT-18, recombinant human CD22 monoclonal antibody (iv infusion), Lonn Ryonn Pharma/SinoMab Bioscience (Shenzhen), RA-Curcusome, recombinant human interleukin-1 receptor antagonist (rheumatoid arthritis), recombinant human interleukin-2 recombinant TNF receptor 2-Fc fusion protein mutant, RG-6125, RhuDex, rifabutin+clarithromycin+clofazimine, rituximab, rituximab biosimilar, Toritz, rituximab follow-on biologic, RPI-78, SAN-300, sarilumab, SBI-087, seliciclib, SHR-0302, sirukumab, spebrutinib, SR-047, SSS-07, KDDF-201110-06, Syn-1002, T-5224, TAB-08, tacrolimus, TAK-020, TAK-079, tarenflurbil (transdermal spraygel, skin disease/rheumatoid arthritis), technetium Tc 99m tilmanocept, technetium[99Tc] methylenediphosphonate, tenoxicam, Debio-0512, tocilizumab, tofacitinib, tofacitinib citrate, TQG-2813, *Trichuris suis* ova, umbilical cord-derived mesenchymal stem cells (iv, RA/liver disease), ustekinumab, VAY-736, VB-201, WF-10, XmAb-5871, YH-1713, YHB-1411-2, YRA-1909, and ZM-008, or a pharmaceutically acceptable salt of any of the foregoing, or any combination thereof.

In some embodiments, the compounds provided herein, or pharmaceutically acceptable salts thereof, may be combined with one, two, three, or four additional therapeutic agents selected from:

14-3-3 protein eta inhibitors, including but not limited to anti-AGX-020 mAbs (rheumatoid arthritis) and Augurex;

5-Lipoxygenase inhibitors, including but not limited to darbufelone, tebufelone, ZD-2138, etalocib, PGV-20229, L-708780, T-0757, T-0799, ZM-216800, L-699333, BU-4601A, and SKF-104351;

5-Lipoxygenase/Cyclooxygenase inhibitors, including but not limited to tenoxicam, licofelone, tenidap, tepoxalin, flobufen, SKF-86002, WY-28342, and CI-986;

5-Lipoxygenase/PPAR gamma agonists, including but not limited to etalocib;

Abl tyrosine kinase inhibitors/Bcr protein inhibitors/Kit tyrosine kinase inhibitors/PDGF receptor antagonists/Signal transduction inhibitors, including but not limited to imatinib;

ACTH receptor agonists/Adrenocorticotrophic hormone ligands/Opioid growth factor receptor agonists, including but not limited to FAR-404 and metenkefalin acetate+tridecactide acetate;

adenosine A1 receptor antagonist, including but not limited to CP-25;

adenosine A3 receptor agonists, including but not limited to CF-101 (piclidenoson);

adenosine deaminase inhibitors, cladribine, pentostatin, and FR-221647;

ADP ribosyl cyclase-1 inhibitors, including but not limited to daratumumab;

ADP ribosyl cyclase-1 modulators/syndecan-1 inhibitors, including but not limited to indatuximab ravtansine;

ADP ribosylation factor 6 inhibitors, including but not limited to NAV-2729;

adrenocorticotrophic hormone ligands, including but not limited to corticotropin and Mallinckrodt;

aggrecanase-2/TNF gene inhibitors, including but not limited to GIBH-R-001-2;

albumin modulators, including but not limited to ONS-1210;

albumin modulators/IL-6 antagonists, including but not limited to ALX-0061 (vobarilizumab);

albumin modulators/TNF alpha ligand inhibitors, including but not limited to HOT-3010;

AP1 transcription factor/nuclear factor kappa B inhibitors, including but not limited to tarenflurbil and SP-100030;

anti-TNF steroid antibody-drug conjugates (anti-TNF-GRM), including but not limited to ABBV-3373 and ABBV-154;

basigin inhibitors/branched amino acid aminotransferase 1/metalloprotease-9 inhibitors/metalloprotease-2 inhibitors, including but not limited to ERG-240;

BET inhibitors, including but not limited to GSK-3358699;

bispecific anti-CD86/IL-10, including but not limited to APVO-210;

bispecific humanized monoclonal antibody targeted against BAFF and IL-17A, including but not limited to tibulizumab;

bispecific antibody-peptide conjugate (BAFF/ICOSL), including but not limited to AMG-570;

B-lymphocyte antigen CD19 inhibitors, including but not limited to MDX-1342;

B-lymphocyte antigen CD19 inhibitors/immunoglobulin gamma Fc receptor IIB antagonists, including but not limited to XmAb-5871;

B-lymphocyte antigen CD20 inhibitors, including but not limited to ocrelizumab, ofatumumab, rituximab, ABP-798, Maball, Mabtas, Reditux, Zytux, veltuzumab, ocaratuzumab, BLX-301, IDEC-102, ABP-798, GP-2013, MK-8808, HLX-01, CT-P10, TL-011, PF-05280586, IBPM-001RX, IBI-301, AME-133v, BCD-020, BT-D004, SAIT-101, and JHL-1101;

B-lymphocyte antigen CD20 modulators, including but not limited to SBI-087, TRU-015, DXL-625, and MabionCD20;

B-lymphocyte cell adhesion molecule inhibitor, including but not limited to SM-06;

B-lymphocyte stimulator ligand inhibitors, including but not limited to belimumab, RCT-18, blisibimod, tabalumab, and briobacept;

B-lymphocyte stimulator ligand/Tumor necrosis factor ligand 13 inhibitors, including but not limited to atacicept;

bradykinin receptor modulators/histone deacetylase inhibitors/P2X7 purinoceptor agonists, including but not limited to givinostat;

BRAF gene/MEK protein kinase/PERK gene inhibitors, including but not limited to binimetinib;

Bromodomain containing protein inhibitors, including but not limited to RVX-297, ZEN-003694

Btk tyrosine kinase inhibitors, including but not limited to AC-0058, acalabrutinib, HM-71224, spebrutinib, BMS-986142, TAK-020, tirabrutinib (ONO-4059), TAS-5315, ABBV-105, GDC-0834, EBI-1459, BMS-986195, evobrutinib, fenebrutinib, SIMM-016, and YZJ-3058;

Btk tyrosine kinase inhibitors/Syk tyrosine kinase inhibitors/VEGF-2 receptor antagonists, including but not limited to CG-026806;

Btk tyrosine kinase inhibitors/IL-6 antagonists, including but not limited to RN-486;

Btk tyrosine kinase/Jak1 tyrosine kinase inhibitors, including but not limited to upadacitinib+ABBV-105;

Btk tyrosine kinase/Jak3 tyrosine kinase inhibitors, including but not limited to AC-0025;

cadherin-11 antagonists, including but not limited to RG-6125;

calcineurin inhibitors, including but not limited to ciclosporin;

calcineurin inhibitors/opioid receptor delta antagonists, including but not limited to HS-378;

calcium channel inhibitors, including but not limited to RP-3128;

calreticulin inhibitor, including but not limited to ALB-001 and ZYBK-2;

carbonic anhydrase/cyclooxygenase 2 inhibitors, including but not limited to polmacoxib;

cathepsin K inhibitors, including but not limited to CRA-013783 and VEL-0230;

cathepsin K/cathepsin S inhibitors, including but not limited to AM-3876 and NPI-2019;

cathepsin S inhibitors, including but not limited to MIV-247 and RWJ-445380;

CCR1 chemokine antagonists, including but not limited to BX-471, BMS-817399, BI-638683, CCX-354, MLN-3701, MLN-3897, CP-481715, and PS-375179;

CCR2 chemokine antagonists, including but not limited to MK-0812 and AZD-6942;

CCR3 gene modulators/eotaxin 2 ligand inhibitors, including but not limited to CM-102;

CCR5 chemokine antagonists, including but not limited to OHR-118, NIBR-6465, AZD-5672, and AZD-8566;

CD29 modulators/interleukin-10 ligands, including but not limited to PF-06687234;

CD3 modulators, including but not limited to otelixizumab;

CD39/CD73 agonists, including but not limited to AAV5-CD39/CD73 (rheumatoid arthritis), and Arthrogen;

CCR5 chemokine antagonists/CD4 agonists/HIV-1 gp120 protein inhibitors, including but not limited to maraviroc;

CD4 antagonists, including but not limited to zanolimumab, MTRX-1011A, BW-4162W94, EP-1645, clenoliximab, and DerG-PG275Cit;

CD40 ligand inhibitors, including but not limited to dapirolizumab pegol, and TNX-1500;

CD40 ligand receptor antagonists, including but not limited to BI-655064, anti-CD40-XTEN, teneliximab, VIB-4920, and iscalimab;

CD40 ligand receptor modulators/immunoglobulin G1 modulators, including but not limited to CFZ-533;

CD52 antagonists/clusterin stimulators, including but not limited to alemtuzumab;

bispecific CD32B/CD79B antibody, including but not limited to PRV-3279 (MGD-010);

CD80 antagonists, including but not limited to abatacept biobetter;

CD80 antagonists/T cell surface glycoprotein CD28 inhibitors, including but not limited to RhuDex;

CD80 antagonists/CD86 antagonists, including but not limited to XENP-9523 and ASP-2408;

CD86 antagonists, including but not limited to abatacept biosuperior;

CD86 antagonists/cytotoxic T-lymphocyte protein-4 modulators, including but not limited to ES-210;

CD95 antagonists, including but not limited to DE-098 and CS-9507;

Cell adhesion molecule inhibitors, including but not limited to alicaforsen, NPC-17923, TK-280, and PD-144795;

Chemokine receptor antagonists, including but not limited to PF-06835375;
Complement C5 factor inhibitors, including but not limited to eculizumab,
Complement C5 factor inhibitors/IL-1 antagonists, including but not limited to antisense oligonucleotides (rheumatoid arthritis) and Leiden University Medical Center Complement Factor stimulators, including but not limited to CM-101;
C-reactive protein inhibitors, including but not limited to ISIS-353512;
C-reactive protein inhibitors/cyclooxygenase 2 inhibitors/Nuclear factor kappa B inhibitors/immunoglobulin M antagonists/IL-2 receptor antagonists/PGE2 antagonists: IB-RACSF-1 antagonists, including but not limited to masitinib, FPA-008, JNJ-27301937, JNJ-40346527, PLX-5622, CT-1578, PD-360324, and JNJ-28312141;
CSF-1 antagonists/Fyn tyrosine kinase inhibitors/Kit tyrosine kinase inhibitors/Lyn tyrosine kinase inhibitors/NK cell receptor modulators/PDGF receptor antagonists, including but not limited to masitinib;
CXC10 chemokine ligand inhibitors, including but not limited to 946414-98-8 and BMS-936557;
CXCR4 chemokine antagonists, including but not limited to plerixafor;
CDK-2/7/9 inhibitors/MCL1 gene inhibitors, including but not limited to seliciclib;
CDK-1/2/5/7/9 inhibitors, including but not limited to BP-14;
Chaperonin modulator, including but not limited to IRL-201805;
cyclooxygenase 2 inhibitors, including but not limited to celecoxib, etoricoxib, meloxicam, and lumiracoxib;
cyclooxygenase 2/oxidoreductase inhibitors, including but not limited to etodolac;
cyclooxygenase 2 modulators, including but not limited to DRGT-46;
cyclooxygenase inhibitors, including but not limited to aceclofenac, diclofenac, naproxcinod, naproxen etemesil, nabumetone, Aleve, pelubiprofen, LY-210073, NS-398, bromfenac, L-746483, LY-255283, ibuprofen, flurbiprofen, SC-57666, and bermoprofen;
cyclooxygenase inhibitors/H+K+ ATPase inhibitors, including but not limited to naproxen+esomeprazole strontium;
cyclooxygenase inhibitors/PGE1 agonists, including but not limited to misoprostol+diclofenac;
cyclooxygenase inhibitors/oxidoreductase inhibitors, including but not limited to imidazole salicylate;
cytosolic phospholipase A2 inhibitors/phospholipase A2 inhibitors, including but not limited to AVX-002;
cytotoxic T-lymphocyte protein-4 stimulators/T cell surface glycoprotein CD28 inhibitors, including but not limited to abatacept, BMS-188667, and belatacept;
deoxyribonuclease gamma stimulator, including but not limited to NTR-441;
DHFR inhibitors, including but not limited to MPI-2505, Jylamvo, and ZeNEO-Methotrexate;
DHFR inhibitors/folate antagonists/transferrin modulators, including but not limited to methotrexate;
diamine acetyltransferase inhibitors, including but not limited to diminazene aceturate;
dihydroorotate dehydrogenase inhibitors, including but not limited to ASLAN-003, HWA-486, and ABR-224050;
dihydroorotate dehydrogenase/protein tyrosine kinase inhibitors, including but not limited to leflunomide;
DYRK-1 alpha protein kinase inhibitor, including but not limited to VRN-02;
elongation factor 2 inhibitors/interleukin-2 ligands/NAD ADP ribosyltransferase stimulators, including but not limited to denileukin diftitox;
enolase 1 inhibitor, including but not limited to HuL-001;
EP4 prostanoid receptor antagonists, including but not limited to CR-6086;
erythropoietin receptor agonists, including but not limited to cibinetide;
Fas ligands, including but not limited to AP-300;
FGF-2 ligand inhibitors, including but not limited to RBM-007;
FK506 binding protein-12 modulators/mTOR inhibitors, including but not limited to temsirolimus;
folate antagonists/transferrin modulators/DHFR inhibitors, including but not limited to MBP-Y003;
folate receptor modulators, including but not limited to technetium (99mTc) etarfolatide;
fractalkine ligand inhibitors, including but not limited to E-6011;
Fyn tyrosine kinase inhibitors/GABA A receptor modulators/cyclooxygenase 2 inhibitors/dihydroorotate dehydrogenase inhibitors, including but not limited to laflunimus;
glucocorticoid agonists, including but not limited to prednisone, prednisolone, and fosdagrocorat;
glucocorticoid antagonists, including but not limited to REC-200;
glucocorticoid induced leucine zipper stimulators, including but not limited to ART-G01;
GM-CSF ligand inhibitors, including but not limited to namilumab, gimsilumab (MORAb-022), and TJM-2;
GM-CSF receptor antagonists, including but not limited to mavrilimumab;
GM-CSF receptor modulators, including but not limited to GSK-3196165 and otilimab;
growth regulated protein alpha ligand inhibitors/AP1 transcription factor inhibitors/IL-6 antagonists/interleukin-1 beta ligand inhibitors/cathepsin K inhibitors/NFAT gene inhibitors, including but not limited to T-5224;
H+K+ ATPase inhibitors, including but not limited to naproxen+esomeprazole, ketoprofen+omeprazole, KEO-25001, HC-1004, and PN-40020;
histamine H4 receptor antagonists, including but not limited to toreforant and GD-48;
histone deacetylase inhibitors, including but not limited to CHR-5154 (GSK-3117391) and NIPEP-CARE;
histone deacetylase-6 inhibitors, including but not limited to CKD-506;
HLA class II antigen DQ-2 alpha modulators, including but not limited to NexVax2;
HLA class II antigen inhibitors, including but not limited to HLA-DR1/DR4 inhibitors (rheumatoid arthritis) and Provid;
HLA class II antigen modulators, including but not limited to recombinant T-cell receptor ligand (rheumatoid arthritis) and Artielle;
Hsp 70 family inhibitors, including but not limited to gusperimus trihydrochloride;
hypoxia inducible factor-1 inhibitors/VEGF receptor antagonists, including but not limited to 2-methoxyestradiol;

IFNB gene stimulators, including but not limited to ART-102;

I-kappa B kinase beta inhibitors, including but not limited to IMD-2560;

I-kappa B kinase beta inhibitors/Nuclear factor kappa B inhibitors, including but not limited to IMD-0560;

I-kappa B kinase inhibitors/NFE2L2 gene stimulators/Nuclear factor kappa B inhibitors/STAT3 gene inhibitors, including but not limited to bardoxolone methyl;

IL-1 antagonists, including but not limited to recombinant human interleukin-1 receptor antagonist (rheumatoid arthritis), Shanghai Fudan-Zhangjiang Bio-Pharmaceutical;

IL-1 antagonists/interleukin-1 beta ligand inhibitors, including but not limited to rilonacept;

IL-10 agonists, including but not limited to peg-ilodecakin;

IL-11 agonists/PDGF receptor agonists, including but not limited to oprelvekin;

IL-12 antagonists/IL-23 antagonists, including but not limited to ustekinumab and briakinumab;

IL-15 antagonists, including but not limited to AMG-714;

IL-17 antagonists, including but not limited to ixekizumab and secukinumab;

IL-17 receptor modulators, including but not limited to CNTO-6785;

IL-2 receptor agonists, including but not limited to interleukin-2 follow-on biologic (IL-2), Anteluke, and Interking;

IL-2/IL-21/IL-15 antagonists, including but not limited to BNZ-132-2;

IL-21 antagonists, including but not limited to NN-8828;

IL-4 agonists, including but not limited to SER-130-AMI;

IL-6 antagonists, including but not limited to BCD-089, olokizumab, clazakizumab, sirukumab, SA-237, FB-704A, OP-R003, peptide IL-6 antagonist, MEDI-5117, AMG-220, FM-101, BLX-1025, esonarimod, TA-383, and sarilumab;

IL-6 antagonists/interleukin-1 beta ligand inhibitors/TNF alpha ligand inhibitors, including but not limited to K-832;

IL-6 antagonists/insulin sensitizers/interleukin-1 beta ligand inhibitors, including but not limited to BLX-1002;

IL-6 receptor antagonists/modulators, including but not limited to tocilizumab, HS-628, and LusiNEX;

IL-6 receptor modulators, including but not limited to BAT-1806 and RO-4877533;

immunoglobulin antagonists, including but not limited to iguratimod;

immunoglobulin G1 agonists, including but not limited to BX-2922 and HF-1020;

immunoglobulin G1 agonists/interleukin-1 beta ligand inhibitors, including but not limited to canakinumab;

immunoglobulin G1 agonists/TNF alpha ligand inhibitors, including but not limited to STI-002;

immunoglobulin G1 antagonists/TNF alpha ligand inhibitors, including but not limited to YHB-1411-2;

immunoglobulin G1 modulators/GM-CSF ligand inhibitors/immunoglobulin kappa modulators, including but not limited to lenzilumab;

immunoglobulin G2 antagonists/NF kappa B inhibitor stimulators/osteoclast differentiation factor antagonists/osteoclast differentiation factor ligand inhibitors/TNFSF11 gene inhibitors, including but not limited to denosumab;

immunoglobulin gamma Fc receptor II modulators, including but not limited to MGD-010;

inducible nitric oxide synthase inhibitors/cyclooxygenase 2 inhibitors/MAP kinase modulators/nuclear factor kappa B inhibitors, including but not limited to SKLB-023;

inosine monophosphate dehydrogenase inhibitors, including but not limited to mizoribine;

insulin sensitizers/nuclear factor kappa B inhibitors/interleukin ligand inhibitors, including but not limited to HE-3286;

integrin alpha-1/beta-1 antagonists, including but not limited to SAN-300;

integrin alpha-4/beta-1 antagonists/cell adhesion molecule inhibitors, including but not limited to natalizumab;

integrin alpha-9 antagonist, including but not limited to ASP-5094;

integrin antagonists, including but not limited to PEG-HM-3 and CY-9652;

interferon beta ligands, including but not limited to recombinant interferon beta-1a;

interferon beta ligands/IL-6 antagonists, including but not limited to TA-383;

interferon gamma ligands, including but not limited to Li Zhu Yin De Fu and Clongamma;

interleukin 17A ligand inhibitors/tumor necrosis factor ligand inhibitors, including but not limited to ABT-122 and ABBV-257;

interleukin 17F ligand inhibitors, including but not limited to bimekizumab;

interleukin 18 ligand inhibitors, including but not limited to tadekinig alfa;

interleukin 23A inhibitors, including but not limited to guselkumab;

interleukin ligands/IL-1 antagonists, including but not limited to IBPB-007-IL;

interleukin receptor 17A antagonists, including but not limited to brodalumab;

interleukin-1 beta ligand inhibitors, including but not limited to gevokizumab, LY-2189102, CDP-484, and AR-100;

interleukin-1 beta ligand inhibitors/TNF alpha ligand inhibitors, including but not limited to PMI-001;

interleukin-1 beta ligands/TNF alpha ligand modulators, including but not limited to PUR-0110;

interleukin-2 ligands, including but not limited to recombinant interleukin-2 and CUG-252;

IL-2 modulators, including but not limited to AMG-592;

interleukin-4 ligands/tenascin modulator, including but not limited to Tetravil;

interleukin-6 ligand inhibitors, including but not limited to gerilimzumab and PF-4236921;

IRAK-4 protein kinase inhibitor, including but not limited to BAY-1830839, BAY-1834845, PF-06650833, and KT-474;

Itk tyrosine kinase inhibitors, including but not limited to JTE-051;

Itk tyrosine kinase inhibitors/Jak3 tyrosine kinase inhibitors, including but not limited to ARN-4079;

JAK tyrosine kinase inhibitors, including but not limited to deuterated tofacitinib analog, SD-900, and WXSH-0150;

JAK tyrosine kinase inhibitors/Syk tyrosine kinase inhibitors, including but not limited to cerdulatinib and CVXL-0074;

Jak1 tyrosine kinase inhibitors, including but not limited to ABT-494 (upadacitinib), ruxolitinib, filgotinib, itacitinib, NIP-585, YJC-50018, GLPG-0555, MRK-12, and SHR-0302;

Jak1/3 tyrosine kinase inhibitors, including but not limited to tofacitinib, tofacitinib citrate, peficitinib, CKD-374, and CS-944X;

JAK 1/3 inhibitor/ROCK1/2 inhibitor: CPL-409116

Jak1/2 tyrosine kinase inhibitors, including but not limited to baricitinib, ruxolitinib, LW-104, and TLL-018;

Jak2 tyrosine kinase inhibitors/CSF-1 antagonists, including but not limited to CT-1578;

JAK3 gene inhibitors, including but not limited to PF-06651600;

Jak3 tyrosine kinase inhibitors, including but not limited to decernotinib, DNX-04042, MTF-003, and PS-020613;

Jun N terminal kinase inhibitors, including but not limited to IQ-1S;

KCNA voltage-gated potassium channel-3 modulators, including but not limited to MRAD-P1;

Kelch like ECH associated protein 1 modulators/Nuclear erythroid 2-related factor 2 stimulators, including but not limited to dimethyl fumarate;

LanC like protein 2 modulators, including but not limited to BT-11 and BT-104;

LDL receptor related protein-1 stimulator, including but not limited to SP-16;

leukotriene BLT receptor antagonists/complement C5 factor inhibitors, including but not limited to nomacopan;

LITAF gene inhibitors/JAK3 gene inhibitors/MAP3K2 gene inhibitors/TNF antagonists, including but not limited to GBL-5b;

Lymphocyte function antigen-3 receptor antagonists, including but not limited to alefacept;

Macrophage mannose receptor 1 modulators, including but not limited to technetium Tc 99m tilmanocept;

MAdCAM inhibitors/immunoglobulin G2 modulators, including but not limited to PF-547659;

MAPKAPK5 inhibitors/matrix metalloprotease inhibitors, including but not limited to GLPG-0259;

MEK protein kinase inhibitors, including but not limited to AD-GL0001;

membrane copper amine oxidase inhibitors, including but not limited to BTT-1023, PRX-167700, and vepalimomab;

metalloprotease-9 inhibitors, including but not limited to GS-5745;

microbiome modulator, including but not limited to EDP-1815;

midkine ligand inhibitors, including but not limited to CAB-102;

mitochondrial 10 kDa heat shock protein stimulators, including but not limited to INV-103;

mTOR inhibitors, including but not limited to everolimus;

NAMPT gene inhibitors, including but not limited to ART-D01;

Nicotinic acetylcholine receptor antagonists, including but not limited to RPI-78 and RPI-MN;

NKG2 A B activating NK receptor antagonists, including but not limited to monalizumab;

NKG2 D activating NK receptor antagonists, including but not limited to NNC-0142-002;

nuclear factor kappa B inhibitors, including but not limited to dehydroxymethylepoxyquinomicin, MP-42, VGX-1027, SP-650003, MG-132, SIM-916, VGX-350, VGX-300, GIT-027, MLN-1145, and NVP-IKK-005;

nuclear factor kappa B modulators/nuclear factor kappa B p105 inhibitors/transcription factor RelB inhibitors/transcription factor p65 inhibitors, including but not limited to REM-1086;

osteoclast differentiation factor antagonists, including but not limited to cyclic peptidomimetics (rheumatoid arthritis/osteoporosis), University of Michigan;

p38 aMAP kinase alpha inhibitors, including but not limited to VX-745, BMS-582949, and BMS-751324;

p38 MAP kinase inhibitors, including but not limited to BCT-197, losmapimod, and ARRY-797;

PDE 4 inhibitors, including but not limited to apremilast;

PDE 5 inhibitors, including but not limited to PDE5 inhibitors (rheumatoid arthritis), University of Rochester;

PDGF-B ligand inhibitors/VEGF receptor antagonists, including but not limited to SL-1026;

phosphoinositide-3 kinase delta inhibitors, including but not limited to CT-732, INK-007, and GNE-293;

phosphoinositide-3 kinase delta/gamma inhibitors, including but not limited to duvelisib and RP-6503;

phospholipase A2 inhibitors, including but not limited to AK-106, varespladib methyl, Ro-31-4493, BM-162353, Ro-23-9358, and YM-26734;

platelet activating factor receptor antagonists, including but not limited to piperidone hydrochloridum;

PPAR gamma agonists, including but not limited to rosiglitazone XR;

PPAR gamma agonists/insulin sensitizers, including but not limited to rosiglitazone;

programmed cell death protein 1 modulators, including but not limited to INSIX RA;

prostaglandin D synthase stimulators, including but not limited to HF-0220;

protein tyrosine kinase inhibitors, including but not limited to tairuimide;

PurH purine biosynthesis protein inhibitors/inosine monophosphate dehydrogenase inhibitors, including but not limited to mycophenolate mofetil;

Rev protein modulators, including but not limited to ABX-464;

RIP-1 kinase inhibitors, including but not limited to GSK-2982772 and VRN-04;

IL-17 antagonist/rho associated protein kinase 2 inhibitor, including but not limited to KD-025;

signal transducer CD24 modulators, including but not limited to CD24-IgFc;

sodium glucose transporter-2 inhibitors/PPAR gamma agonists/insulin sensitizers, including but not limited to THR-0921;

STAT3 gene inhibitors, including but not limited to vidofludimus;

STAT-3 inhibitors, including but not limited to HL-237;

Superoxide dismutase stimulators, including but not limited to imisopasem manganese;

SYK family tyrosine kinase inhibitors/Zap70 tyrosine kinase inhibitors, including but not limited to MK-8457;

Syk tyrosine kinase inhibitors, including but not limited to fostamatinib, entospletinib, KDDF-201110-06, HMPL-523, AB-8779, GS-9876, PRT-2607, CG-103065, and SKI-0-703;

T cell receptor antagonists, including but not limited to TCR inhibiting SCHOOL peptides (systemic/topical, rheumatoid arthritis/dermatitis/scleroderma), SignaBlok and CII modified peptide (rheumatoid arthritis);

T cell receptor modulators/HLA class II antigen modulators, including but not limited to ARG-301;

T cell surface glycoprotein CD28 stimulators, including but not limited to TAB-08 and theralizumab;

TAK1 binding protein modulators, including but not limited to epigallocatechin 3-gallate;

Talin modulators, including but not limited to short-form talin regulators (rheumatoid arthritis), KayteeBio;

T-cell differentiation antigen CD6 inhibitors, including but not limited to itolizumab;

T-cell surface glycoprotein CD8 inhibitors/TGF beta agonists/CD4 antagonists, including but not limited to tregalizumab;

thymulin agonists, including but not limited to Syn-1002;

TLR-2/TLR-4 antagonists, including but not limited to VB-201;

TLR-4 antagonists, including but not limited to NI-0101;

TLR-2/4/9 antagonists, including but not limited to P-13;

TNF agonists/TNF antagonists/type II TNF receptor modulators, including but not limited to Lifmior;

TNF alpha ligand inhibitors, including but not limited to Adfrar, FKB-327, Exemptia, Cinnora, Mabura, adalimumab, infliximab, Flixabi, PF-06438179, hadlima, recombinant humanized anti-TNF-alpha monoclonal antibody, CMAB-008, CT-P13, GB-242, golimumab (CNTO-148), ozoralizumab, AT-132, ISIS-104838, ISU-202, CT-P17, MB-612, Debio-0512, anti-TNF alpha human monoclonal antibody, UB-721, KN-002, DA-3113, BX-2922, R-TPR-015, BOW-050, PF-06410293, CKD-760, CHS-1420, GS-071, ABP-710, BOW-015, HLX-03, BI-695501, MYL-1401A, ABP-501, BAX-2923, SCH-215596, ABT-D2E7, BAT-1406, XPro-1595, Atsttrin, SSS-07, golimumab biosimilar, TA-101, BLX-1002, ABX-0401, TAQ-588, TeHL-1, placulumab, CYT-007-TNFQb, SSR-150106, PassTNF, Verigen, DOM-0200, DOM-0215, AME-527, anti-TNF-alpha mAb, GENZ-38167, BLX-1028, CYT-020-TNFQb, CC-1080, CC-1069, LBAL, GP-2017, Idacio, IBI-303, HS-016, TNF-2, and IA-14069;

TNF alpha ligand inhibitors/TNF antagonists/type II TNF receptor modulators, including but not limited to BAX-2200;

TNF alpha ligand inhibitors/Type II TNF receptor modulators, including but not limited to Eucept, TNF alpha ligand modulators: MM-A01-01, CDP-571, camobucol, and JNJ-63823539;

TNF antagonists, including but not limited to DNX-114, TNF antagonist+IL-12 antagonist (rheumatoid arthritis), University of Oxford, BN-006, pegsunercept, ACE-772, onercept, DE-096, PN-0615, lenercept, ITF-1779, MDL-201112, HD-203, Qiangke, and TNF a Fc;

TNF antagonists/type II TNF receptor modulators, including but not limited to Altebrel, Intacept, QL-0902, etanercept, Erelzi, opinercept, YISAIPU, Anbainuo, Benepali, YLB-113, SCB-808, DA-3853, and SCB-131;

TNF antagonists/TNF alpha ligand inhibitors, including but not limited to certolizumab pegol;

TNF receptor modulators, including but not limited to recombinant TNF receptor 2-Fc fusion protein mutant, T-0001;

TNF receptor modulators/TNF alpha ligand inhibitors, including but not limited to tgAAV-TNFR:Fc;

tumor necrosis factor 13C receptor antagonists, including but not limited to VAY-736;

tumor necrosis factor 15 ligand inhibitors, including but not limited to anti-TL1A antibodies (rheumatoid arthritis/inflammatory bowel disease), NIAMS;

tumor necrosis factor ligand inhibitors, including but not limited to etanercept biosimilar;

type I IL-1 receptor antagonists, including but not limited to anakinra, IL-1 $R^a$, anakinra follow-on biologic, and AXXO;

type I TNF receptor antagonists, including but not limited to NM-940 and EN-2001;

type II TNF receptor modulators, including but not limited to LBEC-0101, DMB-3853, DWP-422, and BT-D001;

unspecified GPCR agonists, including but not limited to NCP-70X;

VEGF receptor antagonists, including but not limited to NSC-650853;

VEGF-2 receptor modulators, including but not limited to VEGFR2 neutralizing antibody (rheumatoid arthritis), University of Rochester;

VEGF-B ligand inhibitors, including but not limited to CSL-346;

X-linked inhibitor of apoptosis protein inhibitors, including but not limited to IAP inhibitors (oral), Pharmascience; and Zap70 tyrosine kinase inhibitors, including but not limited to CT-5332.

Inflammatory Bowel Disease Combination Therapy

In some embodiments, the compounds provided herein, or pharmaceutically acceptable salts thereof, may be combined with one or more additional therapeutic agents that treat or ameliorate inflammatory bowel disease (IBD).

The term "inflammatory bowel disease" or "IBD" as used herein is a collective term describing inflammatory disorders of the gastrointestinal tract, the most common forms of which are ulcerative colitis and Crohn's disease. Other forms of IBD that can be treated with the compounds provided herein, or pharmaceutically acceptable salts thereof, or pharmaceutical compositions provided herein include, but are not limited to, diversion colitis, ischemic colitis, infectious colitis, chemical colitis, microscopic colitis (including collagenous colitis and lymphocytic colitis), atypical colitis, pseudomembranous colitis, fulminant colitis, autistic enterocolitis, indeterminate colitis, Behçet's disease, gastroduodenal CD, jejunoileitis, ileitis, ileocolitis, Crohn's (granulomatous) colitis, irritable bowel syndrome, mucositis, radiation induced enteritis, short bowel syndrome, celiac disease, stomach ulcers, diverticulitis, pouchitis, proctitis, and chronic diarrhea.

Treating or preventing IBD also includes ameliorating or reducing one or more symptoms of IBD. As used herein, the term "symptoms of IBD" refers to detected symptoms such as abdominal pain, diarrhea, rectal bleeding, weight loss, fever, loss of appetite, and other more serious complications, such as dehydration, anemia and malnutrition. A number of such symptoms are subject to quantitative analysis (e.g. weight loss, fever, anemia, etc.). Some symptoms are readily determined from a blood test (e.g. anemia) or a test that detects the presence of blood (e.g. rectal bleeding). The term "wherein said symptoms are reduced" refers to a qualitative or quantitative reduction in detectable symptoms, including but not limited to a detectable impact on the rate of recovery from disease (e.g. rate of weight gain). The diagnosis is typically determined by way of an endoscopic observation of the mucosa, and pathologic examination of endoscopic biopsy specimens.

The course of IBD varies and is often associated with intermittent periods of disease remission and disease exacerbation. Various methods have been described for characterizing disease activity and severity of IBD as well as response to treatment in subjects having IBD. Treatment according to the present methods and uses is generally applicable to a subject having IBD of any level or degree of disease activity.

The methods and uses provided herein can also be applied at any point in the course of the disease. In some embodiments, the methods and uses are applied to a subject having IBD during a time period of remission (i.e., inactive disease). In some embodiments, the present methods and uses provided herein provide benefit by extending the time period of remission (e.g., extending the period of inactive disease) or by preventing, reducing, or delaying the onset of active disease. In some embodiments, the methods and uses provided herein may be applied to a subject having IBD during a period of active disease. In some embodiments, the methods and uses provided herein provide benefit by reducing the duration of the period of active disease, reducing or ameliorating one or more symptoms of IBD, or treating IBD.

Measures for determining efficacy of treatment of IBD in clinical practice have been described and include, for example, the following: symptom control; fistula closure; extent of corticosteroid therapy required; and improvement in quality of life. Heath-related quality of life (HRQL) can be assessed using the Inflammatory Bowel Disease Questionnaire (IBDQ), which is extensively used in clinical practice to assess quality of life in a subject with IBD. (See Guyatt et al. (1989) Gastroenterology 96:804-810.)

In some embodiments, the compounds provided herein, or pharmaceutically acceptable salts thereof, may be combined with one or more additional therapeutic agents that treat or ameliorate IBD. Non-limiting examples of therapeutic agents that treat or ameliorate IBC include allogeneic bone marrow-derived MSC therapy, AMP activated protein kinase stimulator, aryl hydrocarbon receptor agonist and T cell receptor modulator, ASK1 inhibitors, beta adrenoceptor antagonists, BTK inhibitors, beta-catenin stimulator, beta-glucuronidase inhibitors, bradykinin receptor modulators, calcineurin inhibitors, calcium channel inhibitors, cathepsin S inhibitors, CCR3 chemokine antagonists, CD40 ligand receptor antagonists, chemokine CXC ligand inhibitors, CHST15 gene inhibitors, collagen modulators, CXCR3 chemokine antagonist, CSF-1 antagonists, cyclooxygenase inhibitors, cytochrome P450 3A4 inhibitors, DYRK-1 alpha protein kinase inhibitor, endothelial dysfunction and vascular leakage blocker, enolase 1 inhibitor, eotaxin ligand inhibitors, EP4 prostanoid receptor agonists, erythropoietin receptor agonists, exportin 1 inhibitor, fractalkine ligand inhibitors, free fatty acid receptor 2 antagonists, GATA 3 transcription factor inhibitors, glucagon-like peptide 2 agonists, glucocorticoid agonists, guanylate cyclase receptor agonists, histone deacetylase inhibitors, HLA class II antigen modulators, IL-12 antagonists, IL-13 antagonists, Interleukin-2 ligand, IL-23 antagonists, IL-6 antagonists, IL-6 receptor modulators, interleukin-7 receptor modulators, IL-7 antagonists, IL-8 antagonists, integrin alpha-4/beta-1 antagonists, integrin alpha-4/beta-7 antagonists, integrin alpha-E antagonists, integrin antagonists, integrin beta-7 antagonists, interleukin ligand inhibitors, Interleukin-10 ligand, interleukin receptor 17A antagonists, Interleukin 23A inhibitor, interleukin-1 beta ligands, interleukin-1 beta ligand modulators, IRAK4 inhibitors, JAK tyrosine kinase inhibitors, Jak1 tyrosine kinase inhibitors, Jak3 tyrosine kinase inhibitors, LanC like protein 2 modulators, lipoxygenase modulators, acrophage mannose receptor 1 modulator, MAdCAM inhibitors, matrix metalloprotease inhibitors, melanocortin agonists, metalloprotease-9 inhibitors, NADPH oxidase inhibitor, natriuretic peptide receptor C agonists, NC-301, next-generation intestinal microbiota therapy, neuregulin-4 ligands, NKG2 D activating NK receptor antagonists, Non receptor tyrosine kinase TYK2 antagonist, opioid receptor antagonists, opioid receptor delta antagonists, oxidoreductase inhibitors, P2X7 purinoceptor agonists, PDE 4 inhibitors, phagocytosis stimulating peptide modulators, potassium channel inhibitors, PPAR alpha agonists, PPAR delta agonists, PPAR gamma agonists, protein fimH inhibitors, P-selectin glycoprotein ligand-1 inhibitors, RNA polymerase inhibitors, sphingosine 1 phosphate phosphatase 1 stimulators, sphingosine 1 phosphate phosphatase modulators, sphingosine-1-phosphate receptor-1 agonists, sphingosine-1-phosphate receptor-1 antagonists, sphingosine-1-phosphate receptor-1 modulators, sphingosine-1-phosphate receptor-5 modulators, STAT3 gene inhibitors, stem cell antigen-1 inhibitors, superoxide dismutase modulators, superoxide dismutase stimulators, SYK inhibitors, TGF beta 1 ligand inhibitors, thymulin agonists, TLR antagonists, TNF alpha ligand inhibitors, TNF antagonists, tumor necrosis factor 14 ligand modulators, type II TNF receptor modulators, Tpl 2 inhibitors, X box binding protein 1 stimulator, and Zonulin inhibitors.

In some embodiments, the compounds provided herein, or pharmaceutically acceptable salts thereof, may be combined with one or more additional therapeutic agents selected from ABX-464, adalimumab; ALLO-ASC-CD, AMG-966, AMT-101, anakinra, apremilast; Alequel; ALV-304, AMG-139; amiselimod, anti-CXCR3 mAb, ASD-003, ASP-3291, AX-1505, balsalazide; beclomethasone dipropionate; BI-655130, BMC-321, BMC-322, BMS-986184; BT-051, budesonide; CBX-11, CEQ-508; certolizumab; cibinetide, *Clostridium butyricum*; ChAdOx2-HAV, CU-06, CUG-252 dexamethasone sodium phosphate, DNVX-078, EB-7020, EM-101, etanercept; ENERGI-F704, ETX-201, golimumab; GS-4997, GS-5718, GS-9876, GS-4875, GS-4059, infliximab; IMS-001, mesalazine, HLD-400, IBI-112, IMM-H013, KB-295, LFS-829, LYC-30937 EC; IONIS-JBI1-2.5Rx, JNJ-64304500, JNJ-66525433, JNJ-4447; mesalamine, MET-642, MVA-HAV, naltrexone; natalizumab; neihulizumab, olsalazine; NOS-1244, NTG-A-009, PH-46-A, propionyl-L-carnitine; PTG-100; remestemcel-L; tacrolimus; teduglutide; tofacitinib; ASP-1002; ustekinumab; vedolizumab; AVX-470; INN-108; SGM-1019; PF-06480605; PF-06651600; PR-600; RBX-8225, R-2187, RG-6287, SER-287; TOP-1288; VBY-129; 99mTc-annexin V-128; bertilimumab; DLX-105; dolcanatide; quetmolimab (E-6011); FFP-104; filgotinib; foralumab; GED-0507-34-Levo; givinostat; GLPG-0974; iberogast; ICP-330, JNJ-40346527; K(D)PT; KAG-308; KHK-4083; KRP-203; larazotide acetate; LY-3074828, midismase; olokizumab; OvaSave; P-28-GST; PF-547659; prednisolone; QBECO; RG-7835; RBX-2660, RO7049665, JKB-122; SYGN-313, SB-012; STNM-01; SZN-1326, TJC-0434, Debio-0512; TRK-170; ABT-494; Ampion; BI-655066; carotegast methyl; cobitolimod; elafibranor; etrolizumab; GS-5745; HMPL-004; LP-02, ozanimod; peficitinib; QX-004-N, RHB-104; SEFA-1024, tildrakizumab; TOP-1890, tralokinumab; brodalumab; laquinimod; and plecanatide; or a pharmaceutically acceptable salt of any of the foregoing; or any combination thereof.

VII. Compound Preparation

Some embodiments of the present disclosure are directed to processes and intermediates useful for preparing the compounds provided herein or pharmaceutically acceptable salts thereof.

Compounds described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography.

During any of the processes for preparation of the compounds provided herein, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4$^{th}$ ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used.

The methods of the present disclosure generally provide a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or diastereomerically pure.

Representative syntheses of compounds of the present disclosure are described in the schemes below, and the particular examples that follow.

Certain abbreviations and acronyms are used in describing the experimental details. Although a person of ordinary skill in the art will readily recognize and understand most of the abbreviations and acronyms, the below list provides many of the meanings of the abbreviations and acronyms.

| List of Abbreviations and Acronyms | |
| --- | --- |
| Abbreviation | Meaning |
| Ac | acetate |
| AcOH | acetic acid |
| ACN | acetonitrile |
| AmPhos | di-tert-butyl(4-dimethylaminophenyl)phosphine |
| Bn | benzyl |
| Bpin | (pinacolato)boron |
| $B_2Pin_2$ | bis(pinacolato)diboron |
| Boc | tert-butoxycarbonyl |
| $Boc_2O$ | di-tert-butyl dicabonate |
| Bu | Butyl |
| Bz | benzoyl |
| BzCl | benzoyl chloride |
| cataCXium ® A Pd G3 | Mesylate[(di(1-adamantyl)-n-butylphosphine)-2-(2'-amino-1,1'-biphenyl)]palladium(II) |
| CDI | 1,1'-carbonyldiimidazole |
| DBAD | di-tert-butyl azodicarboxylate |
| DBU | 1,8-Diazabicyclo[5.4.0]undec-7-ene |
| DCE | 1,2-dichloroethane |
| DCM | dichloromethane |
| DEA | diethylamine |
| Deoxofluor | Bis(2-methoxyethyl)aminosulfur trifluoride |
| DIPEA | N,N-diisopropylethylamine |
| DMA | dimethylacetamide |
| 4-DMAP | 4-dimethylaminopyridine |
| DME | dimethoxyethane |
| DMF | dimethylformamide |
| DMF-DMA | N,N-dimethylformamide dimethyl acetal |
| DMSO | dimethylsulfoxide |
| dppf | 1,1'-Ferrocenediyl-bis(diphenylphosphine) |
| dtbbpy | 4,4'-Di-tert-butyl-2,2'-dipyridyl |
| EDC | N-(3-dimethylaminopropyl)-N'-ethylcarbodiimide hydrochloride |
| EDCI | N-(3-dimethylaminopropyl)-N'-ethylcarbodiimide hydrochloride |
| ES/MS | electron spray mass spectrometry |
| Et | ethyl |
| HATU | 1-[Bis(dimethylamino)methylene]-1H-1,2,3-triazolo[4,5-b]pyridinium 3-oxide hexafluorophosphate |
| HNMR | hydrogen nuclear magnetic resonance |
| IPA | isopropanol |
| JohnPhos | (2-Biphenyl)di-tert-butylphosphine |

| List of Abbreviations and Acronyms | |
| --- | --- |
| Abbreviation | Meaning |
| KOtBu | potassium tert-butoxide |
| LC | liquid chromatography |
| LCMS | liquid chromatography/mass spectrometry |
| MCPBA | meta-chloroperbenzoic acid |
| Me | methyl |
| Ms | methanesulfonyl |
| m/z | mass to charge ratio |
| MS or ms | mass spectrum |
| NBS | N-bromosuccinimide |
| NCS | N-chlorosuccinimide |
| NIS | N-iodosuccinimide |
| NMP | N-methyl-2-pyrrolidone |
| NMR | nuclear magnetic resonance |
| Pd(AmPhos)$_2$Cl$_2$ | Bis(di-tert-butyl(4-dimethylaminophenyl)phosphine)dichloropalladium(II) |
| Pd(dppf)Cl$_2$ | [1,1'-Bis(diphenylphosphino)ferrocene]dichloropalladium(II) |
| Ph | phenyl |
| Ph$_3$P | triphenylphosphine |
| Pg | Protecting group |
| pin | pinacol |
| Piv | pivaloyl |
| PMB | para-methoxybenzyl |
| Pyr | pyridine |
| RBF | round bottom flask |
| RP-HPLC | reverse phase high performance liquid chromatography |
| RT | room temperature |
| SEM | [2-(trimethylsilyl)ethoxy]methyl |
| SFC | supercritical fluid chromatography |
| STAB | Sodium triacetoxyborohydride |
| TBAI | Tetrabutylammonium iodide |
| TLC | thin layer chromatography |
| tBuXPhos Pd G3 | [(2-Di-tert-butylphosphino-2',4',6'-triisopropyl-1,1'-biphenyl)-2-(2'- amino-1,1'-biphenyl)] palladium(II) methanesulfonate |
| XantPhos | 4,5-Bis(diphenylphosphino)-9,9-dimethylxanthene |
| XPhos Pd G2 | Chloro(2-dicyclohexylphosphino-2',4',6'-triisopropyl-1,1'-biphenyl)[2-(2'-amino-1,1'-biphenyl)]palladium(II) |
| XPhos Pd G3 | (2-Dicyclohexylphosphino-2',4',6'-triisopropyl-1,1'-biphenyl)[2-(2'-amino-1,1'-biphenyl)]palladium(II) methanesulfonate |
| TBAF | Tetrabutylammonium fluoride |
| TCFH | Chloro-N,N,N',N'-tetramethylformamidinium hexafluorophosphate |
| TEA | triethylamine |
| TFA | trifluoroacetic acid |
| THF | tetrahydrofuran |
| Tf | trifluoromethanesulfonyl |
| Ts | 4-toluenesulfonyl |
| δ | parts per million referenced to residual solvent peak |

General Synthetic Schemes

General Reaction Schemes 1-14 are provided as further embodiments of the present disclosure and illustrate general methods which were used to prepare certain compounds of the present disclosure and which can be used to prepare additional compounds of the present disclosure. Each of the variables (e.g. $R^1$, $R^2$, $R^3$, $R^4$) of the compounds disclosed in General Reaction Schemes 1-13 are as defined herein.

The compounds of the present disclosure may be prepared using the methods disclosed herein and routine modifications thereof, which will be apparent to a skilled artisan given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers. In general, compounds described herein are typically stable and isolatable at room temperature and pressure.

Typical embodiments of compounds disclosed herein may be synthesized using the general reaction schemes described below. It will be apparent to a skilled artisan given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments disclosed in the present disclosure, inspection of the structure of the compound to be synthesized will provide the identity of each substituent group. The identity of the final product will generally render apparent the identity of the necessary starting materials by a simple process of inspection, given the examples herein.

The terms "solvent", "inert organic solvent", or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, and the like). Unless specified to the contrary, the solvents used in the reactions of the present disclosure are inert organic solvents, and the reactions are carried out under an inert gas, preferably nitrogen or argon.

Intermediate 1.1 (where M is —B, —Sn, —Zn, —Si, or —Mg) may be reacted with Intermediate 2 in the presence of a suitable palladium catalyst to deliver intermediate 1.3. Intermediate 1.4 may be reacted in the presence of a metalating reagent (e.g. iPrMgBr, n-BuLi) and di-tertbutyl azodicarboxylate to afford Intermediate 1.6. Intermediate 1.3 may be reacted with intermediate 1.6 at elevated temperatures in the presence of acid (e.g. PTSA) to afford Intermediate 1.7.

-continued

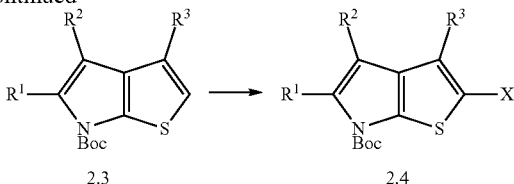

2.3 → 2.4

Intermediate 1.7 can be reacted in the presence of a suitable base (e.g. LiOH, Me₃SnOH) and heat to produce Intermediate 2.1. Intermediate 2.1 may then be reacted in the presence of a suitable base (e.g. DBU) and heat for produce intermediate 2.2. Alternatively, Intermediate 2.2 may be furnished by reacting Intermediate 1.7 in the presence of a suitable base (e.g. LiOH) and extended heating. Intermediate 2.2 may be reacted with Boc-anhydride in the presence of a suitable base (e.g. DMAP) to afford Intermediate 2.3. Intermediate 2.3 may be reacted in the presence of suitable halogenating reagent (e.g., NBS, NIS, NCS) to produce intermediate 2.4, where X=I, Br, or Cl.

General Reaction Scheme 4

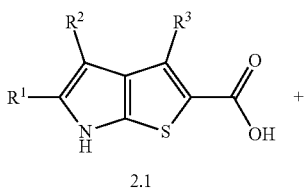

2.1

General Reaction Scheme 3

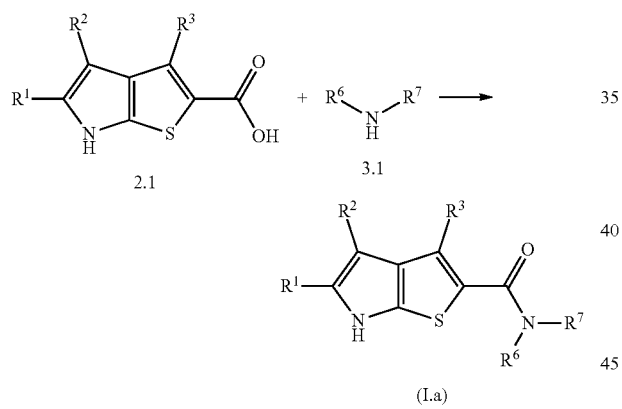

(I.a)

Compounds of formula (I.a) can be assembled by the combination of intermediate 2.1 with a suitable primary or secondary amine 3.1, in the presence of a suitable peptide coupling reagent (e.g., HATU, TCFH, EDC) and a suitable base (e.g., N,N-diisopropylethylamine, triethylamine). If the compound of the formula (I.a) contains a tert-butylcarbamate functional group, this can be subsequently removed by treatment with acid (e.g., trifluoroacetic acid or hydrochloric acid) to reveal a compound of formula (I.a) that contains a primary or secondary amine. If the compound of the formula (I.a) contains a benzyl-amine functional group, this can be subsequently removed (e.g., using a metal catalyst and H₂ gas), to reveal a compound of formula (I.a) that contains a primary or secondary amine.

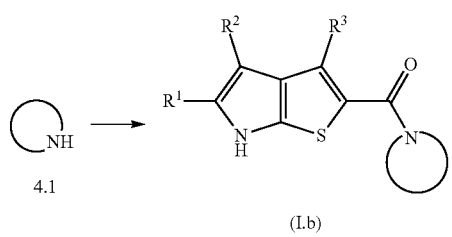

4.1 → (I.b)

Compounds of formula (I.b) can be assembled by the combination of intermediate 2.1 with a suitable cyclic secondary amine 4.1, in the presence of a suitable peptide coupling reagent (e.g., HATU, TCFH, EDC) and a suitable base (e.g., N,N-diisopropylethylamine, triethylamine). If the compound of the formula (I.b) contains a tert-butylcarbamate functional group, this can be subsequently removed by treatment with acid (e.g., trifluoroacetic acid or hydrochloric acid) to reveal a compound of formula (I.b) that contains a primary or secondary amine. If the compound of the formula (I.b) contains a benzyl-amine functional group, this can be subsequently removed (e.g., using a metal catalyst and H₂ gas), to reveal a compound of formula (I.b) that contains a primary or secondary amine.

General Reaction Scheme 5

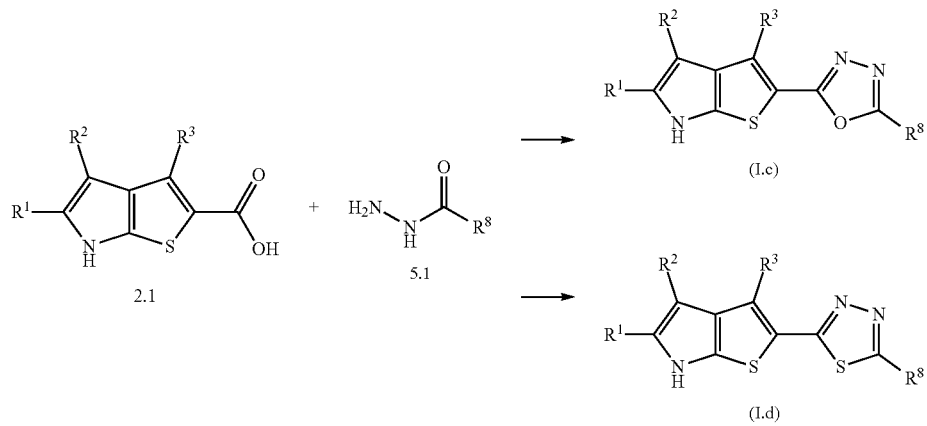

Compounds of the formula (I.c) that contain an (1,3,4)-oxadiazole moiety may be assembled by reacting intermediate 2.1 with an intermediate 5.1 first in the presence of a suitable peptide coupling reagent (e.g., HATU, TCFH, EDC, CDI) and a suitable base (e.g., N,N-diisopropylethylamine, triethylamine), and then subsequently in the presence of an oxidant (e.g., Burgess reagent). Alternatively, compounds of the formula (I.d) that contain a (1,3,4)-thiadiazole moiety may be assembled by reacting intermediate 2.1 with an intermediate 5.1 first in the presence of a suitable peptide coupling reagent (e.g., HATU, TCFH, EDC, CDI) and a suitable base (e.g., N,N-diisopropylethylamine, triethylamine), and then subsequently in the presence of an sulfur reagent (e.g., Lawesson's reagent, $P_2S_5$). If the compound of the formula (I.c) or (I.d) contains a tert-butylcarbamate functional group, this can be subsequently removed by treatment with acid (e.g., trifluoroacetic acid or hydrochloric acid) to reveal a compound of formula (I.c) or (I.d) that contains a primary or secondary amine. If the compound of the formula (I.c) or (I.d) contains a benzyl-amine functional group, this can be subsequently removed (e.g., using a metal catalyst and $H_2$ gas), to reveal a compound of formula (I.c) or (I.d) that contains a primary or secondary amine.

General Reaction Scheme 6

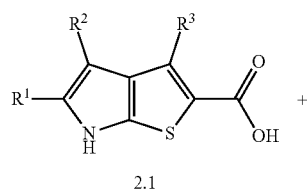

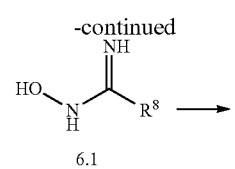

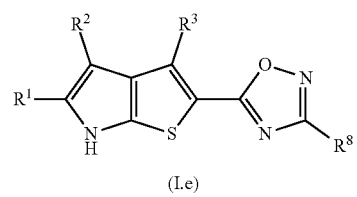

Compounds of the formula (I.e) that contain an (1,2,4)-oxadiazole moiety may be assembled by reacting intermediate 2.1 with an intermediate 6.1 first in the presence of a coupling reagent (e.g., CDI) and heat. If the compound of the formula (I.e) contains a tert-butylcarbamate functional group, this can be subsequently removed by treatment with acid (e.g., trifluoroacetic acid or hydrochloric acid) to reveal a compound of formula (I.e) that contains a primary or secondary amine. If the compound of the formula (I.e) contains a benzyl-amine functional group, this can be subsequently removed (e.g., using a metal catalyst and $H_2$ gas), to reveal a compound of formula (I.e) that contains a primary or secondary amine.

General Reaction Scheme 7

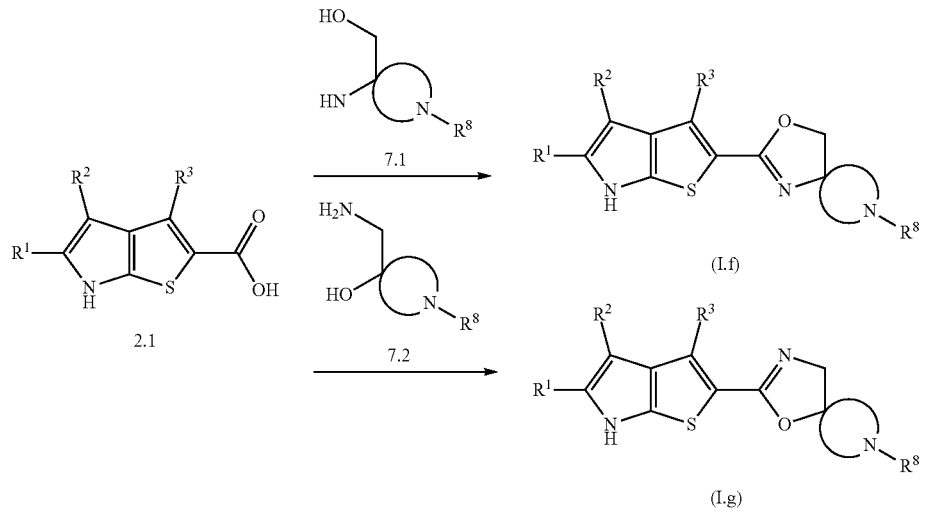

Compounds of the formula (I.f) that contain an oxazoline moiety may be assembled by reacting intermediate 2.1 with an intermediate 7.1 first in the presence of a suitable peptide coupling reagent (e.g., HATU, TCFH, EDC, CDI) and a suitable base (e.g., N,N-diisopropylethylamine, triethylamine), and then subsequently in the presence of an oxidant (e.g., Burgess reagent). Alternatively, compounds of the formula (I.g) that contain an oxazoline moiety may be assembled by reacting intermediate 2.1 with an intermediate 7.2 first in the presence of a suitable peptide coupling reagent (e.g., HATU, TCFH, EDC, CDI) and a suitable base (e.g., N,N-diisopropylethylamine, triethylamine), and then subsequently in the presence of an oxidant (e.g., Burgess reagent). If the compound of the formula (I.f) or (I.g) contains a tert-butylcarbamate functional group, this can be subsequently removed by treatment with acid (e.g., trifluoroacetic acid or hydrochloric acid) to reveal a compound of formula (I.f) or (I.g) that contains a primary or secondary amine. If the compound of the formula (I.f) or (I.g) contains a benzyl-amine functional group, this can be subsequently removed (e.g., using a metal catalyst and $H_2$ gas), to reveal a compound of formula (I.f) or (I.g) that contains a primary or secondary amine.

General Reaction Scheme 8

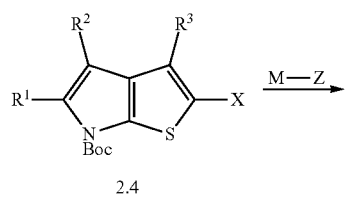

-continued

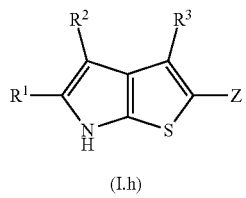

Compounds of formula (I.h) can be assembled by the combination of intermediate 2.4 with a suitable metallated coupling partner M-Z (where Z is aryl, heteroaryl, alkenyl, and M is —B, —Sn, —Zn, —Si, or —Mg) using a suitable palladium catalyst and a base (e.g., cesium carbonate, potassium phosphate tribasic, sodium carbonate) to deliver compounds of formula (I.h). If the compound of formula (I.h) contains an alkene, this can be subsequently removed (e.g., using a metal catalyst and $H_2$ gas). If the compound of the formula (I.h) contains a tert-butylcarbamate functional group, this can be subsequently removed by treatment with acid (e.g., trifluoroacetic acid or hydrochloric acid) to reveal a compound of formula (I.h) that contains a primary or secondary amine. If the compound of the formula (I.h) contains a benzyl-amine functional group, this can be subsequently removed (e.g., using a metal catalyst and $H_2$ gas), to reveal a compound of formula (I.h) that contains a primary or secondary amine.

General Reaction Scheme 9

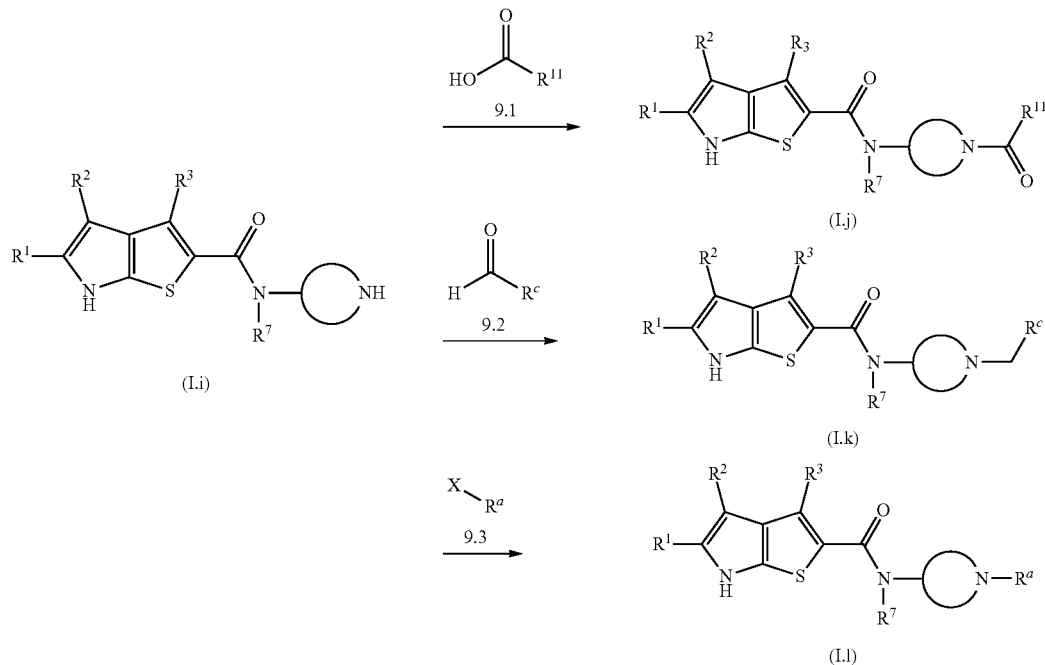

Compounds of formula (I.j) can be assembled by the combination of a compound of formula (L.i) (produced via one of the methods elaborated above, such as Scheme 3) with a suitable carboxylic acid 9.1, in the presence of a suitable peptide coupling reagent (e.g., HATU, TCFH, EDC) and a suitable base (e.g., N,N-diisopropylethylamine, triethylamine). Alternatively, compounds of formula (I.k) can be assembled by the combination of compounds of formula (I.i) with a suitable aldehyde 9.2, in the presence of a suitable reducing reagent (e.g., $NaBH_4$, $Na(OAc)_3BH$, $Na(CN)_3BH$). Alternatively, compounds of formula (I.l) can be assembled by the combination of compounds of formula (I.i) with an intermediate 9.3, where X is a leaving group (e.g. —Cl, —Br, —I, OTs, —OMs), in the presence of a base (e.g., N,N-diisopropylethylamine, triethylamine, $K_2CO_3$, $CsCO_3$). If the compound of the formula (I.j), (I.k), or (I.l) contains a tert-butylcarbamate functional group, this can be subsequently removed by treatment with acid (e.g., trifluoroacetic acid or hydrochloric acid) to reveal a compound of formula (I.j), (I.k), or (I.l) that contains a primary or secondary amine. If the compound of the formula (I.j), (I.k), or (I.l) contains a benzyl-amine functional group, this can be subsequently removed (e.g., using a metal catalyst and $H_2$ gas), to reveal a compound of formula (I.j), (I.k), or (I.l) that contains a primary or secondary amine.

General Reaction Scheme 10

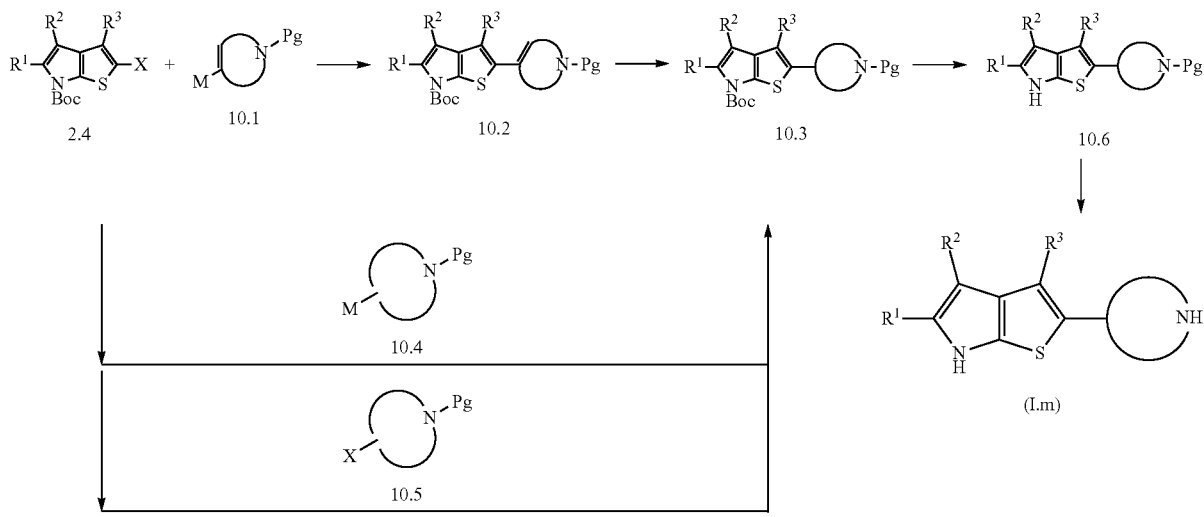

Intermediate 2.4 can be coupled with intermediate 10.1 (where -M is —B, —Sn, or —Zn, and Pg is Boc or Bn) in the presence of a palladium catalyst and a base (e.g., cesium carbonate, potassium phosphate tribasic, sodium carbonate) to produce intermediate 10.2. Intermediate 10.2 may be reacted in the presence of a metal catalyst (e.g., palladium) and $H_2$ gas to produce Intermediate 10.3. Alternatively, Intermediate 2.4 can be coupled with intermediate 10.4 (where -M is —B or —Zn, and Pg is Boc or Bn) in the presence of a palladium catalyst to produce intermediate 10.3. Alternatively, Intermediate 2.4 can be coupled with intermediate 10.5 (where —X is —Cl, —Br, —I, OMs, —OTs, —OTf, and Pg is Boc or Bn) in the presence of a palladium or nickel catalyst to produce intermediate 10.3. Intermediate 10.3 may be reacted in the presence of aqueous base (e.g. potassium carbonate) to afford Intermediate 10.6. If Pg=Boc, Intermediate 10.6 may be reacted in the presence of acid (e.g., TFA, HCl) to produce a compound of formula (I.m). Alternatively, if Pg=Bn, Intermediate 10.6 may be reacted in the presence of a metal catalyst (e.g., palladium) and $H_2$ gas to produce a compound of formula (I.m).

General Reaction Scheme 11

Compounds of formula (I.n) can be assembled by the combination of a compound of formula (I.m) (produced via one of the methods elaborated above, such as Scheme 10) with a suitable carboxylic acid 11.1, in the presence of a suitable peptide coupling reagent (e.g., HATU, TCFH, EDC) and a suitable base (e.g., N,N-diisopropylethylamine, triethylamine). Alternatively, compounds of formula (I.o) can be assembled by the combination of compounds of formula (I.m) with a suitable aldehyde or ketone 11.2, in the presence of a suitable reducing reagent (e.g., $NaBH_4$, $Na(OAc)_3BH$, $Na(CN)_3BH$). Alternatively, compounds of formula (I.p) can be assembled by the combination of compounds of formula (I.m) with an intermediate 10.3, where X is a leaving group (e.g. —Cl, 0Br, —I, OTs, —OMs), in the presence of a base (e.g., N,N-diisopropylethylamine, triethylamine, $K_2CO_3$, $CsCO_3$). If the compound of the formula (I.n), (I.o), or (I.p) contains a tert-butylcarbamate functional group, this can be subsequently removed by treatment with acid (e.g., trifluoroacetic acid or hydrochloric acid) to reveal a compound of formula (I.n), (I.o), or (I.p) that contains a primary or secondary amine. If the compound of the formula (I.n), (I.o), or (I.p) contains a benzyl-amine functional group, this can be subsequently removed (e.g., using a metal catalyst and $H_2$ gas), to reveal a compound of formula (I.n), (I.o), or (I.p) that contains a primary or secondary amine.

General Reaction Scheme 12

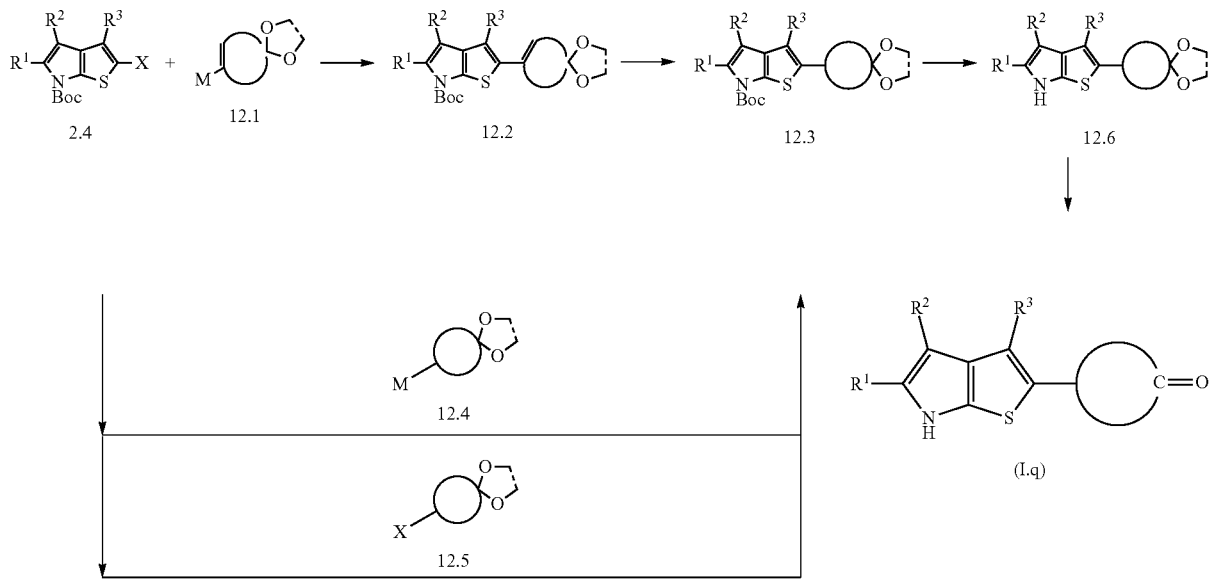

Intermediate 2.4 can be coupled with intermediate 12.1 (where -M is —B, —Sn, or —Zn, and the ketal moiety may or may not be cyclized to form a ring) in the presence of a palladium catalyst and a base (e.g., cesium carbonate, potassium phosphate tribasic, sodium carbonate) to produce intermediate 12.2. Intermediate 12.2 may be reacted in the presence of a metal catalyst (e.g., palladium) and $H_2$ gas to produce Intermediate 12.3. Alternatively, Intermediate 2.4 can be coupled with intermediate 12.4 (where -M is —B or —Zn, and the ketal moiety may or may not be cyclized to form a ring) in the presence of a palladium catalyst to produce intermediate 12.3. Alternatively, Intermediate 2.4 can be coupled with intermediate 12.5 (where —X is —Cl, —Br, —I, OMs, —OTs, —OTf, and the ketal moiety may or may not be cyclized to form a ring) in the presence of a palladium or nickel catalyst to produce intermediate 12.3. Intermediate 12.3 may be reacted in the presence of aqueous base (e.g. potassium carbonate) to afford Intermediate 12.6. Intermediate 12.6 may be reacted in the presence of acid (e.g., TFA, HCl) to produce a compound of formula (I.q).

Compounds of formula (I.r) can be assembled by the combination of compounds of formula (I.q) with a suitable primary or secondary amine 3.1, in the presence of a suitable reducing reagent (e.g., $NaBH_4$, $Na(OAc)_3BH$, $Na(CN)_3BH$). Compounds of formula (I.s) can be assembled by the combination of compounds of formula (I.q) with a suitable cyclic amine 4.1, in the presence of a suitable reducing reagent (e.g., $NaBH_4$, $Na(OAc)_3BH$, $Na(CN)_3BH$). If the compound of the formula (I.r) or (I.s) contains a tert-butylcarbamate functional group, this can be subsequently removed by treatment with acid (e.g., trifluoroacetic acid or hydrochloric acid) to reveal a compound of formula (I.r) or (I.s) that contains a primary or secondary amine. If the compound of the formula (I.r) or (I.s) contains a benzyl-amine functional group, this can be subsequently removed (e.g., using a metal catalyst and $H_2$ gas), to reveal a compound of formula (I.r) or (I.s) that contains a primary or secondary amine.

General Reaction Scheme 13

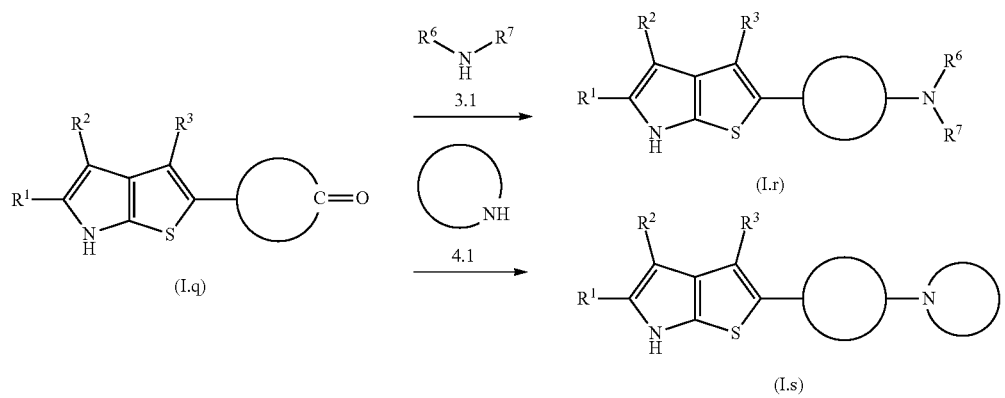

171

General Reaction Scheme 14

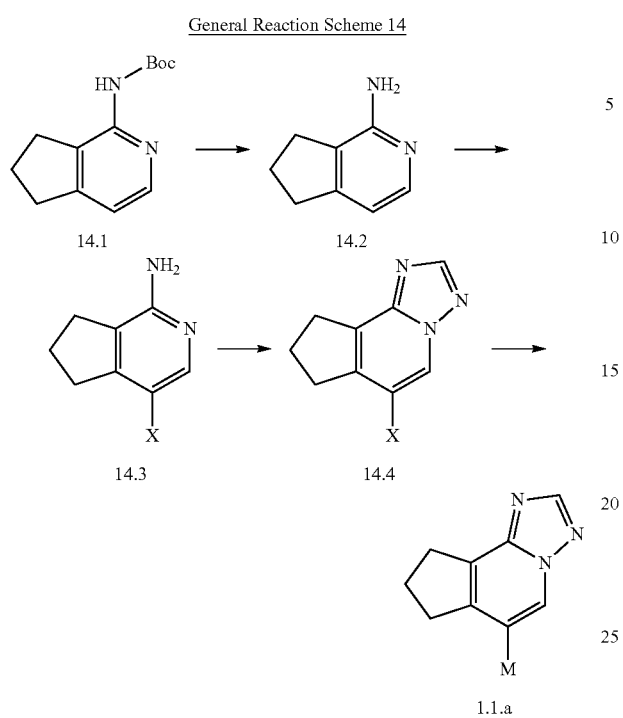

Intermediate 14.2 may be synthesized by reacting Intermediate 14.1 in the presence of acid (e.g., HCl, TFA). Intermediate 14.2 may be reacted in the presence of suitable halogenating reagent (e.g., NBS, NIS, NCS) to produce intermediate 14.3, where X=I, Br, or Cl. Intermediate 14.3 may be reacted in the presence of DMF-DMA and hydroxyamine-O-sulfonic acid to afford Intermediate 14.4. Intermediates of the formula 1.1.a may be furnished by reacting Intermediate 14.4 in the presence of a suitable boron reagent (e.g. B$_2$Pin$_2$, HBPin), a suitable base (e.g. potassium acetate, potassium propionate, triethylamine), and a suitable palladium catalyst.

VIII. Examples

Exemplary chemical entities of the present disclosure are provided in the specific examples that follow. Those skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

In the following description of the Examples, specific embodiments are described. These embodiments are described in sufficient detail to enable those skilled in the art to practice certain embodiments of the present disclosure. Other embodiments may be utilized and logical and other changes may be made without departing from the scope of the disclosure. The following description is, therefore, not intended to limit the scope of the present disclosure.

Intermediates

Preparation of Intermediate I-1

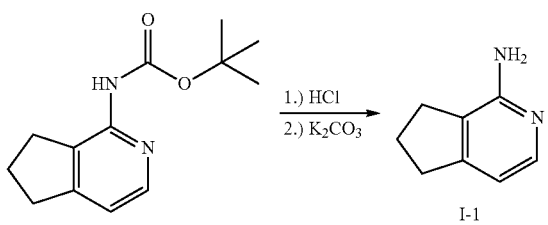 [SMILES: CC(C)(C)OC(=O)Nc1nccc2c1CCC2 ; Nc1nccc2c1CCC2 ; [I-]]

6,7-dihydro-5H-cyclopenta[c]pyridin-1-amine (I-1): To a solution of tert-butyl (6,7-dihydro-5H-cyclopenta[c]pyridin-1-yl)carbamate (prepared according to the literature procedure in WO 2015/058160, paragraph 00843) (6 g, 25.6 mmol) dissolved in dioxane (50 mL) and methanol (75 mL) was added hydrochloric acid (4M in dioxane, 25.6 mL, 102 mmol), and the reaction mixture was stirred for 24 h at room temperature. The reaction mixture was concentrated under reduced pressure, and the crude residue was dissolved in dichloromethane (100 mL) and 50% aqueous potassium carbonate (20 mL). The mixture was stirred for 30 minutes at room temperature, and the pH was checked to be >8. The layers were separated, and the aq. layer was extracted with dichloromethane (2×50 mL). The combined organic layers were dried over MgSO$_4$, filtered, and concentrated under reduced pressure to give the title compound.

Preparation of Intermediate I-2

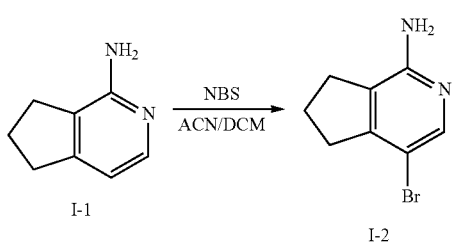

4-bromo-6,7-dihydro-5H-cyclopenta[c]pyridin-1-amine (I-2): To a solution of 6,7-dihydro-5H-cyclopenta[c]pyridin-1-amine (I-1) (3.4 g, 25.3 mmol) in acetonitrile (100 mL) and dichloromethane (100 mL) cooled to 0° C. was added a solution of N-bromosuccinimide (4.51 g, 25.3 mmol) dissolved in acetonitrile (30 mL) dropwise, and the reaction mixture was allowed to slowly warm to room temperature and stirred for 1 h. The mixture was concentrated, and the crude mixture was dissolved in dichloromethane (150 mL). The organic layer was washed with 50% aq. NaHCO3 (40 mL), and once with water (40 mL). The combined aqueous layers were extracted with DCM (50 mL). The combined organic layers were dried over magnesium sulfate, filtered and concentrated under reduced pressure. The crude residue was purified by column chromatography (20-100% EtOAc in hexane) to give the title compound. ES/MS: 215.1 (M$^+$).

Preparation of Intermediate I-3

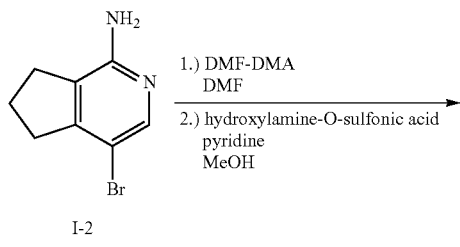

I-2

6-bromo-8,9-dihydro-7H-cyclopenta[c][1,2,4]triazolo[1,5-a]pyridine (I-3): To a solution of 4-bromo-6,7-dihydro-5H-cyclopenta[c]pyridin-1-amine (I-2) (5.4 g, 25.3 mmol) in DMF (14 mL) was added N,N-dimethylformamide dimethyl acetal (DMF-DMA) (16.6 mL, 101 mmol), and the reaction mixture was for 6 hours at 80° C. The mixture was concentrated under reduced pressure, and methanol (10 mL) was added to the crude mixture. The mixture was cooled to 0° C., and pyridine (3.07 mL, 38 mmol) was added, followed by hydroxylamine-O-sulfonic acid (4.3 g, 38 mmol). The mixture was stirred overnight, warming to room temperature. The precipitated product was filtered and saved. The filtrate was concentrated under reduced pressure, and dissolved in DCM (120 mL), EtOAc (20 mL), and sat. aq. sodium bicarbonate (50 mL). The layers were separated, and the aqueous layer was extracted with DCM (2×50 mL). The combined organic layers were washed with brine (40 mL), and were dried over magnesium sulfate, filtered and concentrated under reduced pressure. The crude residue was purified by column chromatography (15-100% EtOAc in hexane) to give the title compound, which was combined with the precipitated product and carried forward. ES/MS: 238.0 (M+). $^1$H NMR (400 MHz, Methanol-d4) δ 8.94 (d, J=1.1 Hz, 1H), 8.37 (s, 1H), 3.40-3.34 (m, 2H), 3.20-3.12 (m, 2H), 2.41-2.30 (m, 2H).

Preparation of Intermediate I-4

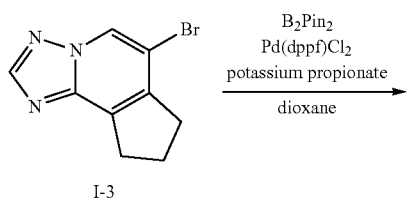

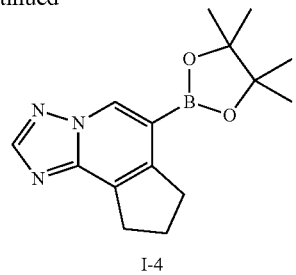

I-4

6-(4,4,5,5-tetramethyl-1,3,2-dioxaborolan-2-yl)-8,9-dihydro-7H-cyclopenta[c][1,2,4]triazolo[1,5-a]pyridine (I-4): To a 250 mL RBF was added 6-bromo-8,9-dihydro-7H-cyclopenta[c][1,2,4]triazolo[1,5-a]pyridine (I-3) (5.37 g, 22.6 mmol), Bis(pinacolato)diboron (8.59 g, 33.8 mmol), [1,1'-Bis(diphenylphosphino)ferrocene]dichloropalladium (II) (1.17 g, 1.58 mmol), and potassium propionate (7.59 g, 67.7 mmol). The mixture was dissolved in 1,4-dioxane (50 mL), and nitrogen was bubbled through the reaction mixture for 5 minutes. The mixture was heated at 95° C. for 1 hour under nitrogen. The mixture was cooled to rt, filtered through celite, and concentrated under reduced pressure. The crude residue was purified by silica gel chromatography (eluent: EtOAc/hexanes) to provide the product I-4. ES/MS: 286.2 (M+H+). $^1$H NMR (400 MHz, Chloroform-d) δ 8.83 (s, 1H), 8.32 (s, 1H), 3.30-3.18 (m, 4H), 2.28 (p, J=7.6 Hz, 2H), 1.38 (s, 12H).

Preparation of Intermediate I-5

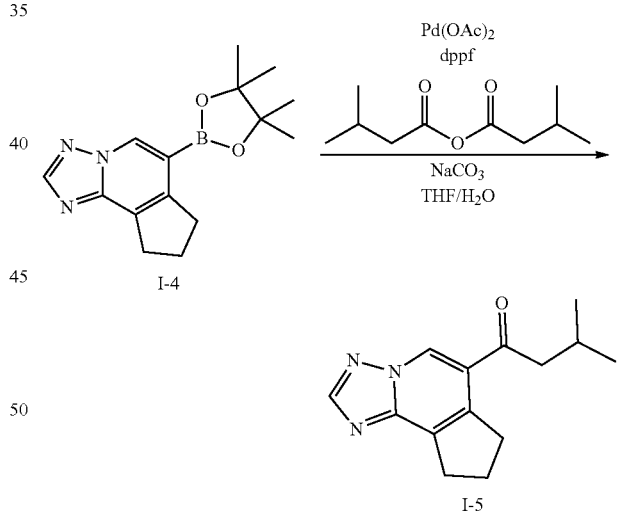

1-(8,9-dihydro-7H-cyclopenta[c][1,2,4]triazolo[1,5-a]pyridin-6-yl)-3-methylbutan-1-one (I-5): To a vial was added 6-(4,4,5,5-tetramethyl-1,3,2-dioxaborolan-2-yl)-8,9-dihydro-7H-cyclopenta[c][1,2,4]triazolo[1,5-a]pyridine (I-4) (4.66 g, 16.3 mmol), palladium acetate (0.220 g, 0.98 mmol), 1,1'-bis(diphenylphosphino)ferrocene (dppf) (0.770 g, 1.39 mmol), and sodium carbonate (0.866 g, 8.17 mmol), followed by THF (50 mL), water (2.06 mL, 114 mmol) and isovaleric anhydride (4.57 mL, 22.9 mmol). Argon was bubbled through the mixture for 4 min and the reaction mixture was heated to 60° C. for 4 h. The reaction mixture was filtered through celite, rinsing with EtOAc and the filtrate was concentrated under reduced pressure. The crude residue was purified by column chromatography (10-70% EtOAc in hexane) to give the title compound. ES/MS: 244.2 (M+H⁺). ¹H NMR (400 MHz, Chloroform-d) δ 9.07 (s, 1H), 8.43 (s, 1H), 3.51-3.37 (m, 2H), 3.36-3.22 (m, 2H), 2.85 (d, J=6.9 Hz, 2H), 2.43-2.22 (m, 3H), 1.04 (d, J=6.6 Hz, 6H).

Preparation of Intermediate I-6

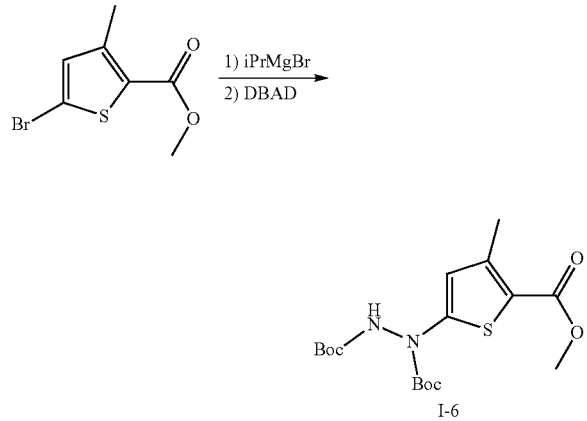

di-tert-butyl 1-(5-(methoxycarbonyl)-4-methylthiophen-2-yl)hydrazine-1,2-dicarboxylate (I-6): To a solution of methyl 5-bromo-3-methyl-thiophene-2-carboxylate (3.90 g, 16.6 mmol) in THF (50 mL) cooled to −40° C. was added isopropylmagnesium bromide in 2-MeTHF (2.90 mol/L, 8.01 mL, 23.2 mmol) dropwise and the solution was stirred for 30 min at −40° C. Di-tert-butylazodicarboxylate (4.58 g, 19.9 mmol) was then added as a solution in THF (50 mL) dropwise and the reaction was stirred for 15 min at −40° C. The reaction was quenched by the addition of saturated aqueous ammonium chloride and the mixture was extracted with DCM (3×). The combined organic extracts were washed with brine, dried over sodium sulfate, filtered and the filtrate was concentrated under reduced pressure. The crude residue was purified by column chromatography (0-50% EtOAc in hexane) to give the title compound. ES/MS: 387.2 (M+H⁺). ¹H NMR (400 MHz, Methanol-d₄) δ 6.62 (s, 1H), 3.82 (s, 3H), 2.46 (s, 3H), 1.60-1.51 (m, 18H).

Preparation of Intermediate I-7

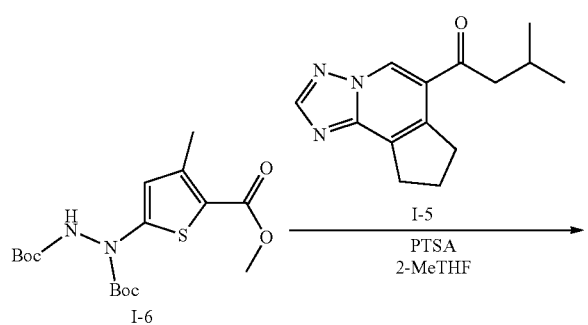

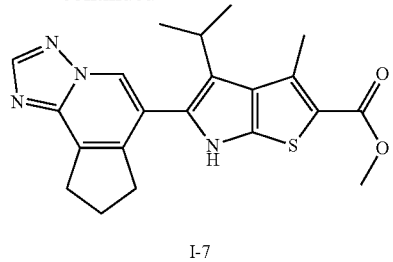

methyl 4-isopropyl-3-methyl-5-(8-methyl-[1,2,4]triazolo[1,5-a]pyridin-6-yl)-6H-thieno[2,3-b]pyrrole-2-carboxylate (I-7): To a solution of di-tert-butyl 1-(5-(methoxycarbonyl)-4-methylthiophen-2-yl)hydrazine-1,2-dicarboxylate (I-6) (5.69 g, 14.7 mmol) and p-Toluenesulfonic Acid, monohydrate (15.2 g, 88.3 mmol) in 2-MeTHF (150 mL) in a 500 mL round-bottomed flask was added 1-(8,9-dihydro-7H-cyclopenta[c][1,2,4]triazolo[1,5-a]pyridin-6-yl)-3-methylbutan-1-one (I-5) (3.58 g, 14.7 mmol) and the reaction mixture was heated to 90° C. for 16 h with a reflux condenser. The reaction mixture was concentrated under reduced pressure, taken up in EtOAc and washed with sat. aq. sodium bicarbonate. The layers were separated, the aqueous layer was extracted with EtOAc (2×) and the combined organic layers were washed with brine, dried over sodium sulfate, filtered and the filtrate was concentrated under reduced pressure. The crude residue was purified by column chromatography (15-100% EtOAc in hexane) to give the title compound. ES/MS: 395.2 (M+H⁺). ¹H NMR (400 MHz, Methanol-d4) δ 8.63 (d, J=1.1 Hz, 1H), 8.43 (s, 1H), 3.85 (s, 3H), 3.32-3.27 (m, 2H), 3.24-3.11 (m, 1H), 3.00 (t, J=7.5 Hz, 2H), 2.87 (s, 3H), 2.31 (q, J=7.6 Hz, 2H), 1.32 (d, J=7.1 Hz, 6H).

Preparation of Intermediate I-8

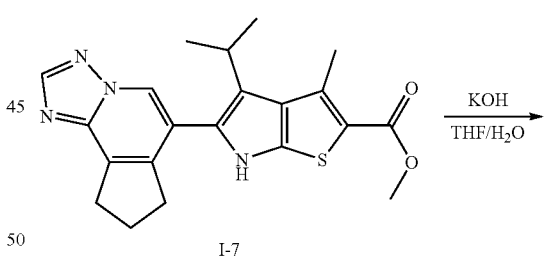

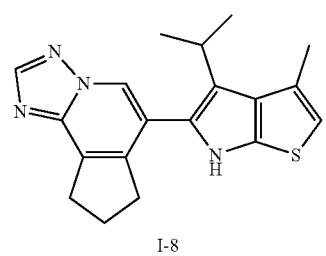

5-(8,9-dihydro-7H-cyclopenta[c][1,2,4]triazolo[1,5-a]pyridin-6-yl)-4-isopropyl-3-methyl-6H-thieno[2,3-b]pyrrole (I-8): To a solution of methyl 4-isopropyl-3-methyl-5-(8-methyl-[1,2,4]triazolo[1,5-a]pyridin-6-yl)-6H-thieno[2,3-b]pyrrole-2-carboxylate (I-7) (3.1 g, 7.86 mmol) in ethanol (150 mL) and water (20 mL) was added potassium hydroxide (2.65 g, 47.1 mmol) and the reaction mixture was heated to 90° C. for 16 h. The reaction mixture was concentrated under reduced pressure then diluted with hydrochloric acid (1.00 mol/L, 63 mL, 62.9 mmol) and cooled to 0° C. for 30 minutes to facilitate precipitation. The precipitate was collected by filtration, rinsed once with water, and air-dried for 1 h to give the title product. The material was further dried overnight in a lyophilizer to complete the drying process. ES/MS: 337.2 (M+H$^+$).

Preparation of Intermediate I-9

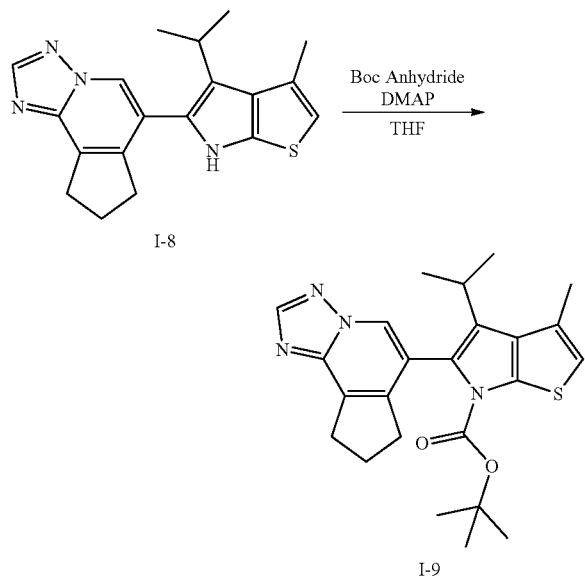

tert-butyl 5-(8,9-dihydro-7H-cyclopenta[c][1,2,4]triazolo[1,5-a]pyridin-6-yl)-4-isopropyl-3-methyl-6H-thieno[2,3-b]pyrrole-6-carboxylate (I-9): To a solution of 5-(8,9-dihydro-7H-cyclopenta[c][1,2,4]triazolo[1,5-a]pyridin-6-yl)-4-isopropyl-3-methyl-6H-thieno[2,3-b]pyrrole (I-8) (1.89 g, 5.62 mmol) in THF (150 mL) was added N,N-dimethylpyridin-4-amine (DMAP) (0.961 g, 7.86 mmol), and tert-butoxycarbonyl tert-butyl carbonate (1.59 mg, 7.30 mmol). The mixture was stirred at rt overnight. The mixture was concentrated under reduced pressure. The crude residue product was purified by flash chromatography (eluent: EtOAc/hexanes) to provide the product. ES/MS: 437.2 (M+H$^+$).

Preparation of Intermediate I-10

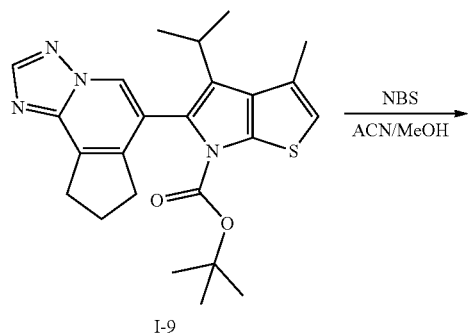

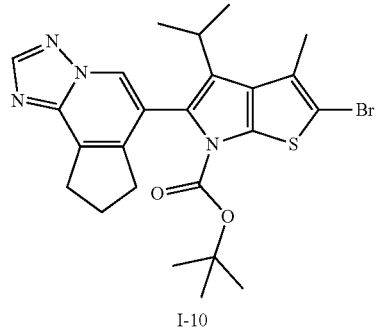

tert-butyl 2-bromo-5-(8,9-dihydro-7H-cyclopenta[c][1,2,4]triazolo[1,5-a]pyridin-6-yl)-4-isopropyl-3-methyl-6H-thieno[2,3-b]pyrrole-6-carboxylate (I-10): To a solution of tert-butyl 5-(8,9-dihydro-7H-cyclopenta[c][1,2,4]triazolo[1,5-a]pyridin-6-yl)-4-isopropyl-3-methyl-6H-thieno[2,3-b]pyrrole-6-carboxylate (I-9) (1.64 g, 3.76 mmol) in ACN (100 mL) and methanol (100) cooled to 0° C. was added N-bromosuccinimide (0.67 g, 3.76 mmol) dissolved in ACN (30 mL) dropwise and the reaction mixture was monitored by LCMS for reaction completion. The reaction was diluted with DCM and quenched by the addition of 10% aqueous thiosulfate and the layers separated. The aqueous layer was extracted with DCM (2×). The combined organic extracts were washed with brine, dried over sodium sulfate, filtered and the filtrate was concentrated under reduced pressure. The crude residue was purified by column chromatography (0-100% EtOAc in hexane) to give the title compound. ES/MS: 391.1 (M$^+$). $^1$H NMR (400 MHz, Methanol-d4) δ 8.63 (s, 1H), 8.47 (s, 1H), 7.59 (s, 1H), 3.31-3.23 (m, 2H), 2.69 (s, 3H), 2.48 (s, 3H), 1.40 (dd, J=7.1, 1.0 Hz, 6H).

Preparation of Intermediate I-11

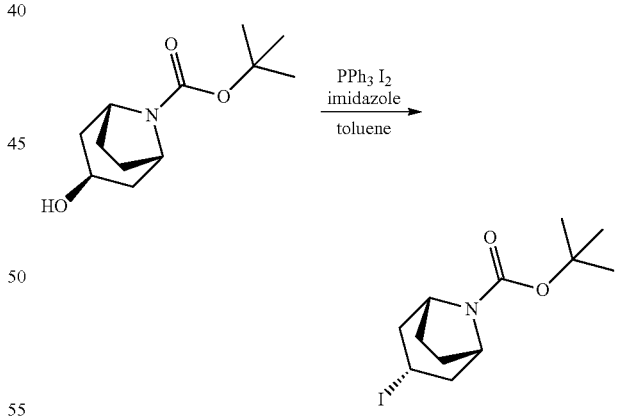

tert-butyl (1R,5S)-3-iodo-8-azabicyclo[3.2.1]octane-8-carboxylate (I-11): To a solution of tert-butyl (1R,5S)-3-hydroxy-8-azabicyclo[3.2.1]octane-8-carboxylate (1.5 g, 6.6 mmol) in toluene (50 mL) was added triphenylphosphine (1.96 g, 7.92 mmol), molecular iodine (2.01 g, 7.92 mmol) and imidazole (899 mg, 13.2 mmol). The mixture was stirred at reflux overnight. The mixture was concentrated under reduced pressure. The crude residue product was purified by flash chromatography (eluent: EtOAc/hexanes) to provide the product. ES/MS: 282.0 (M+H$^+$) (mass minus tert-butyl).

Preparation of Intermediate I-12

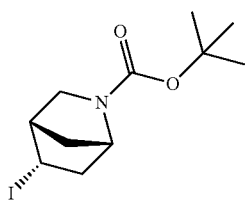

tert-butyl (1S,4S,5S)-5-iodo-2-azabicyclo[2.2.1]heptane-2-carboxylate (I-12): Prepared analogously to I-11, substituting tert-butyl (1R,5S)-3-hydroxy-8-azabicyclo[3.2.1]octane-8-carboxylate with tert-butyl (1S,4S,5R)-5-hydroxy-2-azabicyclo[2.2.1]heptane-2-carboxylate. ES/MS: 268.0 (M+H$^+$) (mass minus tert-butyl).

Preparation of Intermediate I-13

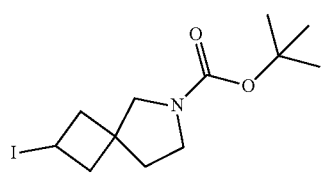

tert-butyl 2-iodo-6-azaspiro[3.4]octane-6-carboxylate (I-13): Prepared analogously to I-11, substituting tert-butyl (1R,5S)-3-hydroxy-8-azabicyclo[3.2.1]octane-8-carboxylate with tert-butyl 2-hydroxy-6-azaspiro[3.4]octane-6-carboxylate. ES/MS: 282.1 (M+H$^+$) (mass minus tert-butyl).

Preparation of Intermediate I-14

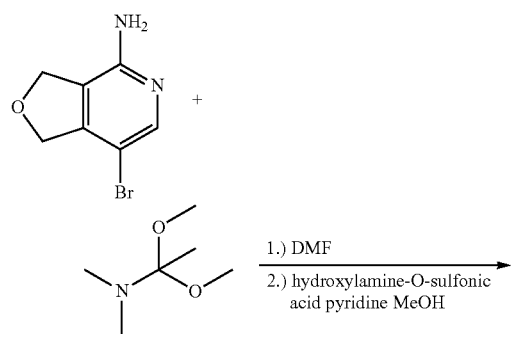

6-bromo-2-methyl-7,9-dihydrofuro[3,4-c][1,2,4]triazolo[1,5-a]pyridine (I-14): To a solution of 7-bromo-1,3-dihydrofuro[3,4-c]pyridin-4-amine (1.5 g, 6.98 mmol) in DMF (6 mL) was added 1,1-dimethoxy-N,N-dimethylethanamine (4.13 mL, 27.9 mmol), and the reaction mixture was stirred for 3 hours at 100° C. The mixture was concentrated under reduced pressure, and methanol (5 mL) was added to the crude mixture. The mixture was cooled to 0° C., and pyridine (0.85 mL, 10.5 mmol) was added, followed by hydroxylamine-O-sulfonic acid (1.18 g, 10.5 mmol). The mixture was stirred overnight, warming to room temperature. The precipitated product was filtered and saved. The filtrate was concentrated under reduced pressure, and dissolved in DCM (60 mL), EtOAc (20 mL), and sat. aq. sodium bicarbonate (25 mL). The layers were separated, and the aqueous layer was extracted with DCM (2×25 mL). The combined organic layers were washed with brine (20 mL), and were dried over magnesium sulfate, filtered and concentrated under reduced pressure. The crude residue was purified by column chromatography (15-100% EtOAc in hexane) to give the title compound, which was combined with the precipitated product and carried forward. ES/MS: 254.0 (M$^+$)

Preparation of Intermediate I-15

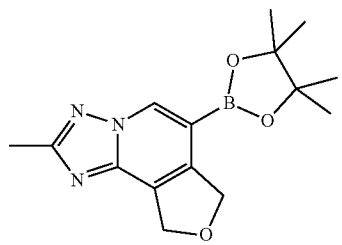

2-methyl-6-(4,4,5,5-tetramethyl-1,3,2-dioxaborolan-2-yl)-7,9-dihydrofuro[3,4-c][1,2,4]triazolo[1,5-a]pyridine (I-15): Prepared analogously to I-4, substituting 6-bromo-8,9-dihydro-7H-cyclopenta[c][1,2,4]triazolo[1,5-a]pyridine (I-3) with 6-bromo-2-methyl-7,9-dihydrofuro[3,4-c][1,2,4]triazolo[1,5-a]pyridine (I-15) ES/MS: 302.2 (M+H$^+$) $^1$H NMR (400 MHz, Chloroform-d) δ 4.20 (s, 1H), 4.08 (ddd, 1H), 3.29 (dd, 1H), 3.06 (d, 1H), 2.90-2.84 (m, 1H), 2.59-2.47 (m, 1H), 2.26 (dt, 1H), 2.10 (d, 1H), 1.78 (dd, 1H), 1.46 (d, 9H).

Preparation of Intermediate I-16

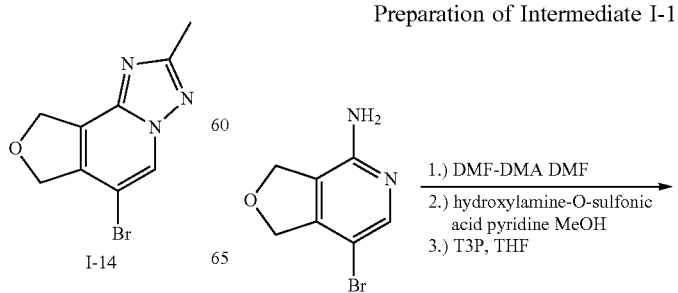

-continued

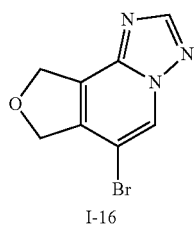

I-16

6-bromo-7,9-dihydrofuro[3,4-c][1,2,4]triazolo[1,5-a]pyridine (I-16): To a solution of 7-bromo-1,3-dihydrofuro[3,4-c]pyridin-4-amine (I-15) (2.0 g, 9.30 mmol) in DMF (3 mL) was added N,N-dimethylformamide dimethyl acetal (DMF-DMA) (3.74 mL, 27.9 mmol), and the reaction mixture was stirred overnight at 130° C. After cooling to room temperature, the volatiles were removed under reduced pressure to afford the intermediate imine product. To an ice-cooled, stirred solution of the crude intermediate in methanol (20 mL) and pyridine (1.5 mL) was added hydroxylamine-O-sulfonic acid (1.58 g, 14.0 mmol). The reaction mixture was allowed to warm to room temperature and was stirred overnight. The volatiles were removed under reduced pressure, and the residue was partitioned between sat. aq. sodium bicarbonate (50 mL) and EtOAc (50 mL). The aqueous layer was further extracted with EtOAc (3×20 mL), and the combined organic layers were washed sequentially with water (100 mL) and brine (100 mL), dried over magnesium sulfate, and concentrated under reduced pressure to yield a mixture of the desire product and the hydroxy-imine intermediate. The mixture of the product and the intermediate was re-dissolved in THF (5 mL) and to the solution T3P [(1-propanephosphonic acid cyclic anhydride) 50% in DMF] (1 mL) was added, and the reaction was stirred overnight at 50° C. The reaction mixture was concentrated under reduced pressure. The crude product was directly purified by flash chromatography (eluent: EtOAc/hexane) to provide the product. ES/MS: 240.0 (M+). $^1$H NMR (400 MHz, CDCl$_3$) δ 8.75 (t, J=1.1 Hz, 1H), 8.36 (s, 1H), 5.59 (tt, J=2.6, 1.1 Hz, 2H), 5.27 (dd, J=4.0, 3.1 Hz, 2H).

Preparation of Intermediate I-17

 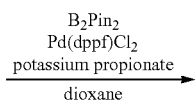

I-16

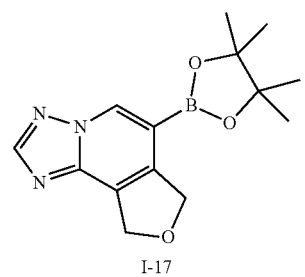

I-17

6-(4,4,5,5-tetramethyl-1,3,2-dioxaborolan-2-yl)-7,9-dihydrofuro[3,4-c][1,2,4]triazolo[1,5-a]pyridine (I-17): Prepared analogously to I-4, substituting 6-bromo-8,9-dihydro-7H-cyclopenta[c][1,2,4]triazolo[1,5-a]pyridine (I-3) with 6-bromo-7,9-dihydrofuro[3,4-c][1,2,4]triazolo[1,5-a]pyridine (I-16). ES/MS: 288.2 [M+H$^+$]. $^1$H NMR (400 MHz, CDCl3) δ 8.94 (s, 1H), 8.39 (s, 1H), 5.81-5.23 (m, 4H), 1.38 (s, 12H).

Preparation of Intermediate I-18

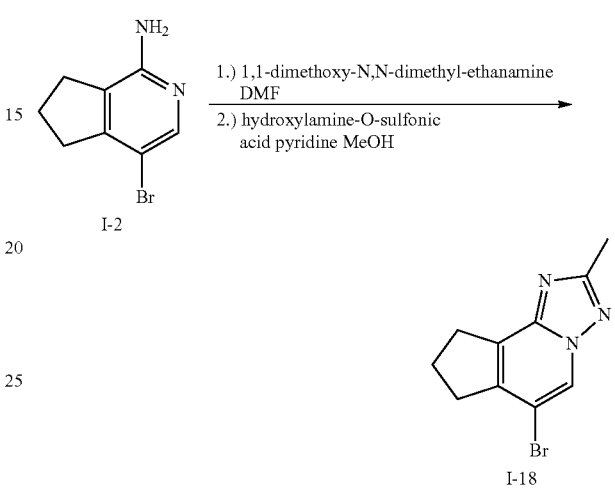

8-Bromo-4-methyl-3,5,6-triazatricyclo[7.3.0.02,6]dodeca-1(9),2,4,7-tetraene (I-18): Prepared analogously to I-2, substituting DMF-DMA with 1,1-dimethoxy-N,N-dimethyl-ethanamine. ES/MS: 254.1 [M+2H$^+$]. $^1$H NMR (400 MHz, CDCl$_3$) δ 8.53 (d, J=1.3 Hz, 1H), 3.41-3.32 (m, 2H), 3.10 (td, J=7.6, 1.4 Hz, 2H), 2.60 (d, J=1.0 Hz, 3H), 2.31 (p, J=7.6 Hz, 2H).

Preparation of Intermediate I-19

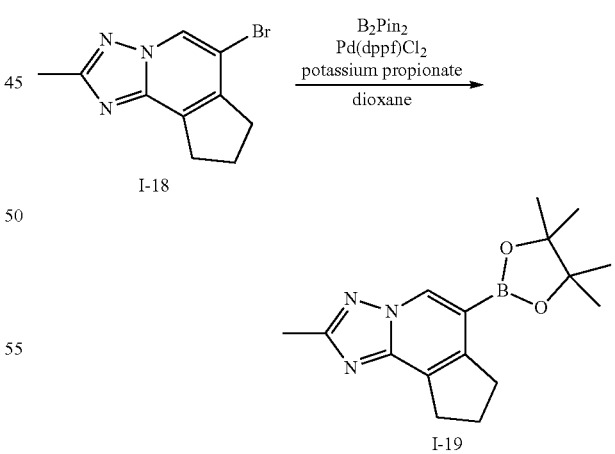

2-Methyl-6-(4,4,5,5-tetramethyl-1,3,2-dioxaborolan-2-yl)-8,9-dihydro-7H-cyclopenta[c][1,2,4]triazolo[1,5-a]pyridine (I-19): Prepared analogously to I-4, substituting 6-bromo-8,9-dihydro-7H-cyclopenta[c][1,2,4]triazolo[1,5-a]pyridine (I-3) with 8-Bromo-4-methyl-3,5,6-triazatricyclo[7.3.0.02,6]dodeca-1(9),2,4,7-tetraene (I-18). ES/MS: 300.2 [M+H$^+$]

Preparation of Intermediate I-20

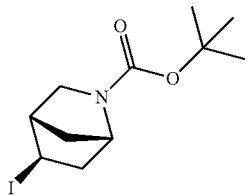

tert-butyl (1S,4S,5R)-5-iodo-2-azabicyclo[2.2.1]heptane-2-carboxylate (I-20): Prepared analogously to I-11, substituting tert-butyl (1R,5S)-3-hydroxy-8-azabicyclo[3.2.1]octane-8-carboxylate with tert-butyl (1S,4S,5S)-5-hydroxy-2-azabicyclo[2.2.1]heptane-2-carboxylate. ES/MS: 268.0 (M+H$^+$) (mass minus tert-butyl)$^1$H NMR (400 MHz, Chloroform-d) δ 4.20 (s, 1H), 4.08 (ddd, 1H), 3.29 (dd, 1H), 3.06 (d, 1H), 2.90-2.84 (m, 1H), 2.59-2.47 (m, 1H), 2.26 (dt, 1H), 2.10 (d, 1H), 1.78 (dd, 1H), 1.46 (d, 9H).

Preparation of Intermediate I-21

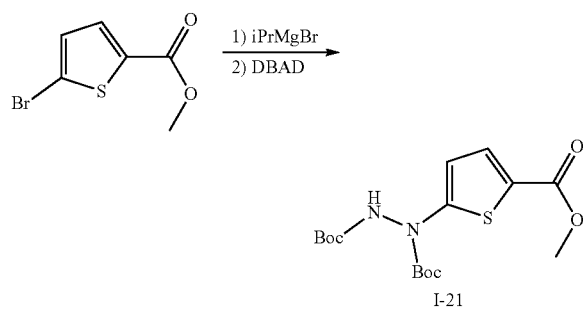

di-tert-butyl 1-(5-(methoxycarbonyl)thiophen-2-yl)hydrazine-1,2-dicarboxylate (I-21): The reaction was performed analogously to that of I-6 starting from methyl 5-bromothiophene-2-carboxylate to give the title compound. ES/MS: 373.2 (M+H$^+$)

Preparation of Intermediate I-22

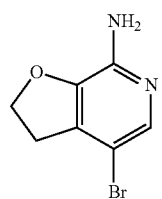

4-bromo-2,3-dihydrofuro[2,3-c]pyridin-7-amine (I-22): Prepared analogously to I-2, substituting 6,7-dihydro-5H-cyclopenta[c]pyridin-1-amine (I-1) with 2,3-dihydrofuro[2,3-c]pyridin-7-amine. ES/MS: 215.0 (M$^+$). 1H NMR (400 MHz, Chloroform-d) δ 7.71 (s, 1H), 4.68 (t, J=9.0 Hz, 2H), 3.26 (t, J=9.0 Hz, 2H).

Preparation of Intermediate I-23

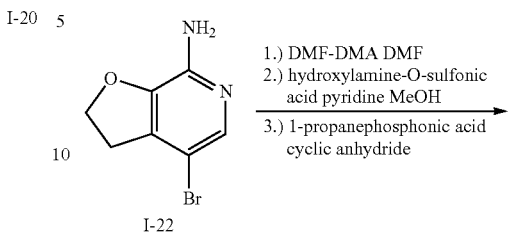

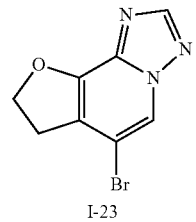

6-bromo-7,8-dihydrofuro[2,3-c][1,2,4]triazolo[1,5-a]pyridine (I-23): To a solution of 4-bromo-2,3-dihydrofuro[2,3-c]pyridin-7-amine (I-22) (1.1 g, 5.12 mmol) in DMF (3 mL) was added N,N-dimethylformamide dimethyl acetal (DMF-DMA) (3.35 mL, 20.5 mmol), and the reaction mixture was stirred for 6 hours at 80° C. The mixture was concentrated under reduced pressure, and methanol (3 mL) was added to the crude mixture. The mixture was cooled to 0° C., and pyridine (0.62 mL, 7.67 mmol) was added, followed by hydroxylamine-O-sulfonic acid (0.87 g, 7.67 mmol). The mixture was stirred overnight, warming to room temperature. The precipitated material was filtered. The precipitate was added to a 50 mL RBF, and THF (15 mL) was added. 1-Propanephosphonic acid (T3P) (50% solution in 2-MeTHF, 3.3 mL) was added dropwise, and the mixture was stirred overnight at 55° C. The mixture was diluted with EtOAc (50 mL), and the organic layer was washed with sat. aq. NaHCO$_3$ (20 mL) and brine (10 mL), and then the organic layer was dried over magnesium sulfate, filtered and concentrated under reduced pressure. The crude residue was purified by column chromatography (15-100% EtOAc in hexane) to give the title compound. ES/MS: 240.0 (M$^+$)

Preparation of Intermediate I-24

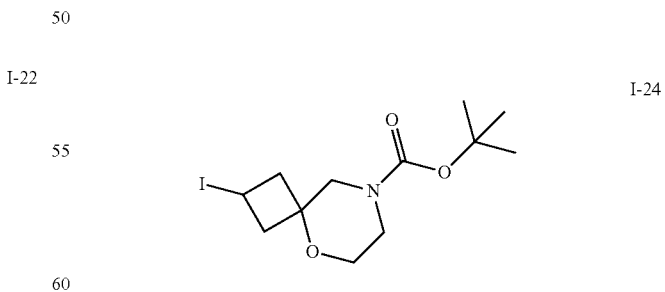

tert-butyl 2-iodo-5-oxa-8-azaspiro[3.5]nonane-8-carboxylate (I-24): Prepared analogously to I-11, substituting tert-butyl (1R,5S)-3-hydroxy-8-azabicyclo[3.2.1]octane-8-carboxylate with tert-butyl 2-hydroxy-5-oxa-8-azaspiro[3.5]nonane-8-carboxylate. ES/MS: 298.0 (M+H$^+$) (mass minus tert-butyl)

Preparation of Intermediate I-25

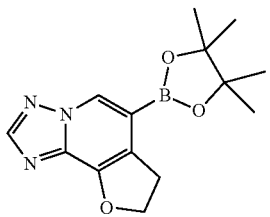

I-25

6-(4,4,5,5-tetramethyl-1,3,2-dioxaborolan-2-yl)-7,8-dihydrofuro[2,3-c][1,2,4]triazolo[1,5-a]pyridine (I-25): Prepared analogously to I-4, substituting 6-bromo-8,9-dihydro-7H-cyclopenta[c][1,2,4]triazolo[1,5-a]pyridine (I-3) with 6-bromo-7,8-dihydrofuro[2,3-c][1,2,4]triazolo[1,5-a]pyridine (I-23). ES/MS: 288.1 (M+H$^+$)

Preparation of Intermediate I-26

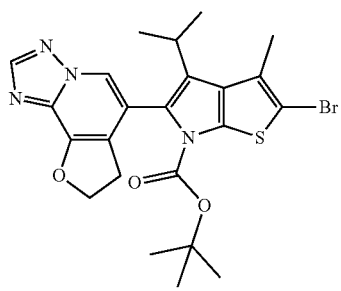

I-26 tert-butyl 2-bromo-5-(7,8-dihydrofuro[2,3-c][1,2,4]triazolo[1,5-a]pyridin-6-yl)-4-isopropyl-3-methyl-6H-thieno[2,3-b]pyrrole-6-carboxylate (I-26): Prepared analogously to I-5, I-7, I-8, I-9, and I-10, substituting 6-(4,4,5,5-tetramethyl-1,3,2-dioxaborolan-2-yl)-8,9-dihydro-7H-cyclopenta[c][1,2,4]triazolo[1,5-a]pyridine (I-4) with 6-(4,4,5,5-tetramethyl-1,3,2-dioxaborolan-2-yl)-7,8-dihydrofuro[2,3-c][1,2,4]triazolo[1,5-a]pyridine (I-25). ES/MS: 517.1 (M$^+$) 1H NMR (400 MHz, Chloroform-d) δ 8.37 (s, 1H), 8.21 (s, 1H), 5.03-4.64 (m, 2H), 3.13 (qdd, J=15.7, 10.1, 8.1 Hz, 2H), 2.97 (p, J=7.1 Hz, 1H), 2.48 (s, 3H), 1.41 (s, 9H), 1.28-1.25 (m, 3H), 1.23 (d, J=7.1 Hz, 3H).

Preparation of Intermediate I-27

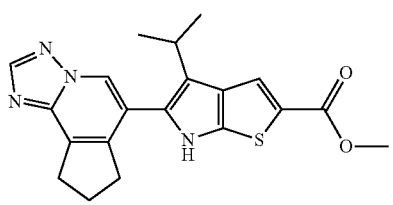

I-27 methyl 5-(8,9-dihydro-7H-cyclopenta[c][1,2,4]triazolo[1,5-a]pyridin-6-yl)-4-isopropyl-6H-thieno[2,3-b]pyrrole-2-carboxylate (I-27): Prepared analogously to I-7, substituting di-tert-butyl 1-(5-(methoxycarbonyl)-4-methylthiophen-2-yl)hydrazine-1,2-dicarboxylate (I-6) with di-tert-butyl 1-(5-(methoxycarbonyl)thiophen-2-yl)hydrazine-1,2-dicarboxylate (I-21). ES/MS: 381.1 (M+H$^+$)

Preparation of Intermediate I-28

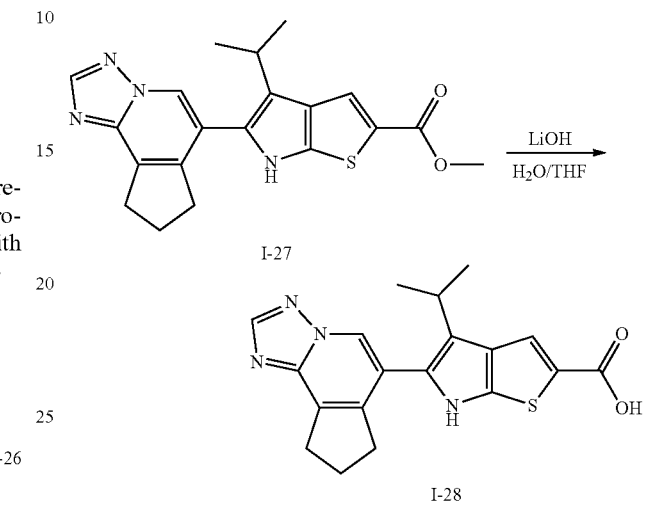

5-(8,9-dihydro-7H-cyclopenta[c][1,2,4]triazolo[1,5-a]pyridin-6-yl)-4-isopropyl-6H-thieno[2,3-b]pyrrole-2-carboxylic acid (I-28): To a solution of methyl 5-(8,9-dihydro-7H-cyclopenta[c][1,2,4]triazolo[1,5-a]pyridin-6-yl)-4-isopropyl-6H-thieno[2,3-b]pyrrole-2-carboxylate (1 g, 2.63 mmol) (I-27) in THF (20 mL) was added lithium hydroxide monohydrate (221 mg, 5.26 mmol) (dissolved in 17 mL water) and the reaction mixture was stirred for 16 h at 70° C. The reaction mixture was concentrated under reduced pressure, then diluted with hydrochloric acid (1.00 mol/L, 6.57 mL, 6.57 mmol), cooled to 0° C., and the precipitate was collected by filtration to give the title compound which was used directly in the next step. ES/MS: 367.1 (M+H$^+$)

Preparation of Intermediate I-29

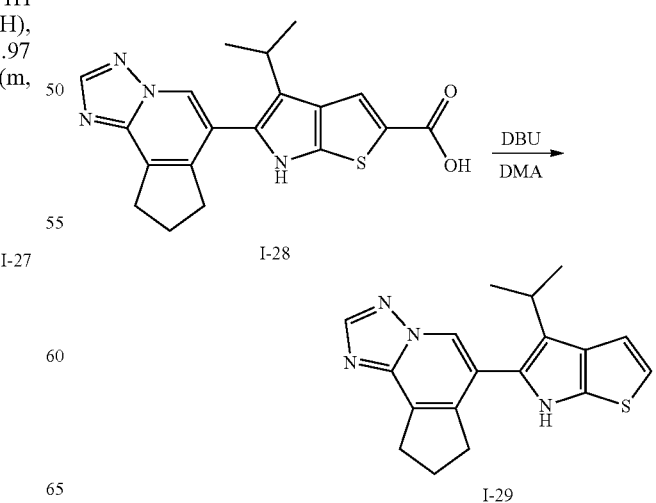

5-(8,9-dihydro-7H-cyclopenta[c][1,2,4]triazolo[1,5-a]pyridin-6-yl)-4-isopropyl-6H-thieno[2,3-b]pyrrole (I-29): To a solution of 5-(8,9-dihydro-7H-cyclopenta[c][1,2,4]triazolo[1,5-a]pyridin-6-yl)-4-isopropyl-6H-thieno[2,3-b]pyrrole-2-carboxylic acid (I-28) (500 mg, 1.36 mmol) in DMA (3 mL) was added DBU (0.611 mL, 4.09 mmol), and the resulting reaction mixture was stirred at 150° C. for 2 h. The reaction mixture was allowed to cool to room temperature, diluted with EtOAc (60 mL) and extracted with brine (2×20 mL). The aqueous layers were combined and extracted with EtOAc (60 mL). The combined organic layer was dried over Na$_2$SO$_4$, concentrated under reduced pressure, and purified by flash column chromatography ES/MS: 323.1 (M+H$^+$).

Preparation of Intermediate I-30

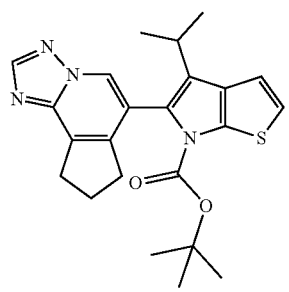

I-30 tert-butyl 5-(8,9-dihydro-7H-cyclopenta[c][1,2,4]triazolo[1,5-a]pyridin-6-yl)-4-isopropyl-6H-thieno[2,3-b]pyrrole-6-carboxylate (I-30): Prepared analogously to I-9, substituting 5-(8,9-dihydro-7H-cyclopenta[c][1,2,4]triazolo[1,5-a]pyridin-6-yl)-4-isopropyl-3-methyl-6H-thieno[2,3-b]pyrrole (I-8) with 5-(8,9-dihydro-7H-cyclopenta[c][1,2,4]triazolo[1,5-a]pyridin-6-yl)-4-isopropyl-6H-thieno[2,3-b]pyrrole (I-29). ES/MS: 423.2 (M+H$^+$)

Preparation of Intermediate I-31

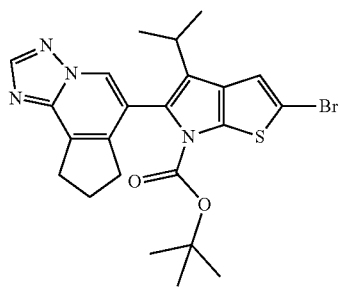

I-31 tert-butyl 2-bromo-5-(8,9-dihydro-7H-cyclopenta[c][1,2,4]triazolo[1,5-a]pyridin-6-yl)-4-isopropyl-6H-thieno[2,3-b]pyrrole-6-carboxylate (I-31): Prepared analogously to I-10, substituting tert-butyl 5-(8,9-dihydro-7H-cyclopenta[c][1,2,4]triazolo[1,5-a]pyridin-6-yl)-4-isopropyl-3-methyl-6H-thieno[2,3-b]pyrrole-6-carboxylate (I-9) with tert-butyl 5-(8,9-dihydro-7H-cyclopenta[c][1,2,4]triazolo[1,5-a]pyridin-6-yl)-4-isopropyl-6H-thieno[2,3-b]pyrrole-6-carboxylate (I-30). ES/MS: 501.1 (M$^+$)

Preparation of Intermediate I-32

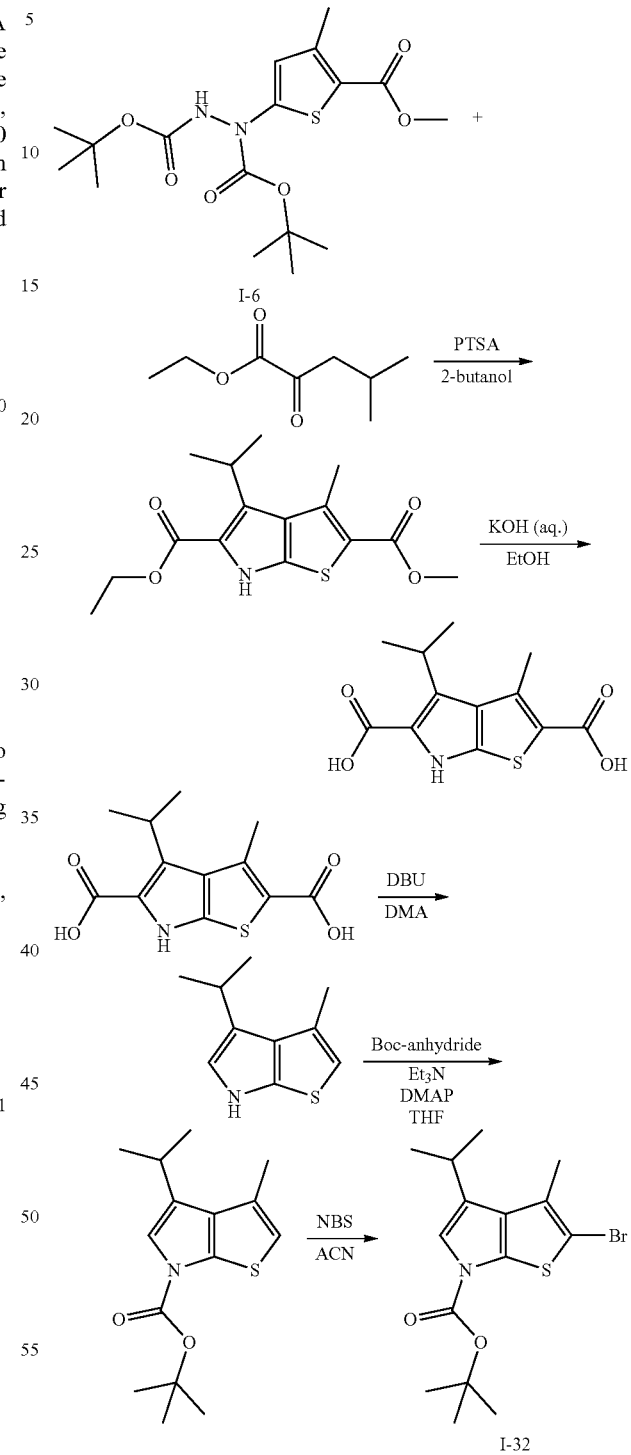

5-ethyl 2-methyl 4-isopropyl-3-methyl-6H-thieno[2,3-b]pyrrole-2,5-dicarboxylate: To a solution of di-tert-butyl 1-(5-(methoxycarbonyl)-4-methylthiophen-2-yl)hydrazine-1,2-dicarboxylate (I-6) (32.2 g, 83 mmol) and p-Toluenesulfonic Acid, monohydrate (66.1 g, 348 mmol) in a 500 mL round-bottomed flask in 2-butanol (140 mL) was added ethyl 4-methyl-2-oxo-pentanoate (11 g, 69.5 mmol) and the reaction mixture was heated to 90° C. for 16 h with a reflux condenser. The reaction mixture was concentrated under reduced pressure, taken up in EtOAc and water. The layers were separated, the aqueous layer was extracted with EtOAc (2×) and the combined organic layers were washed with brine, dried over sodium sulfate, filtered and the filtrate was concentrated under reduced pressure. The crude product was used for the next step. ES/MS: 310.0 (M+H⁺)

4-isopropyl-3-methyl-6H-thieno[2,3-b]pyrrole-2,5-dicarboxylic acid: To a solution of 5-ethyl 2-methyl 4-isopropyl-3-methyl-6H-thieno[2,3-b]pyrrole-2,5-dicarboxylate (21 g, 67.9 mmol) in ethanol (150 mL) was added potassium hydroxide (339 mL, 1M aq.) and the reaction mixture was heated to 100° C. for 24 h. The reaction mixture was concentrated under reduced pressure then diluted with hydrochloric acid (339 mL, 1M aw.) and poured onto a brine solution. The product was extracted from the aqueous phase with EtOAc (2×) and the combined organic layers were washed with brine, dried over sodium sulfate, filtered and the filtrate was concentrated under reduced pressure. The crude product was used for the next step. ES/MS: 268.0 (M+H⁺)

4-isopropyl-3-methyl-6H-thieno[2,3-b]pyrrole: To a solution of 4-isopropyl-3-methyl-6H-thieno[2,3-b]pyrrole-2,5-dicarboxylic acid (18.1 g, 67.7 mmol) in DMA (120 mL) was added DBU (30.3 mL, 203 mmol), and the resulting reaction mixture was stirred at 150° C. for 2 h. The reaction mixture was allowed to cool to room temperature, diluted with EtOAc (30 mL) and extracted with brine (2×20 mL). The aqueous layers were combined and extracted with EtOAc (30 mL). The combined organic layers were dried over Na₂SO₄ and concentrated under reduced pressure. The crude residue product was purified by flash chromatography (eluent: EtOAc/hexanes) to provide the product. ES/MS: 180.1 (M+H⁺)

tert-butyl 4-isopropyl-3-methyl-6H-thieno[2,3-b]pyrrole-6-carboxylate: To a solution of 4-isopropyl-3-methyl-6H-thieno[2,3-b]pyrrole. (12.1 g, 67.5 mmol) in THF (150 mL) was added N,N-dimethylpyridin-4-amine (DMAP) (2.0 g, 16.9 mmol), triethylamine (9.41 mL, 67.5 mmol), and tert-butoxycarbonyl tert-butyl carbonate (15.5 g, 70.9 mmol). The mixture was stirred at rt for 16 h. The mixture was concentrated under reduced pressure. The crude residue product was purified by flash chromatography (eluent: EtOAc/hexanes) to provide the product. 1H NMR (400 MHz, Chloroform-d) δ 7.00 (s, 1H), 6.57 (s, 1H), 3.14 (pd, J=6.8, 1.0 Hz, 1H), 2.43 (s, 3H), 1.67 (s, 9H), 1.32 (d, J=6.8 Hz, 6H).

tert-butyl 2-bromo-4-isopropyl-3-methyl-thieno[2,3-b]pyrrole-6-carboxylate (I-32):To an solution of tert-butyl 4-isopropyl-3-methyl-6H-thieno[2,3-b]pyrrole-6-carboxylate (7.02 g, 25.1 mmol) in acetonitrile (70.1 mL) at 0° C. was added NBS (4.47 g, 25.1 mmol) dissolved in acetonitrile (10 mL) dropwise until LCMS showed completion of reaction. The reaction mixture was diluted with EtOAc (150 mL) and the resultant mixture was extracted with aq. sodium thiosulfate solution (30 mL). The organic layer was then successively washed with water (2×30 mL) and brine (30 mL), dried over Na₂SO₄, filtered, and evaporated under reduced pressure and the crude residue was purified by column chromatography (eluent: EtOAc in hexane) to give the product. ES/MS: 302.0 (M⁺) (mass minus tert-butyl) ¹H NMR (400 MHz, DMSO-d₆) δ 7.18 (s, 1H), 3.21-2.97 (m, 1H), 2.32 (s, 3H), 1.59 (s, 9H), 1.24 (d, J=6.8 Hz, 6H).

Preparation of Intermediate I-33

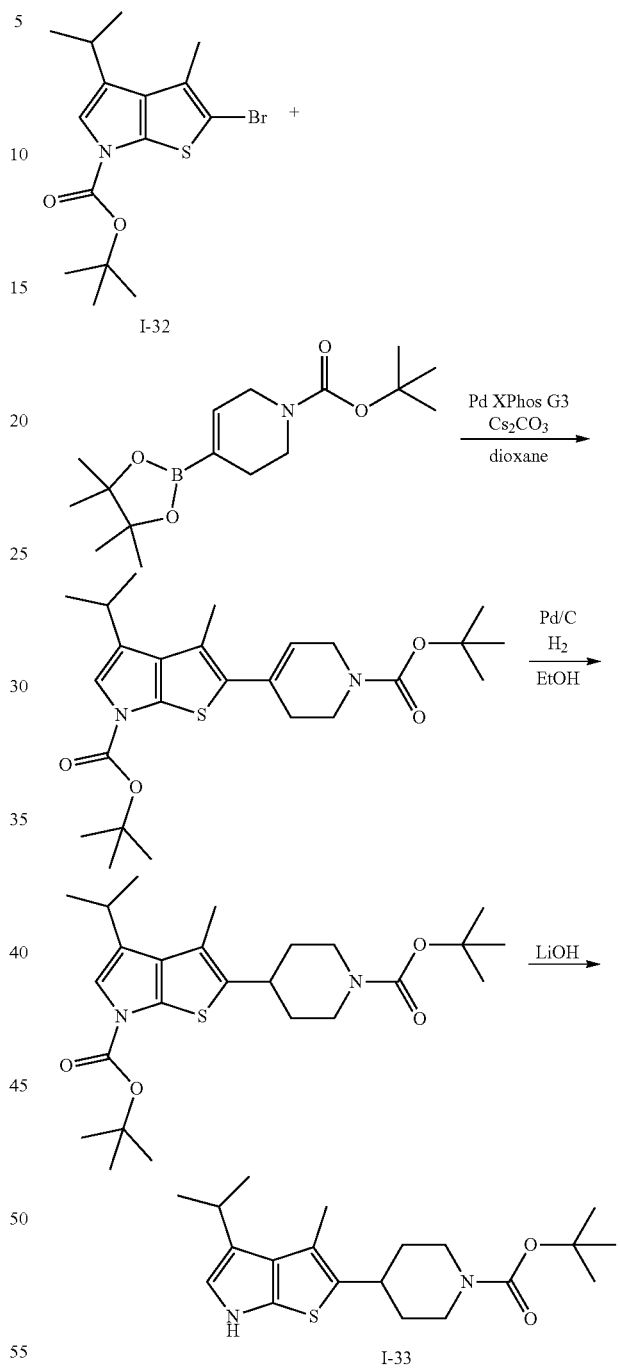

tert-butyl 2-(1-tert-butoxycarbonyl-3,6-dihydro-2H-pyridin-4-yl)-4-isopropyl-3-methyl-thieno[2,3-b]pyrrole-6-carboxylate: To tert-butyl 2-bromo-4-isopropyl-3-methyl-thieno[2,3-b]pyrrole-6-carboxylate (I-32) (4.1 g, 11.4 mmol) in 10:1 dioxane (100 ml) and water (10 mL) was added tert-butyl 4-(4,4,5,5-tetramethyl-1,3,2-dioxaborolan-2-yl)-3,6-dihydro-2H-pyridine-1-carboxylate (4.6 g, 14.8 mmol), XPhos Pd G3 (859 mg, 1.1 mmol) and cesium carbonate (11.1 g, 34.2 mmol). The reaction mixture was degassed with argon, and heated to 110° C. for 2 hours. The reaction mixture was diluted with EtOAc (150 mL) and the resultant mixture was extracted with aq. sodium thiosulfate solution (30 mL). The organic layer was then washed with water (2×30 mL) and brine (30 mL), dried over $Na_2SO_4$, filtered, and evaporated under reduced pressure. The crude residue was purified by column chromatography (eluent: EtOAc in hexane) to give the product. ES/MS: 461.2 (M+H$^+$)

tert-butyl 2-(1-(tert-butoxycarbonyl)piperidin-4-yl)-4-isopropyl-3-methyl-6H-thieno[2,3-b]pyrrole-6-carboxylate: To a solution of tert-butyl 2-(1-tert-butoxycarbonyl-3,6-dihydro-2H-pyridin-4-yl)-4-isopropyl-3-methyl-thieno[2,3-b]pyrrole-6-carboxylate (4.2 g, 9.12 mmol) in ethyl acetate (25 mL) was added palladium on carbon 10 wt. % (10.0%, 970 mg, 9.12 mmol) and the reaction mixture was stirred at room temp for 24 h under an atmosphere of hydrogen. The reaction mixture was subsequently degassed with argon, diluted with EtOAc, and filtered through celite, rinsing with EtOAc. The filtrate was concentrated under reduced pressure to give the product which was used directly in the next step. ES/MS: 463.3 (M+H$^+$)

tert-butyl 4-(4-isopropyl-3-methyl-6H-thieno[2,3-b]pyrrol-2-yl)piperidine-1-carboxylate (I-33): To tert-butyl 2-(1-tert-butoxycarbonyl-4-piperidyl)-4-isopropyl-3-methyl-thieno[2,3-b]pyrrole-6-carboxylate (4.2 g, 9.1 mmol) in a 1:1:1 mixture of EtOH/THF/water (50 mL) was added LiOH (1.4 g, 54.7 mmol) and the reaction mixture was stirred for 16 h at 80° C. The reaction mixture was diluted with EtOAc (150 mL) and the organic layer was then successively washed with water (2×50 mL) and brine (50 mL), dried over $Na_2SO_4$, filtered, and evaporated under reduced pressure to provide the product. ES/MS: 363.3 (M+H$^+$)

Preparation of Intermediate I-34

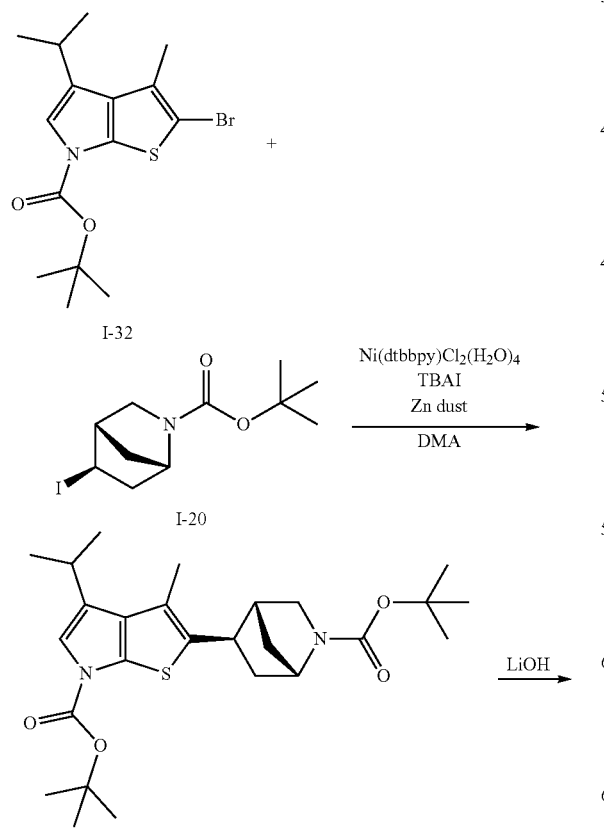

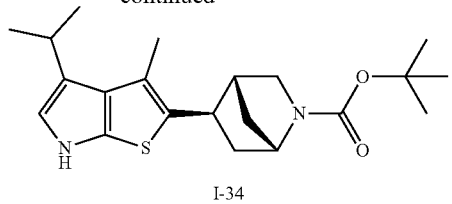

tert-butyl 2-((1S,4R,5R)-2-(tert-butoxycarbonyl)-2-azabicyclo[2.2.1]heptan-5-yl)-4-isopropyl-3-methyl-6H-thieno[2,3-b]pyrrole-6-carboxylate: To dried vial was added tert-butyl 2-bromo-4-isopropyl-3-methyl-6H-thieno[2,3-b]pyrrole-6-carboxylate (I-32) (250 mg, 0.7 mmol), tert-butyl (1S,4S,5R)-5-iodo-2-azabicyclo[2.2.1]heptane-2-carboxylate (I-20) (451 mg, 1.4 mmol), tetrabutylammonium iodide (TBAI) (309 mg, 0.837 mmol), Ni(dtbbpy)(H$_2$O)$_4$Cl$_2$ (32.8 mg, 0.07 mmol), and zinc dust (272 mg, 4.19 mmol). Dry DMA (2.5 mL) was added, and the mixture was degassed for 1 minute with argon. The vial was sealed, and the reaction was stirred at 70° C. for 16 h. Afterward, the reaction was cooled, and the crude mixture was purified directly by silica chromatography (eluent: EtOAc/hexanes) to provide the product.

tert-butyl (1S,4R,5R)-5-(4-isopropyl-3-methyl-6H-thieno[2,3-b]pyrrol-2-yl)-2-azabicyclo[2.2.1]heptane-2-carboxylate (I-34): To a solution of tert-butyl 2-((1S,4R,5R)-2-(tert-butoxycarbonyl)-2-azabicyclo[2.2.1]heptan-5-yl)-4-isopropyl-3-methyl-6H-thieno[2,3-b]pyrrole-6-carboxylate (320 mg, 0.67 mmol) in THF (1 mL) and MeOH (2 mL) was added LiOH monohydrate (100 mg, 2.38 mmol) (dissolved in 1 mL water) and the reaction mixture was stirred for 6 h at 90° C. The reaction mixture was diluted with EtOAc (50 mL) and the organic layer was then successively washed with water (15 mL) and brine (5 mL), dried over MgSO$_4$, filtered, and evaporated under reduced pressure to provide the product. ES/MS: 375.2 (M+H$^+$)

Preparation of Intermediate I-35

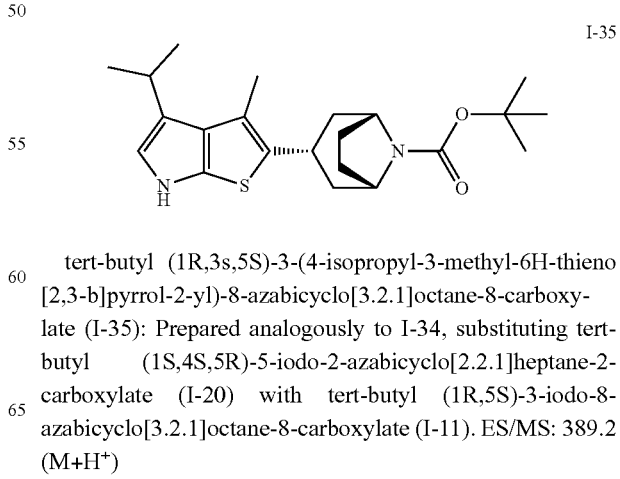

tert-butyl (1R,3s,5S)-3-(4-isopropyl-3-methyl-6H-thieno[2,3-b]pyrrol-2-yl)-8-azabicyclo[3.2.1]octane-8-carboxylate (I-35): Prepared analogously to I-34, substituting tert-butyl (1S,4S,5R)-5-iodo-2-azabicyclo[2.2.1]heptane-2-carboxylate (I-20) with tert-butyl (1R,5S)-3-iodo-8-azabicyclo[3.2.1]octane-8-carboxylate (I-11). ES/MS: 389.2 (M+H$^+$)

193
Preparation of Intermediate I-36

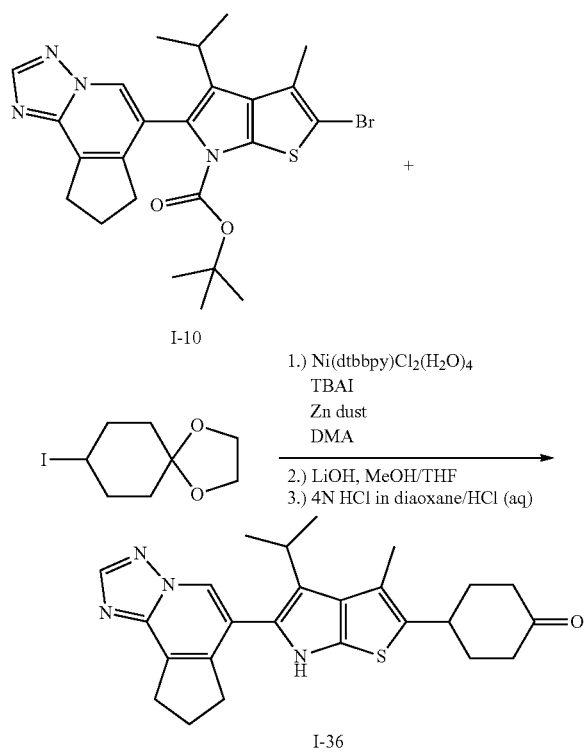

I-36

4-(5-(8,9-dihydro-7H-cyclopenta[c][1,2,4]triazolo[1,5-a]pyridin-6-yl)-4-isopropyl-3-methyl-6H-thieno[2,3-b]pyrrol-2-yl)cyclohexan-1-one (I-36): To dried vial was added tert-butyl 2-bromo-5-(8,9-dihydro-7H-cyclopenta[c][1,2,4]triazolo[1,5-a]pyridin-6-yl)-4-isopropyl-3-methyl-6H-thieno[2,3-b]pyrrole-6-carboxylate (I-10) (200 mg, 0.39 mmol), 8-iodo-1,4-dioxaspiro[4.5]decane (208 mg, 0.78 mmol), tetrabutylammonium iodide (TBAI) (172 mg, 0.47 mmol), Ni(dtbbpy)(H₂O)₄Cl₂ (721.9 mg, 0.047 mmol) and zinc dust (151 mg, 2.33 mmol). Dry DMA (2 mL) was added, and the mixture was degassed for 1 minute with argon. The vial was sealed, and the reaction was stirred at 70° C. for 16 h. Afterward, the reaction was cooled, and the crude mixture was purified directly by silica chromatography (eluent: EtOAc/hexanes). To a solution of the purified product in MeOH (1 mL) and THF (1 mL), LiOH (excess) was added and the resulting reaction mixture was stirred at 80° C. for 3 hr. The reaction mixture was cooled down to room temperature, diluted with EtOAc (30 mL) and water (5 mL). The layers were separated, and the organic layer was washed once with brine (5 mL). The organic layer was dried over MgSO₄, filtered and concentrated. To a solution of the crude product in DCM (2 mL), 4N HCl in dioxane (5 mL) and 1N aq. HCl (0.1 mL) was added and stirred at room temperature for 2 hr. The reaction mixture was diluted with DCM (20 mL), washed sequentially with aq. NaHCO₃ (2×10 mL), water (20 mL), brine (10 mL), dried over NaSO₄ and concentrated under reduced pressure to provide the title compound. ES/MS: 433.1 (M+H⁺)

194
Final Procedures

Procedure 1, Example 1

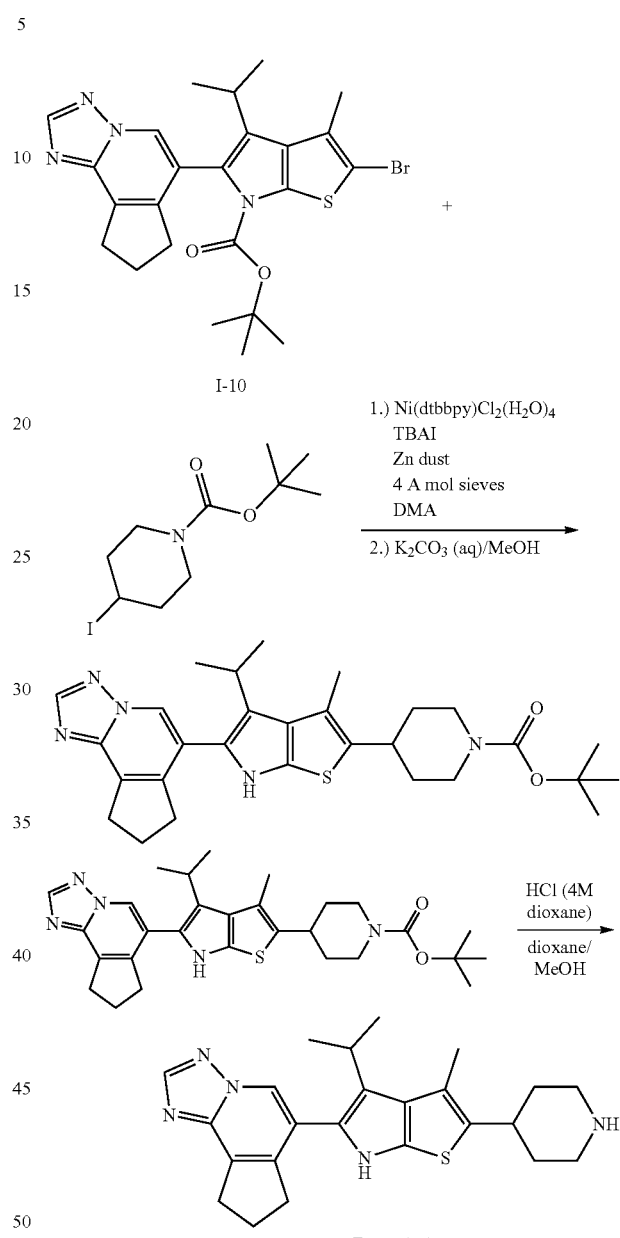

Example 1 tert-butyl 4-(5-(8,9-dihydro-7H-cyclopenta[c][1,2,4]triazolo[1,5-a]pyridin-6-yl)-4-isopropyl-3-methyl-6H-thieno[2,3-b]pyrrol-2-yl)piperidine-1-carboxylate: To a dried vial was added tert-butyl 2-bromo-5-(8,9-dihydro-7H-cyclopenta[c][1,2,4]triazolo[1,5-a]pyridin-6-yl)-4-isopropyl-3-methyl-6H-thieno[2,3-b]pyrrole-6-carboxylate (I-10) (113 mg, 0.219 mmol tert-butyl 4-iodopiperidine-1-carboxylate (102 mg, 0.329 mmol), tetrabutylammonium iodide (TBAI) (12.1 mg, 0.033 mmol), Ni(dtbbpy)(H₂O)₄Cl₂ (7.2 mg, 0.0153 mmol), zinc dust (72 mg, 1.1 mmol), and 4 Angstrom molecular sieves (40 mg). Dry DMA (1.0 mL) were added, and the mixture was degassed for 1 minute with argon. The vial was sealed, and the reaction was stirred at 70° C. for 16 h. Afterward, the reaction was cooled, and the crude mixture was purified directly by silica chromatography (eluent: EtOAc/hexanes). The purified material was dissolved in MeOH (1.5 mL) and potassium carbonate (sat. aq., 0.25 mL) was added. The mixture was stirred at 40 degrees overnight. LCMS indicated removal of the Boc group, and the mixture was diluted with EtOAc (30 mL) and water (5 mL). The layers were separated, and the organic layer was washed with brine (5 mL). The organic layer was dried over MgSO$_4$, filtered, and concentrated under reduced pressure to afford the product. ES/MS: 520.3 (M+H$^+$).

5-(8,9-dihydro-7H-cyclopenta[c][1,2,4]triazolo[1,5-a]pyridin-6-yl)-4-isopropyl-3-methyl-2-(piperidin-4-yl)-6H-thieno[2,3-b]pyrrole: To a vial with tert-butyl 4-(5-(8,9-dihydro-7H-cyclopenta[c][1,2,4]triazolo[1,5-a]pyridin-6-yl)-4-isopropyl-3-methyl-6H-thieno[2,3-b]pyrrol-2-yl)piperidine-1-carboxylate (90 mg, 0.173 mmol) was added 1,4-dioxane (0.25 mL) and methanol (0.25 mL). HCl (4M in dioxane, 0.52 mL, 2.08 mmol) was added, and the mixture was stirred for 3 hours at rt. LCMS indicated reaction completion, and the volatiles were evaporated under reduced pressure to isolate the HCl salt. To the mixture was added acetonitrile (0.5 mL), water (0.2 mL), and TFA (0.1 mL), and the mixture was filtered through an acrodisc before purification by RP-HPLC (0.1% TFA-ACN in 0.1% TFA Water, Column: Gemini 5 uM, NX-C18 110 Angstrom, 250×21.2 mm) to give the title compound Example 1. ES/MS: 420.2 (M+H$^+$). $^1$H NMR (400 MHz, Methanol-d4) δ 8.56 (s, 1H), 8.44 (s, 1H), 3.58-3.38 (m, 5H), 3.28-3.07 (m, 3H), 3.01 (t, J=7.5 Hz, 2H), 2.48 (s, 3H), 2.31 (p, J=7.7 Hz, 2H), 2.20 (d, J=14.4 Hz, 2H), 1.98-1.82 (m, 2H), 1.32 (d, J=7.1 Hz, 6H).

The following Examples were made in an analogous fashion according to Procedure 1 and are shown below in Table 1. To prepare the below Examples, different reagents/starting materials were used than some of those described in Procedure 1 and are noted in the last column of Table 1—"Changes to Procedure 1: Different Reagents/Starting Materials". A person of ordinary skill in the art will readily recognize which reagents/starting materials of Procedure 1 were replaced with the different reagents/starting materials noted below.

TABLE 1

| Example | Structure | ES/MS m/z | $^1$H-NMR | Changes to Procedure 1: Different Reagents/Starting Materials |
|---|---|---|---|---|
| 2 | 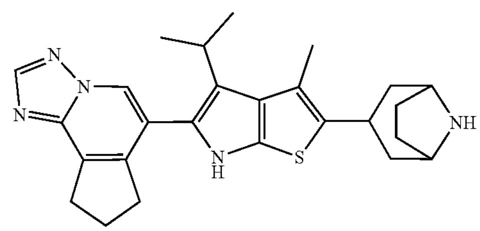 [SMILES: Cc1c(C2CC3CCC(C2)N3)sc2[nH]c(-c3cn4ncnc4c4c3CCC4)c(C(C)C)c12] | 446.3 | $^1$H NMR (400 MHz, Methanol-d4) δ 8.56 (s, 1H), 8.45 (s, 1H), 4.13 (s, 2H), 3.68 (tt, J = 11.8, 6.2 Hz, 1H), 3.42-3.35 (m, 2H), 3.18-3.08 (m, 1H), 3.00 (t, J = 7.5 Hz, 2H), 2.49 (s, 3H), 2.39-2.15 (m, 6H), 2.08 (dd, J = 14.9, 4.5 Hz, 4H), 1.31 (d, J = 7.1 Hz, 6H). | I-11 |
| 3 | 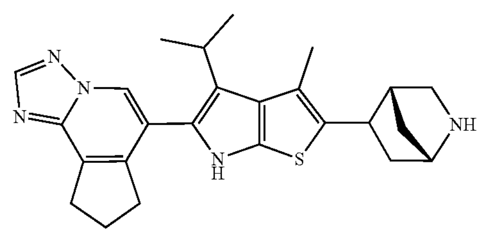 [SMILES: Cc1c(C2C[C@@H]3C[C@H]2CN3)sc2[nH]c(-c3cn4ncnc4c4c3CCC4)c(C(C)C)c12] | 432.2 | $^1$H NMR (400 MHz, Methanol-d4) δ 8.56 (s, 1H), 8.45 (s, 1H), 4.22 (s, 1H), 3.61-3.46 (m, 1H), 3.30-3.21 (m, 3H), 3.17-3.07 (m, 1H), 3.00 (t, J = 7.5 Hz, 2H), 2.79 (s, 1H), 2.48 (s, 3H), 2.48-2.39 (m, 1H), 2.31 (td, J = 14.1, 13.1, 6.8 Hz, 4H), 1.98 (dt, J = 14.8, 3.5 Hz, 1H), 1.82 (d, J = 11.8 Hz, 1H), 1.32 (dd, J = 7.1, 1.2 Hz, 6H). | I-12 |
| 4 | 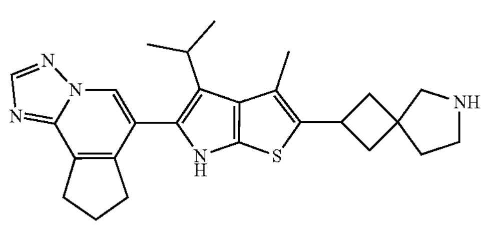 [SMILES: Cc1c(C2CC3(CCNC3)C2)sc2[nH]c(-c3cn4ncnc4c4c3CCC4)c(C(C)C)c12] | 446.3 | $^1$H NMR (400 MHz, MeOD) δ 8.56 (s, 1H), 8.46 (s, 1H), 3.95 (dq, J = 13.3, 8.8 Hz, 1H), 3.47 (s, 1H), 3.38 (t, J = 7.1 Hz, 1H), 3.33 (dq, J = 4.0, 2.0 Hz, 2H), 3.25 (s, 1H), 3.15-2.97 (m, 3H), 2.69-2.51 (m, 2H), 2.39 (d, J = 2.5 Hz, 3H), 2.30 (ddd, J = 10.5, 7.9, 4.9 Hz, 5H), 2.11 (t, J = 7.5 Hz, 1H), 1.31 (d, J = 7.1 Hz, 6H). | I-13 |

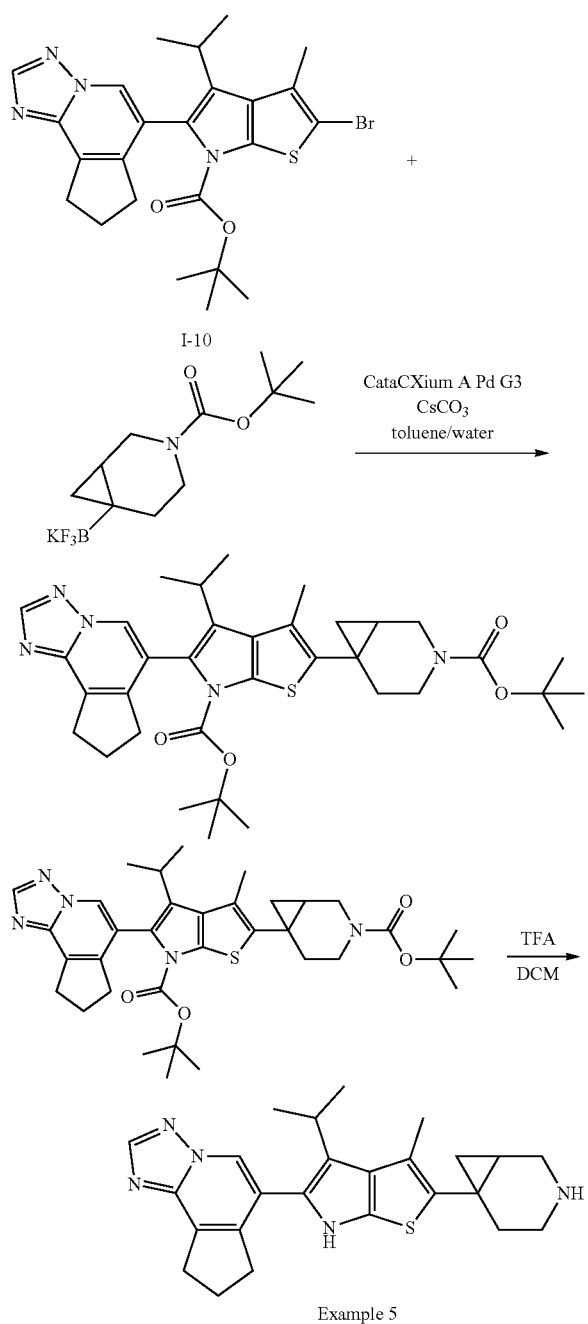

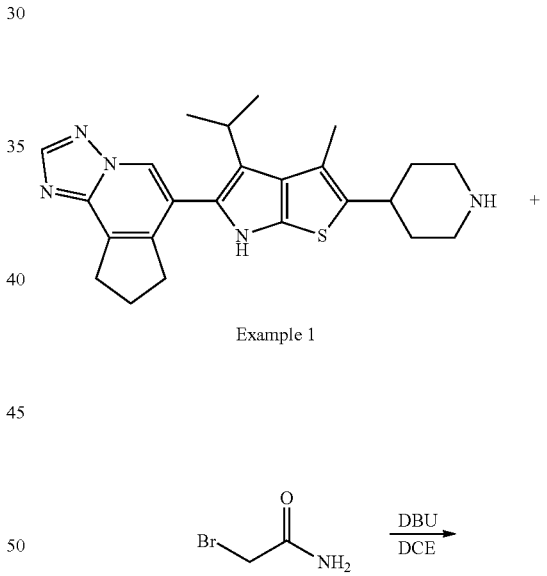

Example 1

Example 6

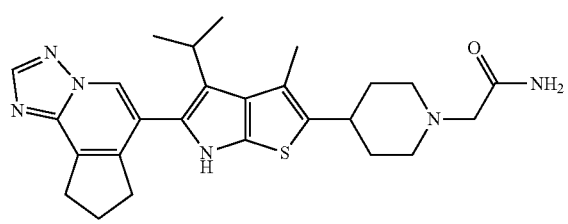

tert-butyl 2-(3-(tert-butoxycarbonyl)-3-azabicyclo[4.1.0]heptan-6-yl)-5-(8,9-dihydro-7H-cyclopenta[c][1,2,4]triazolo[1,5-a]pyridin-6-yl)-4-isopropyl-3-methyl-6H-thieno[2,3-b]pyrrole-6-carboxylate: To a dried vial was added tert-butyl 2-bromo-5-(8,9-dihydro-7H-cyclopenta[c][1,2,4]triazolo[1,5-a]pyridin-6-yl)-4-isopropyl-3-methyl-6H-thieno[2,3-b]pyrrole-6-carboxylate (I-10) (125 mg, 0.242 mmol), tert-butyl 6-(trifluoroboraneyl)-3-azabicyclo[4.1.0]heptane-3-carboxylate, potassium salt (118 mg, 0.388 mmol), CataCXium A Pd G3 (17.7 mg, 0.024 mmol), cesium carbonate (237 mg, 0.727 mmol). Toluene (6.0 mL) and water (0.6 mL) were added, and the mixture was degassed for 4 minutes with argon. The vial was sealed, and the reaction was stirred at 90° C. for 18 h. Afterward, the reaction was cooled, and the crude mixture was filtered through celite, rinsing with EtOAc. The mixture was concentrated under reduced pressure, and the crude residue was purified directly by silica chromatography (eluent: EtOAc/hexanes) to afford the product. ES/MS: 632.4 (M+H$^+$)

2-(3-azabicyclo[4.1.0]heptan-6-yl)-5-(8,9-dihydro-7H-cyclopenta[c][1,2,4]triazolo[1,5-a]pyridin-6-yl)-4-isopropyl-3-methyl-6H-thieno[2,3-b]pyrrole (Example 5): To a vial with tert-butyl 2-(3-(tert-butoxycarbonyl)-3-azabicyclo[4.1.0]heptan-6-yl)-5-(8,9-dihydro-7H-cyclopenta[c][1,2,4]triazolo[1,5-a]pyridin-6-yl)-4-isopropyl-3-methyl-6H-thieno[2,3-b]pyrrole-6-carboxylate (160 mg, 0.253 mmol) was added dichloromethane (4 mL). Trifluoroacetic acid (1 mL) was added, and the mixture was stirred at rt. LCMS indicated reaction completion, and the volatiles were evaporated under reduced pressure. To the mixture was added acetonitrile (0.5 mL), water (0.2 mL), and the mixture was filtered through an acrodisc before purification by RP-HPLC (0.1% TFA-ACN in 0.1% TFA Water, Column: Gemini 5 uM, NX-C18 110 Angstrom, 250×21.2 mm) to give the title compound Example 5. ES/MS: 432.2 (M+H$^+$). $^1$H NMR (400 MHz, MeOD) δ 8.56 (s, 1H), 8.46 (s, 1H), 3.83 (dd, J=13.6, 7.3 Hz, 1H), 3.22 (dt, J=13.2, 5.4 Hz, 1H), 3.10 (p, J=7.1 Hz, 2H), 2.98 (dt, J=17.4, 8.1 Hz, 3H), 2.55 (s, 3H), 2.48-2.25 (m, 5H), 1.73-1.67 (m, 1H), 1.39 (dd, J=9.2, 5.3 Hz, 1H), 1.31 (dd, J=7.1, 1.3 Hz, 6H), 1.23 (t, J=5.5 Hz, 1H).

Procedure 3, Example 6

2-(4-(5-(8,9-dihydro-7H-cyclopenta[c][1,2,4]triazolo[1,5-a]pyridin-6-yl)-4-isopropyl-3-methyl-6H-thieno[2,3-b]pyrrol-2-yl)piperidin-1-yl)acetamide (Example 6): To a solution of 5-(8,9-dihydro-7H-cyclopenta[c][1,2,4]triazolo[1,5-a]pyridin-6-yl)-4-isopropyl-3-methyl-2-(piperidin-4-yl)-6H-thieno[2,3-b]pyrrole (HCl salt) (Example 1) (43 mg, 0.094 mmol) in 1,2-dichloroethane (2 mL) was added 2-bromoacetamide (15.6 mg, 0.113 mmol) and 1,8-diazabicyclo[5.4.0]undec-7-ene (0.056 mL, 0.38 mmol). The mixture was stirred overnight at rt. To the mixture was added 0.2 mL TFA, and the DCE was subsequently removed under reduced pressure. Acetonitrile (0.5 mL), DMSO (0.2 mL) and water (0.2 mL) were added, and the mixture was filtered through an acrodisc before purification by RP-HPLC (0.1% TFA-ACN in 0.1% TFA Water, Column: Gemini 5 uM, NX-C18 110 Angstrom, 250×21.2 mm) to give the title compound Example 6. ES/MS: 477.3 (M+H$^+$). $^1$H NMR (400 MHz, Methanol-d4) δ 8.57 (s, 1H), 8.46 (s, 1H), 3.99 (s, 2H), 3.74 (d, J=12.1 Hz, 2H), 3.62-3.37 (m, 3H), 3.30-3.19 (m, 3H), 3.19-3.08 (m, 2H), 3.01 (t, J=7.5 Hz, 2H), 2.49 (s, 3H), 2.32 (p, J=7.5 Hz, 2H), 2.23 (d, J=14.1 Hz, 2H), 2.09 (q, J=13.2 Hz, 2H), 1.32 (d, J=7.0 Hz, 6H).

The following Examples were made in an analogous fashion according to Procedure 3 and are shown below in Table 2. To prepare the below Examples, different reagents/starting materials were used than some of those described in Procedure 3 and are noted in the last column of Table 2—"Changes to Procedure 3: Different Reagents/Starting Materials". A person of ordinary skill in the art will readily recognize which reagents/starting materials of Procedure 3 were replaced with the different reagents/starting materials noted below.

TABLE 2

| Example | Structure | ES/MS m/z | $^1$H-NMR | Changes to Procedure 3: Different Reagents/Starting Materials |
|---|---|---|---|---|
| 7 | 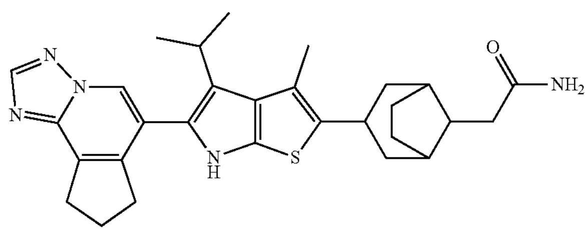 [SMILES: Cc1c(C2CC3CCC(C2)C3CC(N)=O)sc2[nH]c(-c3cn4ncnc4c4c3CCC4)c(C(C)C)c12] | 503.3 | $^1$H NMR (400 MHz, Methanol-d4) δ 8.57 (s, 1H), 8.46 (s, 1H), 4.14 (s, 2H), 3.89 (s, 2H), 3.74 (dq, J = 12.0, 5.8 Hz, 1H), 3.38-3.34 (m, 2H), 3.18-3.07 (m, 1H), 3.01 (t, J = 7.5 Hz, 2H), 2.50 (s, 3H), 2.45-2.23 (m, 8H), 2.18 (d, J = 14.8 Hz, 2H), 1.31 (d, J = 7.1 Hz, 6H). | Example 2 |
| 8 | 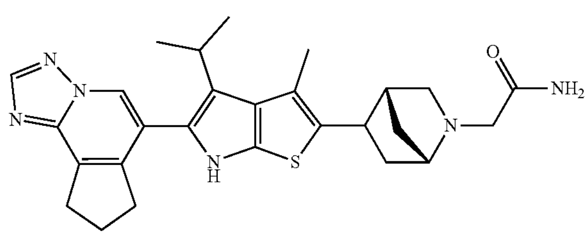 [SMILES: Cc1c(C2C[C@@H]3C[C@H]2CN3CC(N)=O)sc2[nH]c(-c3cn4ncnc4c4c3CCC4)c(C(C)C)c12] | 489.3 | $^1$H NMR (400 MHz, Methanol-d4) δ 8.57 (s, 1H), 8.46 (s, 1H), 4.35-3.96 (m, 3H), 3.76 (dd, J = 25.5, 9.5 Hz, 1H), 3.67-3.46 (m, 1H), 3.21-3.05 (m, 3H), 3.01 (t, J = 7.5 Hz, 2H), 2.86-2.56 (m, 3H), 2.49 (d, J = 4.2 Hz, 3H), 2.40-2.20 (m, 4H), 2.17-1.94 (m, 2H), 1.32 (d, J = 7.1 Hz, 6H). | Example 3 |
| 9 | 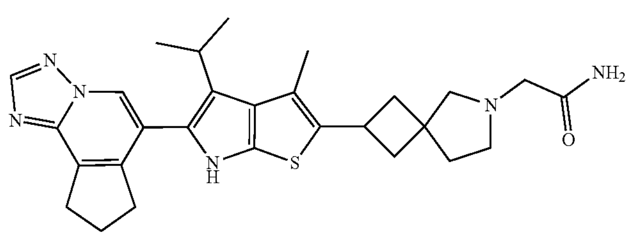 [SMILES: Cc1c(C2CC3(CCN(CC(N)=O)C3)C2)sc2[nH]c(-c3cn4ncnc4c4c3CCC4)c(C(C)C)c12] | 503.3 | $^1$H NMR (400 MHz, MeOD) δ 8.57 (s, 1H), 8.48 (s, 1H), 4.20-3.54 (m, 6H), 3.17-2.91 (m, 4H), 2.85-2.10 (m, 13H), 1.31 (d, J = 7.1 Hz, 6H). | Example 4 |
| 10 | 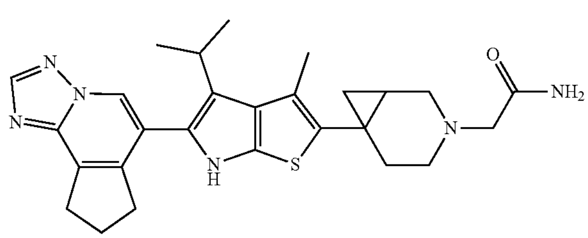 [SMILES: Cc1c(C23CCN(CC(N)=O)CC2C3)sc2[nH]c(-c3cn4ncnc4c4c3CCC4)c(C(C)C)c12] | 489.3 | $^1$H NMR (400 MHz, MeOD) δ 10.77 (s, 1H), 8.56 (s, 1H), 8.46 (s, 1H), 4.10 (s, 2H), 3.10 (p, J = 7.1 Hz, 2H), 3.00 (t, J = 7.5 Hz, 3H), 2.55 (s, 5H), 2.31 (p, J = 7.6 Hz, 3H), 1.76 (d, J = 7.1 Hz, 1H), 1.42 (s, 1H), 1.31 (dd, J = 7.2, 2.8 Hz, 8H). | Example 5 |

Procedure 4, Example 11

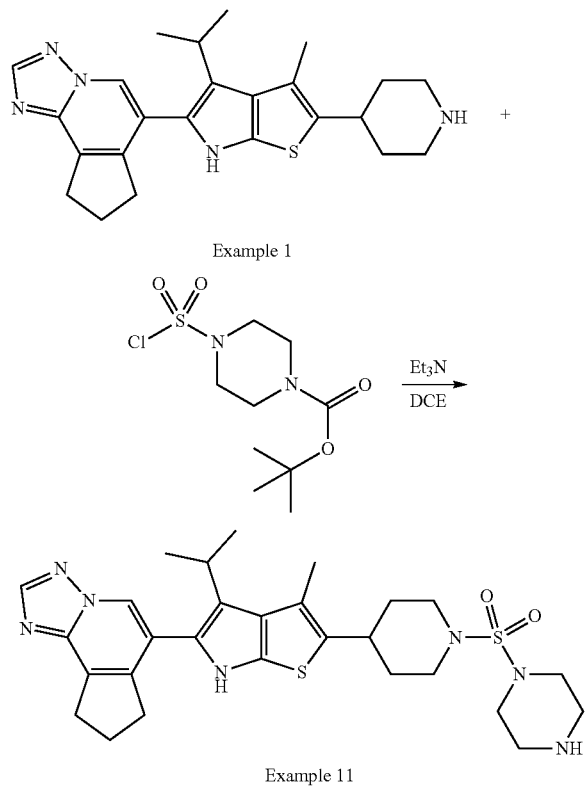

Example 11

5-(8,9-dihydro-7H-cyclopenta[c][1,2,4]triazolo[1,5-a]pyridin-6-yl)-4-isopropyl-3-methyl-2-(1-(piperazin-1-ylsulfonyl)piperidin-4-yl)-6H-thieno[2,3-b]pyrrole (Example 11): To a solution of 5-(8,9-dihydro-7H-cyclopenta[c][1,2,4]triazolo[1,5-a]pyridin-6-yl)-4-isopropyl-3-methyl-2-(piperidin-4-yl)-6H-thieno[2,3-b]pyrrole (HCl salt) (Example 1) (10 mg, 0.022 mmol) in 1,2-dichloroethane (2 mL) was added tert-butyl 4-(chlorosulfonyl)piperazine-1-carboxylate (31 mg, 0.11 mmol) and N,N-diisopropylethylamine (0.02 mL, 0.11 mmol). The mixture was stirred 2 hr at rt. To the mixture was added 0.5 mL TFA, and the DCE was subsequently removed under reduced pressure. Acetonitrile (1.5 mL) and water (0.5 mL) were added, and the mixture was filtered through an acrodisc before purification by RP-HPLC (0.1% TFA-ACN in 0.1% TFA Water, Column: Gemini 5 uM, NX-C18 110 Angstrom, 250×21.2 mm) to give the title compound Example 11. ES/MS: 568.2 (M+H$^+$). $^1$H NMR (400 MHz, Methanol-d4) δ 10.71 (s, 1H), 8.55 (s, 1H), 8.43 (s, 1H), 3.86 (d, 2H), 3.55-3.48 (m, 6H), 3.40-3.35 (m, 5H), 3.15 (dt, 2H), 3.09 (d, 1H), 3.01 (t, 2H), 2.46 (s, 3H), 2.32 (q, 2H), 2.03 (d, 2H), 1.80-1.67 (m, 1H), 1.31 (d, 6H).

Procedure 5, Example 12

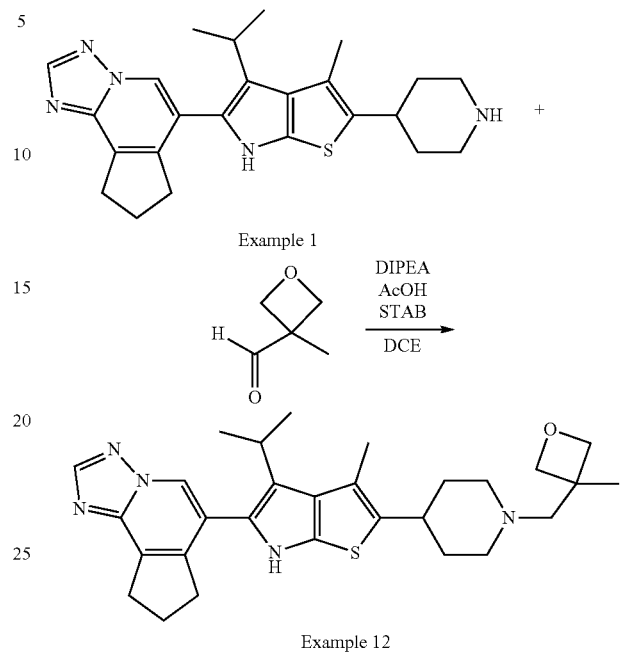

Example 12

5-(8,9-dihydro-7H-cyclopenta[c][1,2,4]triazolo[1,5-a]pyridin-6-yl)-4-isopropyl-3-methyl-2-(1-((3-methyloxetan-3-yl)methyl)piperidin-4-yl)-6H-thieno[2,3-b]pyrrole (Example 12): To a vial with 5-(8,9-dihydro-7H-cyclopenta[c][1,2,4]triazolo[1,5-a]pyridin-6-yl)-4-isopropyl-3-methyl-2-(piperidin-4-yl)-6H-thieno[2,3-b]pyrrole (HCl salt) (Example 1) (10 mg, 0.022 mmol) in 1,2-dichloroethane (1 mL) was added 3-methyloxetane-3-carbaldehyde (4 mg, 0.044 mmol), N,N-diisopropylethylamine (0.008 mL, 0.044 mmol), and acetic acid (1 drop). The mixture was stirred 2 hr at rt. To the mixture was subsequently added sodium triacetoxyborohydride (STAB) (14 mg, 0.066 mmol), and the mixture was stirred overnight at rt. To the mixture was added 0.1 mL TFA, and the DCE was subsequently removed under reduced pressure. Acetonitrile (1.5 mL) and water (0.5 mL) were added, and the mixture was filtered through an acrodisc before purification by RP-HPLC (0.1% TFA-ACN in 0.1% TFA Water, Column: Gemini 5 uM, NX-C18 110 Angstrom, 250×21.2 mm) to give the title compound Example 12. ES/MS: 504.3 (M+H$^+$). $^1$H NMR (400 MHz, Methanol-d4) δ 10.78 (s, 1H), 8.56 (s, 1H), 8.44 (s, 1H), 4.65 (d, 2H), 4.44 (d, 2H), 3.56 (s, 2H), 3.50 (p, 1H), 3.47 (s, 2H), 3.45-3.38 (m, 1H), 3.18-3.08 (m, 2H), 3.00 (t, 2H), 2.49 (s, 3H), 2.31 (p, 2H), 2.23 (d, 2H), 2.11-1.96 (m, 2H), 1.61 (s, 3H), 1.45-1.37 (m, 1H), 1.31 (d, 6H).

The following Examples were made in an analogous fashion according to Procedure 5 and are shown below in Table 3. To prepare the below Examples, different reagents/starting materials were used than some of those described in Procedure 5 and are noted in the last column of Table 3—"Changes to Procedure 5: Different Reagents/Starting Materials". A person of ordinary skill in the art will readily recognize which reagents/starting materials of Procedure 5 were replaced with the different reagents/starting materials noted below.

TABLE 3

| Example | Structure | ES/MS m/z | ¹H-NMR | Changes to Procedure 5: Different Reagents/ Starting Materials |
|---|---|---|---|---|
| 13 | 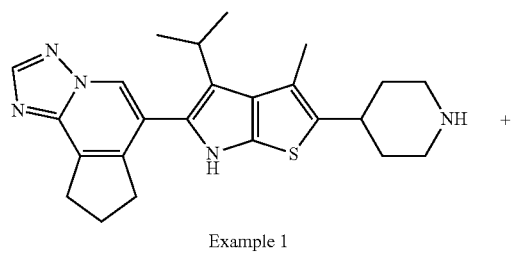 | 514.3 | ¹H NMR (400 MHz, Methanol-d4) δ 10.77 (s, 1H), 8.56 (s, 1H), 8.46 (s, 1H), 7.72 (d, 1H), 6.49 (d, 1H), 4.35 (s, 2H), 3.97 (s, 3H), 3.67 (d, 2H), 3.50 (p, 1H), 3.45-3.38 (m, 1H), 3.27-3.17 (m, 1H), 3.17-3.05 (m, 1H), 3.00 (t, 2H), 2.47 (s, 3H), 2.31 (p, 2H), 2.23 (d, 2H), 2.03-1.86 (m, 2H), 1.31 (d, 6H). | 1-methyl-pyrazole-3-carbaldehyde |

Procedure 6, Example 14

(R)-(4-(5-(8,9-dihydro-7H-cyclopenta[c][1,2,4]triazolo[1,5-a]pyridin-6-yl)-4-isopropyl-3-methyl-6H-thieno[2,3-b]pyrrol-2-yl)piperidin-1-yl)(morpholin-3-yl)methanone (Example 14): To a vial with 5-(8,9-dihydro-7H-cyclopenta[c][1,2,4]triazolo[1,5-a]pyridin-6-yl)-4-isopropyl-3-methyl-2-(piperidin-4-yl)-6H-thieno[2,3-b]pyrrole (HCl salt) (Example 1) (15 mg, 0.033 mmol) in 1,2-dichloroethane (2 mL) was added (R)-4-(tert-butoxycarbonyl)morpholine-3-carboxylic acid (11 mg, 0.049 mmol), 2-(7-Aza-1H-benzotriazole-1-yl)-1,1,3,3-tetramethyluronium hexafluorophosphate (HATU) (19 mg, 0.049 mmol), N,N-diisopropylethylamine (0.02 mL, 0.099 mmol). The mixture was stirred 5 hr at rt. To the mixture was added TFA (0.5 mL), and the mixture was stirred 2 hr at rt. LCMS indicated removal of the Boc group. The crude mixture was concentrated under reduced pressure, and acetonitrile (1.5 mL) and water (0.5 mL) were added. The mixture was filtered through an acrodisc before purification by RP-HPLC (0.1% TFA-ACN in 0.1% TFA Water, Column: Gemini 5 uM, NX-C18 110 Angstrom, 250×21.2 mm) to give the title compound Example 14. ES/MS: 533.3 (M+H⁺). ¹H NMR (400 MHz, Methanol-d4) δ 10.71 (s, 1H), 8.57 (s, 1H), 8.48 (s, 1H), 4.72 (dd, 1H), 4.65 (d, 2H), 4.28 (dd, 1H), 4.06 (t, 2H), 3.86-3.75 (m, 1H), 3.74-3.56 (m, 1H), 3.42-3.36 (m, 2H), 3.18-3.07 (m, 1H), 3.01 (t, 2H), 2.90 (t, 1H), 2.48 (s, 3H), 2.31 (p, 2H), 2.21-2.01 (m, 3H), 1.79-1.51 (m, 2H), 1.32 (d, 7H).

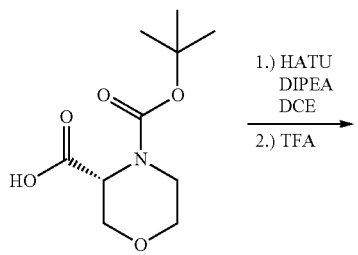

Example 1

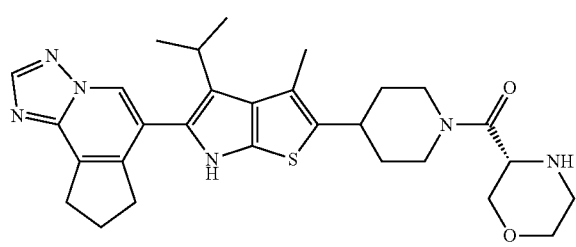

Example 14

The following Examples were made in an analogous fashion according to Procedure 6 and are shown below in Table 4. To prepare the below Examples, different reagents/starting materials were used than some of those described in Procedure 6 and are noted in the last column of Table 4—"Changes to Procedure 6: Different Reagents/Starting Materials". A person of ordinary skill in the art will readily recognize which reagents/starting materials of Procedure 6 were replaced with the different reagents/starting materials noted below.

TABLE 4

| Example | Structure | ES/MS m/z | ¹H-NMR | Changes to Procedure 6: Different Reagents/ Starting Materials |
|---|---|---|---|---|
| 15 | 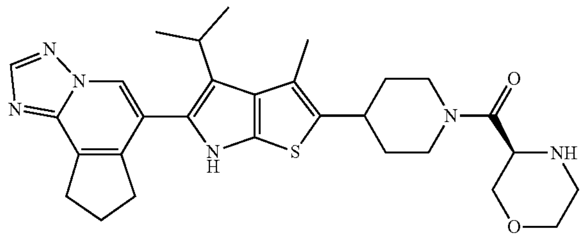 [SMILES: Cc1c(C2CCN(C(=O)[C@@H]3COCCN3)CC2)sc2[nH]c(-c3cn4ncnc4c4c3CCC4)c(C(C)C)c12] | 533.3 | ¹H NMR (400 MHz, Methanol-d₄) δ 8.56 (s, 1H), 8.46 (s, 1H), 4.72 (dd, 1H), 4.65 (d, 1H), 4.28 (dd, 1H), 4.06 (t, 2H), 3.85-3.75 (m, 1H), 3.74-3.66 (m, 1H), 3.66-3.56 (m, 1H), 3.50 (p, 1H), 3.44-3.37 (m, 1H), 3.37-3.35 (m, 4H), 3.17-3.08 (m, 1H), 3.01 (t, 2H), 2.90 (t, 1H), 2.48 (s, 3H), 2.31 (p, 2H), 2.21-2.01 (m, 2H), 1.78-1.52 (m, 2H), 1.32 (d, 6H). | (R)-4-(tert-butoxy-carbonyl) morpholine-3-carboxylic acid |
| 16 | 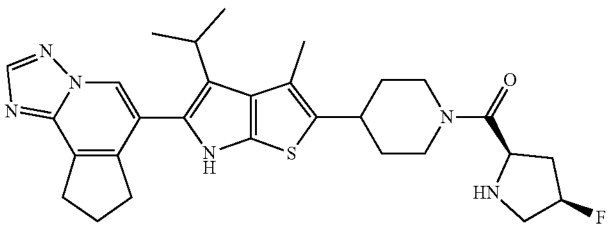 [SMILES: Cc1c(C2CCN(C(=O)[C@H]3C[C@@H](F)CN3)CC2)sc2[nH]c(-c3cn4ncnc4c4c3CCC4)c(C(C)C)c12] | 535.3 | ¹H NMR (400 MHz, Methanol-d4) δ 10.72 (d, 1H), 8.56 (s, 1H), 8.46 (s, 1H), 5.47 (dd, 1H), 4.67 (d, 1H), 3.92-3.78 (m, 2H), 3.61-3.53 (m, 1H), 3.50 (dd, 1H), 3.47-3.37 (m, 1H), 3.17-3.07 (m, 1H), 3.05-2.96 (m, 2H), 2.92-2.78 (m, 1H), 2.48 (s, 3H), 2.46-2.36 (m, 1H), 2.31 (p, 2H), 2.07 (m, 2H), 1.79-1.58 (m, 2H), 1.32 (d, 6H). | (2R,4R)-1-tert-butoxy-carbonyl-4-fluoro-pyrrolidine-2-carboxylic acid |
| 17 | 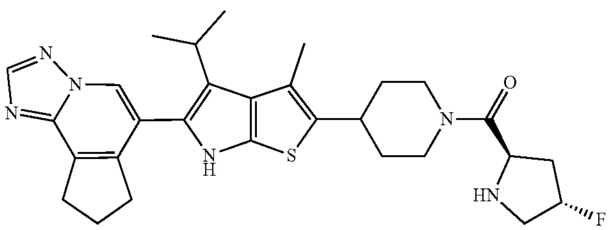 [SMILES: Cc1c(C2CCN(C(=O)[C@H]3C[C@H](F)CN3)CC2)sc2[nH]c(-c3cn4ncnc4c4c3CCC4)c(C(C)C)c12] | 535.3 | ¹H NMR (400 MHz, Methanol-d4) δ 10.72 (d, 1H), 8.56 (s, 1H), 8.47 (s, 1H), 5.54 (dd, 1H), 5.08-4.92 (m, 1H), 4.67 (d, 1H), 3.99 (d, 1H), 3.80-3.68 (m, 1H), 3.68-3.62 (m, 1H), 3.61-3.53 (m, 1H), 3.50 (p, 1H), 3.43-3.36 (m, 1H), 3.17-3.07 (m, 1H), 3.05-2.98 (m, 2H), 2.98-2.87 (m, 1H), 2.48 (s, 3H), 2.31 (p, 2H), 2.12-2.01 (m, 2H), 1.82-1.68 (m, 1H), 1.69-1.53 (m, 2H), 1.32 (d, 6H). | (2R,4S)-1-tert-butoxy-carbonyl-4-fluoro-pyrrolidine-2-carboxylic acid |
| 18 | 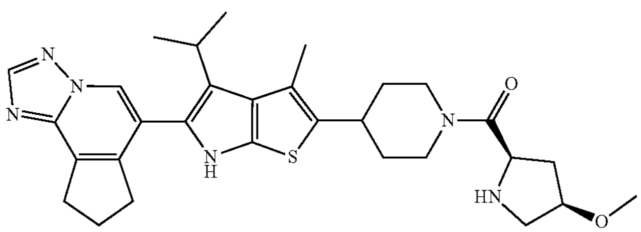 [SMILES: CO[C@H]1CN[C@@H](C(=O)N2CCC(c3sc4[nH]c(-c5cn6ncnc6c6c5CCC6)c(C(C)C)c4c3C)CC2)C1] | 547.3 | ¹H NMR (400 MHz, Methanol-d4) δ 8.56 (s, 1H), 8.46 (s, 1H), 4.75 (dd, 1H), 4.72-4.60 (m, 2H), 4.20 (d, 1H), 3.89 (d, 1H), 3.68 (d, 1H), 3.46-3.35 (m, 3H), 3.18-3.07 (m, 1H), 3.01 (t, 2H), 2.98-2.89 (m, 1H), 2.82-2.68 (m, 1H), 2.48 (s, 3H), 2.31 (p, 2H), 2.21-2.02 (m, 4H), 1.76-1.54 (m, 1H), 1.32 (d, 6H). | (2R,4R)-1-tert-butoxy-carbonyl-4-methoxy-pyrrolidine-2-carboxylic acid |
| 19 | 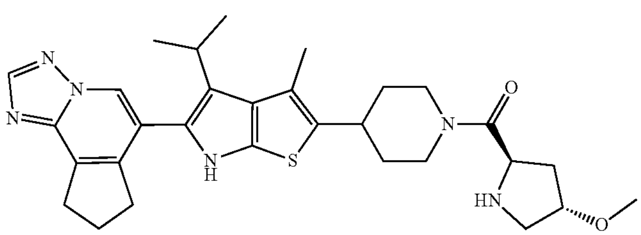 [SMILES: CO[C@@H]1CN[C@@H](C(=O)N2CCC(c3sc4[nH]c(-c5cn6ncnc6c6c5CCC6)c(C(C)C)c4c3C)CC2)C1] | 547.3 | ¹H NMR (400 MHz, Methanol-d4) δ 10.71 (d, 1H), 8.56 (s, 1H), 8.46 (s, 1H), 4.86-4.74 (m, 2H), 4.67 (d, 1H), 4.26 (dt, 1H), 3.97 (d, 1H), 3.55 (dd, 1H), 3.41 (d, 4H), 3.39 (d, 1H), 3.18-3.07 (m, 1H), 3.01 (t, 2H), 2.98-2.87 (m, 1H), 2.85-2.71 (m, 1H), 2.48 (s, 3H), 2.31 (p, 2H), 2.17-1.95 (m, 1H), 1.63 (td, 1H), 1.32 (d, 6H). | (2R,4S)-1-tert-butoxy-carbonyl-4-methoxy-pyrrolidine-2-carboxylic acid |
| 20 | 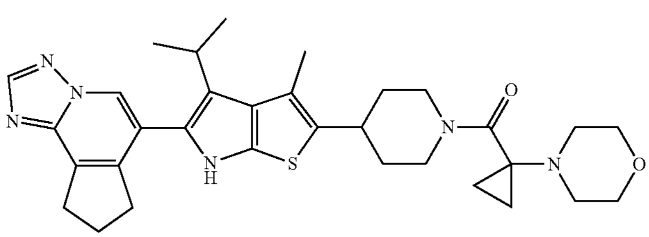 [SMILES: Cc1c(C2CCN(C(=O)C3(N4CCOCC4)CC3)CC2)sc2[nH]c(-c3cn4ncnc4c4c3CCC4)c(C(C)C)c12] | 573.4 | ¹H NMR (400 MHz, Methanol-d4) δ 8.59 (s, 1H), 8.51 (s, 1H), 4.59 (d, 2H), 3.72 (t, 4H), 3.53-3.47 (m, 1H), 3.45-3.36 (m, 1H), 3.19-3.08 (m, 2H), 3.03 (t, 2H), 2.69 (s, 4H), 2.48 (s, 3H), 2.32 (p, 2H), 2.04 (d, 2H), 1.67 (d, 2H), 1.32 (d, 6H), 1.12 (s, 2H), 0.94 (s, 2H). | 1-morpho-lino-cyclo-propane-1-carboxylic acid hydro-chloride |

Procedure 7, Example 21

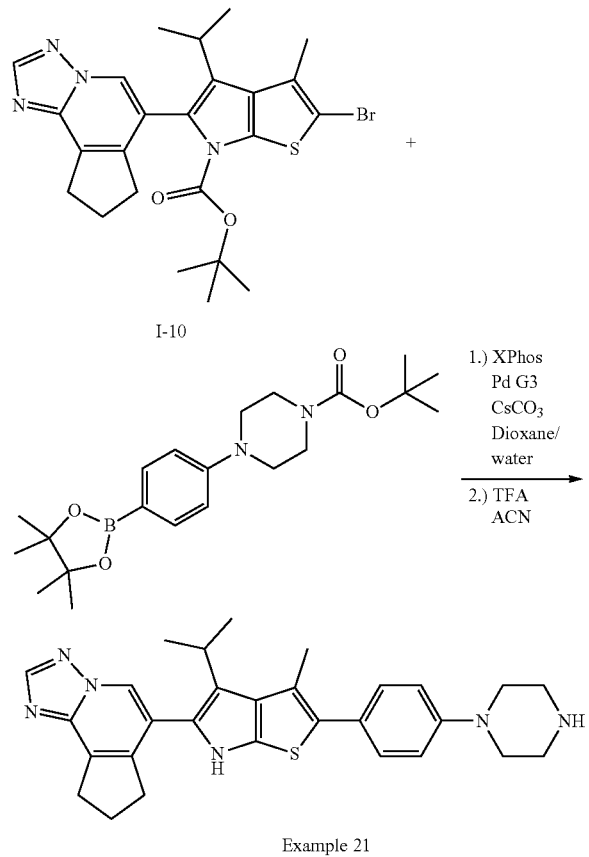

I-10

Example 21

5-(8,9-dihydro-7H-cyclopenta[c][1,2,4]triazolo[1,5-a]pyridin-6-yl)-4-isopropyl-3-methyl-2-(4-(piperazin-1-yl)phenyl)-6H-thieno[2,3-b]pyrrole (Example 21): To a vial was added tert-butyl 2-bromo-5-(8,9-dihydro-7H-cyclopenta[c][1,2,4]triazolo[1,5-a]pyridin-6-yl)-4-isopropyl-3-methyl-6H-thieno[2,3-b]pyrrole-6-carboxylate (I-10) (50 mg, 0.097 mmol), tert-butyl 4-(4-(4,4,5,5-tetramethyl-1,3,2-dioxaborolan-2-yl)phenyl)piperazine-1-carboxylate (45.2 mg, 0.116 mmol), cesium carbonate (95 mg, 0.291 mmol), and XPhos Pd G3 (7.3 mg, 0.0097 mmol). Dioxane (1.8 mL) and water (0.2 mL) were added, and the mixture was degassed with argon for 30 seconds. The vial was sealed, and the mixture was heated at 100° C. for 60 minutes in a microwave. The crude mixture was purified directly by silica chromatography (eluent EtOAc/hexanes). The product was subsequently dissolved in dichloromethane (2 mL). Trifluoroacetic acid (0.5 mL) was added, and the mixture was stirred at rt. LCMS indicated reaction completion (removal of Boc groups), and the volatiles were evaporated under reduced pressure. To the mixture was added acetonitrile (0.5 mL), water (0.2 mL), and the mixture was filtered through an acrodisc before purification by RP-HPLC (0.1% TFA-ACN in 0.1% TFA Water, Column: Gemini 5 uM, NX-C18 110 Angstrom, 250×21.2 mm) to give the title compound Example 21. ES/MS: 497.3 (M+H$^+$). $^1$H NMR (400 MHz, MeOD) δ 8.61 (s, 1H), 8.48 (s, 1H), 7.45-7.41 (m, 2H), 7.14-7.09 (m, 2H), 3.51-3.40 (m, 8H), 3.22-3.13 (m, 1H), 3.05 (t, J=7.5 Hz, 2H), 2.50 (s, 3H), 2.34 (q, J=7.5 Hz, 2H), 1.35 (d, J=7.1 Hz, 7H).

The following Examples were made in an analogous fashion according to Procedure 7 and are shown below in Table 5. To prepare the below Examples, different reagents/starting materials were used than some of those described in Procedure 7 and are noted in the last column of Table 5—"Changes to Procedure 7: Different Reagents/Starting Materials". A person of ordinary skill in the art will readily recognize which reagents/starting materials of Procedure 7 were replaced with the different reagents/starting materials noted below.

TABLE 5

| Example | Structure | ES/MS m/z | $^1$H-NMR | Changes to Procedure 7: Different Reagents/Starting Materials |
|---|---|---|---|---|
| 22 | 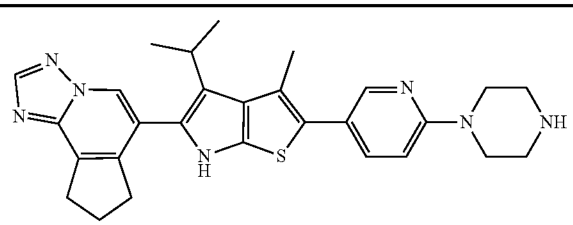 | 498.3 | $^1$H NMR (400 MHz, MeOD) δ 8.64 (s, 1H), 8.54 (s, 1H), 8.26 (d, J = 2.4 Hz, 1H), 7.83 (dd, J = 8.9, 2.4 Hz, 1H), 7.11 (d, J = 8.9 Hz, 1H), 3.90 (t, J = 5.3 Hz, 4H), 3.43-3.37 (m, 4H), 3.17 (p, J = 7.1 Hz, 1H), 3.05 (t, J = 7.5 Hz, 2H), 2.50 (s, 3H), 2.34 (q, J = 7.6 Hz, 2H), 1.34 (d, J = 7.1 Hz, 6H). | tert-butyl 4-[5-(4,4,5,5-tetramethyl-1,3,2-dioxaborolan-2-yl)-2-pyridyl]piperazine-1-carboxylate |
| 23 | 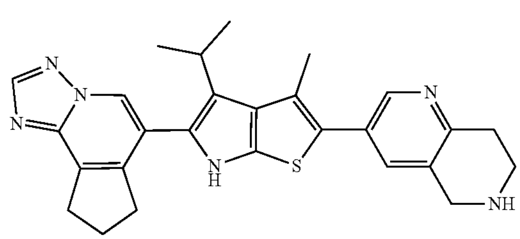 [SMILES: Cc1c(-c2cnc3c(c2)CNCC3)sc2[nH]c(-c3cn4ncnc4c4c3CCC4)c(C(C)C)c12] | 469.4 | $^1$H NMR (400 MHz, MeOD) δ 8.70-8.63 (m, 2H), 8.56 (s, 1H), 7.91 (d, J = 2.1 Hz, 1H), 4.55 (s, 2H), 3.71 (t, J = 6.5 Hz, 2H), 3.33 (dt, J = 3.3, 2.0 Hz, 4H), 3.20 (p, J = 7.2 Hz, 1H), 3.05 (t, J = 7.5 Hz, 2H), 2.58 (s, 3H), 2.35 (p, J = 7.6 Hz, 2H), 1.36 (d, J = 7.1 Hz, 6H). | tert-butyl 3-(4,4,5,5-tetramethyl-1,3,2-dioxaborolan-2-yl)-7,8-dihydro-5H-1,6-naphthyridine-6-carboxylate |

TABLE 5-continued

| Example | Structure | ES/MS m/z | ¹H-NMR | Changes to Procedure 7: Different Reagents/Starting Materials |
|---|---|---|---|---|
| 24 | 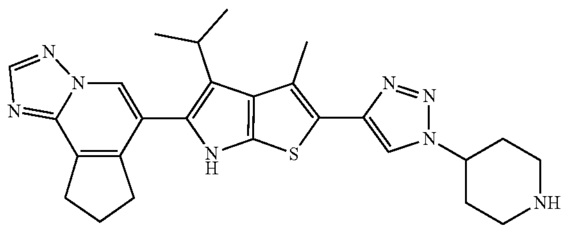 [SMILES: Cc1c(-c2cn(C3CCNCC3)nn2)sc2[nH]c(-c3cn4ncnc4c4c3CCC4)c(C(C)C)c12] | 487.2 | ¹H NMR (400 MHz, MeOD) δ 8.63 (s, 1H), 8.51 (s, 1H), 7.89 (s, 1H), 3.58 (dt, J = 13.2, 4.5 Hz, 2H), 3.33-3.26 (m, 5H), 3.17 (p, J = 7.1 Hz, 1H), 3.05 (t, J = 7.5 Hz, 2H), 2.69 (s, 3H), 2.57-2.27 (m, 6H), 1.35 (d, J = 7.2 Hz, 6H). | tert-butyl 4-[4-(4,4,5,5-tetramethyl-1,3,2-dioxaborolan-2-yl)triazol-1-yl]piperidine-1-carboxylate |

Examples 25-40

The following Examples shown below in Table 6 were made in an analogous fashion according to the Procedure indicated in the column of Table 6 labeled "Procedure." To prepare the below Examples, different reagents/starting materials were used than some of those described in the indicated Procedure and are noted in the last column of Table 6—"Changes to Procedure: Different Reagents/Starting Materials". A person of ordinary skill in the art will readily recognize which reagents/starting materials of the indicated Procedure were replaced with the different reagents/starting materials noted.

TABLE 6

| Example | Structure | ES/MS m/z | ¹H-NMR | Procedure | Changes to Procedure: Different Reagents/Starting Materials |
|---|---|---|---|---|---|
| 25 | 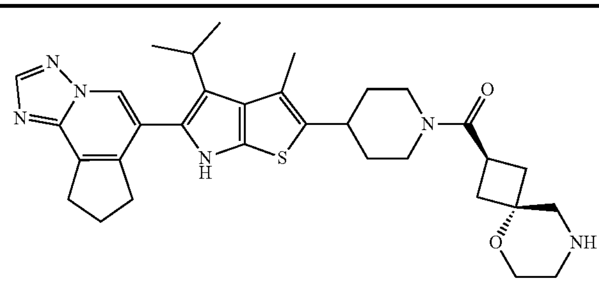 | 573.3 | ¹H NMR (400 MHz, MeOD) δ 8.57 (s, 1H), 8.49 (s, 1H), 4.66 (d, J = 13.1 Hz, 1H), 3.96 (d, J = 13.6 Hz, 1H), 3.86 (dd, J = 6.0, 4.0 Hz, 2H), 3.35 (s, 3H), 3.31-2.98 (m, 8H), 2.88-2.76 (m, 1H), 2.61-2.23 (m, 10H), 2.01 (q, J = 13.4 Hz, 2H), 1.57 (qd, J = 12.4, 6.4 Hz, 2H), 1.32 (d, J = 7.1 Hz, 6H). | 6 | cis-8-tert-butoxy-carbonyl-5-oxa-8-azaspiro[3.5]nonane-2-carboxylic-acid |
| 26 | 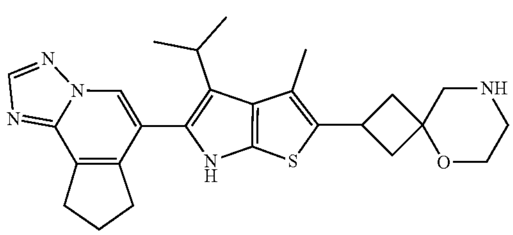 [SMILES: Cc1c(C2CC3(CNCCO3)C2)sc2[nH]c(-c3cn4ncnc4c4c3CCC4)c(C(C)C)c12] | 462.2 | ¹H NMR (400 MHz, MeOD) δ 8.59 (s, 1H), 8.52 (s, 1H), 3.92-3.85 (m, 2H), 3.71-3.57 (m, 1H), 3.43 (s, 2H), 3.30 (s, 2H), 3.25-3.18 (m, 2H), 3.16-2.99 (m, 3H), 2.79 (ddt, J = 11.0, 6.3, 2.4 Hz, 2H), 2.41 (s, 3H), 2.38-2.19 (m, 4H), 1.31 (d, J = 7.1 Hz, 6H). | 1 | I-24 |
| 27 | 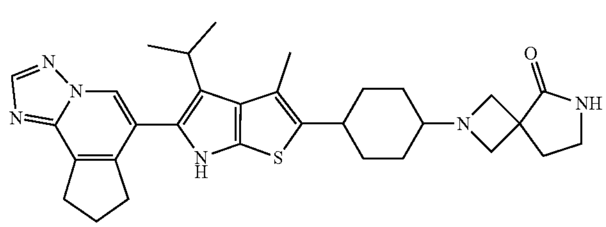 [SMILES: Cc1c(C2CCC(N3CC4(CCNC4=O)C3)CC2)sc2[nH]c(-c3cn4ncnc4c4c3CCC4)c(C(C)C)c12] | 543.3 | ¹H NMR (400 MHz, MeOD) δ 8.57 (d, J = 1.3 Hz, 1H), 8.49 (s, 1H), 4.58-4.11 (m, 4H), 3.69-3.53 (m, 1H), 3.40 (t, J = 6.9 Hz, 2H), 3.30 (s, 1H), 3.12 (p, J = 7.4 Hz, 1H), 3.02 (t, J = 7.5 Hz, 2H), 2.69-2.49 (m, 3H), 2.45 (s, 3H), 2.32 (p, J = 7.6 Hz, 2H), 2.16 (d, J = 14.9 Hz, 1H), 2.10-1.89 (m, 5H), 1.84-1.63 (m, 2H), 1.47 (d, J = 8.8 Hz, 1H), 1.31 (d, J = 7.1 Hz, 6H). | 5 | I-36: 2,6-diazaspiro[3.4]octan-5-one |

TABLE 6-continued

| Example | Structure | ES/MS m/z | ¹H-NMR | Procedure | Changes to Procedure: Different Reagents/Starting Materials |
|---|---|---|---|---|---|
| 28 | 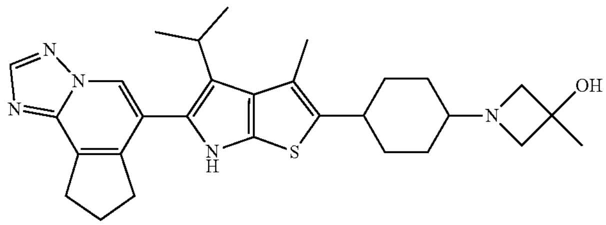 [SMILES: Cc1c(C2CCC(N3CC(C)(O)C3)CC2)sc2[nH]c(-c3cn4ncnc4c4c3CCC4)c(C(C)C)c12] | 504.3 | ¹H NMR (400 MHz, MeOD) δ 8.57 (s, 1H), 8.49 (s, 1H), 4.42-3.82 (m, 5H), 3.51 (s, 1H), 3.30 (s, 2H), 3.12 (p, J = 7.0 Hz, 1H), 3.02 (t, J = 7.5 Hz, 2H), 2.44 (s, 3H), 2.32 (p, J = 7.5 Hz, 2H), 2.21-1.70 (m, 8H), 1.66-1.50 (m, 3H), 1.31 (d, J = 7.1 Hz, 6H). | 5 | I-36; 3-methyl-azetidin-3-ol; hydrochloride |
| 29 | 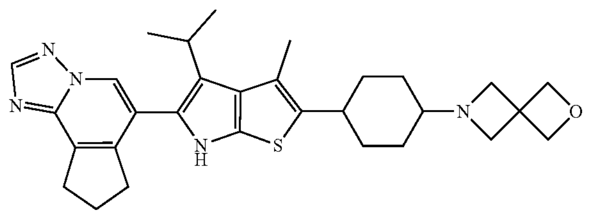 [SMILES: Cc1c(C2CCC(N3CC4(COC4)C3)CC2)sc2[nH]c(-c3cn4ncnc4c4c3CCC4)c(C(C)C)c12] | 516.4 | ¹H NMR (400 MHz, MeOD) δ 8.55 (s, 1H), 8.46 (s, 1H), 4.93 (d, J = 6.7 Hz, 2H), 4.76 (d, J = 7.8 Hz, 2H), 4.50-4.34 (m, 4H), 3.49 (d, J = 10.5 Hz, 1H), 3.27-2.94 (m, 5H), 2.44 (d, J = 1.5 Hz, 3H), 2.31 (p, J = 7.4 Hz, 3H), 2.16 (d, J = 11.6 Hz, 2H), 2.05-1.91 (m, 4H), 1.59 (p, J = 12.3 Hz, 2H), 1.31 (d, J = 7.0 Hz, 6H). | 5 | I-36; 2-oxa-6-azaspiro[3.3]heptane |
| 30 | 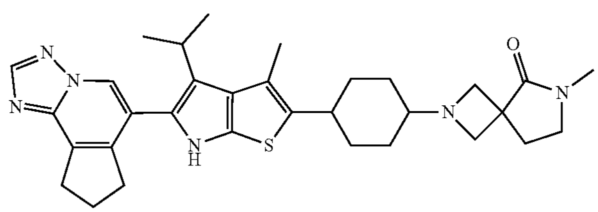 [SMILES: Cc1c(C2CCC(N3CC4(CCN(C)C4=O)C3)CC2)sc2[nH]c(-c3cn4ncnc4c4c3CCC4)c(C(C)C)c12] | 557.4 | ¹H NMR (400 MHz, MeOD) δ 8.56 (s, 1H), 8.45 (s, 1H), 4.38-4.15 (m, 4H), 3.65 (s, 1H), 3.50-3.39 (m, 3H), 3.24 (d, J = 10.0 Hz, 1H), 3.16-3.06 (m, 2H), 3.02 (t, J = 7.5 Hz, 2H), 2.92 (d, J = 4.8 Hz, 3H), 2.57 (t, J = 6.9 Hz, 2H), 2.45 (s, 3H), 2.32 (p, J = 7.5 Hz, 2H), 2.08-1.92 (m, 5H), 1.82-1.61 (m, 3H), 1.31 (d, J = 7.1 Hz, 6H). | 5 | I-36; 6-methyl-2,6-diazaspiro[3.4]octan-5-one |
| 31 | 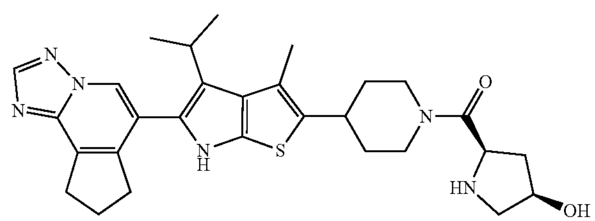 [SMILES: Cc1c(C2CCN(C(=O)[C@H]3C[C@@H](O)CN3)CC2)sc2[nH]c(-c3cn4ncnc4c4c3CCC4)c(C(C)C)c12] | 533.3 | ¹H NMR (400 MHz, Methanol-d4) δ 8.55 (s, 1H), 8.44 (s, 1H), 4.71-4.49 (m, 2H), 3.89 (d, J = 13.8 Hz, 1H), 3.44 (ddt, J = 48.7, 3.5, 1.7 Hz, 4H), 3.14-3.08 (m, 2H), 3.04-2.65 (m, 4H), 2.48 (s, 3H), 2.32 (q, J = 7.5 Hz, 2H), 2.06 (s, 5H), 1.77-1.56 (m, 2H), 1.32 (d, J = 7.1 Hz, 6H). | 6 | (2R,4R)-1-tert-butoxycarbonyl-4-hydroxy-pyrrolidine-2-carboxylic acid |
| 32 | 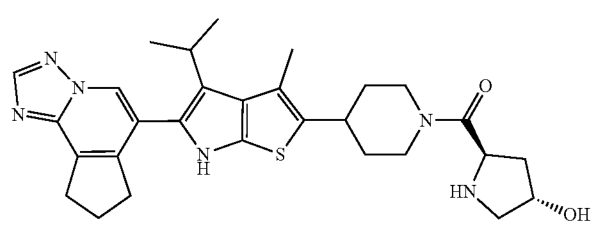 [SMILES: Cc1c(C2CCN(C(=O)[C@H]3C[C@H](O)CN3)CC2)sc2[nH]c(-c3cn4ncnc4c4c3CCC4)c(C(C)C)c12] | 533.3 | ¹H NMR (400 MHz, Methanol-d4) δ 8.55 (s, 1H), 8.45 (s, 1H), 4.64 (d, J = 13.0 Hz, 2H), 3.98 (d, J = 13.8 Hz, 1H), 3.46-3.37 (m, 4H), 3.16-3.08 (m, 2H), 3.04-2.85 (m, 3H), 2.57 (dt, J = 14.1, 7.3 Hz, 1H), 2.48 (s, 3H), 2.31 (p, J = 7.5 Hz, 2H), 2.08 (dd, J = 23.0, 10.5 Hz, 5H), 1.81-1.50 (m, 2H), 1.32 (d, J = 7.1 Hz, 6H). | 6 | (2R,4S)-1-tert-butoxycarbonyl-4-hydroxy-pyrrolidine-2-carboxylic acid |
| 33 | 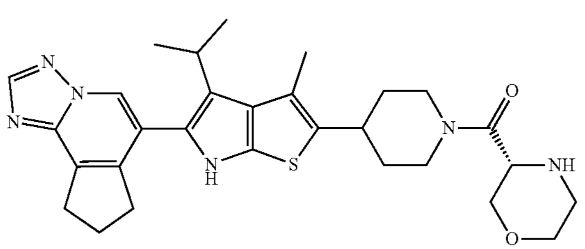 [SMILES: Cc1c(C2CCN(C(=O)[C@H]3COCCN3)CC2)sc2[nH]c(-c3cn4ncnc4c4c3CCC4)c(C(C)C)c12] | 519.3 | ¹H NMR (400 MHz, Methanol-d4) δ 8.54 (s, 1H), 8.45 (s, 1H), 6.92 (d, J = 9.7 Hz, 1H), 4.76-4.51 (m, 2H), 4.28 (d, J = 12.5 Hz, 1H), 4.06 (t, J = 15.6 Hz, 2H), 3.85-3.73 (m, 1H), 3.65 (dt, J = 27.8, 11.9 Hz, 1H), 3.38 (s, 5H), 3.20 (d, J = 11.3 Hz, 1H), 3.06 (t, J = 7.5 Hz, 2H), 2.96-2.85 (m, 2H), 2.39-2.11 (m, 4H), 1.89-1.59 (m, 2H), 1.35 (d, J = 6.9 Hz, 6H). | 1, 6 | I-31 |

TABLE 6-continued

| Example | Structure | ES/MS m/z | ¹H-NMR | Procedure | Changes to Procedure: Different Reagents/ Starting Materials |
|---|---|---|---|---|---|
| 34 | 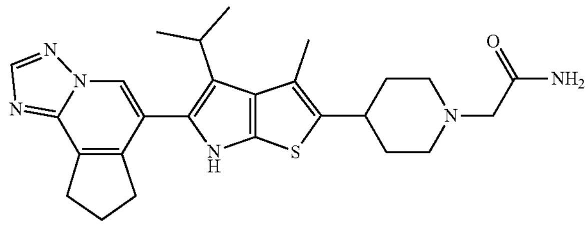 [SMILES: Cc1c(C2CCN(CC(N)=O)CC2)sc2[nH]c(-c3cn4ncnc4c4c3CCC4)c(C(C)C)c12] | 463.5 | ¹H NMR (400 MHz, Methanol-d4) δ 8.56 (s, 1H), 8.48 (s, 1H), 6.97 (s, 1H), 4.00 (s, 2H), 3.75 (d, J = 12.2 Hz, 2H), 3.59-3.39 (m, 2H), 3.31-3.16 (m, 3H), 3.06 (t, J = 7.5 Hz, 2H), 2.92 (p, J = 6.9 Hz, 1H), 2.43-2.24 (m, 4H), 2.24-2.05 (m, 2H), 1.35 (d, J = 6.9 Hz, 6H). | 1, 3 | I-31 |
| 35 | 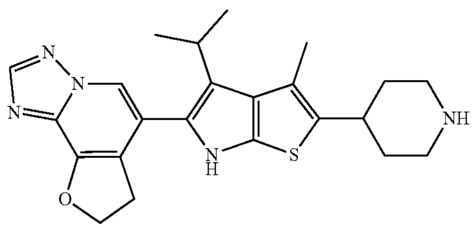 [SMILES: Cc1c(C2CCNCC2)sc2[nH]c(-c3cn4ncnc4c4c3CCO4)c(C(C)C)c12] | 422.2 | ¹H NMR (400 MHz, Methanol-d4) δ 8.40 (s, 1H), 8.35 (s, 1H), 5.01-4.91 (m, 2H), 3.56-3.48 (m, 2H), 3.45-3.39 (m, 2H), 3.27-3.15 (m, 4H), 2.49 (s, 3H), 2.20 (d, J = 14.2 Hz, 2H), 1.97-1.80 (m, 2H), 1.35 (d, J = 7.1 Hz, 6H). | 1 | I-26 |
| 36 | 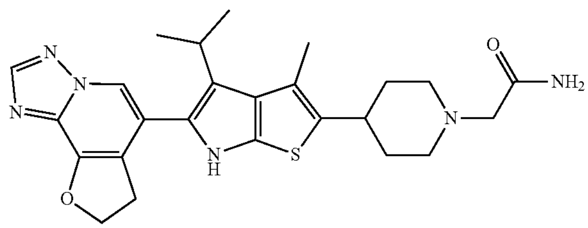 [SMILES: Cc1c(C2CCN(CC(N)=O)CC2)sc2[nH]c(-c3cn4ncnc4c4c3CCO4)c(C(C)C)c12] | 479.2 | ¹H NMR (400 MHz, Methanol-d4) δ 8.40 (s, 1H), 8.35 (s, 1H), 4.94 (d, J = 9.2 Hz, 1H), 3.99 (s, 2H), 3.74 (d, J = 12.0 Hz, 2H), 3.42 (s, 2H), 3.29-3.13 (m, 3H), 2.49 (s, 3H), 2.23 (d, J = 14.3 Hz, 2H), 2.16-1.73 (m, 2H), 1.35 (d, J = 7.1 Hz, 6H). | 3 | Example 35 |
| 37 | 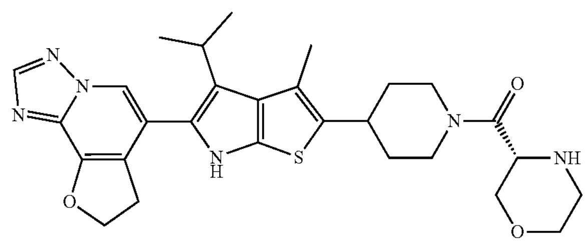 [SMILES: Cc1c(C2CCN(C(=O)[C@H]3COCCN3)CC2)sc2[nH]c(-c3cn4ncnc4c4c3CCO4)c(C(C)C)c12] | 535.3 | ¹H NMR (400 MHz, Methanol-d4) δ 8.40 (s, 1H), 8.34 (s, 1H), 4.94 (d, J = 9.2 Hz, 2H), 4.69 (dd, J = 25.5, 11.5 Hz, 2H), 4.28 (d, J = 13.1 Hz, 1H), 4.06 (t, J = 14.5 Hz, 2H), 3.86-3.75 (m, 1H), 3.75-3.54 (m, 2H), 3.46-3.36 (m, 4H), 3.23-3.12 (m, 2H), 2.90 (t, J = 12.9 Hz, 1H), 2.48 (s, 3H), 2.08 (t, J = 16.9 Hz, 2H), 1.80-1.48 (m, 2H), 1.35 (d, J = 7.1 Hz, 6H). | 6 | Example 35 |
| 38 | 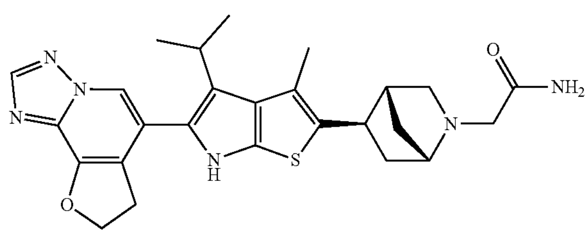 [SMILES: Cc1c([C@@H]2C[C@@H]3C[C@H]2CN3CC(N)=O)sc2[nH]c(-c3cn4ncnc4c4c3CCO4)c(C(C)C)c12] | 491.2 | ¹H NMR (400 MHz, Methanol-d4) δ 8.40 (s, 1H), 8.35 (s, 1H), 4.94 (d, J = 9.2 Hz, 1H), 3.99 (s, 2H), 3.74 (d, J = 12.0 Hz, 2H), 3.42 (s, 2H), 3.29-3.13 (m, 3H), 2.49 (s, 3H), 2.23 (d, J = 14.3 Hz, 2H), 2.16-1.73 (m, 2H), 1.35 (d, J = 7.1 Hz, 6H). | 1, 3 | I-26, I-20 |
| 39 | 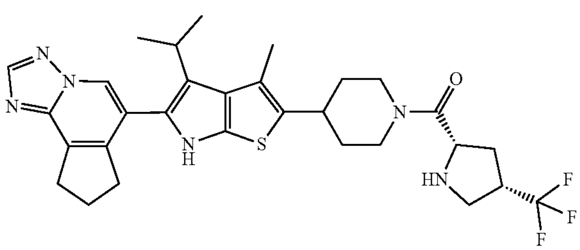 [SMILES: Cc1c(C2CCN(C(=O)[C@@H]3C[C@H](C(F)(F)F)CN3)CC2)sc2[nH]c(-c3cn4ncnc4c4c3CCC4)c(C(C)C)c12] | 585.2 | ¹H NMR (400 MHz, Methanol-d4) δ 10.72 (d, 1H), 8.56 (s, 1H), 8.47 (d, 1H), 4.67 (d, 1H), 3.95 (d, 1H), 3.70 (dd, 1H), 3.64-3.52 (m, 1H), 3.52-3.44 (m, 1H), 3.46-3.37 (m, 1H), 3.17-3.07 (m, 1H), 3.01 (t, 2H), 2.97-2.84 (m, 1H), 2.48 (s, 3H), 2.31 (p, 2H), 2.08 (p, 4H), 1.67 (ddt, 2H), 1.32 (d, 6H). | 6 | (2S,4S)-1-tert-butoxy-carbonyl-4-(trifluoro-methyl)pyrrolidine-2-carboxylic acid |

TABLE 6-continued

| Example | Structure | ES/MS m/z | ¹H-NMR | Procedure | Changes to Procedure: Different Reagents/Starting Materials |
|---|---|---|---|---|---|
| 40 | 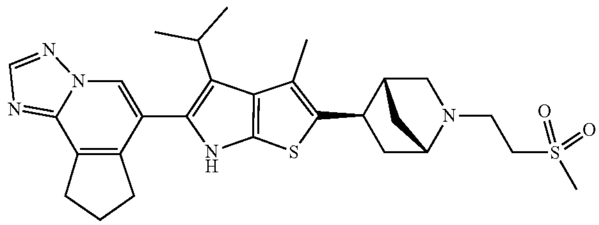 [SMILES: Cc1c([C@@H]2C[C@@H]3C[C@H]2CN3CCS(C)(=O)=O)sc2[nH]c(-c3cn4ncnc4c4c3CCC4)c(C(C)C)c12] | 538.2 | ¹H NMR (400 MHz, MeOD) δ 8.57 (d, J = 1.0 Hz, 1H), 8.47 (s, 1H), 4.34 (s, 1H), 3.92-3.48 (m, 8H), 3.27 (d, J = 21.3 Hz, 5H), 3.18-3.05 (m, 5H), 3.01 (t, J = 7.5 Hz, 2H), 2.84 (s, 2H), 2.49 (s, 4H), 2.32 (p, J = 7.5 Hz, 3H), 2.20 (d, J = 12.8 Hz, 1H), 2.04 (d, J = 16.2 Hz, 2H), 1.32 (dd, J = 7.1, 1.1 Hz, 6H). | 3 | Example 3; 1-bromo-2-methyl-sulfonyl-ethane |

Procedure 8, Example 41

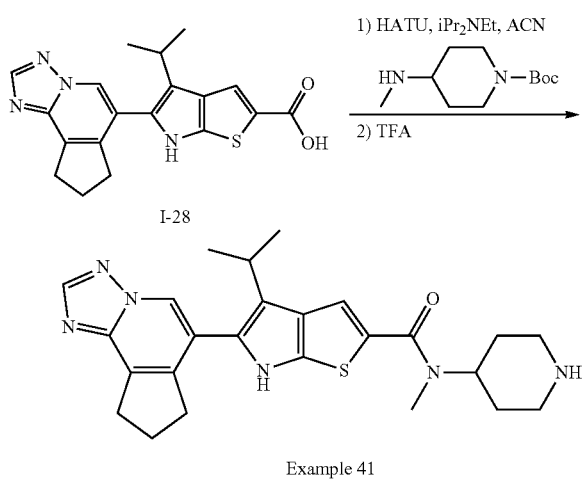

I-28

Example 41

5-(8,9-dihydro-7H-cyclopenta[c][1,2,4]triazolo[1,5-a]pyridin-6-yl)-4-isopropyl-N-methyl-N-(piperidin-4-yl)-6H-thieno[2,3-b]pyrrole-2-carboxamide (Example 41): To a solution of 5-(8,9-dihydro-7H-cyclopenta[c][1,2,4]triazolo[1,5-a]pyridin-6-yl)-4-isopropyl-6H-thieno[2,3-b]pyrrole-2-carboxylic acid (I-28) (12.0 mg, 0.033 mmol) in ACN (0.5 mL) was added tert-butyl 4-(methylamino)piperidine-1-carboxylate (11 mg, 0.05 mmol), HATU (15 mg, 0.04 mmol) and N,N-diisopropylethylamine (0.017 mL, 0.099 mmol) and the reaction mixture was stirred at r.t. overnight. Trifluoroacetic acid (0.25 mL, 3.27 mmol) was added and the reaction mixture was stirred at 35° C. for 2 hours. Acetonitrile (0.7 mL) and water (0.15 mL) were added, and the crude mixture was filtered through an acrodisc before purification by RP-HPLC (0.1% TFA-ACN in 0.1% TFA-Water, Column: Gemini 5 uM, NX-C18 110 Angstrom, 250×21.2 mm) to give the title compound Example 41. ES/MS: 463.2 (M+H⁺)

¹H NMR (400 MHz, Methanol-d4) δ 8.61 (s, 1H), 8.45 (s, 1H), 7.64 (s, 1H), 4.61 (dt, J=11.2, 5.9 Hz, 1H), 3.56 (d, J=12.8 Hz, 2H), 3.39-3.36 (m, 3H), 3.24-3.13 (m, 2H), 3.05 (t, J=7.5 Hz, 2H), 2.96 (p, J=6.9 Hz, 1H), 2.34 (p, J=7.6 Hz, 2H), 2.21-2.07 (m, 6H), 1.39 (d, J=6.9 Hz, 6H).

The following Example was made in an analogous fashion according to Procedure 8 and is shown below in Table 7. To prepare the below Example, a different reagents/starting material was used than some of those described in Procedure 8 and is noted in the last column of Table 7—"Changes to Procedure 8: Different Reagents/Starting Materials". A person of ordinary skill in the art will readily recognize which reagents/starting materials of Procedure 8 were replaced with the different reagents/starting materials noted below.

TABLE 7

| Example | Structure | ES/MS m/z | ¹H-NMR | Changes to Procedure 8: Different Reagents/Starting Materials |
|---|---|---|---|---|
| 42 | 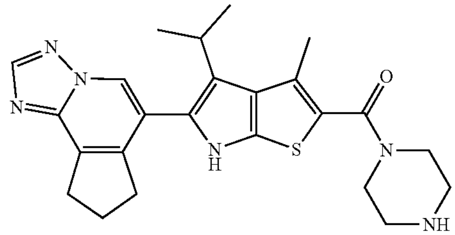 [SMILES: Cc1c(C(=O)N2CCNCC2)sc2[nH]c(-c3cn4ncnc4c4c3CCC4)c(C(C)C)c12] | 435.0 | 1H NMR (400 MHz, Methanol-d4) δ 8.61 (s, 1H), 8.45 (s, 1H), 7.64 (s, 1H), 4.11 (t, J = 5.4 Hz, 4H), 3.40-3.37 (m, 6H), 3.10-2.89 (m, 3H), 2.33 (p, J = 7.6 Hz, 2H), 1.39 (d, J = 6.9 Hz, 6H). | tert-butyl piperazine-1-carboxylate |

Procedure 9: Example 43

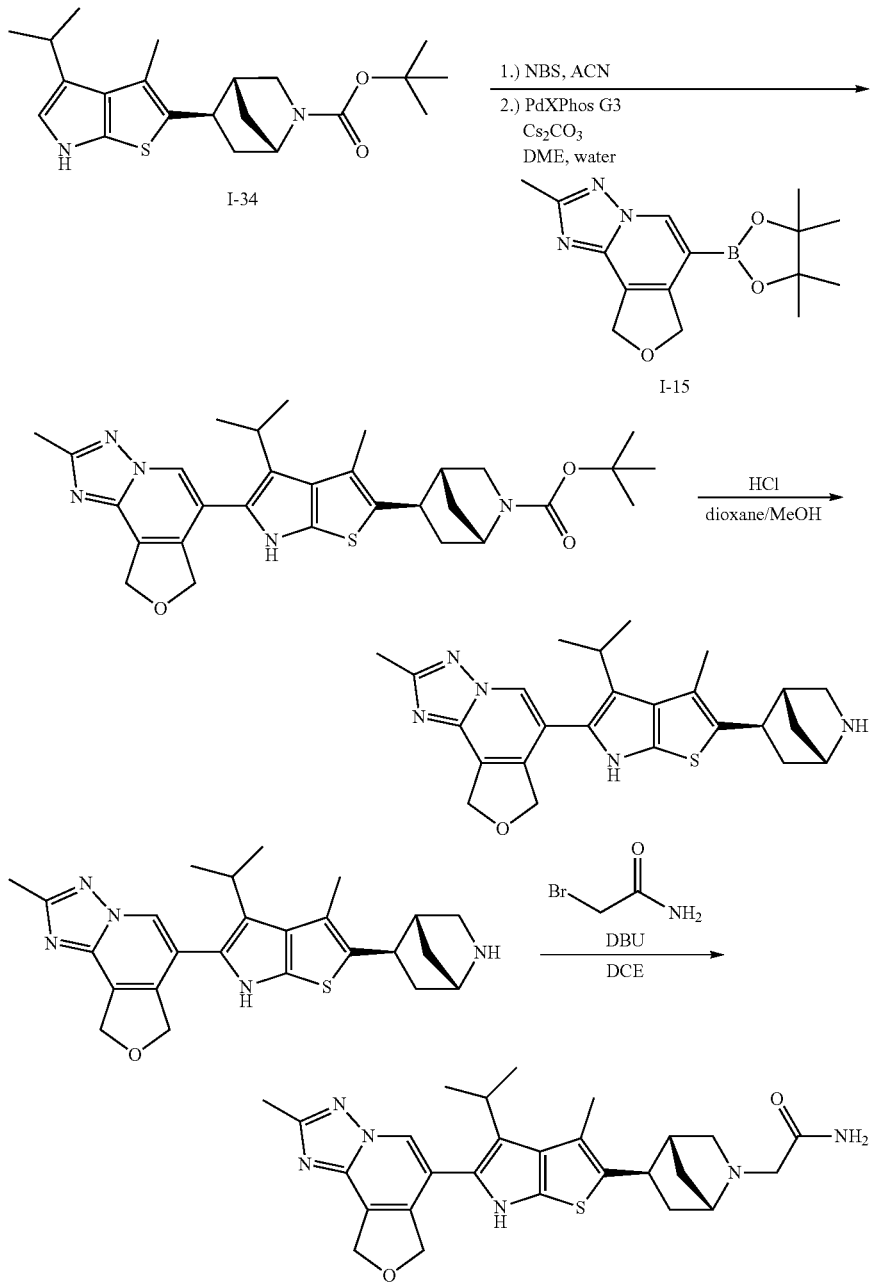

Example 43 tert-butyl (1S,4R,5R)-5-(4-isopropyl-3-methyl-5-(2-methyl-7,9-dihydrofuro[3,4-c][1,2,4]triazolo[1,5-a]pyridin-6-yl)-6H-thieno[2,3-b]pyrrol-2-yl)-2-azabicyclo[2.2.1]heptane-2-carboxylate: A solution of tert-butyl (1S,4R,5R)-5-(4-isopropyl-3-methyl-6H-thieno[2,3-b]pyrrol-2-yl)-2-azabicyclo[2.2.1]heptane-2-carboxylate (I-34) (70 mg, 0.187 mmol) in ACN (3 mL) was cooled to 0° C., and N-bromosuccinimide (28.3 mg, 0.16 mmol) (dissolved in 1 mL ACN) was added dropwise. After completion of addition, LCMS indicated reaction completion. The mixture was quickly concentrated under reduced pressure. The crude residue was dissolved in DME (1 mL) and this solution was added to a MW vial containing 2-methyl-6-(4,4,5,5-tetramethyl-1,3,2-dioxaborolan-2-yl)-7,9-dihydrofuro[3,4-c][1,2,4]triazolo[1,5-a]pyridine (I-15) (96 mg, 0.318 mmol), XPhos Pd G3 (23.7 mg, 0.028 mmol) and cesium carbonate (183 mg, 0.561 mmol). Water (0.2 mL) was added, and the mixture was degassed with argon for 30 seconds. The vial was sealed, and the mixture was heated at 120° C. for 15 minutes in a microwave. The crude mixture was purified directly by silica chromatography (eluent EtOAc/hexanes). ES/MS: 548.3 (M+H$^+$)

6-(2-((1S,4R,5R)-2-azabicyclo[2.2.1]heptan-5-yl)-4-isopropyl-3-methyl-6H-thieno[2,3-b]pyrrol-5-yl)-2-methyl-7, 9-dihydrofuro[3,4-c][1,2,4]triazolo[1,5-a]pyridine: To a vial with tert-butyl (1S,4R,5R)-5-(4-isopropyl-3-methyl-5-(2-methyl-7,9-dihydrofuro[3,4-c][1,2,4]triazolo[1,5-a]pyridin-6-yl)-6H-thieno[2,3-b]pyrrol-2-yl)-2-azabicyclo[2.2.1]heptane-2-carboxylate (47 mg, 0.085 mmol) was added methanol (1 mL) and HCl (4M in dioxane, 0.5 mL). The reaction was stirred at 35° C. for 30 minutes. The crude mixture was concentrated under reduced pressure, and taken forward to the next step. ES/MS: 448.2 (M+H$^+$)

2-((1S,4R,5R)-5-(4-isopropyl-3-methyl-5-(2-methyl-7,9-dihydrofuro[3,4-c][1,2,4]triazolo[1,5-a]pyridin-6-yl)-6H-thieno[2,3-b]pyrrol-2-yl)-2-azabicyclo[2.2.1]heptan-2-yl)acetamide (Example 43): To a solution of 6-(2-((1S,4R,5R)-2-azabicyclo[2.2.1]heptan-5-yl)-4-isopropyl-3-methyl-6H-thieno[2,3-b]pyrrol-5-yl)-2-methyl-7,9-dihydrofuro[3,4-c][1,2,4]triazolo[1,5-a]pyridine (HCl salt) (40 mg, 0.083 mmol) in 1,2-dichloroethane (1 mL) was added 2-bromoacetamide (13.7 mg, 0.1 mmol) and 1,8-diazabicyclo[5.4.0]undec-7-ene (0.049 mL, 0.33 mmol). The mixture was stirred overnight at rt. To the mixture was added 0.2 mL TFA, and the DCE was subsequently removed under reduced pressure. Acetonitrile (0.5 mL), and water (0.2 mL) were added, and the mixture was filtered through an acrodisc before purification by RP-HPLC (0.1% TFA-ACN in 0.1% TFA Water, Column: Gemini 5 uM, NX-C18 110 Angstrom, 250×21.2 mm) to give the title compound Example 43. ES/MS: 505.2 (M+H$^+$). $^1$H NMR (400 MHz, Methanol-d4) δ 8.57 (s, 1H), 5.43 (t, J=3.3 Hz, 2H), 5.14 (t, J=3.3 Hz, 2H), 4.36-3.95 (m, 3H), 3.87-3.68 (m, 1H), 3.68-3.45 (m, 2H), 3.22-3.04 (m, 2H), 2.83-2.62 (m, 1H), 2.60 (s, 3H), 2.52-2.45 (m, 3H), 2.40-1.93 (m, 4H), 1.33 (d, J=7.1 Hz, 6H).

The following Examples were made in an analogous fashion according to Procedure 9 and are shown below in Table 8. To prepare the below Examples, different reagents/starting materials were used than some of those described in Procedure 9 and are noted in the last column of Table 8—"Changes to Procedure 9: Different Reagents/Starting Materials". A person of ordinary skill in the art will readily recognize which reagents/starting materials of Procedure 9 were replaced with the different reagents/starting materials noted below.

TABLE 8

| Example | Structure | ES/MS m/z | $^1$H-NMR | Changes to Procedure 9: Different Reagents/ Starting Materials |
|---|---|---|---|---|
| 44 | 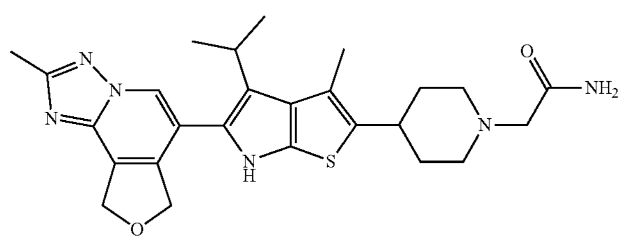 [SMILES: Cc1nc2c3c(c(-c4[nH]c5sc(C6CCN(CC(N)=O)CC6)c(C)c5c4C(C)C)cn2n1)COC3] | 493.2 | 1H NMR (400 MHz, Methanol-d4) δ 10.83 (s, 1H), 8.57 (s, 1H), 5.43 (t, 2H), 5.15 (t, 2H), 3.99 (s, 2H), 3.74 (d, 2H), 3.53-3.37 (m, 1H), 3.31-3.22 (m, 1H), 3.14 (p, 1H), 2.60 (s, 3H), 2.48 (s, 3H), 2.26-2.16 (m, 2H), 2.08 (q, 2H), 1.33 (d, 6H). | I-33 |
| 45 | 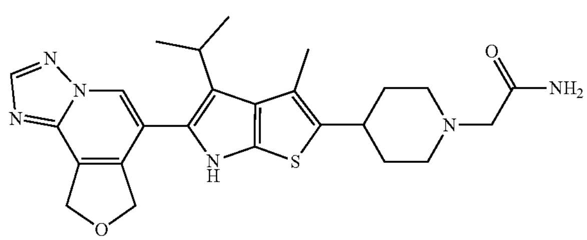 [SMILES: Cc1c(C2CCN(CC(N)=O)CC2)sc2[nH]c(-c3cn4ncnc4c4c3COC4)c(C(C)C)c12] | 479.2 | 1H NMR (400 MHz, MeOD) δ 8.70 (s, 1H), 8.50 (s, 1H), 5.47 (s, 2H), 5.17 (t, J = 3.4 Hz, 2H), 3.97 (s, 2H), 3.71 (s, 2H), 2.48 (s, 3H), 2.28-1.99 (m, 6H), 1.34 (d, J = 7.1 Hz, 5H). | I-33; I-17 |
| 46 | 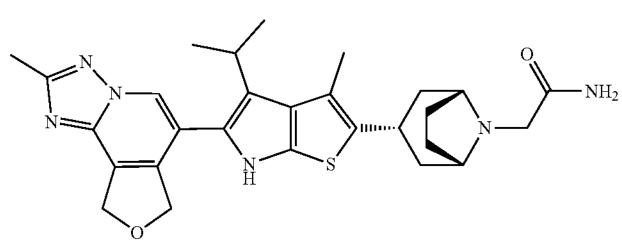 [SMILES: Cc1nc2c3c(c(-c4[nH]c5sc([C@@H]6C[C@H]7CC[C@@H](C6)N7CC(N)=O)c(C)c5c4C(C)C)cn2n1)COC3] | 519.2 | 1H NMR (400 MHz, Methanol-d4) δ 8.57 (s, 1H), 5.43 (s, 2H), 5.15 (d, J = 3.5 Hz, 2H), 4.14 (s, 2H), 3.89 (s, 2H), 3.82-3.66 (m, 1H), 3.22-3.10 (m, 1H), 2.60 (s, 3H), 2.49 (s, 3H), 2.44-2.23 (m, 6H), 2.23-2.13 (m, 2H), 1.33 (d, J = 7.1 Hz, 6H). | I-35 |

TABLE 8-continued

| Example | Structure | ES/MS m/z | ¹H-NMR | Changes to Procedure 9: Different Reagents/Starting Materials |
|---|---|---|---|---|
| 47 | 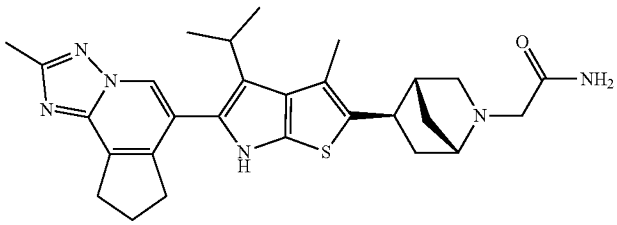 [SMILES: Cc1nc2c3c(c(-c4[nH]c5sc([C@@H]6C[C@@H]7C[C@H]6CN7CC(N)=O)c(C)c5c4C(C)C)cn2n1)CCC3] | 503.3 | 1H NMR (400 MHz, Methanol-d4) δ 8.47 (s, 1H), 4.36-3.88 (m, 3H), 3.76 (dd, J = 25.0, 11.6 Hz, 1H), 3.53 (dd, J = 15.9, 9.0 Hz, 1H), 3.27 (d, J = 7.6 Hz, 2H), 3.24-3.06 (m, 2H), 3.00 (t, J = 7.5 Hz, 2H), 2.86-2.64 (m, 1H), 2.60 (s, 3H), 2.54-2.41 (m, 3H), 2.41-1.90 (m, 6H), 1.31 (d, J = 7.0 Hz, 6H). | I-34; I-19 |
| 48 | 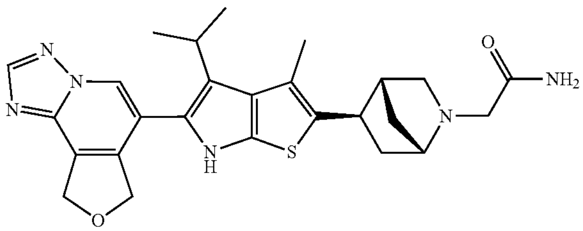 [SMILES: Cc1c([C@@H]2C[C@@H]3C[C@H]2CN3CC(N)=O)sc2[nH]c(-c3cn4ncnc4c4c3COC4)c(C(C)C)c12] | 491.2 | 1H NMR (400 MHz, Methanol-d4) δ 8.70 (s, 1H), 8.50 (s, 1H), 5.47 (t, J = 3.3 Hz, 2H), 5.16 (t, J = 3.5 Hz, 2H), 4.37-3.96 (m, 3H), 3.92-3.67 (m, 1H), 3.67-3.48 (m, 1H), 3.25-3.05 (m, 2H), 2.86-2.56 (m, 2H), 2.49 (d, J = 4.4 Hz, 3H), 2.42-1.92 (m, 3H), 1.34 (d, J = 7.1 Hz, 6H). | I-34; I-17 |
| 49 | 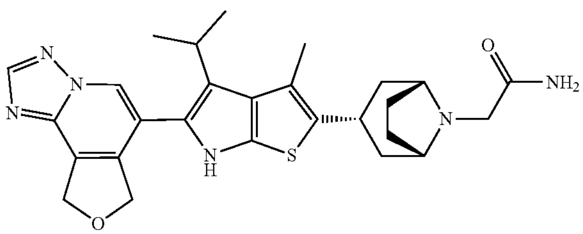 [SMILES: Cc1c([C@@H]2C[C@H]3CC[C@@H](C2)N3CC(N)=O)sc2[nH]c(-c3cn4ncnc4c4c3COC4)c(C(C)C)c12] | 505.2 | 1H NMR (400 MHz, MeOD) δ 8.70 (s, 1H), 8.50 (s, 1H), 5.47 (t, J = 3.4 Hz, 2H), 5.17 (t, J = 3.4 Hz, 2H), 4.14 (s, 2H), 3.90 (s, 2H), 3.73 (tt, J = 11.6, 5.5 Hz, 1H), 3.15 (hept, J = 7.1 Hz, 1H), 2.50 (s, 3H), 2.40-2.06 (m, 8H), 1.34 (d, J = 7.1 Hz, 6H). | I-35; I-17 |
| 50 | 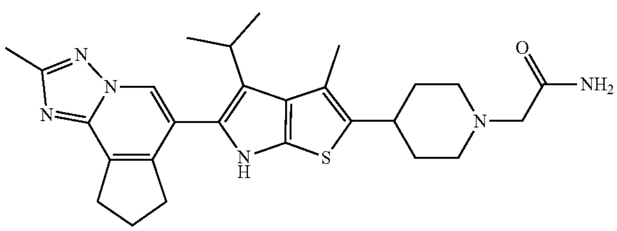 [SMILES: Cc1nc2c3c(c(-c4[nH]c5sc(C6CCN(CC(N)=O)CC6)c(C)c5c4C(C)C)cn2n1)CCC3] | 491.2 | 1H NMR (400 MHz, MeOD) δ 8.57 (s, 1H), 4.00 (s, 2H), 3.74 (d, J = 12.2 Hz, 2H), 3.55-3.36 (m, 2H), 3.32-3.21 (m, 3H), 3.17-3.00 (m, 3H), 2.65 (s, 3H), 2.48 (s, 3H), 2.34 (p, J = 7.6 Hz, 2H), 2.22 (d, J = 14.3 Hz, 2H), 2.08 (td, J = 13.9, 9.5 Hz, 2H), 1.32 (d, J = 7.0 Hz, 6H). | I-19 |

Procedure 10: Example 51

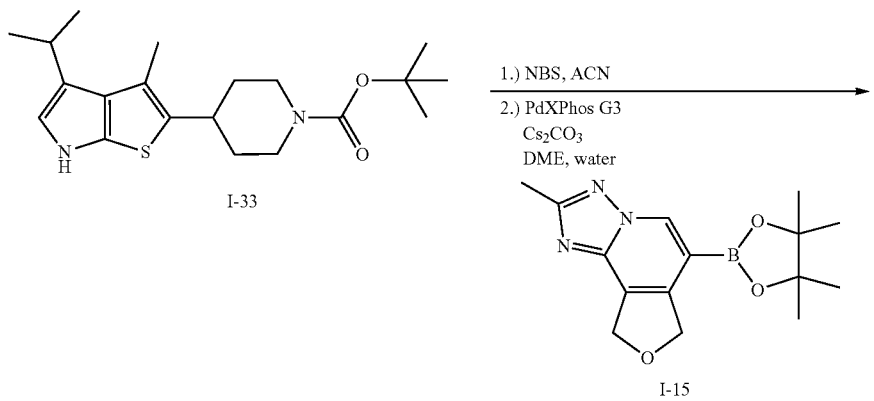

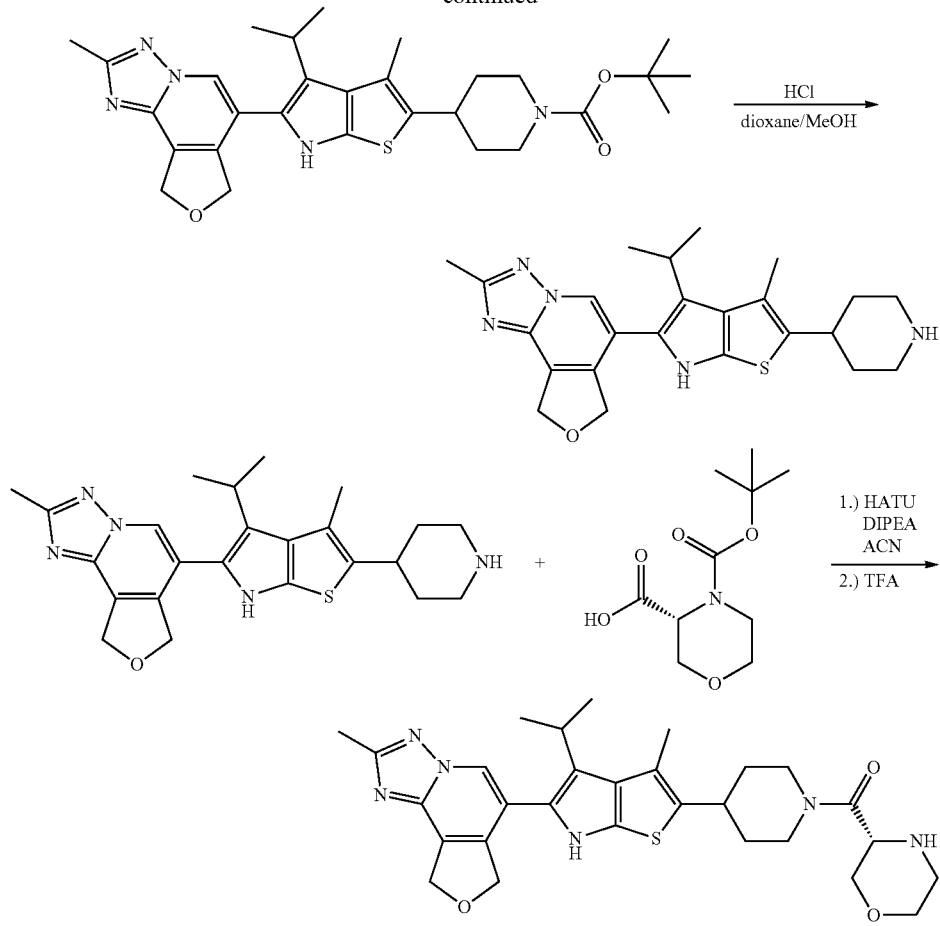

Example 51 tert-butyl 4-(4-isopropyl-3-methyl-5-(2-methyl-7,9-dihydrofuro[3,4-c][1,2,4]triazolo[1,5-a]pyridin-6-yl)-6H-thieno[2,3-b]pyrrol-2-yl)piperidine-1-carboxylate: A solution of tert-butyl 4-(4-isopropyl-3-methyl-6H-thieno[2,3-b]pyrrol-2-yl)piperidine-1-carboxylate (I-33) (147 mg, 0.404 mmol) in ACN (4 mL) was cooled to 0° C., and N-bromosuccinimide (64.7 mg, 0.364 mmol) (dissolved in 2 mL ACN) was added dropwise. After completion of addition, LCMS indicated reaction completion. The mixture was quickly concentrated under reduced pressure. The crude residue was dissolved in DME (2 mL) and this solution was added to a MW vial containing 2-methyl-6-(4,4,5,5-tetramethyl-1,3,2-dioxaborolan-2-yl)-7,9-dihydrofuro[3,4-c][1,2,4]triazolo[1,5-a]pyridine (I-15) (207 mg, 0.687 mmol), XPhos Pd G3 (51.3 mg, 0.0606 mmol) and cesium carbonate (395 mg, 1.21 mmol). Water (0.2 mL) was added, and the mixture was degassed with argon for 30 seconds. The vial was sealed, and the mixture was heated at 120° C. for 15 minutes in a microwave. The crude mixture was purified directly by silica chromatography (eluent EtOAc/hexanes). ES/MS: 536.6 (M+H⁺)

6-(4-isopropyl-3-methyl-2-(piperidin-4-yl)-6H-thieno[2,3-b]pyrrol-5-yl)-2-methyl-7,9-dihydrofuro[3,4-c][1,2,4]triazolo[1,5-a]pyridine: To a vial with tert-butyl 4-(4-isopropyl-3-methyl-5-(2-methyl-7,9-dihydrofuro[3,4-c][1,2,4]triazolo[1,5-a]pyridin-6-yl)-6H-thieno[2,3-b]pyrrol-2-yl)piperidine-1-carboxylate (75 mg, 0.14 mmol) was added methanol (1 mL) and HCl (4M in dioxane, 0.5 mL). The reaction was stirred at 35° C. for 30 minutes. The crude mixture was concentrated under reduced pressure, and taken forward to the next step. ES/MS: 436.2 (M+H⁺)

(R)-(4-(4-isopropyl-3-methyl-5-(2-methyl-7,9-dihydrofuro[3,4-c][1,2,4]triazolo[1,5-a]pyridin-6-yl)-6H-thieno[2,3-b]pyrrol-2-yl)piperidin-1-yl)(morpholin-3-yl)methanone (Example 51): To a vial with 6-(4-isopropyl-3-methyl-2-(piperidin-4-yl)-6H-thieno[2,3-b]pyrrol-5-yl)-2-methyl-7,9-dihydrofuro[3,4-c][1,2,4]triazolo[1,5-a]pyridine (HCl salt) (29 mg, 0.057 mmol) in dichloromethane (1 mL) was added (R)-4-(tert-butoxycarbonyl)morpholine-3-carboxylic acid (20 mg, 0.086 mmol), 2-(7-Aza-1H-benzotriazole-1-yl)-1,1,3,3-tetramethyluronium hexafluorophosphate (HATU) (33 mg, 0.086 mmol), N,N-diisopropylethylamine (0.03 mL, 0.17 mmol). The mixture was stirred 5 hr at rt. To the mixture was added TFA (0.5 mL), and the mixture was stirred 2 hr at rt. The crude mixture was concentrated under reduced pressure, and acetonitrile (1.5 mL) and water (0.5 mL) were added. The mixture was filtered through an acrodisc before purification by RP-HPLC (0.1% TFA-ACN in 0.1% TFA Water, Column: Gemini 5 uM, NX-C18 110 Angstrom, 250×21.2 mm) to give the title compound Example 51. ES/MS: 549.1 (M+H⁺). 1H NMR (400 MHz, Methanol-d4) δ 10.76 (s, 1H), 8.56 (s, 1H), 5.42 (t, 2H), 5.15 (t, 2H), 4.76-4.57 (m, 2H), 4.28 (dd, 1H), 4.06 (t, 2H), 3.84-3.74 (m, 1H), 3.65 (dt, 1H), 3.45-3.37 (m, 4H), 3.14 (p, 1H), 2.90 (t, 1H), 2.60 (s, 3H), 2.47 (s, 3H), 2.19-1.98 (m, 2H), 1.77-1.55 (m, 2H), 1.33 (d, 6H).

The following Examples were made in an analogous fashion according to Procedure 10 and are shown below in Table 9. To prepare the below Examples, different reagents/starting materials were used than some of those described in Procedure 10 and are noted in the last column of Table 9—"Changes to Procedure 10: Different Reagents/Starting Materials". A person of ordinary skill in the art will readily recognize which reagents/starting materials of Procedure 10 were replaced with the different reagents/starting materials noted below.

2-(5-(8,9-dihydro-7H-cyclopenta[c][1,2,4]triazolo[1,5-a]pyridin-6-yl)-4-isopropyl-3-methyl-6H-thieno[2,3-b]pyrrol-2-yl)-5-oxa-8-azaspiro[3.5]nonane (Example 54 and Example 55): 2-(5-(8,9-dihydro-7H-cyclopenta[c][1,2,4]triazolo[1,5-a]pyridin-6-yl)-4-isopropyl-3-methyl-6H-thieno

TABLE 9

| Example | Structure | ES/MS m/z | ¹H-NMR | Changes to Procedure 10: Different Reagents/Starting Materials |
|---|---|---|---|---|
| 52 | 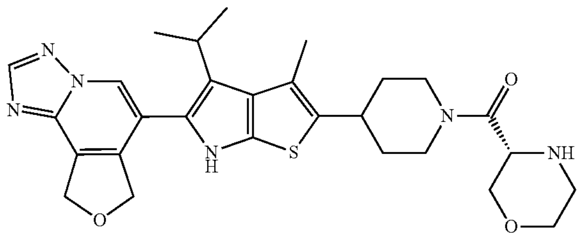 [SMILES: Cc1c(C2CCN(C(=O)[C@H]3COCCN3)CC2)sc2[nH]c(-c3cn4ncnc4c4c3COC4)c(C(C)C)c12] | 535.2 | 1H NMR (400 MeOD) δ 8.69 (s, 1H), 8.50 (s, 1H), 5.47 (t, J = 3.4 Hz, 2H), 5.17 (t, J = 3.4 Hz, 2H), 4.76-4.61 (m, 3H), 4.26 (s, 1H), 4.06 (t, J = 14.3 Hz, 2H), 3.79 (t, J = 13.8 Hz, 1H), 3.65 (dt, J = 34.9, 11.8 Hz, 2H), 3.20-3.08 (m, 2H), 2.90 (t, J = 12.9 Hz, 1H), 2.48 (s, 3H), 2.18-1.99 (m, 3H), 1.76-1.52 (m, 3H), 1.34 (d, J = 7.1 Hz, 6H). | I-17 |
| 53 | 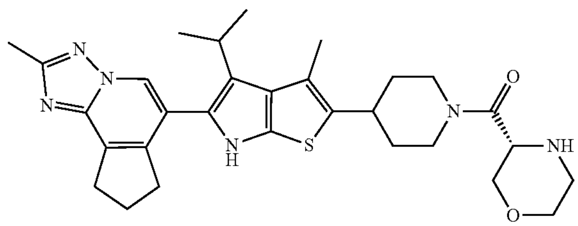 [SMILES: Cc1nc2c3c(c(-c4[nH]c5sc(C6CCN(C(=O)[C@H]7COCCN7)CC6)c(C)c5c4C(C)C)cn2n1)CCC3] | 547.3 | 1H NMR (400 MHz, MeOD) δ 8.55 (s, 1H), 4.76-4.62 (m, 2H), 4.27 (ddd, J = 11.0, 6.8, 3.4 Hz, 1H), 4.11-4.00 (m, 2H), 3.87-3.56 (m, 3H), 3.45-3.24 (m, 5H), 3.22-2.98 (m, 3H), 2.95-2.84 (m, 1H), 2.64 (s, 3H), 2.48 (s, 3H), 2.33 (p, J = 7.6 Hz, 2H), 2.20-1.97 (m, 2H), 1.78-1.51 (m, 2H), 1.32 (d, J = 7.4 Hz, 6H). | I-19 |

Procedure 11: Example 54: and Example 55

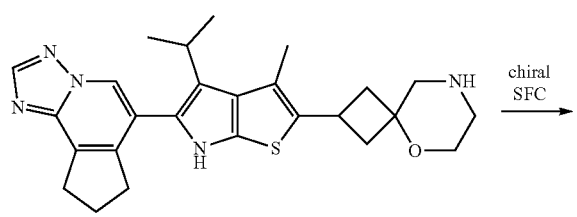

Example 26 chiral SFC →

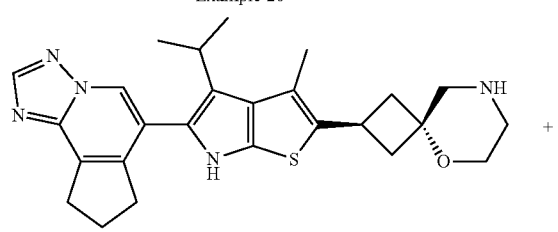

Example 54

+

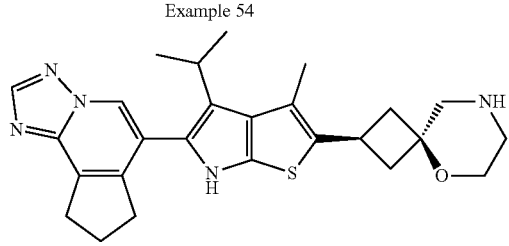

Example 55

[2,3-b]pyrrol-2-yl)-5-oxa-8-azaspiro[3.5]nonane (Example 26) as a mixture of 2 stereoisomers was separated by chiral SFC (Cell 2 4.6×100 mm 5 mic; 45% EtOH)) to give two diastereomers, which were arbitrarily assigned as Isomer 1 and Isomer 2.

Isomer 1: 2-(5-(8,9-dihydro-7H-cyclopenta[c][1,2,4]triazolo[1,5-a]pyridin-6-yl)-4-isopropyl-3-methyl-6H-thieno[2,3-b]pyrrol-2-yl)-5-oxa-8-azaspiro[3.5]nonane (Example 54) ES/MS: 462.2 (M+H⁺). ¹H NMR (400 MHz, MeOD) δ 8.57 (s, 1H), 8.48 (s, 1H), 4.08 (p, J=8.6 Hz, 1H), 3.97 (t, J=5.0 Hz, 2H), 3.33-3.17 (m, 6H), 3.16-2.98 (m, 3H), 2.81-2.71 (m, 2H), 2.39 (s, 3H), 2.30 (ddd, J=13.6, 11.0, 7.7 Hz, 4H), 1.31 (d, J=7.1 Hz, 6H).

Isomer 2: 2-(5-(8,9-dihydro-7H-cyclopenta[c][1,2,4]triazolo[1,5-a]pyridin-6-yl)-4-isopropyl-3-methyl-6H-thieno[2,3-b]pyrrol-2-yl)-5-oxa-8-azaspiro[3.5]nonane (Example 55) ES/MS: 462.2 (M+H⁺). ¹H NMR (400 MHz, MeOD) δ 8.59 (s, 1H), 8.52 (s, 1H), 3.92-3.85 (m, 2H), 3.71-3.57 (m, 1H), 3.43 (s, 2H), 3.30 (s, 2H), 3.25-3.18 (m, 2H), 3.16-2.99 (m, 3H), 2.79 (ddt, J=11.0, 6.3, 2.4 Hz, 2H), 2.41 (s, 3H), 2.38-2.19 (m, 4H), 1.31 (d, J=7.1 Hz, 6H).

BIOLOGICAL EXAMPLES

Example A

TLR7/9 Human Peripheral Blood Mononuclear Cell (PBMC) Cell-Based Assay

Human peripheral blood mononuclear cells (PBMCs) consist of lymphocytes, monocytes and dendritic cells that express TLR7, TLR8 and TLR9. These cells respond to TLR7, TLR8 and TLR9 ligand stimulation and produce cytokines and chemokines in vitro and in vivo. Human PBMCs are therefore suitable to be used in a cell-based assay to assess the in vitro potency of a TLR 7, 8, and/or 9 antagonist. The result is expected to be more translatable to the pharmacodynamics response in vivo than cell line-based assays.

Cryopreserved human PBMCs from healthy donors were thawed and resuspended in RPMI-1640 media with L-glutamine (Corning) supplemented with 10% Fetal Bovine Serum (Hyclone) and 1× Penicillin-Streptomycin (Corning). After counting, the cell density was adjusted to 2 million cells/ml and incubated for 1 hour at 37° C., 5% $CO_2$ for recovery. Following the recovery, the cells were plated by adding 50 µl per well (100,000 cells) to 384-well cell culture plates (Greiner) containing 250 nl of test antagonists in 100% DMSO per well, in a 10 points dose response in quadruplicates. PBMCs were incubated in the presence of test antagonists for one hour at 37° C., 5% $CO_2$ before being stimulated with a TLR7 or TLR9 agonist. GS-986 (Gilead Sciences) was used as the TLR7 agonist at a final concentration of 400 nM. ODN-2216 (InvivoGen) was used as the TLR9 agonist at a final concentration of 3 µM. PBMCs were incubated in the presence of the test antagonist and the TLR7 (or TLR9) agonist for an additional 6 hours at 37° C., 5% $CO_2$. At the end of the incubation, the cell culture plates were centrifuged at 500 g for 5 min, and the cell culture supernatant was collected. The level of cytokines (IL-6 and IFNα) in the supernatant was measured by electrochemiluminescence immunoassays (Mesoscale Discovery) following manufacturer's recommended protocols. The level of cytokine measured was plotted against the test antagonist concentration and fitted to a sigmoidal function to determine the $EC_{50}$, which are shown below in Table 6.

TLR8 Human Peripheral Blood Mononuclear Cell (PBMC) Cell-Based Assay

Cryopreserved human PBMCs from healthy donors were thawed and resuspended in RPMI-1640 media with L-glutamine (Corning) supplemented with 10% Fetal Bovine Serum (Hyclone) and 1× Penicillin-Streptomycin (Corning). After counting, the cell density was adjusted to 2 million cells/ml and incubated for 1 hour at 37° C., 5% $CO_2$ for recovery. Following the recovery, the cells were plated by adding 50 µl per well (100,000 cells) to 384-well cell culture plates (Greiner) containing 250 nl of test antagonists in 100% DMSO per well, in a 10 points dose response in quadruplicates. PBMCs were incubated in the presence of antagonists for one hour at 37° C., 5% $CO_2$ before being stimulated with TLR8 agonist. Compound A (Gilead Sciences, U.S. Pat. No. 10,285,990) was used as the TLR8 agonist at a final concentration of 800 nM. PBMCs were incubated in the presence of antagonist and the TLR8 agonist for an additional 6 hours at 37° C., 5% $CO_2$. At the end of the incubation, the cell culture plates were centrifuged at 500 g for 5 min, and the cell culture supernatant was collected. The level of cytokines (TNFa and IL12p40) in the supernatant was measured by electrochemiluminescence immunoassays (Mesoscale Discovery) following manufacturer's recommended protocols. The level of cytokine measured was plotted against the antagonist concentration and fitted to a sigmoidal function to determine the $EC_{50}$, which are shown below in Table 6. Compound A has the structure:

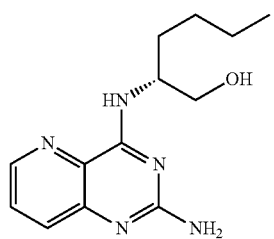

TABLE 6

| Example | TLR-7 $EC_{50}$ (nM) | TLR-8 $EC_{50}$ (nM) |
| --- | --- | --- |
| 1 | 0.11 | 1.89 |
| 2 | 0.95 | 3.94 |
| 3 | 0.77 | 0.31 |
| 4 | 0.46 | 0.27 |
| 5 | 0.23 | 1.76 |
| 6 | 0.35 | 3.06 |
| 7 | 0.78 | 3.91 |
| 8 | 0.69 | 0.14 |
| 9 | 1.17 | 0.32 |
| 10 | 0.26 | 15.32 |
| 11 | 0.32 | 4.70 |
| 12 | 6.08 | 4.74 |
| 13 | 1.44 | 5.84 |
| 14 | 0.58 | 4.87 |
| 15 | 0.29 | 5.26 |
| 16 | 1.46 | 12.48 |
| 17 | 0.68 | 15.23 |
| 18 | 0.44 | 4.42 |
| 19 | 0.14 | 5.42 |
| 20 | 4.63 | 22.31 |
| 21 | 0.51 | 1.32 |
| 22 | 0.23 | 0.66 |
| 23 | 0.33 | 0.08 |
| 24 | 0.94 | 0.21 |
| 25 | 0.05 | 1.38 |
| 26 | 0.11 | 0.54 |
| 27 | 0.26 | 2.55 |
| 28 | 0.15 | 1.57 |
| 29 | 0.10 | 1.00 |
| 30 | 0.86 | 1.29 |
| 31 | 1.33 | 6.38 |
| 32 | 1.50 | 11.27 |
| 33 | 2.33 | 7.57 |
| 34 | 0.58 | 1.57 |
| 35 | 0.33 | 7.88 |
| 36 | 4.50 | 27.61 |
| 37 | 2.95 | 24.48 |
| 38 | 0.58 | 0.81 |
| 39 | 3.40 | 5.01 |
| 40 | 0.27 | 0.11 |
| 41 | 0.49 | 2.56 |
| 42 | 0.78 | 0.69 |
| 43 | 1.10 | 2.05 |
| 44 | 4.09 | 134.97 |
| 45 | 4.00 | 63.58 |
| 46 | 1.21 | 77.92 |
| 47 | 0.24 | 0.05 |
| 48 | 0.39 | 0.36 |
| 49 | 0.41 | 15.19 |
| 50 | 0.78 | 34.59 |
| 51 | 2.46 | 96.57 |
| 52 | 1.17 | 26.67 |
| 53 | 0.62 | 16.19 |
| 54 | 4.69 | 5.06 |
| 55 | 0.07 | 0.18 |

All references, including publications, patents, and patent documents are incorporated by reference herein, as though individually incorporated by reference. The present disclosure provides reference to various embodiments and techniques. However, it should be understood that many variations and modifications may be made while remaining within the spirit and scope of the present disclosure. The description is made with the understanding that it is to be considered an exemplification of the claimed subject matter and is not intended to limit the appended claims to the specific embodiments illustrated.

What is claimed is:
1. A compound selected from the group consisting of:
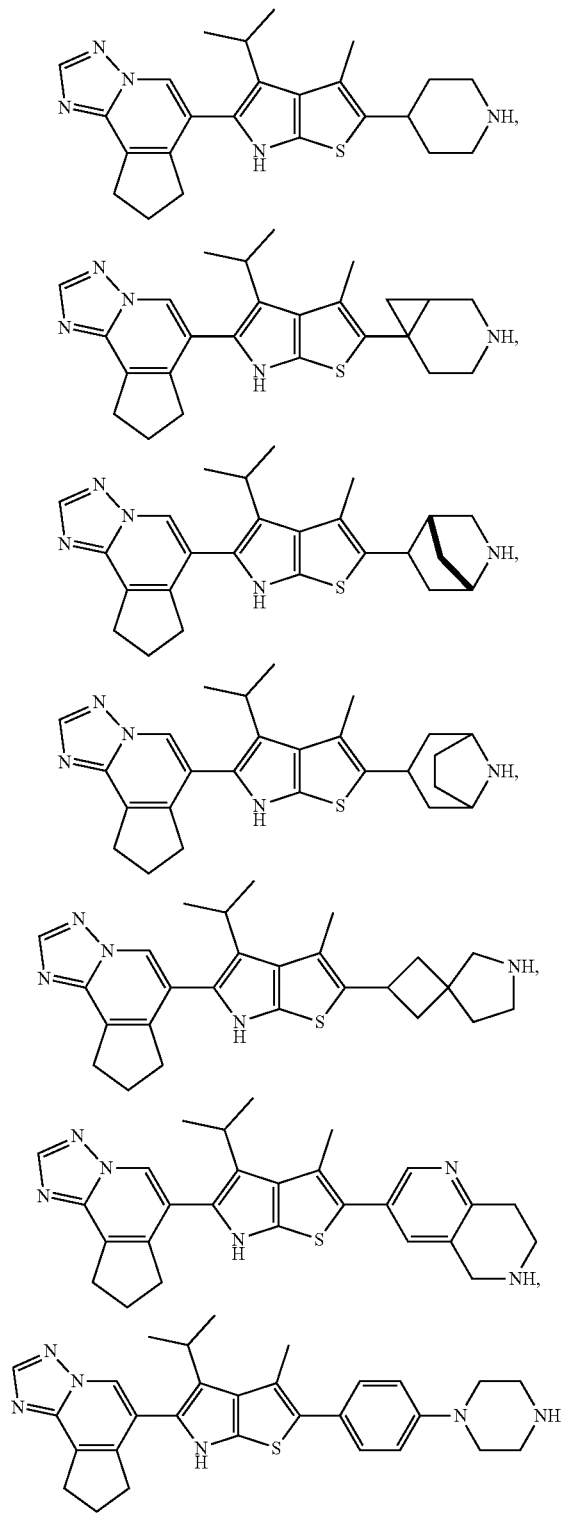
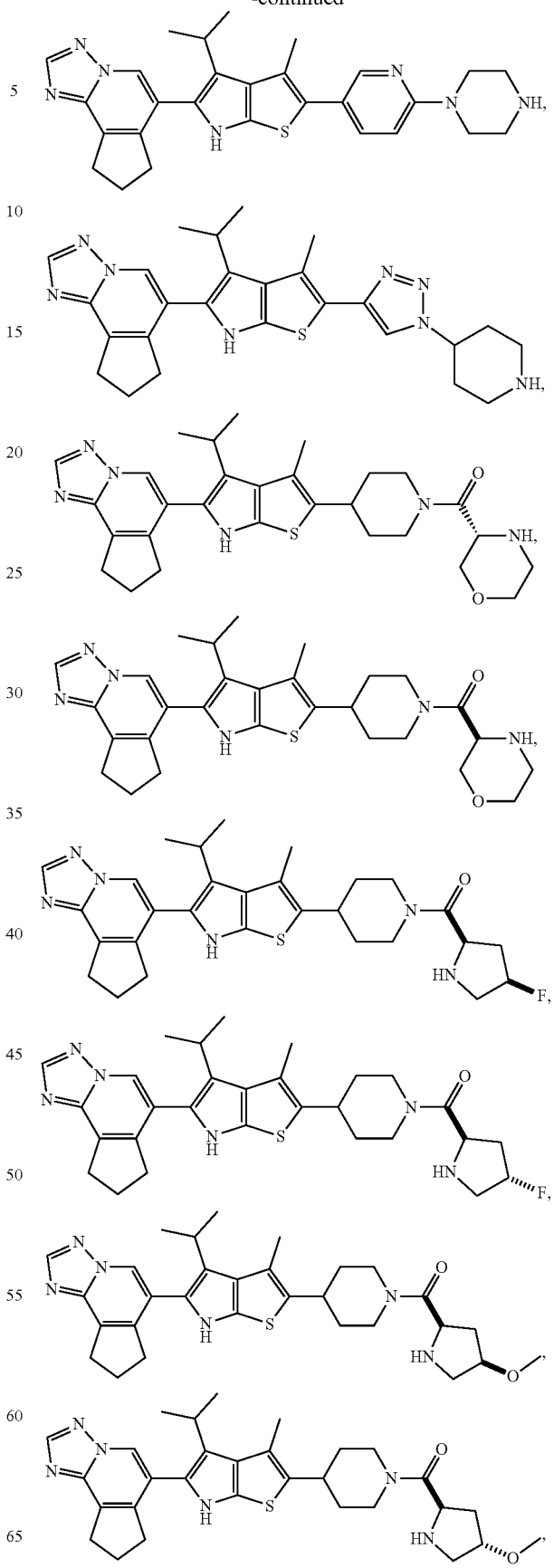

231
-continued
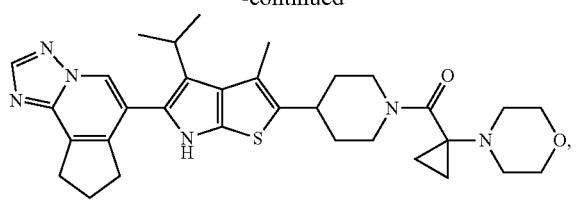
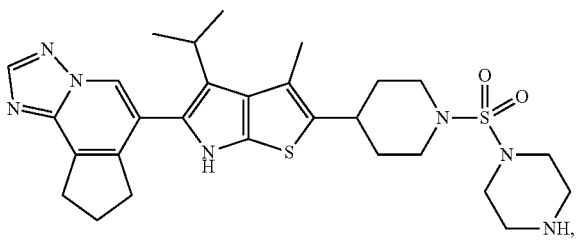
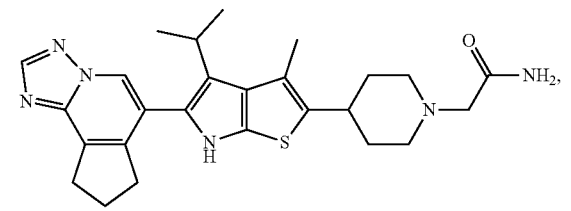
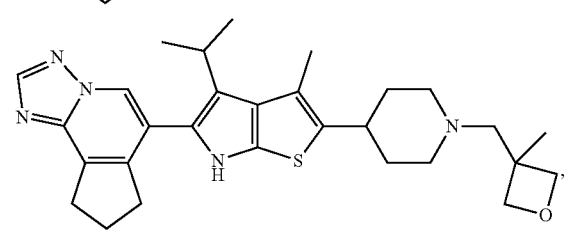
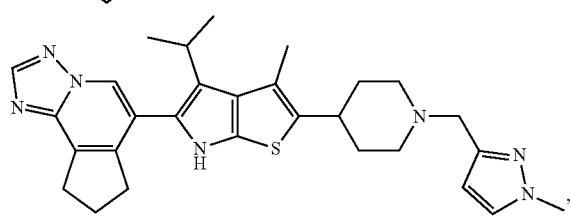
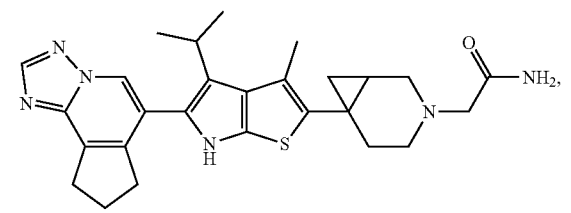
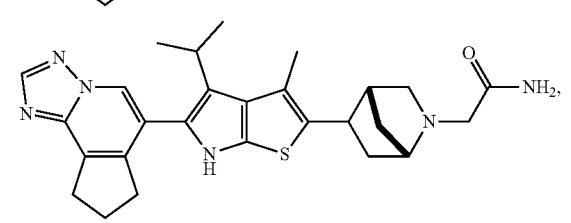
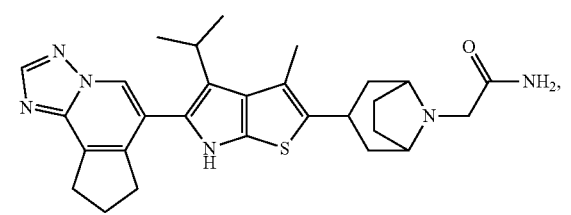
232
-continued
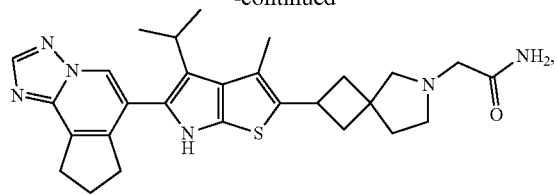
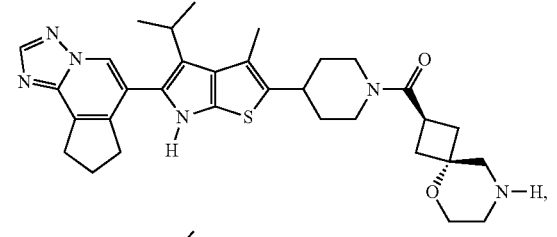
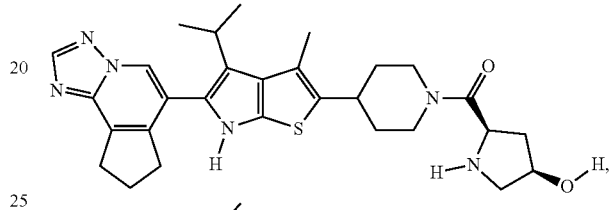
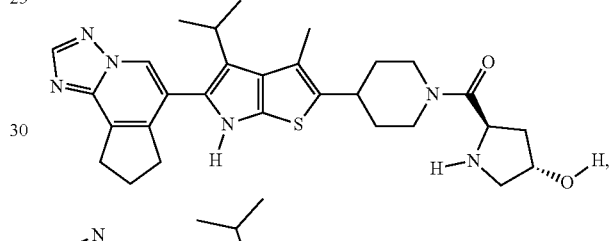
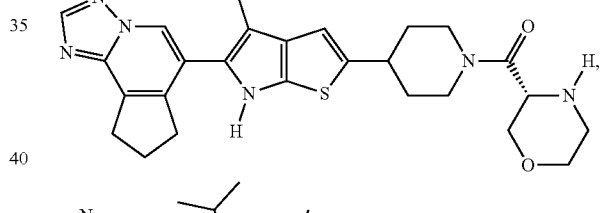
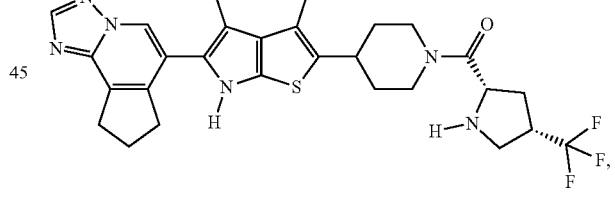
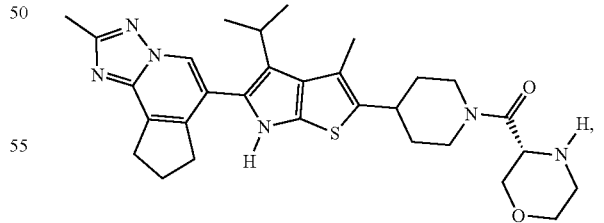
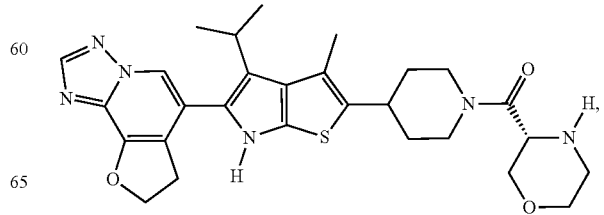

233
-continued
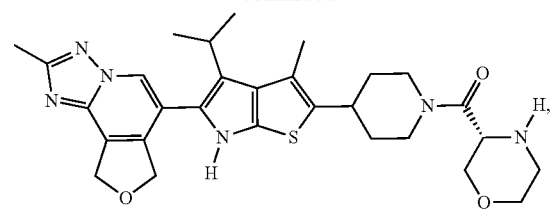
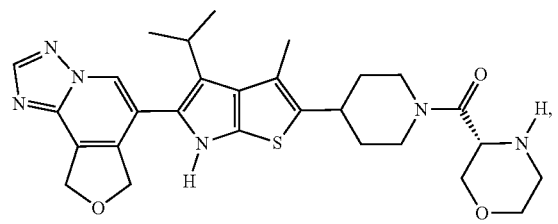
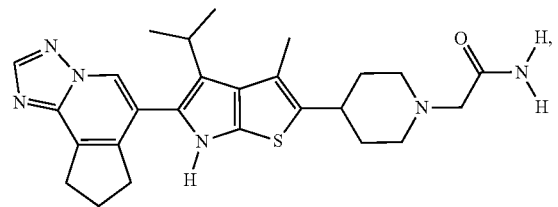
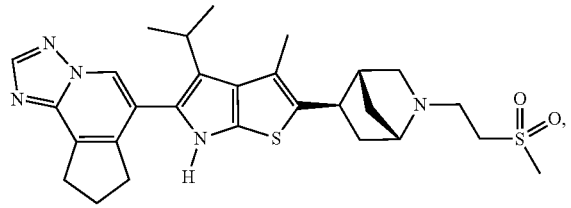
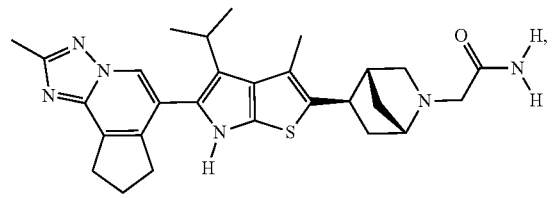
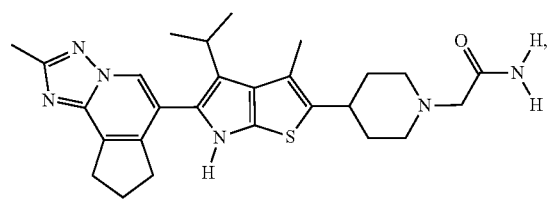
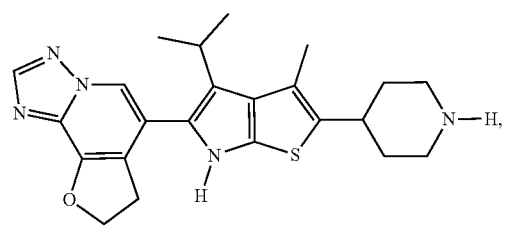
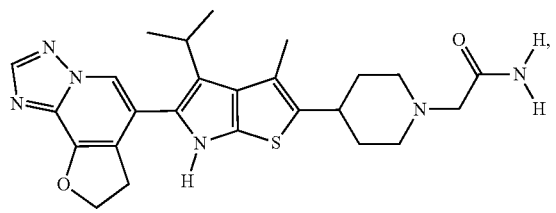
234
-continued
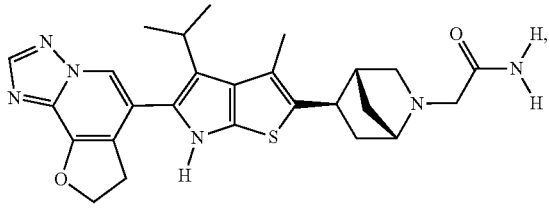
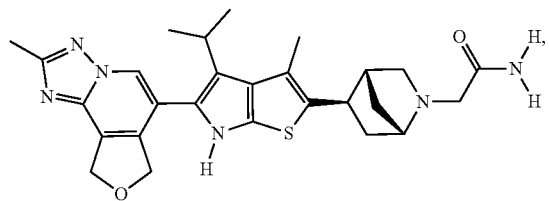
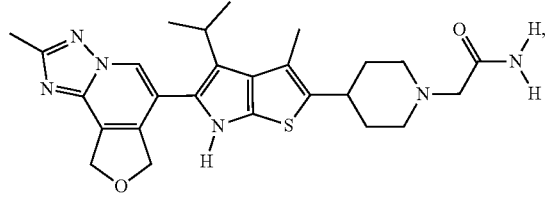
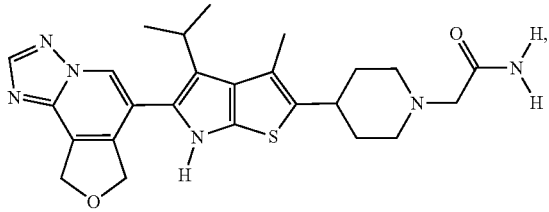
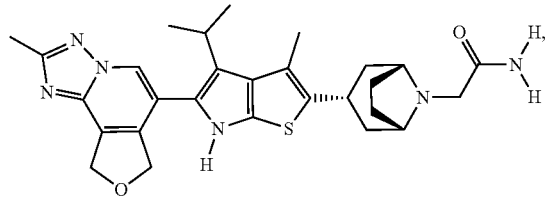
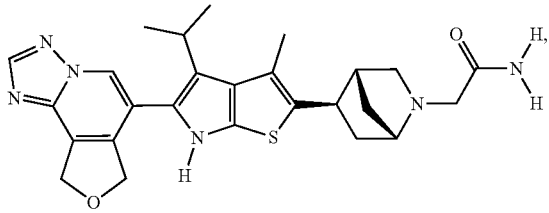
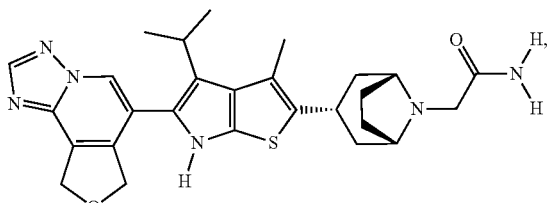
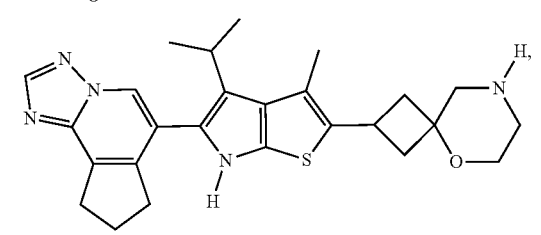

-continued
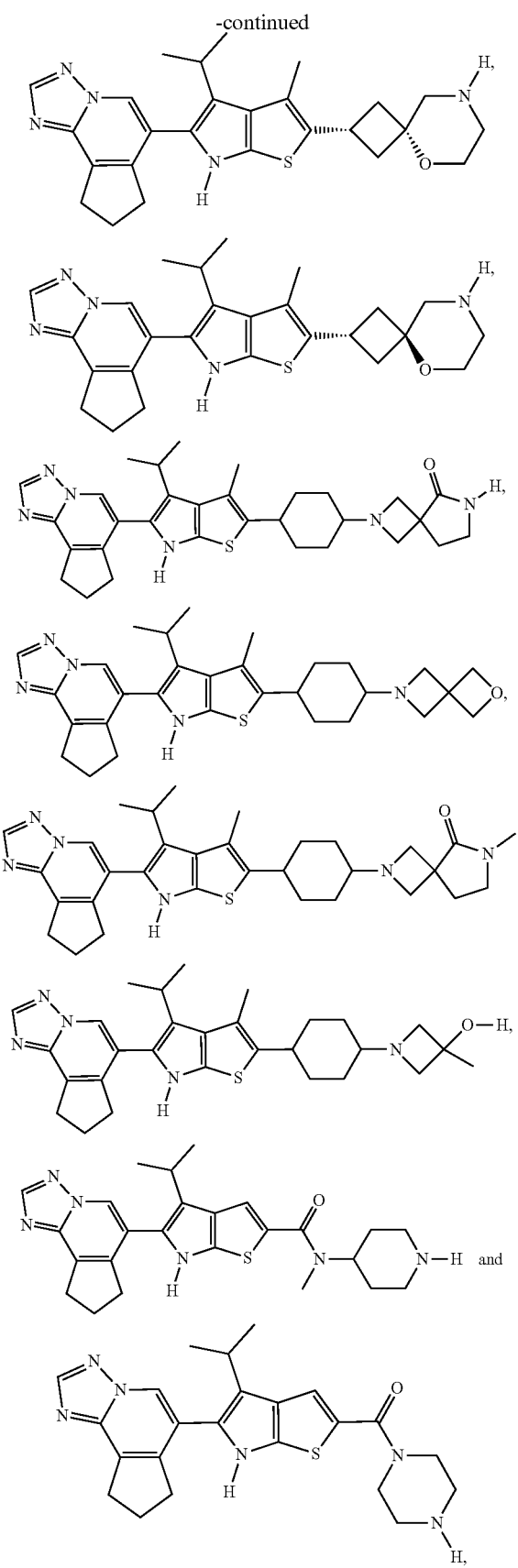
or a pharmaceutically acceptable salt thereof.
2. The compound of claim 1, wherein the compound is selected from the group consisting of:
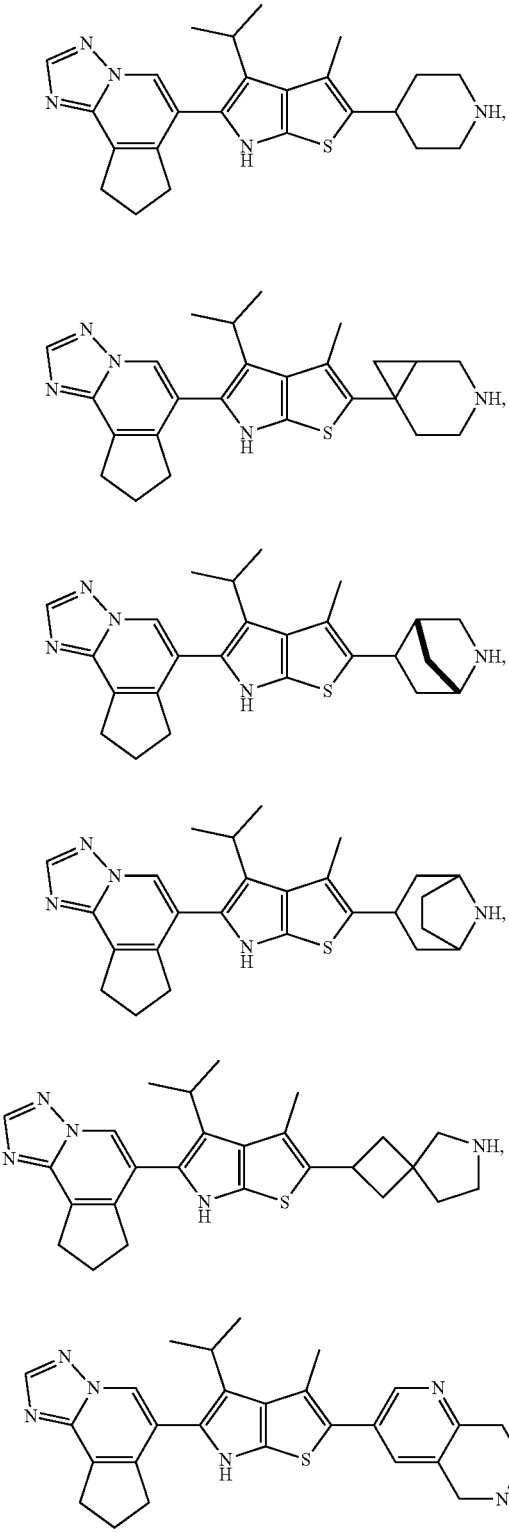
or a pharmaceutically acceptable salt thereof.
3. The compound of claim 1, wherein the compound is selected from the group consisting of:

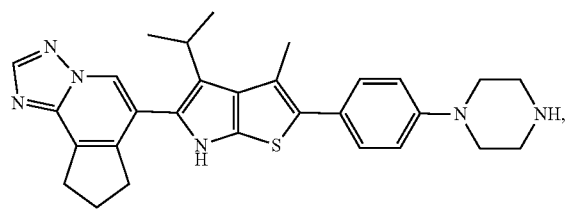
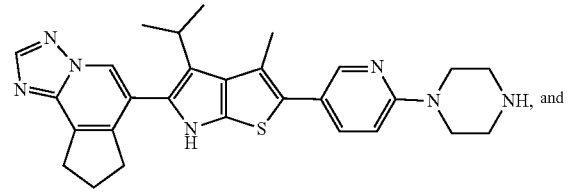, and
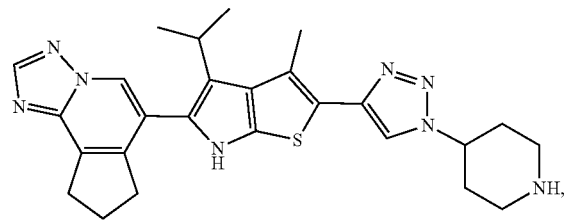
or a pharmaceutically acceptable salt thereof.
4. The compound of claim 1, wherein the compound is selected from the group consisting of:
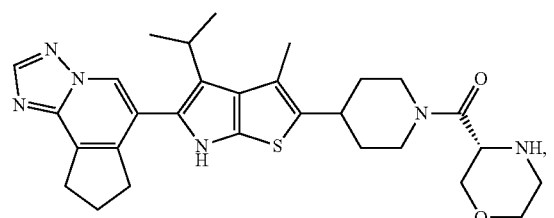
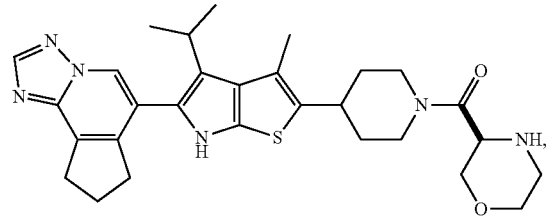
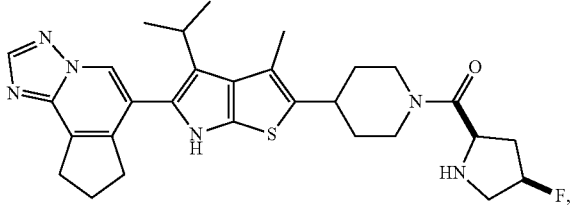
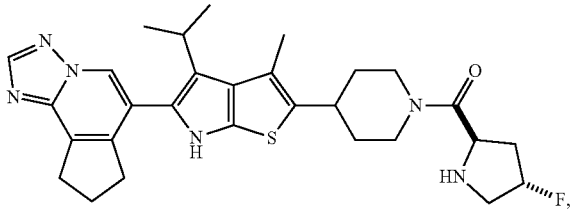
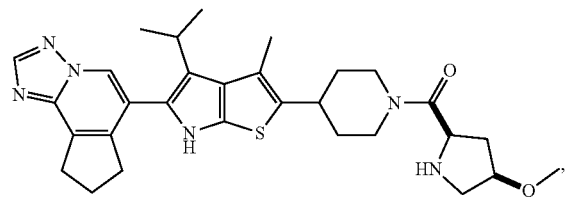
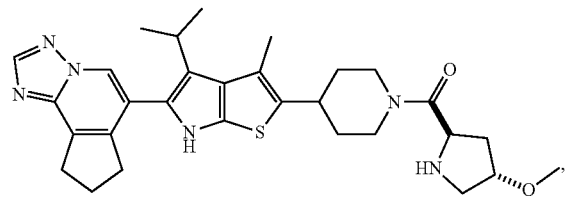
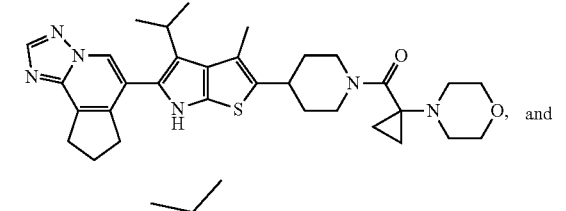, and
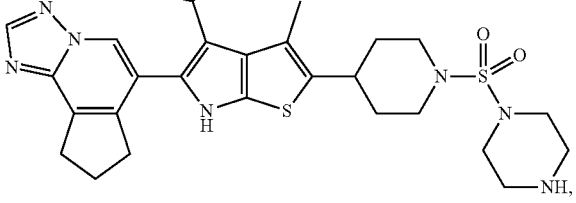
or a pharmaceutically acceptable salt thereof.
5. The compound of claim 1, wherein the compound is selected from the group consisting of:
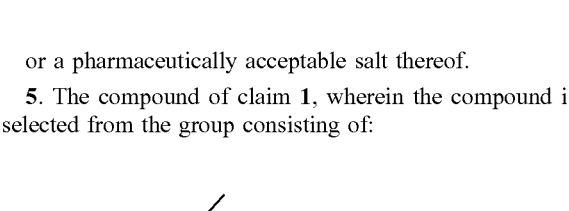
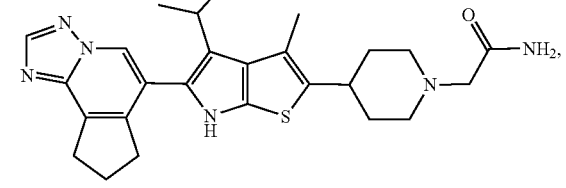
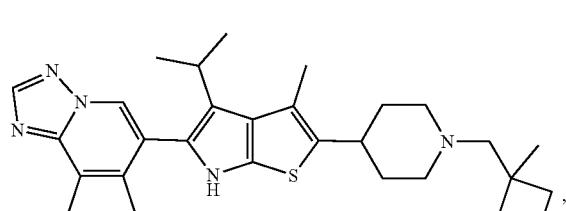
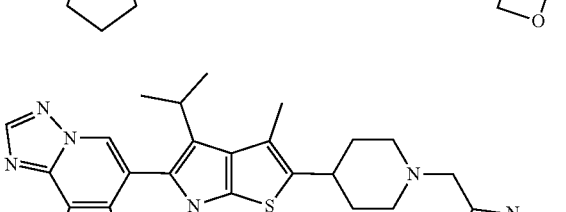

239

-continued

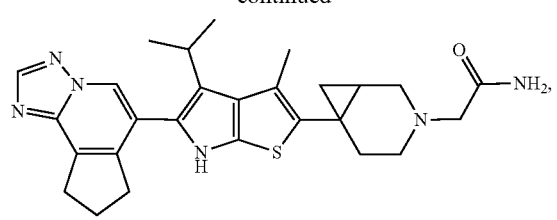

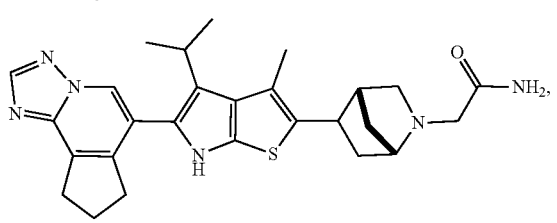

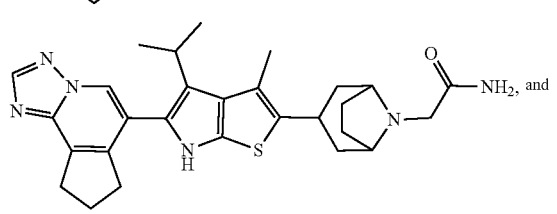

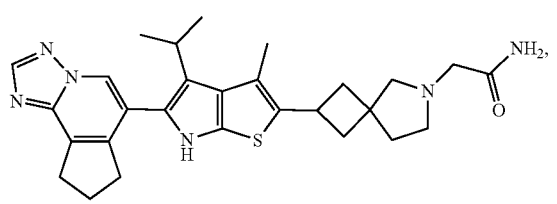

or a pharmaceutically acceptable salt thereof.

6. The compound of claim 1, wherein the compound is selected from the group consisting of:

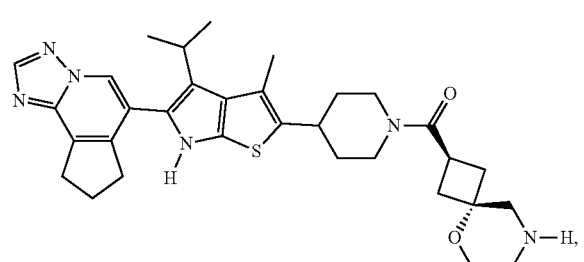

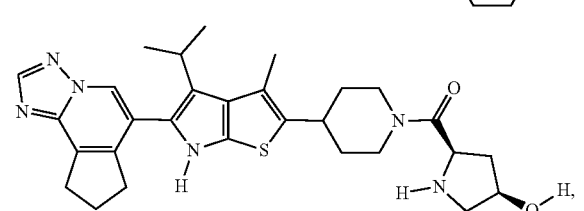

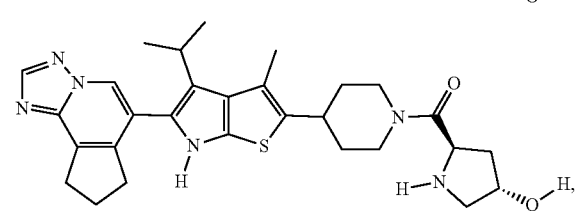

240

-continued

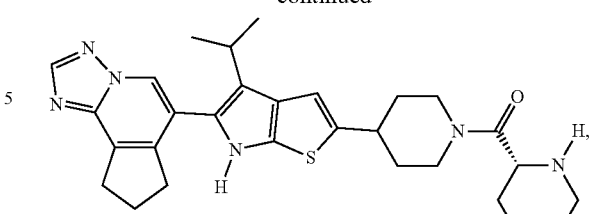

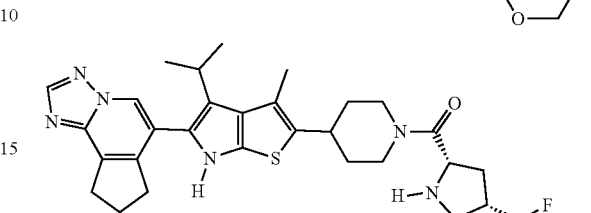

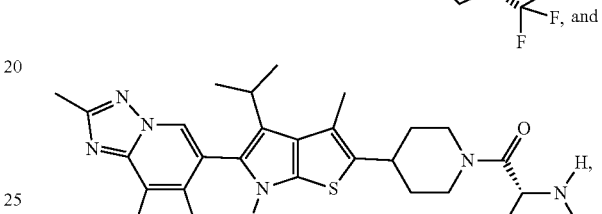

or a pharmaceutically acceptable salt thereof.

7. The compound of claim 1, wherein the compound is selected from the group consisting of:

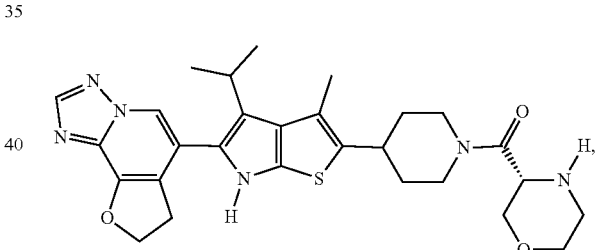

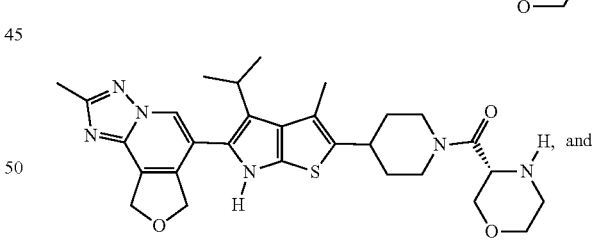

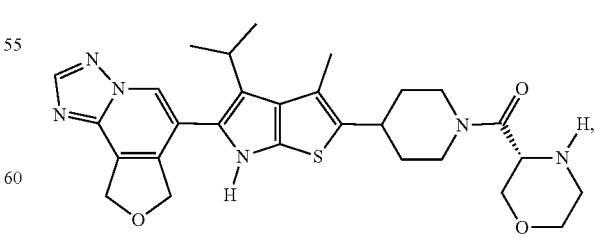

or a pharmaceutically acceptable salt thereof.

8. The compound of claim 1, wherein the compound is selected from the group consisting of:

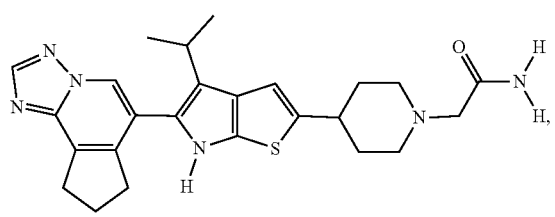
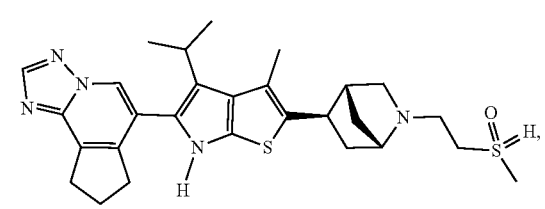
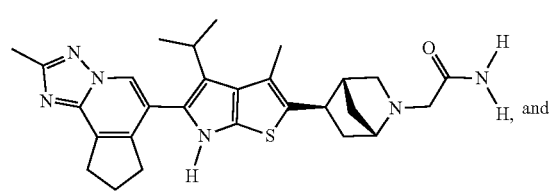
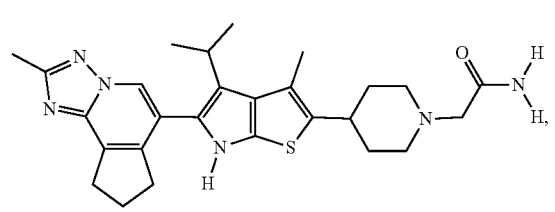
or a pharmaceutically acceptable salt thereof.
9. The compound of claim 1, wherein the compound is selected from the group consisting of:
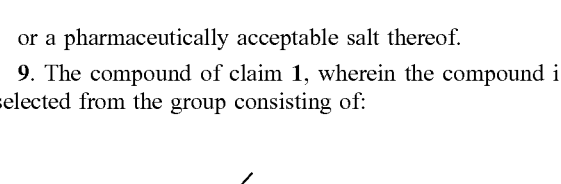
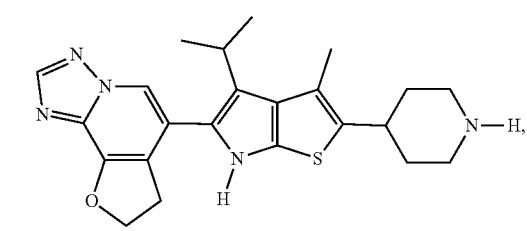
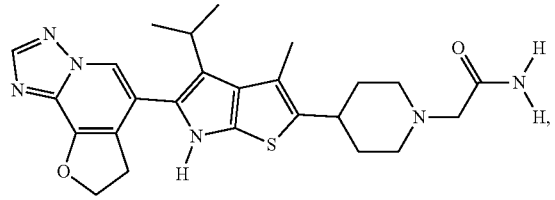
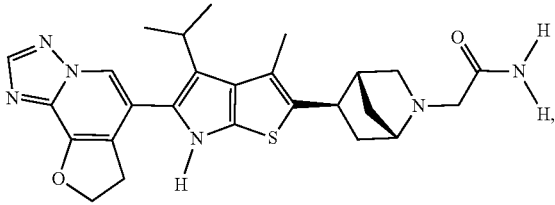
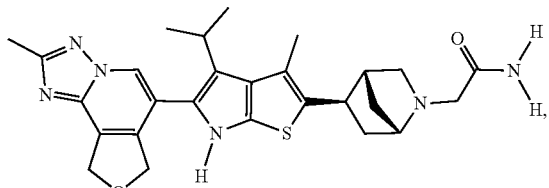
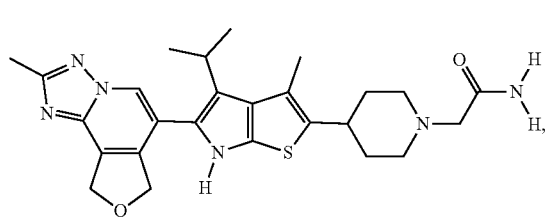
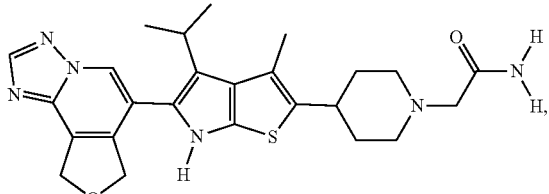
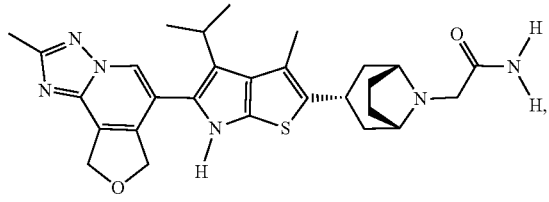
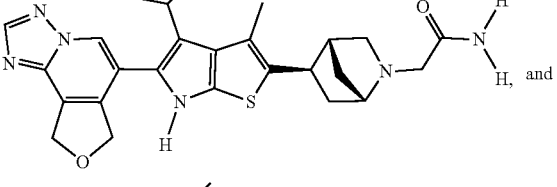
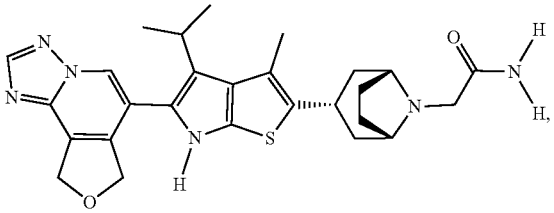
or a pharmaceutically acceptable salt thereof.
10. The compound of claim 1, wherein the compound is selected from the group consisting of:
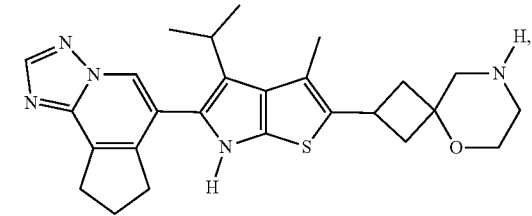

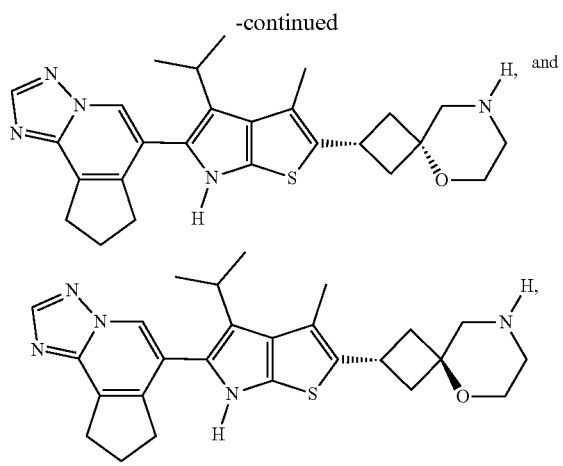

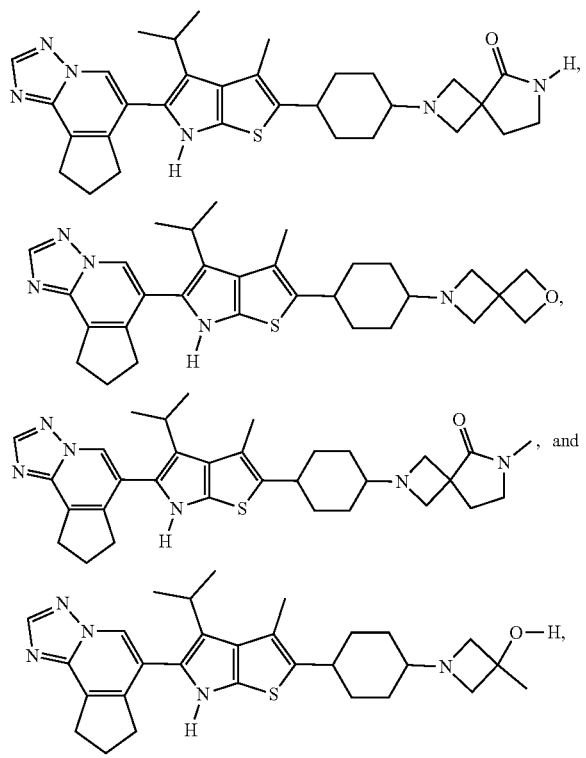

or a pharmaceutically acceptable salt thereof.

11. The compound of claim 1, wherein the compound is selected from the group consisting of:

or a pharmaceutically acceptable salt thereof.

12. The compound of claim 1, wherein the compound is selected from the group consisting of:

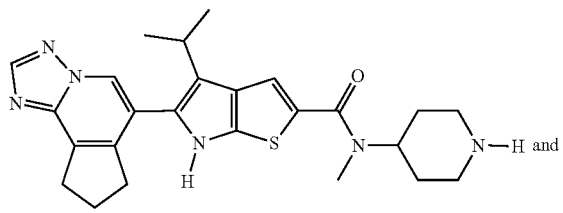

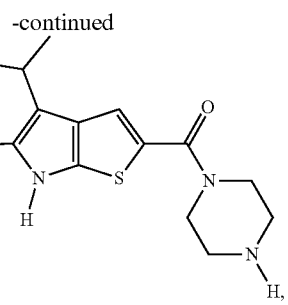

or a pharmaceutically acceptable salt thereof.

13. A pharmaceutical composition comprising the compound of claim 1, or a pharmaceutically acceptable salt thereof, and a pharmaceutically acceptable excipient or carrier.

14. The pharmaceutical composition of claim 13, further comprising one or more additional therapeutic agents, or a pharmaceutically acceptable salt thereof.

15. The pharmaceutical composition of claim 14, wherein the one or more additional therapeutic agents comprises an anti-malarial agent.

16. The pharmaceutical composition of claim 15, wherein the anti-malarial agent is selected from chloroquine and hydroxychloroquine, or a pharmaceutically acceptable salt of each thereof.

17. A method of inhibiting toll-like receptor 7 and/or 8 activity in a subject in need thereof, comprising administering to the subject a therapeutically effective amount of the compound of claim 1, or a pharmaceutically acceptable salt thereof.

18. A method of inhibiting toll-like receptor 7 activity in a subject in need thereof, comprising administering to the subject a therapeutically effective amount of the compound of claim 1, or a pharmaceutically acceptable salt thereof.

19. A method of inhibiting toll-like receptor 8 activity in a subject in need thereof, comprising administering to the subject a therapeutically effective amount of the compound of claim 1, or a pharmaceutically acceptable salt thereof.

20. A method of treating a disease or disorder associated with elevated toll-like receptor 7 and/or 8 activity in a subject in need thereof, comprising administering to the subject a therapeutically effective amount of the compound of claim 1, or a pharmaceutically acceptable salt thereof.

21. A method of treating a disease or disorder associated with elevated toll-like receptor 7 activity in a subject in need thereof, comprising administering to the subject a therapeutically effective amount of the compound of claim 1, or a pharmaceutically acceptable salt thereof.

22. A method of treating a disease or disorder associated with elevated toll-like receptor 8 activity in a subject in need thereof, comprising administering to the subject a therapeutically effective amount of the compound of claim 1, or a pharmaceutically acceptable salt thereof.

23. A method of treating an inflammatory condition in a subject in need thereof, comprising administering to the subject a therapeutically effective amount of the compound of claim 1, or a pharmaceutically acceptable salt thereof.

24. The method of claim 23, wherein the inflammatory condition is selected from inflammatory bowel disease, psoriasis, psoriatic arthritis, rheumatoid arthritis, glomerulonephritis, mixed connective tissue disease (MCTD), dermatomyositis, polymyositis, systemic sclerosis, antineutrophil cytoplasmic antibody-associated vasculitis, antiphospholipid syndrome, autoimmune hemolytic anemia, macrophage activation syndrome driven inflammatory anemia, IgA nephropathy, type I diabetes, non-alcoholic steatohepatitis, and Sjogren's syndrome.

25. A method of treating systemic lupus erythematosus in a subject in need thereof, comprising administering to the subject a therapeutically effective amount of the compound of claim 1, or a pharmaceutically acceptable salt thereof.

26. A method of treating cutaneous lupus erythematosus in a subject in need thereof, comprising administering to the subject a therapeutically effective amount of the compound of claim 1, or a pharmaceutically acceptable salt thereof.

27. A method of treating lupus nephritis in a subject in need thereof, comprising administering to the subject a therapeutically effective amount of the compound of claim 1, or a pharmaceutically acceptable salt thereof.

28. The method of claim 23, further comprising administering a therapeutically effective amount of one or more additional therapeutic agents, or a pharmaceutically acceptable salt thereof.

29. The method of claim 28, wherein the one or more additional therapeutic agents is selected from the group consisting of veltuzumab, PF-06835375, eculizumab, milatuzumab, SM-06, SM-03, BT-063, QX-006-N, BOS-161721, AK-101, TNX-1500, theralizumab, daxdilimab, TAK-079, felzartamab, itolizumab, anifrolumab, iscalimab, dapirolizumab pegol, lanalumab, LY-3361237, JNJ-55920839, UBP-1213, DS-7011, PFI-102, BIIB-059, obexelimab, talacotuzumab, vobarilizumab, TE-2324, PRV-3279, chloroquine, hydroxychloroquine, hydroxychloroquine sulfate, COV-08-0064; GNKS-356, AVO-101, rozibafusp alfa, VRN-02, annexuzlimab, ALPN-101, bendamustine hydrochloride, BMS-986256, NKTR-35, atacicept, telitacicept, BMS-986256, M-5049, KZR-616, KPG-818, verdinexor, ALPN-303, valziflocept, LA-1, cenerimod, prednisone, corticotropin, deucravacitinib, CPL-409116, CS-12192, tofacitinib citrate, ISB-830, DV-1079, ajulemic acid, iberdomide, TAM-01, BML-258, brepocitinib, SDC-1801, SDC-1802, ICP-330, NTR-441, dalazatide, GSK-2646264, SKI-O-703, lanraplenib (GS-9876), GNS-1653, HMPL-523, RSLV-132, interleukin-2 follow-on biologic, interleukin-2 Anteluke, interking recombinant human interleukin-2, ILT-101, CUG-252, DZ-2002, PEGylated HLA-x, AC-0058, fenebrutinib, XNW-1011, tirabrutinib hydrochloride, branebrutinib, elsubrutinib, orelabrutinib, DWP-213388, INV-103, R-salbutamol sulphate, anchorins, NIK-SMI1, X-6, INV-17, Oshadi D, baricitinib, upadacitinib, filgotinib, itacitinib, INCB-54707, delgocitinib, DWP-212525, CKD-971, mometasone, betamethasone, forigerimod, anandamide, DCB-SLE1, arsenic trioxide, tairuimide, TV-4710 (edratide), allogeneic human umbilical cord-derived mesenchymal stem cell therapy, LC-200, BI-705564, SM-934, GX-101, TXR-712, TXR-711, CIT-013, MHV-370, TPX-6001, TPX-7001, artenimol, and AMG-592, or a pharmaceutically acceptable salt of any of the foregoing, or any combination thereof.

* * * * *

UNITED STATES PATENT AND TRADEMARK OFFICE
CERTIFICATE OF CORRECTION

PATENT NO. : 12,070,455 B2
APPLICATION NO. : 17/930538
DATED : August 27, 2024
INVENTOR(S) : Stephen E. Ammann et al.

Page 1 of 1

It is certified that error appears in the above-identified patent and that said Letters Patent is hereby corrected as shown below:

In the Claims

In Claim 8, Column 241, Line 15, please replace " 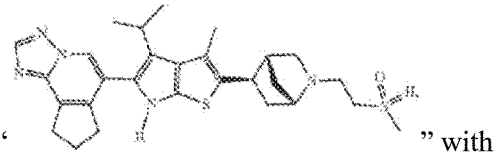 " with

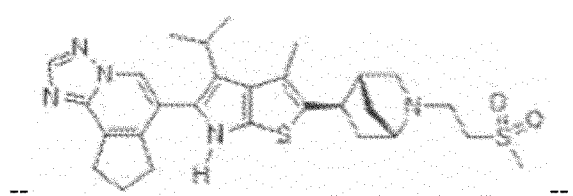

Signed and Sealed this
Twenty-second Day of October, 2024

Katherine Kelly Vidal
*Director of the United States Patent and Trademark Office*